(12) United States Patent
Michaelides et al.

(10) Patent No.: US 8,691,810 B2
(45) Date of Patent: Apr. 8, 2014

(54) PYRROLOPYRIDINE AND PYRROLOPYRIMIDINE INHIBITORS OF KINASES

(75) Inventors: Michael R. Michaelides, Libertyville, IL (US); Andrew S. Judd, Grayslake, IL (US); Shannon R. Fix-Stenzel, Chicago, IL (US); Richard F. Clark, Gurnee, IL (US); Bryan K. Sorensen, Antioch, IL (US); Zhiqin Ji, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 288 days.

(21) Appl. No.: 13/106,076

(22) Filed: May 12, 2011

(65) Prior Publication Data
US 2011/0281842 A1 Nov. 17, 2011

Related U.S. Application Data

(60) Provisional application No. 61/333,850, filed on May 12, 2010.

(51) Int. Cl.
| | | |
|---|---|---|
| A61K 31/5513 | (2006.01) | |
| A61K 31/5377 | (2006.01) | |
| A61K 31/496 | (2006.01) | |
| A61K 31/437 | (2006.01) | |
| C07D 471/04 | (2006.01) | |
| C07D 243/14 | (2006.01) | |
| A61K 31/519 | (2006.01) | |
| C07D 487/04 | (2006.01) | |
| A61P 35/04 | (2006.01) | |

(52) U.S. Cl.
USPC .......... 514/218; 514/234.5; 514/253.04; 514/113; 514/265.1; 546/113; 544/127; 544/280; 540/575

(58) Field of Classification Search
USPC .......................... 544/113; 514/300
See application file for complete search history.

(56) References Cited

FOREIGN PATENT DOCUMENTS

WO    WO2010000364 A1    1/2010

OTHER PUBLICATIONS

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Kolb A.J., et al., "Tyrosine Kinase Assays Adapted to Homogeneous Time-Resolved Fluorescence," Drug Discovery Today, 1998, vol. 3 (7), pp. 333-342.
Mathis G., "HTRF® Technology," Journal of Biomolecular Screening, 1999, vol. 4 (6), pp. 309-314.
Sutton, V.R. et al., "Bcl-2 Prevents Apoptosis Induced by Perforin And Granzyme B, but Not That Mediated by Whole Cytotoxic Lymphocytes," Journal of Immunology, 1997, vol. 158 (12), pp. 5783-5790.
International Search Report and Written Opinion for Application No. PCT/US2011/036298, mailed Aug. 16, 2011, 10 pages.

*Primary Examiner* — Susanna Moore
(74) *Attorney, Agent, or Firm* — Lisa V. Mueller; Michael Best & Friedrich LLP

(57) ABSTRACT

The present invention relates to compounds of formula (I) or pharmaceutical acceptable salts,

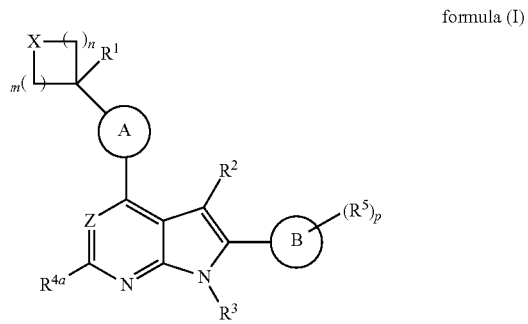

formula (I)

wherein A, B, $R^1$, $R^2$, $R^3$, $R^{4a}$, $R^5$, and Z are defined in the description. The present invention relates also to methods of making said compounds, and compositions containing said compounds which are useful for inhibiting kinases such as aurora.

17 Claims, No Drawings

PYRROLOPYRIDINE AND PYRROLOPYRIMIDINE INHIBITORS OF KINASES

CROSS-REFERENCE TO RELATED APPLICATIONS

This application claims priority to U.S. Provisional Application Ser. No. 61/333,850 filed May 12, 2010, which is incorporated by reference in its entirety.

FIELD OF THE INVENTION

This invention pertains to compounds that inhibit protein kinases such as Aurora-kinases and the VEGFR and PDGFR families of kinases, compositions containing the compounds, and methods of treating diseases using the compounds.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the g-phosphate group of ATP to hydroxyl groups on target proteins. 518 such enzymes exist in the human genome of which ~90 selectively catalyze the phosphorylation of tyrosine hydroxyl groups Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.

RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, -C, -D, -E and placenta growth factor (PlGF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis.

The PDGF receptor (PDGFR) family consists of five RTK's, PDGFR-a and -b, CSF1R, KIT, and FLT3.

The a and b isoforms of the platelet-derived growth factor (PDGF) receptors occur as homodimers or a/b heterodimers and are found most commonly on the surface of fibroblasts and smooth muscle cells. PDGFR-b contributes to tumor angiogenesis through the proliferation and migration of pericytes, the peri-endothelial cells that associate with and stabilize immature blood vessels. In gliomas, autocrine PDGFR stimulation, brought about by the co-expression of PDGF and PDGF receptors, mediates tumor cell proliferation and survival.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention has numerous embodiments. One embodiment of this invention, therefore, pertains to compounds that have formula (I):

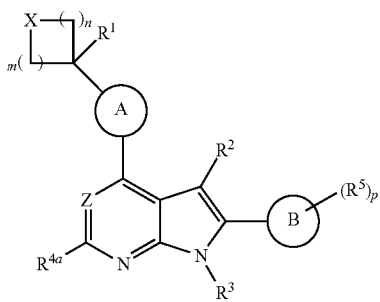

formula (I)

wherein
A is heteroaryl,
B is aryl, heteroaryl, heterocycloalkenyl, or —CH═CH—;
X is —CH$_2$—, —NR$^8$—, —O—, —S—, —S(O)—, or —SO$_2$—;
Z is C—R$^{4b}$ or N;
m is 0, 1, or 2;
n is 1 or 2;
p is 0, 1, 2, 3, or 4;
R$^1$ is halogen, —OR$^9$, or —NR$^{10}$R$^{11}$;
R$^2$ and R$^3$ are independently hydrogen or C$_{1-8}$-alkyl, wherein the C$_{1-8}$ alkyl is optionally substituted with aryl, heterocyclyl, C$_{3-8}$-cycloalkyl, halogen, cyano, hydroxy, C$_{1-4}$-alkoxy, —NH$_2$, —NH(C$_{1-4}$-alkyl), and —N(C$_{1-4}$-alkyl)$_2$;
R$^{4a}$ and R$^{4b}$ are independently hydrogen, nitro, halogen, cyano, C$_{1-4}$-alkyl, C$_{1-4}$-haloalkyl, —OR$^a$, —NR$^b$R$^c$; —C(O)OR$^a$, —C(O)NR$^b$R$^c$, —NR$^b$C(O)R$^c$, —NHC(O)NHR$^b$, or —NHSO$_2$R$^a$;
R$^5$ is R$^6$, nitro, halogen, cyano, C$_{1-4}$-haloalkyl, OR$^d$, —C(O)R$^d$, —C(O)OR$^d$, —OC(O)R$^d$, —NR$^e$R$^f$, —NR$^e$C(O)R$^d$, —NHC(O)NHR$^e$, —NHSO$_2$R$^e$, —C(O)NR$^e$R$^f$, —SR$^c$, —S(O)R$^c$, —SO$_2$R$^c$, or —SO$_2$NR$^c$NR$^d$;
R$^6$ is C$_{1-8}$-alkyl, aryl, or heterocyclyl, wherein the R$^6$ C$_{1-8}$-alkyl substituent is optionally substituted with one or more substituents selected from the group consisting of R$^7$, halogen, cyano, nitro, —OR$^g$, —C(O)R$^g$, —C(O)OR$^g$, —OC(O)R$^g$, —NR$^h$R$^i$, —NR$^h$C(O)R$^g$, —NHC(O)NHR$^b$, —C(O)NR$^h$R$^i$; and wherein (b) the R$^6$ aryl or heterocyclyl substituents are optionally substituted with one or more substituents independently selected from the group consisting of C$_{1-8}$-alkyl, aryl, heterocyclyl, halogen, cyano, nitro, C$_{1-4}$-haloalkyl, —OR$^j$, —C(O)R$^j$, —C(O)OR$^j$, —OC(O)R$^j$, —NR$^k$R$^l$, —NR$^k$C(O)R$^j$, —NHC(O)NHR$^k$, —NHSO$_2$R$^j$, —C(O)NR$^k$R$^l$, —SR$^j$, —S(O)R$^j$, —SO$_2$R$^j$, and —SO$_2$NR$^k$NR$^l$;
R$^7$ is cycloalkyl, aryl, heteroaryl, or heterocycloalkyl, wherein the cycloalkyl, aryl, heteroaryl, or heterocycloalkyl are optionally substituted with C$_{1-8}$-alkyl, halogen, cyano, nitro, C$_{1-4}$-haloalkyl, —OR$^j$, —C(O)R$^j$, —C(O)OR$^j$, —OC(O)R$^j$, —NR$^k$R$^l$, —NR$^k$C(O)R$^j$, —NHC(O)NHR$^k$, —NHSO$_2$R$^j$, —C(O)NR$^k$R$^l$, —SR$^j$, —S(O)R$^j$, —SO$_2$R$^j$, and —SO$_2$NR$^k$NR$^l$,
R$^8$ is hydrogen, C$_{1-8}$-alkyl, or —C(O)C$_{1-8}$-alkyl;
R$^9$ is hydrogen, C$_{1-8}$-alkyl, phenyl, or benzyl, wherein the C$_{1-8}$-alkyl is optionally substituted with —OC$_{1-8}$-alkyl, —C(O)C$_{1-8}$-alkyl, —C(O)OC$_{1-8}$-alkyl, —OC(O)C$_{1-8}$-alkyl, and wherein R$^9$ phenyl or benzyl ring is optionally substituted with —OC$_{1-8}$-alkyl, —C(O)C$_{1-8}$-alkyl, —C(O)OC$_{1-8}$-alkyl, —OC(O)C$_{1-8}$-alkyl;
R$^{10}$ is hydrogen or C$_{1-8}$-alkyl;
R$^{11}$ is hydrogen, C$_{1-8}$-alkyl, —C(O)R$^m$, —C(O)NH$_2$, —C(O)NHR$^m$, —C(O)NR$^m$R$^n$, or —S(O)$_2$R$^m$;
R$^a$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^b$ and R$^c$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^d$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^g$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^h$ and R$^i$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^j$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;
R$^k$ and R$^l$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, $-NH_2$, $-NH(C_{1-8}$-alkyl), and $-N(C_{1-8}$-alkyl)$_2$;

R''' and R'', at each occurrence, are independently selected from the group consisting of hydrogen, $C_{1-8}$-alkyl, phenyl, or benzyl;

or a pharmaceutically acceptable salt thereof.

Also provided are pharmaceutically acceptable compositions comprising a therapeutically effective amount of a compound of formula (I) a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). In yet another embodiment pertains to a method of decreasing tumor volume in a mammal comprising administering thereto a therapeutically acceptable amount of a compound or pharmaceutically acceptable salt of formula (I).

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having formula (I), with or without also administering radiotherapy thereto.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 7 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxy" (alone or in combination with another term(s)) means an ether substituent, and may be depicted as —O—.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "KDR" means kinase insert domain receptor (a type III receptor tyrosine kinase) and is also known as FLK1, VEGFR, VEGFR2, and CD309.

The term "VEGFR" means vascular endothelial growth factor receptor.

The term "PDGFR" means platelet-derived growth factor receptor.

Compounds

In one aspect, the present invention is directed, in part, to a class of compounds having a structure of formula (I):

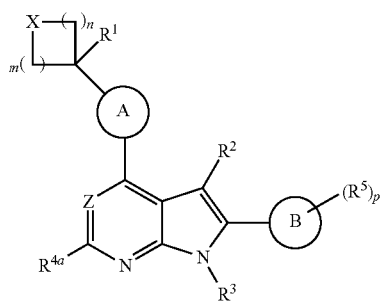

formula (I)

wherein
A is heteroaryl,
B is aryl, heteroaryl, heterocycloalkenyl, or —CH=CH—;
X is —$CH_2$—, —$NR^8$—, —O—, —S—, —S(O)—, or —$SO_2$—;
Z is C—$R^{4b}$ or N;
m is 0, 1, or 2;
n is 1 or 2;
p is 0, 1, 2, 3, or 4;
$R^1$ is halogen, —$OR^9$, or —$NR^{10}R^{11}$;
$R^2$ and $R^3$ are independently hydrogen or $C_{1-8}$-alkyl, wherein the $C_{1-8}$ alkyl is optionally substituted with aryl, heterocyclyl, $C_{3-8}$-cycloalkyl, halogen, cyano, hydroxy, $C_{1-4}$-alkoxy, —$NH_2$, —$NH(C_{1-4}$-alkyl), and —$N(C_{1-4}$-alkyl$)_2$;
$R^{4a}$ and $R^{4b}$ are independently hydrogen, nitro, halogen, cyano, $C_{1-4}$-alkyl, $C_{1-4}$-haloalkyl, —$OR^a$, —$NR^bR^c$; —C(O)$OR^a$, —C(O)$NR^bR^c$, —$NR^bC(O)R^c$, —NHC(O)$NHR^b$, or —$NHSO_2R^a$;
$R^5$ is $R^6$, nitro, halogen, cyano, $C_{1-4}$-haloalkyl, $OR^d$, —C(O)$R^d$, —C(O)$OR^d$, —OC(O)$R^d$, —$NR^eR^f$, —$NR^eC(O)R^d$, —NHC(O)$NHR^e$, —$NHSO_2R^e$, —C(O)$NR^eR^f$, —$SR^c$, —S(O)$R^c$, —$SO_2R^c$, or —$SO_2NR^cNR^d$;
$R^6$ is $C_{1-8}$-alkyl, aryl, or heterocyclyl, wherein the $R^6$ $C_{1-8}$-alkyl substituent is optionally substituted with one or more substituents selected from the group consisting of $R^7$, halogen, cyano, nitro, —$OR^g$, —C(O)$R^g$, —C(O)$OR^g$, —OC(O)$R^g$, —$NR^hR^i$, —$NR^hC(O)R^g$, —NHC(O)$NHR^h$, —C(O)$NR^hR^i$; and wherein (b) the $R^6$ aryl or heterocyclyl substituents are optionally substituted with one or more substituents independently selected from the group consisting of $C_{1-8}$-alkyl, aryl, heterocyclyl, halogen, cyano, nitro, $C_{1-4}$-haloalkyl, —$OR^j$, —C(O)$R^j$, —C(O)$OR^j$, —OC(O)$R^j$, —$NR^kR^l$, —$NR^kC(O)R^j$, —NHC(O)$NHR^k$, —$NHSO_2R^j$, —C(O)$NR^kR^l$, —$SR^j$, —S(O)$R^j$, —$SO_2R^j$, and —$SO_2NR^kNR^l$;

$R^7$ is cycloalkyl, aryl, heteroaryl, or heterocycloalkyl, wherein the cycloalkyl, aryl, heteroaryl, or heterocycloalkyl are optionally substituted with $C_{1-8}$-alkyl, halogen, cyano, nitro, $C_{1-4}$-haloalkyl, —$OR^j$, —C(O)$R^j$, —C(O)$OR^j$, —OC(O)$R^j$, —$NR^kR^l$, —$NR^kC(O)R^j$, —NHC(O)$NHR^k$, —$NHSO_2R^j$, —C(O)$NR^kR^l$, —$SR^j$, —S(O)$R^j$, —$SO_2R^j$, and —$SO_2NR^kNR^l$;
$R^8$ is hydrogen, $C_{1-8}$-alkyl, or —C(O)$C_{1-8}$-alkyl;
$R^9$ is hydrogen, $C_{1-8}$-alkyl, phenyl, or benzyl, wherein the $C_{1-8}$-alkyl is optionally substituted with —O$C_{1-8}$-alkyl, —C(O)$C_{1-8}$-alkyl, —C(O)O$C_{1-8}$-alkyl, —OC(O)$C_{1-8}$-alkyl, and wherein $R^9$ phenyl or benzyl ring is optionally substituted with —O$C_{1-8}$-alkyl, —C(O)$C_{1-8}$-alkyl, —C(O)O$C_{1-8}$-alkyl, —OC(O)$C_{1-8}$-alkyl;
$R^{10}$ is hydrogen or $C_{1-8}$-alkyl;
$R^{11}$ is hydrogen, $C_{1-8}$-alkyl, —C(O)$R^m$, —C(O)$NH_2$, —C(O)$NHR^m$, —C(O)$NR^mR^n$, or —S(O)$_2R^m$;
$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl$)_2$;
$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl$)_2$;
$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl$)_2$;
$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl$)_2$;
$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl$)_2$;
$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^m$ and $R^n$, at each occurrence, are independently selected from the group consisting of hydrogen, $C_{1-8}$-alkyl, phenyl, or benzyl;

or a pharmaceutically acceptable salt thereof.

In one embodiment of formula (I), Z is N. In another embodiment of formula (I), Z is $CR^{4b}$.

In one embodiment of formula (I), A is thiazolyl, pyridinyl, or pyrrolyl. In another embodiment of formula (I), A is thiazolyl.

In one embodiment of formula (I), X is —$CH_2$— and m is 1 and n is 1. In another embodiment of formula (I), X is —$NR^8$— and m is 1 and n is 1 or 2. In another embodiment of formula (I), X is O and m is 1 and n is 1. In another embodiment of formula (I), X is —$SO_2$— and m is 1 and n is 2. In another embodiment of formula (I), X is —S— and m is 1 and n is 2. In another embodiment of formula (I), X is —$CH_2$— or —$NR^8$— and m is 1 and n is 1.

In one embodiment of formula (I), $R^1$ is —$OR^9$ or —$NR^{10}R^{11}$. In another embodiment of formula (I), $R^1$ is —OH or $NH_2$. In another embodiment of formula (I), $R^1$ is fluoro.

In one embodiment of formula (I), $R^2$ is hydrogen.

In one embodiment of formula (I), $R^3$ is hydrogen.

In one embodiment of formula (I), $R^{4a}$ and $R^{4b}$ are each independently hydrogen, hydroxy, nitro, halogen, cyano, trifluoromethyl, trifluoromethoxy, or $C_{1-4}$-alkyl. In another embodiment of formula (I), $R^{4a}$ is hydrogen and $R^{4b}$ is halogen. In yet another embodiment of formula (I), $R^{4a}$ is hydrogen and $R^{4b}$ is chloro. In yet another embodiment of formula (I), $R^{4a}$ is hydrogen and $R^{4b}$ is fluoro.

In another embodiment of formula (I), B is phenyl, pyridyl, tetrahydropyridyl, pyrimidinyl, pyridazinyl, pyrazyl, pyrrolyl, imidazyl, pyrazolyl, triazolyl, furanyl, thiophenyl, oxazolyl, isoxazolyl, thiazolyl, isothiazolyl, oxadiazolyl, or isothiazolyl. In yet another embodiment of formula (I), B is indolyl, isoindolyl, indazolyl, isoindazoyl, quinolinyl, benzoxazolyl, benzofuranyl, benzothiophenyl, benzothiazolyl, benzimidazolyl, benzotriazolyl, 1,2,3,4-tetrahydroquinoline, 1,2,3,4-tetrahydroisoquinoline, isoindolinyl, indolinyl, or pyrazolo[1,5-a]pyridine. In yet another embodiment of formula (I), B is pyridine, tetrahydropyridine, pyrazole, or phenyl.

In one embodiment of formula (I), B is unsubstituted.

In one embodiment of formula (I), B is substituted with $R^5$ and p is 1, wherein $R^5$ is $C_{1-8}$-alkyl, wherein the $C_{1-8}$-alkyl is optionally substituted one or two substituents independently selected from the group consisting of $R^7$, —$OR^g$, —$C(O)OR^g$, —$NR^hR^i$, —$NR^hC(O)R^g$, and —$C(O)NR^hR^i$, wherein $R^7$ is heterocycloalkyl is optionally substituted with $C_{1-8}$-alkyl, $C_{1-4}$-haloalkyl, halogen, —$OR^j$, or —$NR^kR^l$, wherein $R^g$, $R^h$, $R^k$, and $R^l$ are independently selected from hydrogen, $C_{1-8}$-alkyl, aryl, and $C_{3-8}$-cycloalkyl.

In one embodiment of formula (I), B is substituted with $R^5$ and p is 1, wherein $R^5$ is heterocycloalkyl, wherein the heterocycloalkyl is optionally substituted with $C_{1-8}$-alkyl, $C_{1-4}$-haloalkyl, halogen, —$OR^j$, or —$NR^kR^l$, wherein $R^j$, $R^k$, and $R^l$ are independently selected from hydrogen, $C_{1-8}$-alkyl, aryl, and $C_{3-8}$-cycloalkyl.

In yet another embodiment of formula (I), B is substituted with $R^5$ and p is 1, 2, or 3, and $R^5$ is selected from the group consisting of halogen, $C_{1-4}$-haloalkyl, $OR^d$, —$C(O)OR^d$, —$NR^eC(O)R^d$, —$NHSO_2R^e$, —$C(O)NR^eR^f$, —$SO_2R^c$, or —$SO_2NR^cNR^d$; $R^d$, $R^e$, and $R^f$ are independently selected from the group consisting of hydrogen, $C_{1-8}$-alkyl, aryl, and $C_{3-8}$-cycloalkyl, wherein the $C_{1-8}$-alkyl, aryl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$.

Another aspect of the invention is directed to compounds having a structure of formula (II):

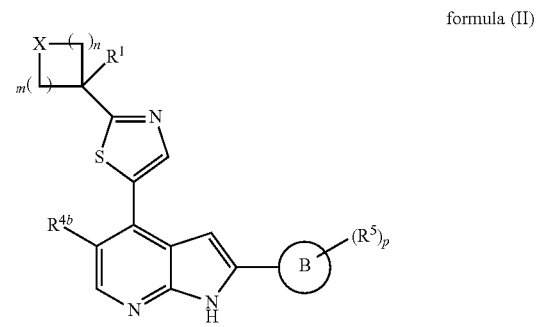

formula (II)

wherein

B is aryl, heteroaryl, heterocycloalkenyl, or —CH=CH—;

X is —$CH_2$—, —$NR^8$—, —O—, —S—, —S(O)—, or —$SO_2$—;

m is 0, 1, or 2;

n is 1 or 2;

p is 0, 1, 2, 3, or 4;

$R^1$ is halogen, —$OR^9$, or —$NR^{10}R^{11}$;

$R^{4b}$ is hydrogen, nitro, halogen, cyano, $C_{1-4}$-alkyl, $C_{1-4}$-haloalkyl, —$OR^a$, —$NR^bR^c$; —$C(O)OR^a$, —$C(O)NR^bR^c$, —$NR^bC(O)R^c$, —$NHC(O)NHR^b$, or —$NHSO_2R^a$;

$R^5$ is $R^6$, nitro, halogen, cyano, $C_{1-4}$-haloalkyl, $OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^e$, —$C(O)NR^eR^f$, —$SR^c$, —$S(O)R^c$, —$SO_2R^c$, or —$SO_2NR^cNR^d$;

$R^6$ is $C_{1-8}$-alkyl, aryl, or heterocyclyl, wherein the $R^6$ $C_{1-8}$-alkyl substituent is optionally substituted with one or more substituents selected from the group consisting of $R^7$, halogen, cyano, nitro, —$OR^g$, —$C(O)R^g$, —$C(O)OR^g$, —$OC(O)R^g$, —$NR^hR^i$, —$NR^hC(O)R^g$, —$NHC(O)NHR^h$, —$C(O)NR^hR^i$; and wherein (b) the $R^6$ aryl or heterocyclyl substituents are optionally substituted with one or more substituents independently selected from the group consisting of $C_{1-8}$-alkyl, aryl, heterocyclyl, halogen, cyano, nitro, $C_{1-4}$-haloalkyl, —$OR^j$, —$C(O)R^j$, —$C(O)OR^j$, —$OC(O)R^j$, —NR$^k$R$^l$, —NR$^k$C(O)R$^j$, —NHC(O)NHR$^k$, —NHSO$_2$R$^j$, —C(O)NR$^k$R$^l$, —SR$^j$, —S(O)R$^j$, —SO$_2$R$^j$, and —SO$_2$NR$^k$NR$^l$;

R$^7$ is cycloalkyl, aryl, heteroaryl, or heterocycloalkyl, wherein the cycloalkyl, aryl, heteroaryl, or heterocycloalkyl are optionally substituted with C$_{1-8}$-alkyl, halogen, cyano, nitro, C$_{1-4}$-haloalkyl, —OR$^j$, —C(O)R$^j$, —C(O)OR$^j$, —OC(O)R$^j$, —NR$^k$R$^l$, —NR$^k$C(O)R$^j$, —NHC(O)NHR$^k$, —NHSO$_2$R$^j$, —C(O)NR$^k$R$^l$, —SR$^j$, —S(O)R$^j$, —SO$_2$R$^j$, and —SO$_2$NR$^k$NR$^l$, R$^8$ is hydrogen, C$_{1-8}$-alkyl, or —C(O)C$_{1-8}$-alkyl;

R$^9$ is hydrogen, C$_{1-8}$-alkyl, phenyl, or benzyl, wherein the C$_{1-8}$-alkyl is optionally substituted with —OC$_{1-8}$-alkyl, —C(O)C$_{1-8}$-alkyl, —C(O)OC$_{1-8}$-alkyl, —OC(O)C$_{1-8}$-alkyl, and wherein R$^g$ phenyl or benzyl ring is optionally substituted with —OC$_{1-8}$-alkyl, —C(O)C$_{1-8}$-alkyl, —C(O)OC$_{1-8}$-alkyl, —OC(O)C$_{1-8}$-alkyl;

R$^{10}$ is hydrogen or C$_{1-8}$-alkyl;

R$^{11}$ is hydrogen, C$_{1-8}$-alkyl, —C(O)R$^m$, —C(O)NH$_2$, —C(O)NHR$^m$, —C(O)NR$^m$R$^n$, or —S(O)$_2$R$^m$;

R$^a$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^b$ and R$^c$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^d$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^g$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^h$ and R$^i$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^j$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^k$ and R$^l$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^m$ and R$^n$, at each occurrence, are independently selected from the group consisting of hydrogen, C$_{1-8}$-alkyl, phenyl, or benzyl;

or a pharmaceutically acceptable salt thereof.

In one embodiment of formula (II), X is —CH$_2$— and m is 1 and n is 1. In another embodiment of formula (II), X is —NR$^8$— and m is 1 and n is 1 or 2. In another embodiment of formula (II), X is O and m is 1 and n is 1. In another embodiment of formula (II), X is —SO$_2$— and m is 1 and n is 2. In another embodiment of formula (II), X is —S— and m is 1 and n is 2.

In another embodiment of formula (II), X is —CH$_2$— or —NR$^8$— and m is 1 and n is 1.

In one embodiment of formula (II), R$^1$ is —OR$^9$ or —NR$^{10}$R$^{11}$. In another embodiment of formula (II), R$^1$ is —OH or NH$_2$. In another embodiment of formula (II), R$^1$ is fluoro.

In one embodiment of formula (II), R$^{4b}$ is chloro. In yet another embodiment of formula (II), R$^{4b}$ is fluoro.

In another embodiment of formula (II), B is phenyl, pyridyl, tetrahydropyridyl, pyrimidinyl, pyridazinyl, pyrazyl, pyrrolyl, imidazyl, pyrazolyl, triazolyl, furanyl, thiophenyl, oxazolyl, isoxazolyl, thiazolyl, isothiazolyl, oxadiazolyl, or isothiazolyl. In yet another embodiment of formula (II), B is indolyl, isoindolyl, indazolyl, isoindazoyl, benzoxazolyl, benzofuranyl, benzothiophenyl, benzothiazolyl, benzimidazolyl, benzotriazolyl, 1,2,3,4-tetrahydroquinoline, 1,2,3,4-tetrahydroisoquinoline, isoindolinyl, indolinyl, or pyrazolo[1,5-a]pyridine. In yet another embodiment of formula (II), B is pyridine, tetrahydropyridine, pyrazole, or phenyl.

In one embodiment of formula (II), B is unsubstituted.

In one embodiment of formula (II), B is substituted with R$^5$ and p is 1, wherein R$^5$ is C$_{1-8}$-alkyl, wherein the C$_{1-8}$-alkyl is optionally substituted one or two substituents independently selected from the group consisting of R$^7$, —OR$^g$, —C(O)OR$^g$, —NR$^h$R$^i$, —NR$^h$C(O)R$^g$, and —C(O)NR$^h$R$^i$, wherein R$^7$ is heterocycloalkyl is optionally substituted with C$_{1-8}$-alkyl, C$_{1-4}$-haloalkyl, halogen, —OR$^j$, or —NR$^k$R$^l$, wherein R$^g$, R$^h$, R$^k$, and R$^l$ are independently selected from hydrogen, C$_{1-8}$-alkyl, aryl, and C$_{3-8}$-cycloalkyl.

In one embodiment of formula (II), B is substituted with R$^5$ and p is 1, wherein R$^5$ is heterocycloalkyl, wherein the heterocycloalkyl is optionally substituted with C$_{1-8}$-alkyl, C$_{1-4}$-haloalkyl, halogen, —OR$^j$, or —NR$^k$R$^l$, wherein R$^j$, R$^k$, and R$^l$ are independently selected from hydrogen, C$_{1-8}$-alkyl, aryl, and C$_{3-8}$-cycloalkyl.

In yet another embodiment of formula (II), B is substituted with $R^5$ and p is 1, 2, or 3, and $R^5$ is selected from the group consisting of halogen, $C_{1-4}$-haloalkyl, $OR^d$, —C(O)$OR^d$, —$NR^eC(O)R^d$, —$NHSO_2R^e$, —C(O)$NR^eR^f$, —$SO_2R^e$, or —$SO_2NR^cNR^d$; $R^d$, $R^e$, and $R^f$ are independently selected from the group consisting of hydrogen, $C_{1-8}$-alkyl, aryl, and $C_{3-8}$-cycloalkyl, wherein the $C_{1-8}$-alkyl, aryl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —NH($C_{1-8}$-alkyl), and —N($C_{1-8}$-alkyl)$_2$.

Another aspect of the invention is directed to compounds having a structure of formula (IIa) or (IIb):

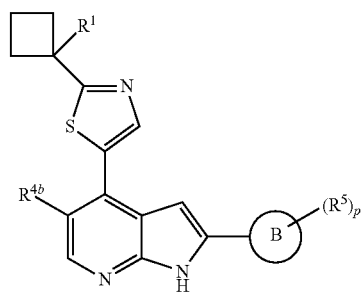

formula (IIa)

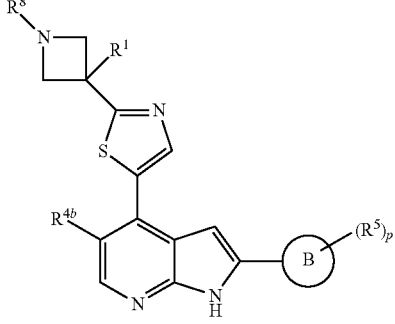

formula (IIb)

wherein B, $R^1$, $R^{4b}$, $R^5$, $R^8$, and p are as defined herein.

In one embodiment of formula (IIa) or formula (IIb), $R^1$ is OH and $NH_2$.

In one embodiment of formula (IIa) or formula (IIb), $R^{4b}$ is chloro or fluoro.

In one embodiment of formula (IIa) or formula (IIb), B is phenyl. In another embodiment of formula (IIa) or formula (IIb), B is pyrazolyl.

Another aspect of the invention is directed to compounds having a structure of formula (III):

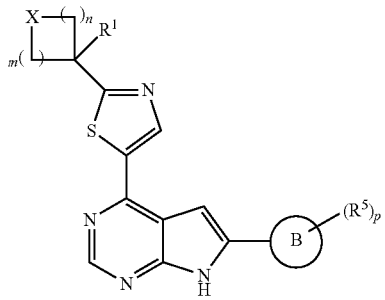

formula (III)

wherein

B is aryl, heteroaryl, heterocycloalkenyl, or —CH=CH—;

X is —$CH_2$—, —$NR^8$—, —O—, —S—, —S(O)—, or —$SO_2$—;

m is 0, 1, or 2;

n is 1 or 2;

p is 0, 1, 2, 3, or 4;

$R^1$ is halogen, —$OR^9$, or —$NR^{10}R^{11}$;

$R^5$ is $R^6$, nitro, halogen, cyano, $C_{1-4}$-haloalkyl, $OR^d$, —C(O)$R^d$, —C(O)$OR^d$, —OC(O)$R^d$, —$NR^eR^f$, —$NR^eC(O)R^d$, —NHC(O)$NHR^e$, —$NHSO_2R^e$, —C(O)$NR^eR^f$, —$SR^e$, —S(O)$R^e$, —$SO_2R^e$, or —$SO_2NR^cNR^d$;

$R^6$ is $C_{1-8}$-alkyl, aryl, or heterocyclyl, wherein the $R^6$ $C_{1-8}$-alkyl substituent is optionally substituted with one or more substituents selected from the group consisting of $R^7$, halogen, cyano, nitro, —$OR^g$, —C(O)$R^g$, —C(O)$OR^g$, —OC(O)$R^g$, —$NR^hR^i$, —$NR^hC(O)R^g$, —NHC(O)$NHR^h$, —C(O)$NR^hR^i$; and wherein (b) the $R^6$ aryl or heterocyclyl substituents are optionally substituted with one or more substituents independently selected from the group consisting of $C_{1-8}$-alkyl, aryl, heterocyclyl, halogen, cyano, nitro, $C_{1-4}$-haloalkyl, —$OR^j$, —C(O)$R^j$, —C(O)$OR^j$, —OC(O)$R^j$, —$NR^kR^l$, —$NR^kC(O)R^j$, —NHC(O)$NHR^k$, —$NHSO_2R^j$, —C(O)$NR^kR^l$, —$SR^j$, —S(O)$R^j$, —$SO_2R^j$, and —$SO_2NR^kNR^l$;

$R^7$ is cycloalkyl, aryl, heteroaryl, or heterocycloalkyl, wherein the cycloalkyl, aryl, heteroaryl, or heterocycloalkyl are optionally substituted with $C_{1-8}$-alkyl, halogen, cyano, nitro, $C_{1-4}$-haloalkyl, —$OR^j$, —C(O)$R^j$, —C(O)$OR^j$, —OC(O)$R^j$, —$NR^kR^l$, —$NR^kC(O)R^j$, —NHC(O)$NHR^k$, —$NHSO_2R^j$, —C(O)$NR^kR^l$, —$SR^j$, —S(O)$R^j$, —$SO_2R^j$, and —$SO_2NR^kNR^l$, $R^8$ is hydrogen, $C_{1-8}$-alkyl, or —C(O)$C_{1-8}$-alkyl;

$R^9$ is hydrogen, $C_{1-8}$-alkyl, phenyl, or benzyl, wherein the $C_{1-8}$-alkyl is optionally substituted with —$OC_{1-8}$-alkyl, —C(O)$C_{1-8}$-alkyl, —C(O)$OC_{1-8}$-alkyl, —OC(O)$C_{1-8}$-alkyl, and wherein $R^9$ phenyl or benzyl ring is optionally substituted with —$OC_{1-8}$-alkyl, —C(O)$C_{1-8}$-alkyl, —C(O)$OC_{1-8}$-alkyl, —OC(O)$C_{1-8}$-alkyl;

$R^{10}$ is hydrogen or $C_{1-8}$-alkyl;

$R^{11}$ is hydrogen, $C_{1-8}$-alkyl, —C(O)$R^m$, —C(O)$NH_2$, —C(O)$NHR^m$, —C(O)$NR^mR^n$, or —$S(O)_2R^m$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —NH($C_{1-8}$-alkyl), and —N($C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —NH($C_{1-8}$-alkyl), and —N($C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —NH$_2$, —NH(C$_{1-8}$-alkyl), and —N(C$_{1-8}$-alkyl)$_2$;

R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^g$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^h$ and R$^i$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^j$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^k$ and R$^l$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$;

R$^m$ and R$^n$, at each occurrence, are independently selected from the group consisting of hydrogen, C$_{1-8}$-alkyl, phenyl, or benzyl;

or a pharmaceutically acceptable salt thereof.

In one embodiment of formula (III), X is —CH$_2$— and m is 1 and n is 1. In another embodiment of formula (III), X is —NR$^8$— and m is 1 and n is 1 or 2. In another embodiment of formula (III), X is O and m is 1 and n is 1. In another embodiment of formula (III), X is —SO$_2$— and m is 1 and n is 2. In another embodiment of formula (III), X is —S— and m is 1 and n is 2.

In another embodiment of formula (III), X is —CH$_2$— or —NR$^8$— and m is 1 and n is 1.

In one embodiment of formula (III), R$^1$ is —OR$^9$ or —NR$^{10}$R$^{11}$. In another embodiment of formula (III), R$^1$ is —OH or NH$_2$. In another embodiment of formula (II), R$^1$ is fluoro.

In another embodiment of formula (III), B is phenyl, pyridyl, tetrahydropyridyl, pyrimidinyl, pyridazinyl, pyrazyl, pyrrolyl, imidazyl, pyrazolyl, triazolyl, furanyl, thiophenyl, oxazolyl, isoxazolyl, thiazolyl, isothiazolyl, oxadiazolyl, or isothiazolyl. In yet another embodiment of formula (III), B is indolyl, isoindolyl, indazolyl, isoindazoyl, quinolinyl, benzoxazolyl, benzofuranyl, benzothiophenyl, benzothiazolyl, benzimidazolyl, benzotriazolyl, 1,2,3,4-tetrahydroquinoline, 1,2,3,4-tetrahydroisoquinoline, isoindolinyl, indolinyl, or pyrazolo[1,5-a]pyridine. In yet another embodiment of formula (II), B is pyridine, tetrahydropyridine, pyrazole, or phenyl.

In one embodiment of formula (III), B is unsubstituted.

In one embodiment of formula (III), B is substituted with R$^5$ and p is 1, wherein R$^5$ is C$_{1-8}$-alkyl, wherein the C$_{1-8}$-alkyl is optionally substituted one or two substituents independently selected from the group consisting of R$^7$, —OR$^g$, —C(O)OR$^g$, —NR$^h$R$^i$, —NR$^h$C(O)R$^g$, and —C(O)NR$^h$R$^i$, wherein R$^7$ is heterocycloalkyl is optionally substituted with C$_{1-8}$-alkyl, C$_{1-4}$-haloalkyl, halogen, —OR$^j$, or —NR$^k$R$^l$, wherein R$^g$, R$^h$R$^i$, R$^j$, R$^k$, and R$^l$ are independently selected from hydrogen, C$_{1-8}$-alkyl, aryl, and C$_{3-8}$-cycloalkyl.

In one embodiment of formula (III), B is substituted with R$^5$ and p is 1, wherein R$^5$ is heterocycloalkyl, wherein the heterocycloalkyl is optionally substituted with C$_{1-8}$-alkyl, C$_{1-4}$-haloalkyl, halogen, —OR$^j$, or —NR$^h$R$^i$, wherein R$^j$, R$^k$, and R$^l$ are independently selected from hydrogen, C$_{1-8}$-alkyl, aryl, and C$_{3-8}$-cycloalkyl.

In yet another embodiment of formula (III), B is substituted with R$^5$ and p is 1, 2, or 3, and R$^5$ is selected from the group consisting of halogen, C$_{1-4}$-haloalkyl, OR$^d$, —C(O)OR$^d$, —NR$^e$C(O)R$^d$, —NHSO$_2$R$^e$, —C(O)NR$^e$R$^f$, —SO$_2$R$^c$, or —SO$_2$NR$^c$NR$^d$; R$^d$, R$^e$, and R$^f$ are independently selected from the group consisting of hydrogen, C$_{1-8}$-alkyl, aryl, and C$_{3-8}$-cycloalkyl, wherein the C$_{1-8}$-alkyl, aryl, and C$_{3-8}$-cycloalkyl are optionally substituted with one or more substituents independently selected from the group consisting of aryl, heterocyclyl, C$_{3-8}$-cycloalkyl, halogen, cyano, hydroxy, C$_{1-8}$-alkoxy, —NH$_2$, —NH(C$_{1-8}$-alkyl), and —N(C$_{1-8}$-alkyl)$_2$.

Another aspect of the invention is directed to compounds having a structure of formula (IIIa) or (IIIb):

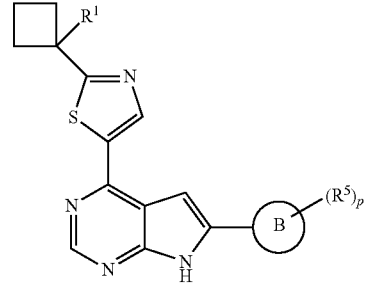

formula (IIIa)

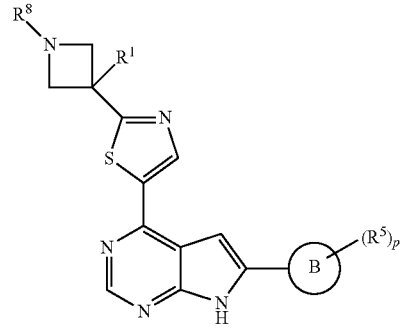

formula (IIIb)

wherein B, R$^1$, R$^5$, R$^8$, and p are as defined herein.

In one embodiment of formula (IIIa) or formula (IIIb), R$^1$ is OH and NH$_2$.

In one embodiment of formula (IIIa) or formula (IIIb), B is phenyl. In another embodiment of formula (IIIa) or formula (IIIb), B is pyrazolyl.

Specific embodiments contemplated as part of the invention include, but are not limited to, compounds of formula (I), for example:

1-(5-{5-chloro-2-[1-(2-morpholin-4-ylethyl)-1H-pyrazol-4-yl]-1H-pyrrolo[2,3-b]pyridin-4-yl}-1,3-thiazol-2-yl)cyclobutanol;

1-{5-[5-fluoro-2-(4-piperazin-1-ylphenyl)-1H-pyrrolo[2,3-b]pyridin-4-yl]-1,3-thiazol-2-yl}cyclobutanol;

1-(5-{2-[4-(morpholin-4-ylmethyl)phenyl]-1H-pyrrolo[2,3-b]pyridin-4-yl}-1,3-thiazol-2-yl)cyclobutanol;

5-chloro-4-{2-[1-(methoxymethoxy)cyclobutyl]-1,3-thiazol-5-yl}-2-[4-(morpholin-4-ylmethyl)phenyl]-1H-pyrrolo[2,3-b]pyridine;

1-(5-{5-chloro-2-[4-(morpholin-4-ylmethyl)phenyl]-1H-pyrrolo[2,3-b]pyridin-4-yl}-1,3-thiazol-2-yl)cyclobutanol;

1-{5-[5-chloro-2-(4-piperazin-1-ylphenyl)-1H-pyrrolo[2,3-b]pyridin-4-yl]-1,3-thiazol-2-yl}cyclobutanol;

5-chloro-4-[2-(1-methoxycyclobutyl)-1,3-thiazol-5-yl]-2-(4-piperazin-1-ylphenyl)-1H-pyrrolo[2,3-b]pyridine;

1-(5-{5-chloro-2-[4-(pyrrolidin-1-ylmethyl)phenyl]-1H-pyrrolo[2,3-b]pyridin-4-yl}-1,3-thiazol-2-yl)cyclobutanol;

1-(5-{5-fluoro-2-[1-(2-morpholin-4-ylethyl)-1H-pyrazol-4-yl]-1H-pyrrolo[2,3-b]pyridin-4-yl}-1,3-thiazol-2-yl)cyclobutanol;

1-(5-{5-fluoro-2-[4-(morpholin-4-ylmethyl)phenyl]-1H-pyrrolo[2,3-b]pyridin-4-yl}-1,3-thiazol-2-yl)cyclobutanol;

3-(5-{5-chloro-2-[4-(morpholin-4-ylmethyl)phenyl]-1H-pyrrolo[2,3-b]pyridin-4-yl}-1,3-thiazol-2-yl)oxetan-3-ol;

3-(5-{5-chloro-2-[1-(2-morpholin-4-ylethyl)-1H-pyrazol-4-yl]-1H-pyrrolo[2,3-b]pyridin-4-yl}-1,3-thiazol-2-yl)oxetan-3-ol;

1-(5-{5-chloro-2-[1-(1,3-dioxolan-2-ylmethyl)-1H-pyrazol-4-yl]-1H-pyrrolo[2,3-b]pyridin-4-yl}-1,3-thiazol-2-yl)cyclobutanol;

1-[5-(5-chloro-2-{1-[2-(dimethylamino)ethyl]-1H-pyrazol-4-yl}-1H-pyrrolo[2,3-b]pyridin-4-yl)-1,3-thiazol-2-yl]cyclobutanol;

1-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)cyclobutanol;

4-{5-chloro-4-[2-(1-hydroxycyclobutyl)-1,3-thiazol-5-yl]-1H-pyrrolo[2,3-b]pyridin-2-yl}benzoic acid;

1-{5-[5-chloro-2-(1-{2-[cyclopropyl(methyl)amino]ethyl}-1H-pyrazol-4-yl)-1H-pyrrolo[2,3-b]pyridin-4-yl]-1,3-thiazol-2-yl}cyclobutanol;

1-(5-{5-chloro-2-[6-(4-methylpiperazin-1-yl)pyridin-3-yl]-1H-pyrrolo[2,3-b]pyridin-4-yl}-1,3-thiazol-2-yl)cyclobutanol;

1-[5-(5-chloro-2-{4-[(4-methylpiperazin-1-yl)carbonyl]phenyl}-1H-pyrrolo[2,3-b]pyridin-4-yl)-1,3-thiazol-2-yl]cyclobutanol;

5-chloro-4-(2-{3-[(4-methoxybenzyl)oxy]oxetan-3-yl}-1,3-thiazol-5-yl)-2-[1-(2-pyrrolidin-1-ylethyl)-1H-pyrazol-4-yl]-1H-pyrrolo[2,3-b]pyridine;

3-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)oxetan-3-ol;

1-{5-[5-chloro-2-(5-piperidin-3-yl-1,2,4-oxadiazol-3-yl)-1H-pyrrolo[2,3-b]pyridin-4-yl]-1,3-thiazol-2-yl}cyclobutanol;

N~1~-(4-{5-chloro-4-[2-(1-hydroxycyclobutyl)-1,3-thiazol-5-yl]-1H-pyrrolo[2,3-b]pyridin-2-yl}phenyl)-N~2~,N~2~-dimethylglycinamide;

1-(5-{5-chloro-2-[3-fluoro-4-(pyrrolidin-1-ylmethyl)phenyl]-1H-pyrrolo[2,3-b]pyridin-4-yl}-1,3-thiazol-2-yl)cyclobutanol;

1-[5-(5-chloro-2-{4-[(dimethylamino)methyl]-3-fluorophenyl}-1H-pyrrolo[2,3-b]pyridin-4-yl)-1,3-thiazol-2-yl]cyclobutanol;

1-(4-{5-chloro-4-[2-(1-hydroxycyclobutyl)-1,3-thiazol-5-yl]-1H-pyrrolo[2,3-b]pyridin-2-yl}-2-fluorobenzyl)pyrrolidin-3-ol;

1-[5-(5-chloro-2-{3-fluoro-4-[(3-fluoropyrrolidin-1-yl)methyl]phenyl}-1H-pyrrolo[2,3-b]pyridin-4-yl)-1,3-thiazol-2-yl]cyclobutanol;

1-[5-(5-chloro-2-{3-fluoro-4-[(2-methylpyrrolidin-1-yl)methyl]phenyl}-1H-pyrrolo[2,3-b]pyridin-4-yl)-1,3-thiazol-2-yl]cyclobutanol;

1-{5-[5-chloro-2-(4-{[cyclopropyl(methyl)amino]methyl}-3-fluorophenyl)-1H-pyrrolo[2,3-b]pyridin-4-yl]-1,3-thiazol-2-yl}cyclobutanol;

1-[5-(5-chloro-2-{3-fluoro-4-[(4-fluoropiperidin-1-yl)methyl]phenyl}-1H-pyrrolo[2,3-b]pyridin-4-yl)-1,3-thiazol-2-yl]cyclobutanol;

1-[5-(5-chloro-2-{4-[(4,4-difluoropiperidin-1-yl)methyl]-3-fluorophenyl}-1H-pyrrolo[2,3-b]pyridin-4-yl)-1,3-thiazol-2-yl]cyclobutanol;

1-[5-(5-chloro-2-phenyl-1H-pyrrolo[2,3-b]pyridin-4-yl)-1,3-thiazol-2-yl]cyclobutanol;

1-{5-[5-chloro-2-(1-methyl-1H-pyrazol-4-yl)-1H-pyrrolo[2,3-b]pyridin-4-yl]-1,3-thiazol-2-yl}cyclobutanol;

1-[5-(5-chloro-2-pyridin-4-yl-1H-pyrrolo[2,3-b]pyridin-4-yl)-1,3-thiazol-2-yl]cyclobutanol;

1-(5-{5-chloro-2-[4-(ethylsulfonyl)phenyl]-1H-pyrrolo[2,3-b]pyridin-4-yl}-1,3-thiazol-2-yl)cyclobutanol;

3-{5-chloro-4-[2-(1-hydroxycyclobutyl)-1,3-thiazol-5-yl]-1H-pyrrolo[2,3-b]pyridin-2-yl}benzoic acid;

(4-{5-chloro-4-[2-(1-hydroxycyclobutyl)-1,3-thiazol-5-yl]-1H-pyrrolo[2,3-b]pyridin-2-yl}phenyl)acetic acid;

(4-{5-chloro-4-[2-(1-hydroxycyclobutyl)-1,3-thiazol-5-yl]-1H-pyrrolo[2,3-b]pyridin-2-yl}-1H-pyrazol-1-yl)acetic acid;

1-(5-{5-chloro-2-[1-(2-hydroxyethyl)-1H-pyrazol-4-yl]-1H-pyrrolo[2,3-b]pyridin-4-yl}-1,3-thiazol-2-yl)cyclobutanol;

1-{5-[5-chloro-2-(2-methylphenyl)-1H-pyrrolo[2,3-b]pyridin-4-yl]-1,3-thiazol-2-yl}cyclobutanol;

1-{5-[5-chloro-2-(3-methylphenyl)-1H-pyrrolo[2,3-b]pyridin-4-yl]-1,3-thiazol-2-yl}cyclobutanol;

1-{5-[5-chloro-2-(2-methoxyphenyl)-1H-pyrrolo[2,3-b]pyridin-4-yl]-1,3-thiazol-2-yl}cyclobutanol;

1-{5-[5-chloro-2-(3-methoxyphenyl)-1H-pyrrolo[2,3-b]pyridin-4-yl]-1,3-thiazol-2-yl}cyclobutanol;

1-{5-[5-chloro-2-(3-fluorophenyl)-1H-pyrrolo[2,3-b]pyridin-4-yl]-1,3-thiazol-2-yl}cyclobutanol;

1-{5-[5-chloro-2-(1,2,3,4-tetrahydroisoquinolin-7-yl)-1H-pyrrolo[2,3-b]pyridin-4-yl]-1,3-thiazol-2-yl}cyclobutanol;

1-{5-[5-chloro-2-(3-piperidin-4-yl-1,2,4-oxadiazol-5-yl)-1H-pyrrolo[2,3-b]pyridin-4-yl]-1,3-thiazol-2-yl}cyclobutanol;

1-{5-[5-chloro-2-(1-methyl-1H-pyrazol-4-yl)-3-(pyrrolidin-1-ylmethyl)-1H-pyrrolo[2,3-b]pyridin-4-yl]-1,3-thiazol-2-yl}cyclobutanol;

N~1~-(4-{5-chloro-4-[2-(1-hydroxycyclobutyl)-1,3-thiazol-5-yl]-1H-pyrrolo[2,3-b]pyridin-2-yl}-3-methylphenyl)-N~2~,N~2~-dimethylglycinamide;

N~1~-(4-{5-chloro-4-[2-(1-hydroxycyclobutyl)-1,3-thiazol-5-yl]-1H-pyrrolo[2,3-b]pyridin-2-yl}-2-methoxyphenyl)-N~2~,N~2~-dimethylglycinamide;

1-{5-[5-chloro-2-(1-piperidin-4-yl-1H-pyrazol-4-yl)-1H-pyrrolo[2,3-b]pyridin-4-yl]-1,3-thiazol-2-yl}cyclobutanol;

3-{5-chloro-4-[2-(1-hydroxycyclobutyl)-1,3-thiazol-5-yl]-1H-pyrrolo[2,3-b]pyridin-2-yl}benzonitrile;

1-(5-{5-chloro-2-[1-(N,N-dimethylglycyl)-2,3-dihydro-1H-indol-5-yl]-1H-pyrrolo[2,3-b]pyridin-4-yl}-1,3-thiazol-2-yl)cyclobutanol;

1-{5-[5-chloro-2-(2,3-dihydro-1H-indol-5-yl)-1H-pyrrolo[2,3-b]pyridin-4-yl]-1,3-thiazol-2-yl}cyclobutanol;

3-(5-{5-fluoro-2-[1-(2-pyrrolidin-1-ylethyl)-1H-pyrazol-4-yl]-1H-pyrrolo[2,3-b]pyridin-4-yl}-1,3-thiazol-2-yl)azetidin-3-ol;

1-(5-{5-chloro-2-[3-fluoro-4-(hydroxymethyl)phenyl]-1H-pyrrolo[2,3-b]pyridin-4-yl}-1,3-thiazol-2-yl)cyclobutanol;

1-(5-{5-chloro-2-[4-(2-pyrrolidin-1-ylethyl)phenyl]-1H-pyrrolo[2,3-b]pyridin-4-yl}-1,3-thiazol-2-yl)cyclobutanol;

1-[5-(5-chloro-2-{4-[(4-methyl-1,4-diazepan-1-yl)carbonyl]phenyl}-1H-pyrrolo[2,3-b]pyridin-4-yl)-1,3-thiazol-2-yl]cyclobutanol;

1-[5-(5-chloro-2-{4-[4-(dimethylamino)piperidin-1-yl]phenyl}-1H-pyrrolo[2,3-b]pyridin-4-yl)-1,3-thiazol-2-yl]cyclobutanol;

1-{5-[5-fluoro-2-(1-methyl-1H-pyrazol-4-yl)-1H-pyrrolo[2,3-b]pyridin-4-yl]-1,3-thiazol-2-yl}cyclobutanol;

N~1~-(4-{5-chloro-4-[2-(1-hydroxycyclobutyl)-1,3-thiazol-5-yl]-1H-pyrrolo[2,3-b]pyridin-2-yl}-3-fluorophenyl)-N~2~,N~2~-dimethylglycinamide;

N~1~-(3-chloro-4-{5-chloro-4-[2-(1-hydroxycyclobutyl)-1,3-thiazol-5-yl]-1H-pyrrolo[2,3-b]pyridin-2-yl}phenyl)-N~2~,N~2~-dimethylglycinamide;

N~1~-(4-{5-chloro-4-[2-(1-hydroxycyclobutyl)-1,3-thiazol-5-yl]-1H-pyrrolo[2,3-b]pyridin-2-yl}-2-methylphenyl)-N~2~,N~2~-dimethylglycinamide;

N~1~-(2-chloro-4-{5-chloro-4-[2-(1-hydroxycyclobutyl)-1,3-thiazol-5-yl]-1H-pyrrolo[2,3-b]pyridin-2-yl}phenyl)-N~2~,N~2~-dimethylglycinamide;

N~1~-(4-{5-chloro-4-[2-(1-hydroxycyclobutyl)-1,3-thiazol-5-yl]-1H-pyrrolo[2,3-b]pyridin-2-yl}-2-fluorophenyl)-N~2~,N~2~-dimethylglycinamide;

1-[5-(5-fluoro-2-{1-[2-(4-methylpiperazin-1-yl)-2-oxoethyl]-1H-pyrazol-4-yl}-1H-pyrrolo[2,3-b]pyridin-4-yl)-1,3-thiazol-2-yl]cyclobutanol;

2-(4-{5-fluoro-4-[2-(1-hydroxycyclobutyl)-1,3-thiazol-5-yl]-1H-pyrrolo[2,3-b]pyridin-2-yl}-1H-pyrazol-1-yl)-N-(methylsulfonyl)acetamide;

1-[5-(5-chloro-2-{1-[(1-methylpiperidin-4-yl)carbonyl]-1,2,3,6-tetrahydropyridin-4-yl}-1H-pyrrolo[2,3-b]pyridin-4-yl)-1,3-thiazol-2-yl]cyclobutanol;

N~1~-(4-{5-chloro-4-[2-(1-hydroxycyclobutyl)-1,3-thiazol-5-yl]-1H-pyrrolo[2,3-b]pyridin-2-yl}-3-methoxyphenyl)-N~2~,N~2~-dimethylglycinamide;

1-(5-{5-chloro-2-[4-(tetrahydrofuran-3-yloxy)phenyl]-1H-pyrrolo[2,3-b]pyridin-4-yl}-1,3-thiazol-2-yl)cyclobutanol;

1-(5-{5-chloro-2-[4-(tetrahydrofuran-2-ylmethoxy)phenyl]-1H-pyrrolo[2,3-b]pyridin-4-yl}-1,3-thiazol-2-yl)cyclobutanol;

1-(5-{5-chloro-2-[4-(1,4-dioxan-2-ylmethoxy)phenyl]-1H-pyrrolo[2,3-b]pyridin-4-yl}-1,3-thiazol-2-yl)cyclobutanol;

1-[5-(5-chloro-2-{4-[(1-methylpiperidin-4-yl)oxy]phenyl}-1H-pyrrolo[2,3-b]pyridin-4-yl)-1,3-thiazol-2-yl]cyclobutanol;

1-[5-(5-fluoro-2-{1-[2-(4-methyl-1,4-diazepan-1-yl)-2-oxoethyl]-1H-pyrazol-4-yl}-1H-pyrrolo[2,3-b]pyridin-4-yl)-1,3-thiazol-2-yl]cyclobutanol;

1-{5-[5-chloro-2-(1,5-dimethyl-1H-pyrazol-4-yl)-1H-pyrrolo[2,3-b]pyridin-4-yl]-1,3-thiazol-2-yl}cyclobutanol;

1-{5-[5-chloro-2-(2,3-dihydro-1,4-benzodioxin-6-yl)-1H-pyrrolo[2,3-b]pyridin-4-yl]-1,3-thiazol-2-yl}cyclobutanol;

1-[5-(5-chloro-2-{4-[(3,3-difluoropiperidin-1-yl)methyl]-3-fluorophenyl}-1H-pyrrolo[2,3-b]pyridin-4-yl)-1,3-thiazol-2-yl]cyclobutanol;

4-(4-{5-chloro-4-[2-(1-hydroxycyclobutyl)-1,3-thiazol-5-yl]-1H-pyrrolo[2,3-b]pyridin-2-yl}-2-fluorobenzyl)piperazin-2-one;

1-{5-[5-chloro-2-(4-{[3-(dimethylamino)pyrrolidin-1-yl]methyl}-3-fluorophenyl)-1H-pyrrolo[2,3-b]pyridin-4-yl]-1,3-thiazol-2-yl}cyclobutanol;

1-{5-[5-chloro-2-(3-fluoro-4-{[4-(trifluoromethyl)piperidin-1-yl]methyl}phenyl)-1H-pyrrolo[2,3-b]pyridin-4-yl]-1,3-thiazol-2-yl}cyclobutanol;

1-{5-[5-chloro-2-(3-fluoro-4-{[3-(trifluoromethyl)piperidin-1-yl]methyl}phenyl)-1H-pyrrolo[2,3-b]pyridin-4-yl]-1,3-thiazol-2-yl}cyclobutanol;

1-[5-(5-chloro-2-{3-fluoro-4-[(2-methylpiperidin-1-yl)methyl]phenyl}-1H-pyrrolo[2,3-b]pyridin-4-yl)-1,3-thiazol-2-yl]cyclobutanol;

1-(5-{5-chloro-2-[3-fluoro-4-(piperazin-1-ylmethyl)phenyl]-1H-pyrrolo[2,3-b]pyridin-4-yl}-1,3-thiazol-2-yl)cyclobutanol;

1-[5-(5-chloro-2-{4-[(4-fluoropiperidin-1-yl)methyl]phenyl}-1H-pyrrolo[2,3-b]pyridin-4-yl)-1,3-thiazol-2-yl]cyclobutanol;

1-(5-{5-chloro-2-[1-(pyridin-2-ylmethyl)-1H-pyrazol-4-yl]-1H-pyrrolo[2,3-b]pyridin-4-yl}-1,3-thiazol-2-yl)cyclobutanol;

1-(5-{5-chloro-2-[1-(pyridin-3-ylmethyl)-1H-pyrazol-4-yl]-1H-pyrrolo[2,3-b]pyridin-4-yl}-1,3-thiazol-2-yl)cyclobutanol;

1-(5-{5-chloro-2-[1-(pyridin-4-ylmethyl)-1H-pyrazol-4-yl]-1H-pyrrolo[2,3-b]pyridin-4-yl}-1,3-thiazol-2-yl)cyclobutanol;

1-[5-(5-chloro-2-pyrazolo[1,5-a]pyridin-3-yl-1H-pyrrolo[2,3-b]pyridin-4-yl)-1,3-thiazol-2-yl]cyclobutanol;

3-[5-(5-fluoro-1H-pyrrolo[2,3-b]pyridin-4-yl)-1,3-thiazol-2-yl]azetidin-3-ol;

1-{5-[5-chloro-2-(1,2,3,6-tetrahydropyridin-4-yl)-1H-pyrrolo[2,3-b]pyridin-4-yl]-1,3-thiazol-2-yl}cyclobutanol;

1-{5-[5-fluoro-2-(3,4,5-trimethoxyphenyl)-1H-pyrrolo[2,3-b]pyridin-4-yl]-1,3-thiazol-2-yl}cyclobutanol;

1-(5-{5-fluoro-2-[3-(methylsulfonyl)phenyl]-1H-pyrrolo[2,3-b]pyridin-4-yl}-1,3-thiazol-2-yl)cyclobutanol;

1-[5-(5-fluoro-2-quinolin-6-yl-1H-pyrrolo[2,3-b]pyridin-4-yl)-1,3-thiazol-2-yl]cyclobutanol;

1-{5-[5-fluoro-2-(5-methoxy-1H-indol-3-yl)-1H-pyrrolo[2,3-b]pyridin-4-yl]-1,3-thiazol-2-yl}cyclobutanol;

3-[5-(5-fluoro-2-pyridin-4-yl-1H-pyrrolo[2,3-b]pyridin-4-yl)-1,3-thiazol-2-yl]azetidin-3-ol;

3-{5-[5-fluoro-2-(1-methyl-1H-pyrazol-4-yl)-1H-pyrrolo[2,3-b]pyridin-4-yl]-1,3-thiazol-2-yl}azetidin-3-ol;

3-(5-{2-[4-(ethylsulfonyl)phenyl]-5-fluoro-1H-pyrrolo[2,3-b]pyridin-4-yl}-1,3-thiazol-2-yl)azetidin-3-ol;

3-(5-{5-fluoro-2-[3-fluoro-4-(morpholin-4-ylmethyl)phenyl]-1H-pyrrolo[2,3-b]pyridin-4-yl}-1,3-thiazol-2-yl)azetidin-3-ol;

3-[5-(5-fluoro-2-phenyl-1H-pyrrolo[2,3-b]pyridin-4-yl)-1,3-thiazol-2-yl]azetidin-3-ol;

3-[5-(2-{4-[(3,3-difluoropiperidin-1-yl)methyl]phenyl}-5-fluoro-1H-pyrrolo[2,3-b]pyridin-4-yl)-1,3-thiazol-2-yl]azetidin-3-ol;

3-[5-(5-fluoro-2-{4-[(2-methylpyrrolidin-1-yl)methyl]phenyl}-1H-pyrrolo[2,3-b]pyridin-4-yl)-1,3-thiazol-2-yl]azetidin-3-ol;

3-[5-(5-fluoro-1H-pyrrolo[2,3-b]pyridin-4-yl)-1,3-thiazol-2-yl]-1-methylazetidin-3-ol;

1-(5-{5-chloro-2-[1-(1,4-dioxan-2-ylcarbonyl)-1,2,3,6-tetrahydropyridin-4-yl]-1H-pyrrolo[2,3-b]pyridin-4-yl}-1,3-thiazol-2-yl)cyclobutanol;

1-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)cyclobutanol;

1-{5-[5-fluoro-2-(5-methoxy-1-methyl-1H-indol-3-yl)-1H-pyrrolo[2,3-b]pyridin-4-yl]-1,3-thiazol-2-yl}cyclobutanol;

1-{5-[2-(5-fluoro-1-methyl-1H-indol-3-yl)-1H-pyrrolo[2,3-b]pyridin-4-yl]-1,3-thiazol-2-yl}cyclobutanol;

3-(5-{5-chloro-2-[4-(pyrrolidin-1-ylmethyl)phenyl]-1H-pyrrolo[2,3-b]pyridin-4-yl}-1,3-thiazol-2-yl)oxetan-3-ol;

3-{5-[5-chloro-2-(1-methyl-1H-pyrazol-4-yl)-1H-pyrrolo[2,3-b]pyridin-4-yl]-1,3-thiazol-2-yl}oxetan-3-ol;

1-(5-{2-[3-(methylsulfonyl)phenyl]-1H-pyrrolo[2,3-b]pyridin-4-yl}-1,3-thiazol-2-yl)cyclobutanol;

1-{5-[2-(1-methyl-1H-pyrazol-4-yl)-1H-pyrrolo[2,3-b]pyridin-4-yl]-1,3-thiazol-2-yl}cyclobutanol;

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N-(4-methoxybenzyl)amine;

1-{1-[5-chloro-2-(1-methyl-1H-pyrazol-4-yl)-1H-pyrrolo[2,3-b]pyridin-4-yl]-1H-pyrazol-4-yl}cyclobutanol;

5-chloro-4-[2-(1-fluorocyclobutyl)-1,3-thiazol-5-yl]-2-[1-(2-morpholin-4-ylethyl)-1H-pyrazol-4-yl]-1H-pyrrolo[2,3-b]pyridine;

5-chloro-4-[2-(1-fluorocyclobutyl)-1,3-thiazol-5-yl]-2-[4-(morpholin-4-ylmethyl)phenyl]-1H-pyrrolo[2,3-b]pyridine;

5-chloro-4-[2-(1-fluorocyclobutyl)-1,3-thiazol-5-yl]-2-[1-(2-pyrrolidin-1-ylethyl)-1H-pyrazol-4-yl]-1H-pyrrolo[2,3-b]pyridine;

3-{5-[5-chloro-2-(1-methyl-1H-pyrazol-4-yl)-1H-pyrrolo[2,3-b]pyridin-4-yl]-1,3-thiazol-2-yl}-1-methylpyrrolidin-3-ol;

3-(5-{5-chloro-2-[4-(morpholin-4-ylmethyl)phenyl]-1H-pyrrolo[2,3-b]pyridin-4-yl}-1,3-thiazol-2-yl)-1-methylpyrrolidin-3-ol;

1-(5-{5-fluoro-2-[2-(4-oxa-1-azabicyclo[3.2.1]oct-5-yl)-1,3-thiazol-5-yl]-1H-pyrrolo[2,3-b]pyridin-4-yl}-1,3-thiazol-2-yl)cyclobutanol;

1-{5-[5-chloro-2-(1-methyl-1H-pyrazol-4-yl)-1H-pyrrolo[2,3-b]pyridin-4-yl]-1,3-thiazol-2-yl}cyclobutanamine;

N-(1-{-5-[5-chloro-2-(1-methyl-1H-pyrazol-4-yl)-1H-pyrrolo[2,3-b]pyridin-4-yl]-1,3-thiazol-2-0yl}cyclobutyl)acetamide;

N-(1-{-5-[5-chloro-2-(1-methyl-1H-pyrazol-4-yl)-1H-pyrrolo[2,3-b]pyridin-4-yl]-1,3-thiazol-2-yl}cyclobutyl)benzamide;

N-(1-{-5-[5-chloro-2-(1-methyl-1H-pyrazol-4-yl)-1H-pyrrolo[2,3-b]pyridin-4-yl]-1,3-thiazol-2-yl}cyclobutyl)-N'-ethylurea;

N-(1-{5-[5-chloro-2-(1-methyl-1H-pyrazol-4-yl)-1H-pyrrolo[2,3-b]pyridin-4-yl]-1,3-thiazol-2-yl}cyclobutyl)methanesulfonamide;

3-{5-[5-chloro-2-(1-methyl-1H-pyrazol-4-yl)-1H-pyrrolo[2,3-b]pyridin-4-yl]-1,3-thiazol-2-yl}-1-methylazetidin-3-ol;

3-(5-{5-chloro-2-[4-(morpholin-4-ylmethyl)phenyl]-1H-pyrrolo[2,3-b]pyridin-4-yl}-1,3-thiazol-2-yl)-1-methylazetidin-3-ol;

1-(1-{5-chloro-2-[4-(pyrrolidin-1-ylmethyl)phenyl]-1H-pyrrolo[2,3-b]pyridin-4-yl}-1H-pyrazol-4-yl)cyclobutanol;

N-(1-{5-[5-chloro-2-(1-methyl-1H-pyrazol-4-yl)-1H-pyrrolo[2,3-b]pyridin-4-yl]-1,3-thiazol-2-yl}cyclobutyl)urea;

N'-(1-{5-[5-chloro-2-(1-methyl-1H-pyrazol-4-yl)-1H-pyrrolo[2,3-b]pyridin-4-yl]-1,3-thiazol-2-yl}cyclobutyl)-N,N-dimethylurea;

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N,N-dimethylamine;

3-{5-[5-chloro-2-(1-methyl-1H-pyrazol-4-yl)-1H-pyrrolo[2,3-b]pyridin-4-yl]-1,3-thiazol-2-yl}-1-ethylpyrrolidin-3-ol;

1-acetyl-3-(5-{5-chloro-2-[4-(morpholin-4-ylmethyl)phenyl]-1H-pyrrolo[2,3-b]pyridin-4-yl}-1,3-thiazol-2-yl)pyrrolidin-3-ol;

3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol 1,1-dioxide;

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N'-phenylurea;

N-benzyl-N'-(1-{5-[5-chloro-2-(1-methyl-1H-pyrazol-4-yl)-1H-pyrrolo[2,3-b]pyridin-4-yl]-1,3-thiazol-2-yl}cyclobutyl)urea;

3-(5-{5-chloro-2-[3-(pyrrolidin-1-ylmethyl)phenyl]-1H-pyrrolo[2,3-b]pyridin-4-yl}-1,3-thiazol-2-yl)-1-methylpyrrolidin-3-ol;

1-{3-[5-chloro-2-(1-methyl-1H-pyrazol-4-yl)-1H-pyrrolo[2,3-b]pyridin-4-yl]-1,2,4-oxadiazol-5-yl}cyclobutanol;

3-(5-{5-chloro-2-[4-(pyrrolidin-1-ylmethyl)phenyl]-1H-pyrrolo[2,3-b]pyridin-4-yl}-1,3-thiazol-2-yl)-1-methylpyrrolidin-3-ol;

3-(5-{5-chloro-2-[4-(pyrrolidin-1-ylmethyl)phenyl]-1H-pyrrolo[2,3-b]pyridin-4-yl}-1,3-thiazol-2-yl)-1-methylazetidin-3-ol;

3-(5-{5-chloro-2-[3-(pyrrolidin-1-ylmethyl)phenyl]-1H-pyrrolo[2,3-b]pyridin-4-yl}-1,3-thiazol-2-yl)-1-methylazetidin-3-ol;

3-[5-(5-chloro-1H-pyrrolo[2,3-b]pyridin-4-yl)-1,3-thiazol-2-yl]-1-methylpyrrolidin-3-ol;

1-(5-{5-chloro-2-[4-(pyrrolidin-1-ylmethyl)phenyl]-1H-pyrrolo[2,3-b]pyridin-4-yl}pyridin-2-yl)cyclobutanol;

3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol;

3-(1-{5-chloro-2-[4-(pyrrolidin-1-ylmethyl)phenyl]-1H-pyrrolo[2,3-b]pyridin-4-yl}-1H-pyrazol-4-yl)oxetan-3-ol;

3-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)oxetan-3-ol;

3-(5-{5-chloro-2-[1-(1-methyl-L-prolyl)-1,2,3,6-tetrahydropyridin-4-yl]-1H-pyrrolo[2,3-b]pyridin-4-yl}-1,3-thiazol-2-yl)oxetan-3-ol;

2-[4-{5-chloro-4-[2-(3-hydroxyoxetan-3-yl)-1,3-thiazol-5-yl]-1H-pyrrolo[2,3-b]pyridin-2-yl}-3,6-dihydropyridin-1(2H)-yl]-N,N-dimethylacetamide;

3-[5-(5-chloro-2-{1-[(1,1-dioxidotetrahydrothien-3-yl)carbonyl]-1,2,3,6-tetrahydropyridin-4-yl}-1H-pyrrolo[2,3-b]pyridin-4-yl)-1,3-thiazol-2-yl]oxetan-3-ol;
3-[5-(5-chloro-2-{1-[(1-methylpyrrolidin-3-yl)carbonyl]-1,2,3,6-tetrahydropyridin-4-yl}-1H-pyrrolo[2,3-b]pyridin-4-yl)-1,3-thiazol-2-yl]oxetan-3-ol;
3-(5-{5-chloro-2-[4-(pyrrolidin-1-ylmethyl)phenyl]-1H-pyrrolo[2,3-b]pyridin-4-yl}-1,3-thiazol-2-yl)tetrahydrothiophene-3-ol 1,1-dioxide;
N-[3-(2-{5-chloro-2-[4-(pyrrolidin-1-ylmethyl)phenyl]-1H-pyrrolo[2,3-b]pyridin-4-yl}-1,3-thiazol-5-yl)oxetan-3-yl]-N'-phenylurea;
3-{2-[5-chloro-2-(1-methyl-1H-pyrazol-4-yl)-1H-pyrrolo[2,3-b]pyridin-4-yl]-1,3-thiazol-5-yl}oxetan-3-amine;
N-(3-{2-[5-chloro-2-(1-methyl-1H-pyrazol-4-yl)-1H-pyrrolo[2,3-b]pyridin-4-yl]-1,3-thiazol-5-yl}oxetan-3-yl)acetamide;
N-(3-{2-[5-chloro-2-(1-methyl-1H-pyrazol-4-yl)-1H-pyrrolo[2,3-b]pyridin-4-yl]-1,3-thiazol-5-yl}oxetan-3-yl)-N'-phenylurea;
N-(3-{2-[5-chloro-2-(1-methyl-1H-pyrazol-4-yl)-1H-pyrrolo[2,3-b]pyridin-4-yl]-1,3-thiazol-5-yl}oxetan-3-yl)urea;
3-(2-{5-chloro-2-[4-(pyrrolidin-1-ylmethyl)phenyl]-1H-pyrrolo[2,3-b]pyridin-4-yl}-1,3-thiazol-5-yl)oxetan-3-amine;
N-[3-(2-{5-chloro-2-[4-(pyrrolidin-1-ylmethyl)phenyl]-1H-pyrrolo[2,3-b]pyridin-4-yl}-1,3-thiazol-5-yl)oxetan-3-yl]acetamide;
1-(5-{5-chloro-2-[(1E)-3-pyrrolidin-1-ylprop-1-enyl]-1H-pyrrolo[2,3-b]pyridin-4-yl}-1,3-thiazol-2-yl)cyclobutanol;
1-{5-[6-(1-methyl-1H-pyrazol-4-yl)-7H-pyrrolo[2,3-d]pyrimidin-4-yl]-1,3-thiazol-2-yl}cyclobutanol;
1-[5-(6-{4-[(4-methylpiperazin-1-yl)carbonyl]phenyl}-7H-pyrrolo[2,3-d]pyrimidin-4-yl)-1,3-thiazol-2-yl]cyclobutanol;
1-(5-{6-[4-(4-methylpiperazin-1-yl)phenyl]-7H-pyrrolo[2,3-d]pyrimidin-4-yl}-1,3-thiazol-2-yl)cyclobutanol;
1-{5-[6-(4-morpholin-4-ylphenyl)-7H-pyrrolo[2,3-d]pyrimidin-4-yl]-1,3-thiazol-2-yl}cyclobutanol; and
1-(5-{6-[4-(morpholin-4-ylmethyl)phenyl]-7H-pyrrolo[2,3-d]pyrimidin-4-yl}-1,3-thiazol-2-yl)cyclobutanol.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

Scheme 1

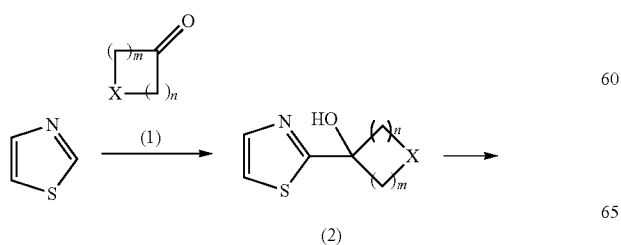

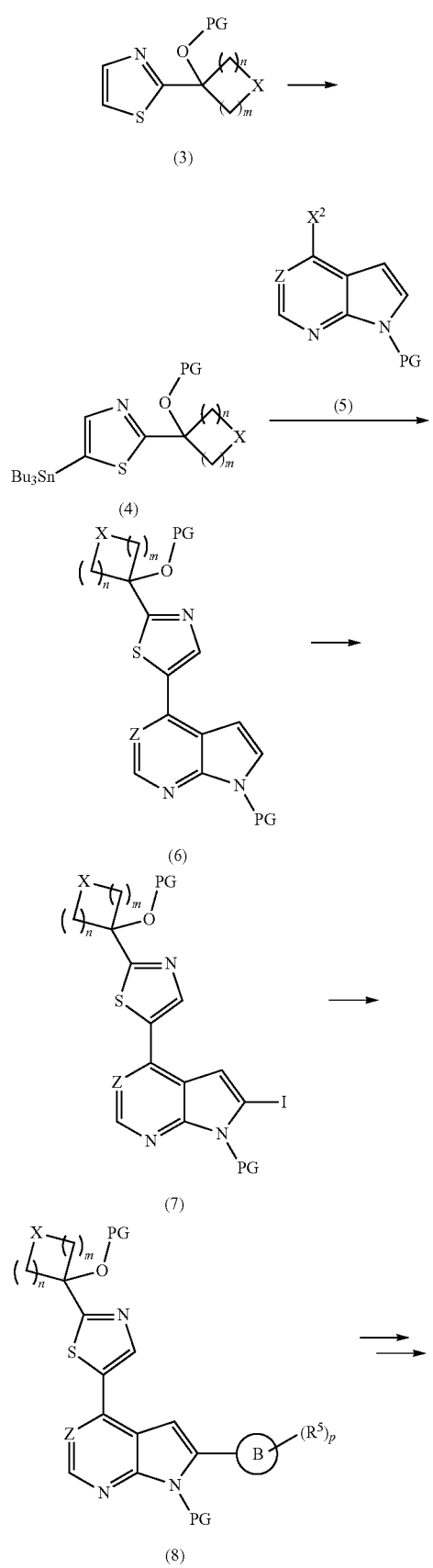

-continued

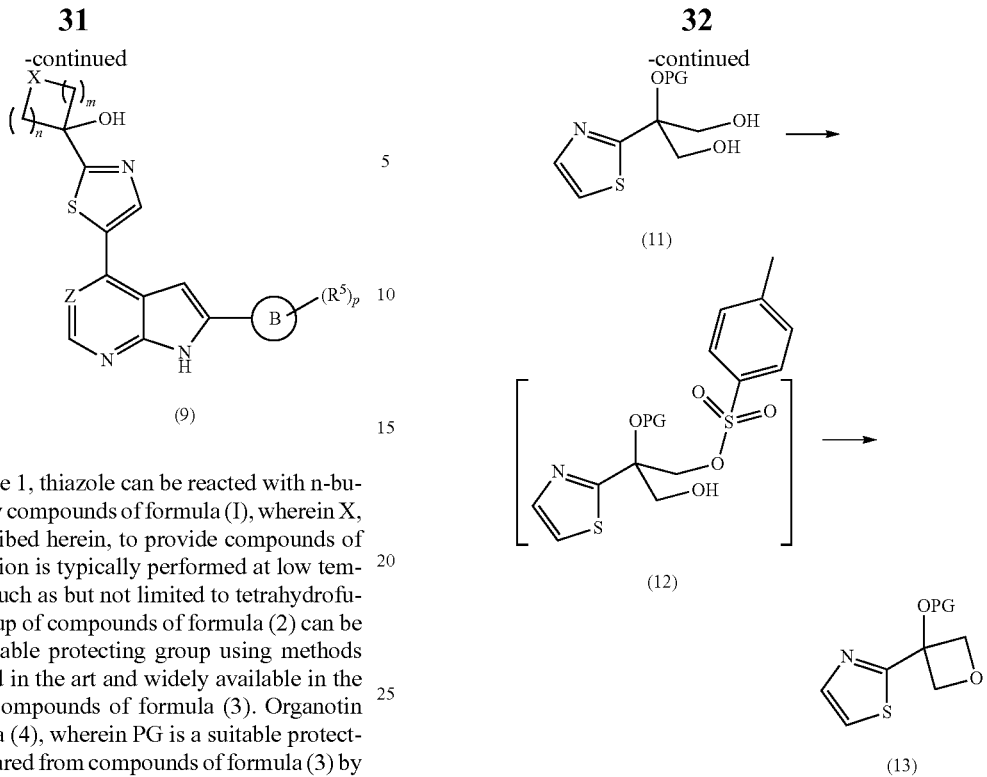

As shown in Scheme 1, thiazole can be reacted with n-butyllithium, followed by compounds of formula (1), wherein X, n, and m, are as described herein, to provide compounds of formula (2). The reaction is typically performed at low temperature in a solvent such as but not limited to tetrahydrofuran. The hydroxyl group of compounds of formula (2) can be protected using a suitable protecting group using methods known to those skilled in the art and widely available in the literature to provide compounds of formula (3). Organotin compounds of formula (4), wherein PG is a suitable protecting group, can be prepared from compounds of formula (3) by reacting the latter at low temperature with n-butyllithium, followed by tributyltin chloride. The reaction is typically performed in a solvent such as but not limited to tetrahydrofuran. Compounds of formula (4) can be reacted with compounds of formula (5), wherein Z is as described herein, $X^2$ is a suitable halogen, and PG is a suitable protecting group, using Stille coupling conditions known to those skilled in the art and widely available in the literature, to provide compounds of formula (6). Compounds of formula (7) can be prepared from compounds of formula (6) by reacting the latter with lithium diisopropylamide at low temperature, followed by iodine. The reaction is typically performed in a solvent such as but not limited to tetrahydrofuran. Compounds of formula (7) can be reacted with an appropriate organotin compound or boronic acid using methods known to those skilled in the art and widely available in the literature for Stille or Suzuki coupling reactions, to provide compounds of formula (8) wherein B, $R^5$ and p are as described herein. Compounds of formula (8) can be deprotected using methods known to those skilled in the art and widely available in the literature to provide compounds of formula (9), which are representative of the compounds of this invention.

As shown in Scheme 2, thiazole can be reacted with n-butyllithium, followed by 2,2-dimethyl-1,3-dioxan-5-one, to provide 2,2-dimethyl-5-(thiazol-2-yl)-1,3-dioxan-5-ol. The reaction is typically performed at low temperature in a solvent such as but not limited to tetrahydrofuran. 2,2-Dimethyl-5-(thiazol-2-yl)-1,3-dioxan-5-ol can be protected using a suitable protecting group, PG, using methods known to those skilled in the art and widely available in the literature to provide compounds of formula (10). Compounds of formula (10) can be reacted with copper(II) chloride dihydrate to provide compounds of formula (11). The reaction is typically performed at elevated temperature in a solvent such as but not limited to methanol. Compounds of formula (13) can be prepared from compounds of formula (11) by reacting the latter with n-butyllithium followed by para-toluenesulfonyl chloride, followed by additional n-butyllithium at an elevated temperature. The reaction is typically performed in a solvent such as but not limited to tetrahydrofuran.

Scheme 3

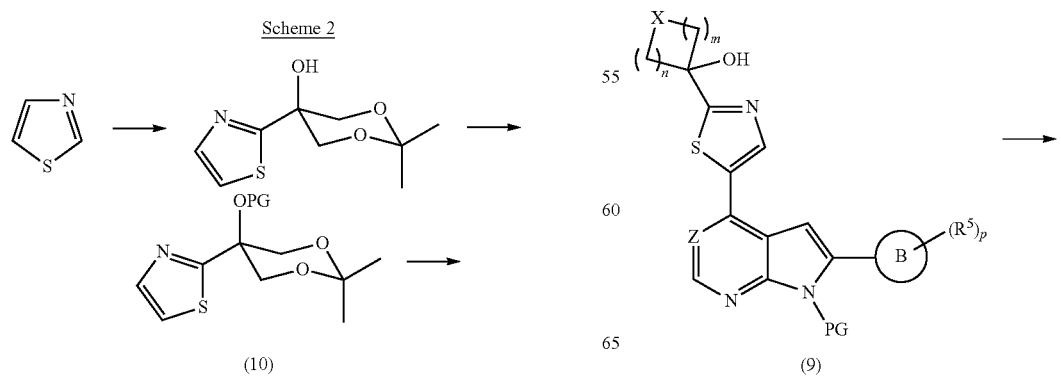

-continued

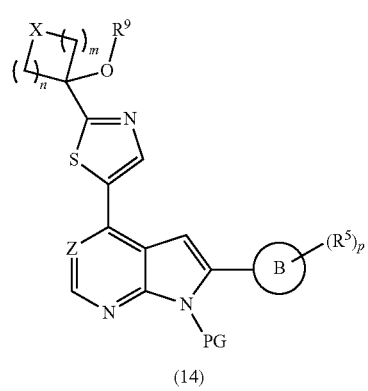

(14)

As shown in Scheme 3, compounds of formula (9), wherein X Z, B, $R^5$, p, m, and n are as described herein and PG is a suitable protecting group, which can be prepared as described in Scheme 1, can be reacted with sodium hydride followed by compounds of formula $R^9$—$X^1$, wherein $X^1$ is a suitable halide and $R^9$ is as described herein, to provide compounds of formula (14). The reaction is typically performed at ambient temperature in a solvent such as but not limited to N,N-dimethylformamide.

Scheme 4

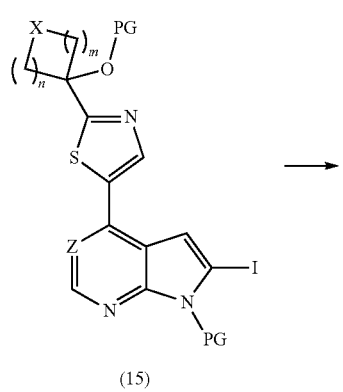

(15)

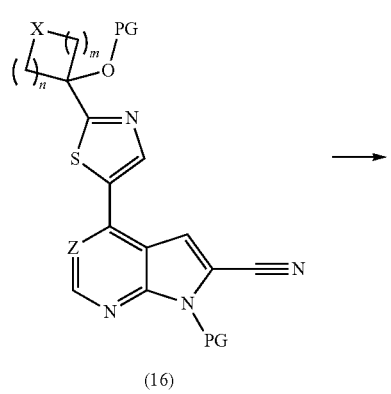

(16)

-continued

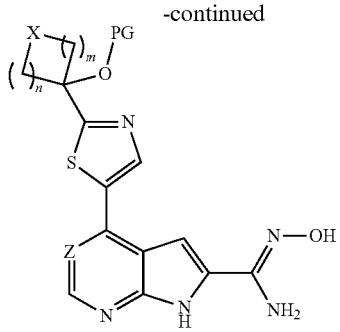

(17)

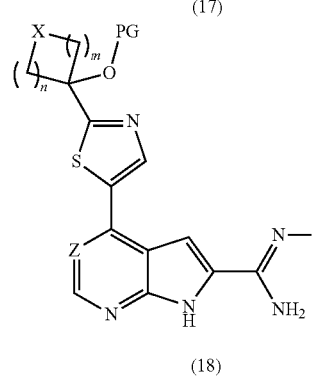

(18)

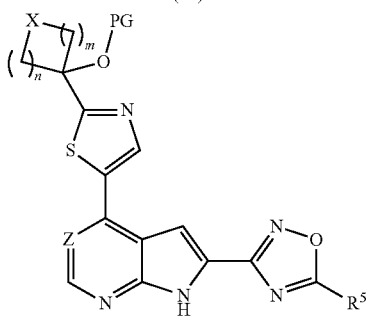

(19)

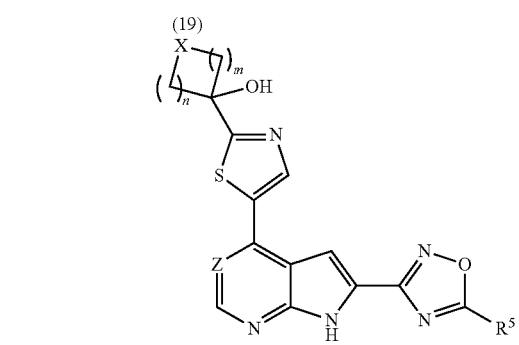

(20)

As shown in Scheme 4, compounds of formula (16) wherein X, Z, m, and n are as described herein, and PG is a suitable protecting group, can be prepared from compounds of formula (15) by treating the latter with zinc cyanide and tetrakis(triphenylphosphine)palladium. The reaction is typically performed in a solvent such as but not limited to 1-methyl-2-pyrrolidinone at an elevated temperature in a microwave reactor. Compounds of formula (16) can be reacted with hydroxylamine hydrochloride in the presence of a base such as but not limited to triethylamine to provide compounds of formula (17). The reaction is typically performed at an elevated temperature in a solvent such as but not limited to ethanol, water, or mixtures thereof. Compounds of formula (17) can be coupled with compounds of formula $R^5C(O)OH$, wherein $R^5$ is as described herein, using methods known to those skilled in the art and widely available in the literature to provide compounds of formula (18). Compounds of formula (18) can be heated at an elevated temperature to provide compounds of formula (19). The reaction is typically performed in a solvent such as but not limited to toluene. Removal of the protecting group, PG, can be performed using methods known to those skilled in the art and widely available in the literature to provide compounds of formula (20), which are representative of the compounds of this invention.

Scheme 5

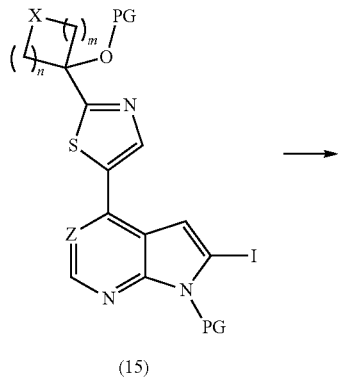

(15)

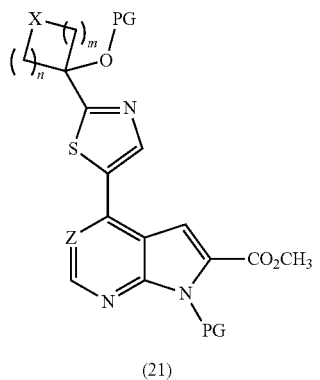

(21)

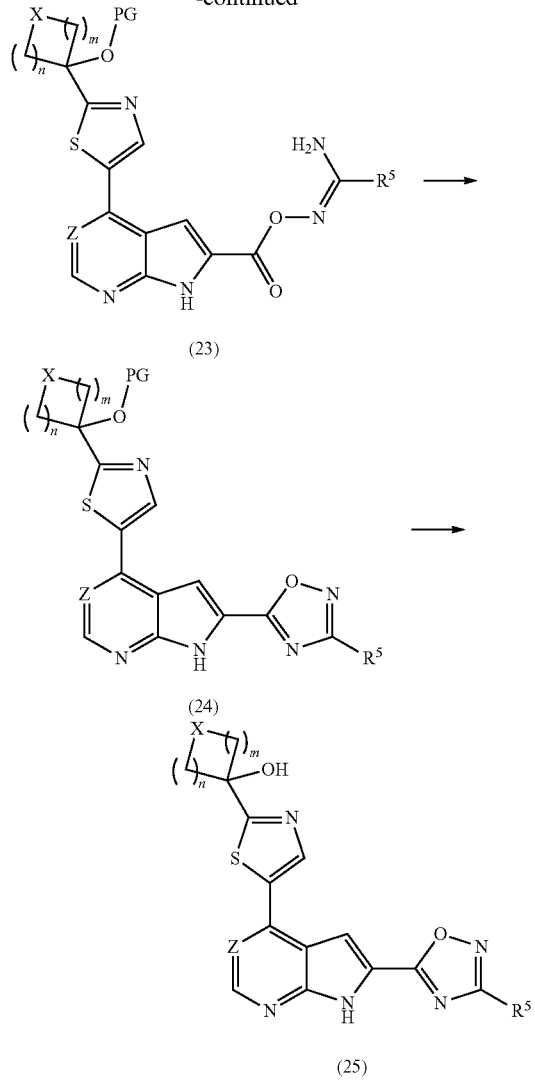

As shown in Scheme 5, compounds of formula (15) wherein X, Z, m, and n are as described herein, and PG is a suitable protecting group, can be reacted with carbon monoxide and methanol, in the presence of a base such as but not limited to triethylamine and a catalyst such as but not limited to [1,1'-bis(diphenylphosphino)ferrocene]dichloropalladium(II) to provide compounds of formula (21). The reaction is typically performed at elevated temperature and pressure in a solvent such as but not limited to methanol, acetonitrile or mixtures thereof. Compounds of formula (22) can be prepared from compounds of formula (21) by reacting the latter with an aqueous base such as but not limited to sodium hydroxide. Compounds of formula (22) can be coupled with compounds of formula $R^5C(NH_2)\!\!=\!\!NOH$, wherein $R^5$ is as described herein, using methods known to those skilled in the art and widely available in the literature to provide compounds of formula (23). Compounds of formula (23) can be heated at an elevated temperature to provide compounds of formula (24). The reaction is typically performed in a solvent such as but not limited to 1-methyl-2-pyrrolidinone. Removal of the protecting group, PG, can be performed using methods known to those skilled in the art and widely available in the literature to provide compounds of formula (25), which are representative of the compounds of this invention.

Scheme 6

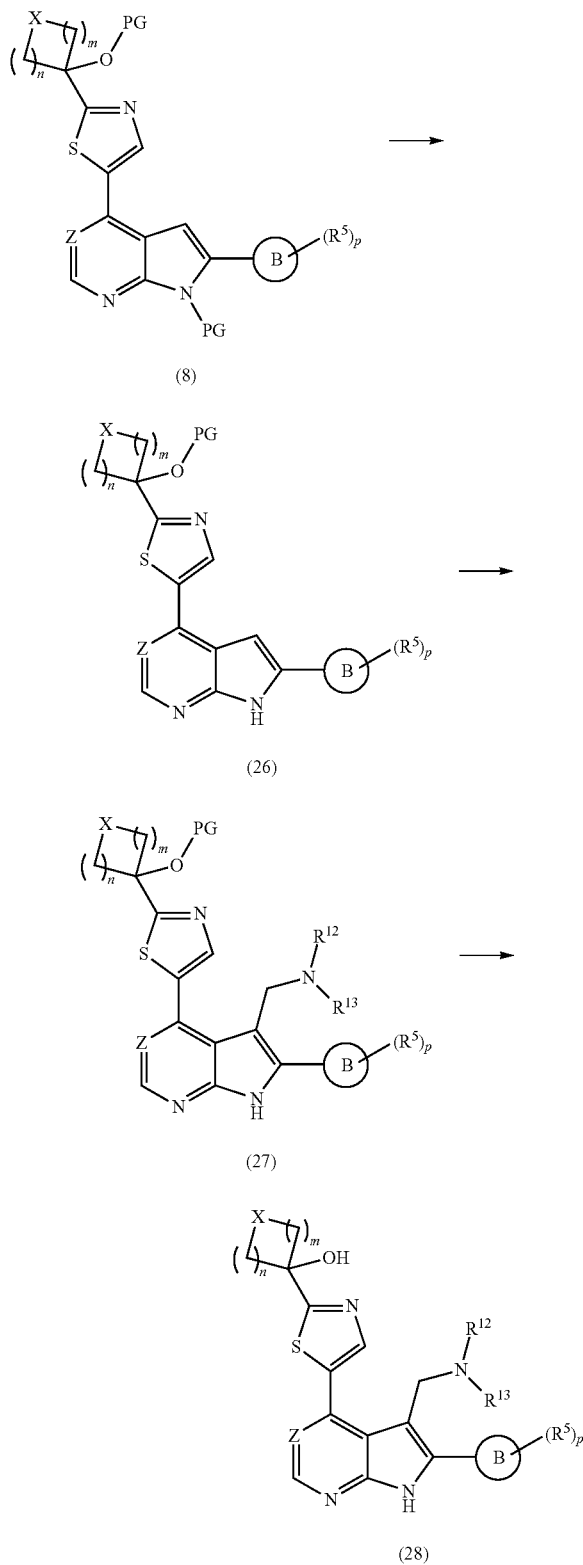

skilled in the art and widely available in the literature to provide compounds of formula (26). Compounds of formula (26) can be reacted with formalin and an amine of formula $NHR^{12}R^{13}$, wherein $R^{12}$ and $R^{13}$ are each independently hydrogen, alkyl or together form a heterocycle, in the presence of an acid such as but not limited to acetic acid to provide compounds of formula (27). The reaction is typically performed at elevated temperatures. Removal of the protecting group, PG, can be performed using methods known to those skilled in the art and widely available in the literature to provide compounds of formula (28), which are representative of the compounds of this invention.

Scheme 7

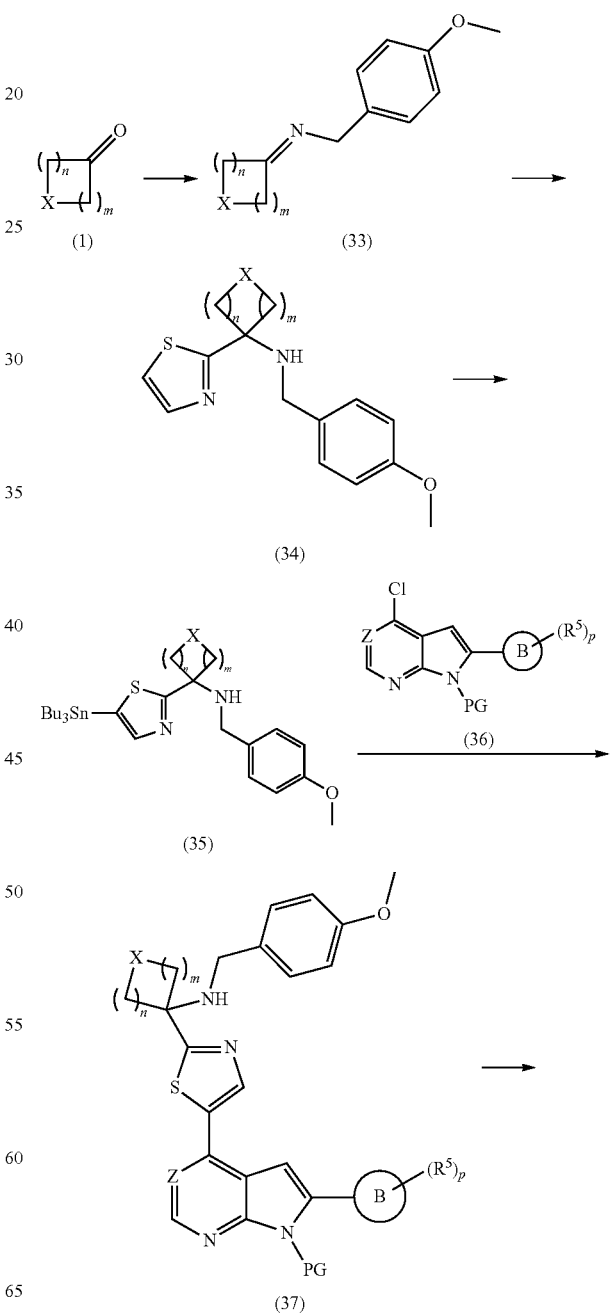

As shown in Scheme 6, removal of one protecting group, PG, in compounds of formula (8), wherein X, Z, B, $R^5$, p, m, and n are as described herein and PG is a suitable protecting group, can be performed using methods known to those -continued

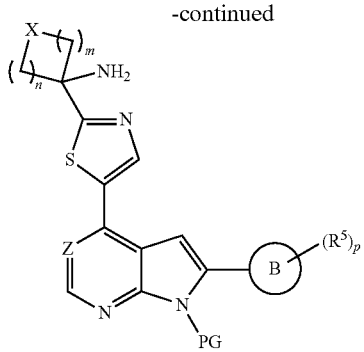

(38)

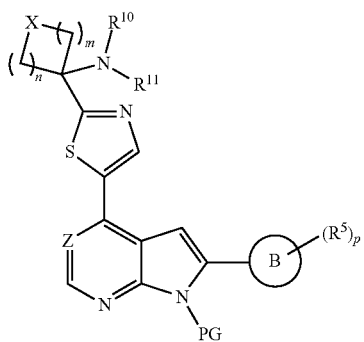

(39)

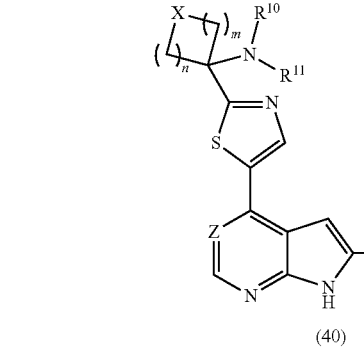

(40)

As shown in Scheme 7, compounds of formula (I) wherein X, n, and m, are as described herein, can be reacted with (4-methoxyphenyl)methanamine in the presence of molecular sieves to provide compounds of formula (33). The reaction is typically performed at room temperature in an anhydrous solvent such as but not limited to diethyl ether. Thiazole can be reacted with n-butyllithium at low temperatures followed by a mixture of compounds of formula (33) and boron trifluoride diethyl etherate to provide compounds of formula (34). The reaction is typically performed in an anhydrous solvent such as but not limited to tetrahydrofuran, toluene, or mixtures thereof. Organotin compounds of formula (35) can be prepared from compounds of formula (34) by reacting the latter at low temperature with lithium diisopropylamide, followed by tributyltin chloride. The reaction is typically performed in a solvent such as but not limited to tetrahydrofuran. Compounds of formula (35) can be reacted with compounds of formula (36), wherein Z, B, $R^5$, and p, are as described herein, and PG is a suitable protecting group and which can be prepared as described herein, using Stille coupling conditions known to those skilled in the art and widely available in the literature, to provide compounds of formula (37). Compounds of formula (38) can be prepared from compounds of formula (37) by reacting the latter with 2,3-dichloro-5,6-dicyano-1,4-benzoquinone. The reaction is typically performed at ambient temperature in a solvent such as but not limited to dichloromethane, water, or mixtures thereof. Compounds of formula (38) can be alkylated or acylated using conditions known to those skilled in the art and widely available in the literature, to provide compounds of formula (39). Removal of the protecting group, PG, using conditions known to those skilled in the art and widely available in the literature, will provide compounds of formula (40), which are representative of the compounds of this invention.

Scheme 8

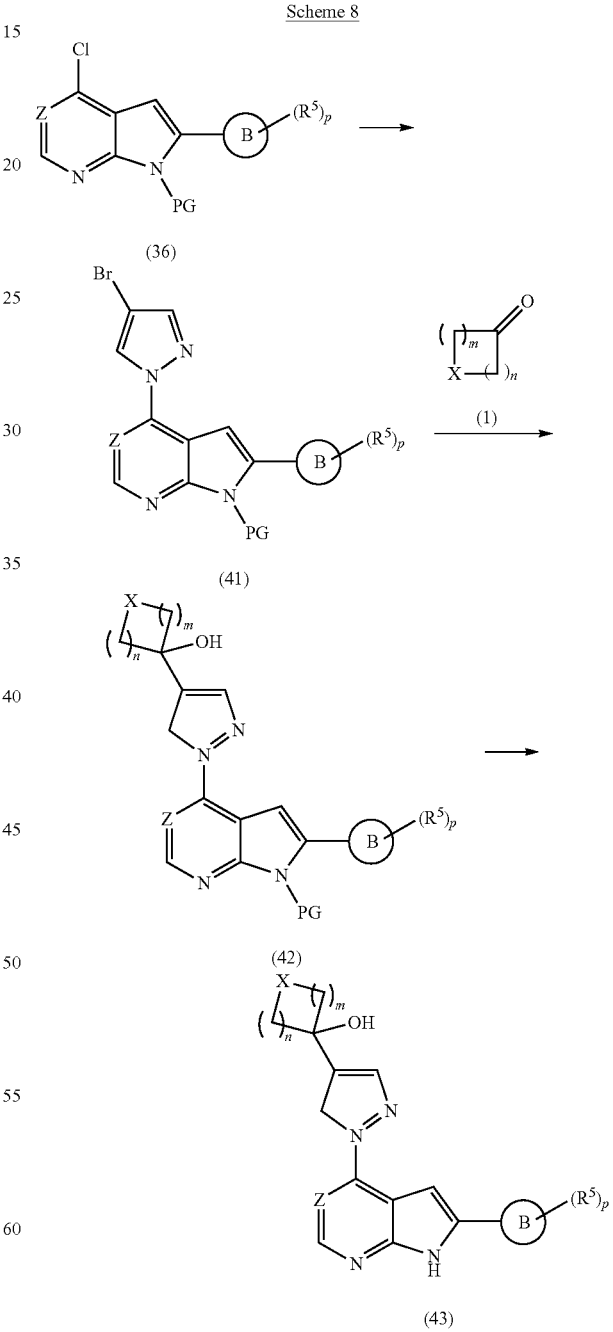

As shown in scheme 8, compounds of formula (36), wherein Z, B, $R^5$, and p are as described herein and PG is a suitable protecting group, can be reacted with 4-bromo-1H-pyrazole in the presence of a base such as but not limited to potassium carbonate to provide compounds of formula (41). The reaction is typically performed at elevated temperatures in a solvent such as but not limited to 1-methyl-2-pyrrolidinone. Compounds of formula (I) wherein X, n, and m, are as described herein, can be reacted with a solution of n-butyl-lithium and compounds of formula (41) to provide compounds of formula (33). The reaction is typically performed at low temperatures in a solvent such as but not limited to tetrahydrofuran. Removal of the protecting group, PG, using conditions known to those skilled in the art and widely available in the literature, will provide compounds of formula (43), which are representative of the compounds of this invention.

Scheme 9

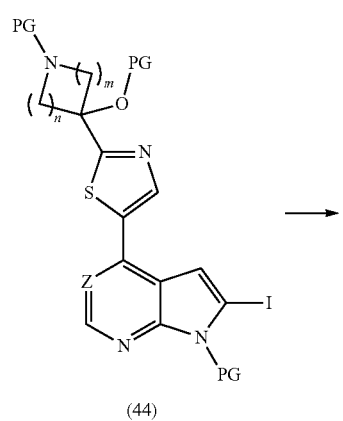

(44)

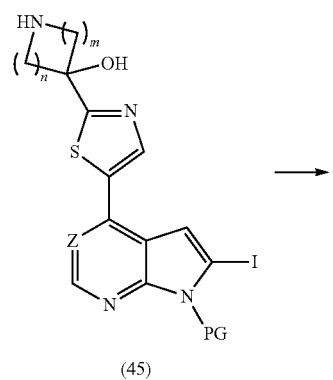

(45)

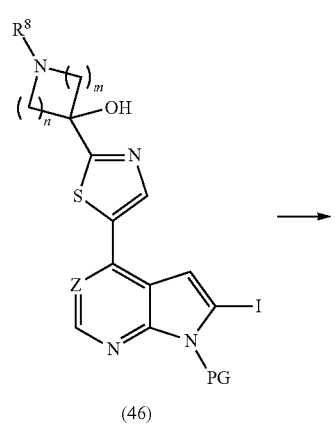

(46)

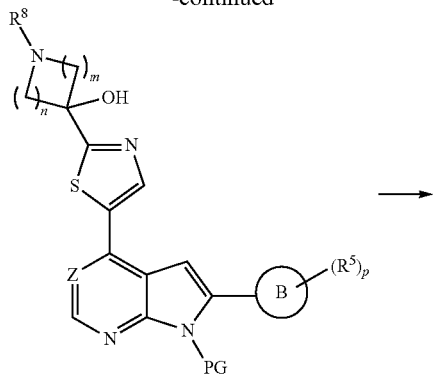

(47)

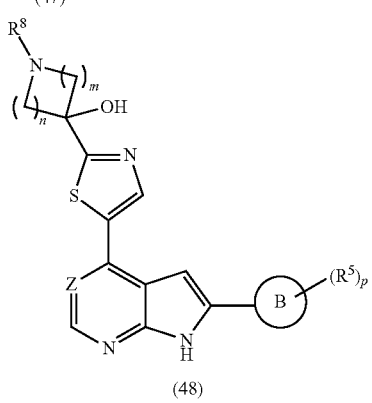

(48)

As shown in Scheme 9, removal of two of the protecting groups, PG, in compounds of formula (44), wherein Z, m, and n are as described herein and each PG is a suitable protecting group, can be performed using methods known to those skilled in the art and widely available in the literature to provide compounds of formula (45). Compounds of formula (46) can be prepared from compounds of formula (45) by reacting the latter with an aldehyde of formula $R^8C(O)H$ under reductive amination conditions known to those skilled in the art and widely available in the literature, or with a acid of formula $R^8C(O)OH$ under coupling conditions known to those skilled in the art and widely available in the literature, to provide compounds of formula (46). Compounds of formula (47) can be prepared from compounds of formula (46) wherein B, $R^5$, and p are as described herein, by reacting the latter with an appropriate organotin compound or boronic acid using methods known to those skilled in the art and widely available in the literature for Stille or Suzuki coupling reactions, to provide compounds of formula (47). Removal of the final protecting group, PG, can be performed using methods known to those skilled in the art and widely available in the literature to provide compounds of formula (48), which are representative of the compounds of this invention.

Scheme 10

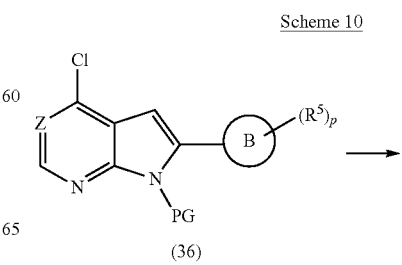

(36)

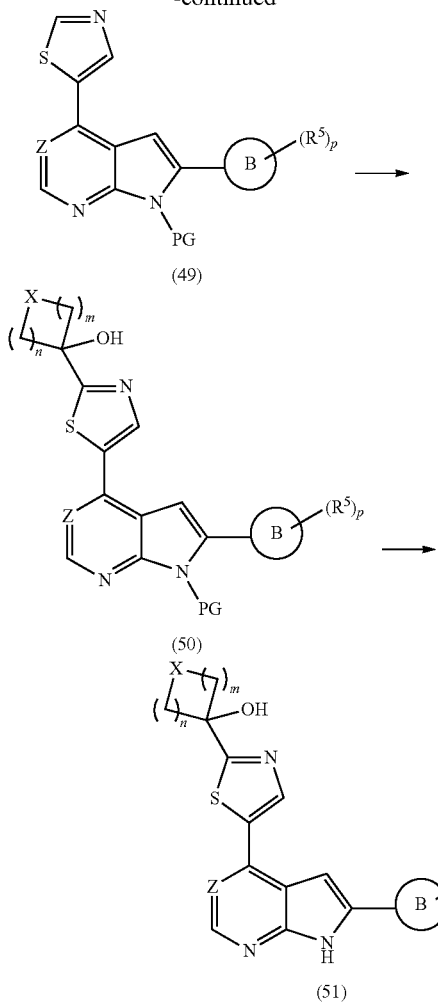

(49)

(50)

(51)

As shown in Scheme 10, compounds of formula (36), wherein Z, B, $R^5$, and p are as described herein and PG is a suitable protecting group, can be reacted with 5-(tributylstannyl)thiazole using Stille coupling conditions known to those skilled in the art and widely available in the literature, to provide compounds of formula (49). Compounds of formula (49) can be treated with n-butyllithium followed by compounds of formula (I) wherein X, n, and m are as described herein, to provide compounds of formula (50). The reaction is typically performed at low temperatures in a solvent such as but not limited to tetrahydrofuran. Removal of the final protecting group, PG, can be performed using methods known to those skilled in the art and widely available in the literature to provide compounds of formula (51), which are representative of the compounds of this invention.

Scheme 11

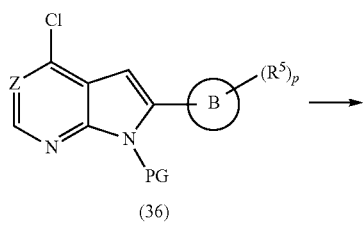

(36)

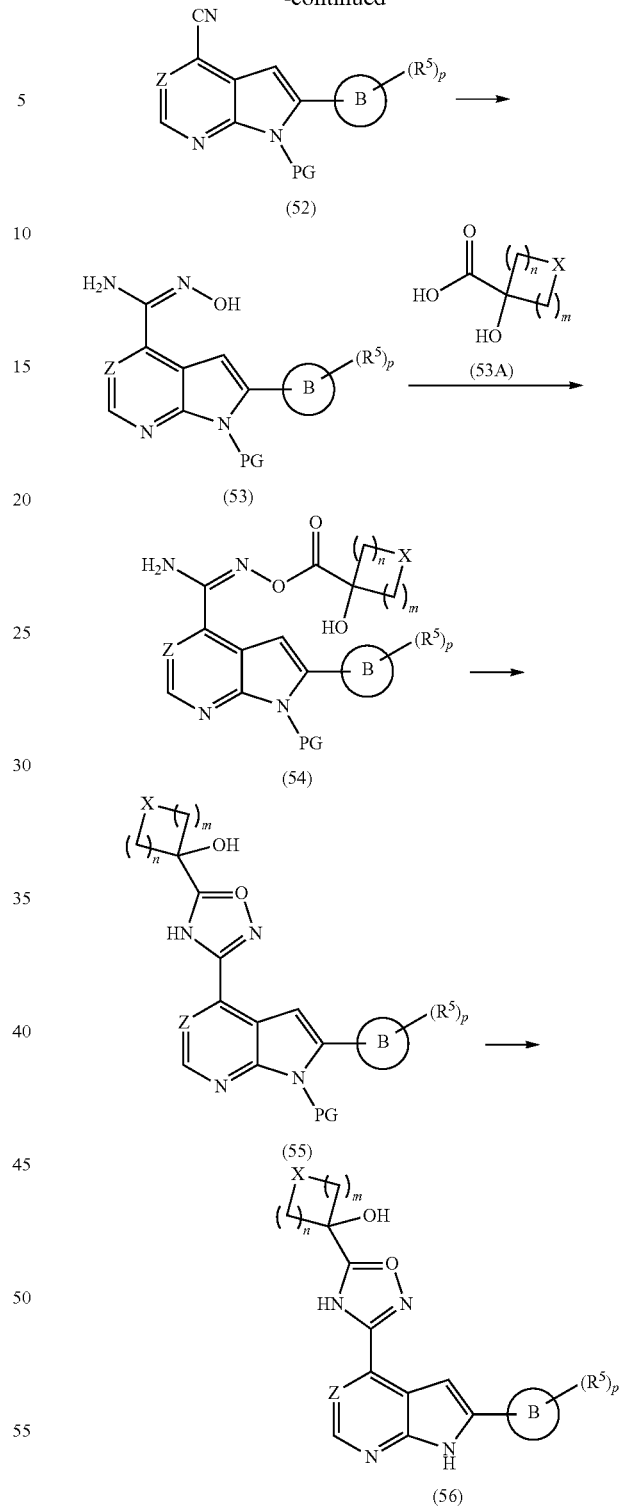

(52)

(53)

(54)

(55)

(56)

As shown in Scheme 11, compounds of formula (36), wherein Z, B, $R^5$, and p are as described herein and PG is a suitable protecting group, can be reacted with zinc cyanide and tetrakis(triphenylphosphine)palladium to provide compounds of formula (52). The reaction is typically performed at elevated temperature in a microwave synthesizer, in a solvent such as but not limited to N-methylpyrrolidine. Compounds of formula (53) can be prepared by reacting compounds of formula (52) with hydroxylamine hydrochloride in the presence of a base such as but not limited to triethylamine. The reaction is typically performed at elevated temperatures in a solvent such as but not limited to as ethanol, water or mixtures thereof. Compounds of formula (53) can be reacted with compounds of formula (53A) wherein X, n, and m are as described herein, using coupling conditions known to those skilled in the art and widely available in the literature, to provide compounds of formula (54). Compounds of formula (55) can be prepared by heating compounds of formula (54) in a solvent such as but not limited to toluene. Removal of the final protecting group, PG, can be performed using methods known to those skilled in the art and widely available in the literature to provide compounds of formula (56), which are representative of the compounds of this invention.

As shown in Scheme 12, 5-bromo-2-iodopyridine can be reacted with a Grignard reagent such as but not limited to isopropyl magnesium chloride, followed by compounds of formula (I) wherein X, n, and m are as described herein, and then n-butyllithium followed by tributyltin chloride to provide compounds of formula (58). The reaction is typically performed in "one pot" without isolation of the intermediates at low temperatures in a solvent such as but not limited to tetrahydrofuran. Compounds of formula (37), wherein Z, B, $R^5$, and p are as described herein and PG is a suitable protecting group, can be reacted with compounds of formula (58) using Stille coupling conditions known to those skilled in the art and widely available in the literature, to provide compounds of formula (59). Removal of the final protecting group, PG, can be performed using methods known to those skilled in the art and widely available in the literature to provide compounds of formula (60), which are representative of the compounds of this invention.

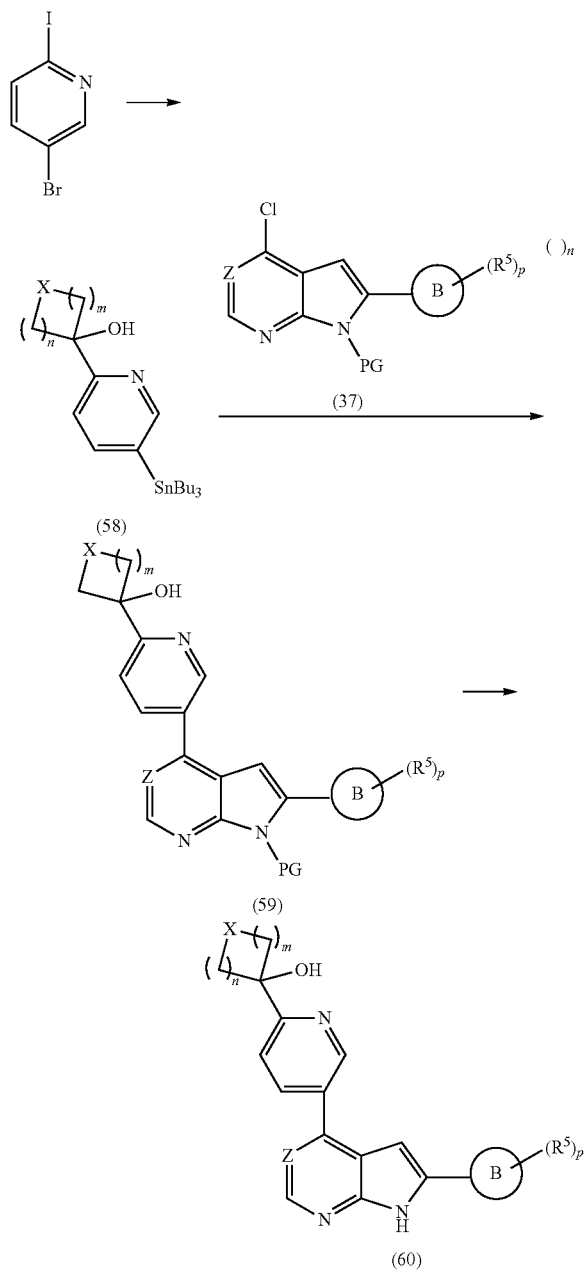

Scheme 12

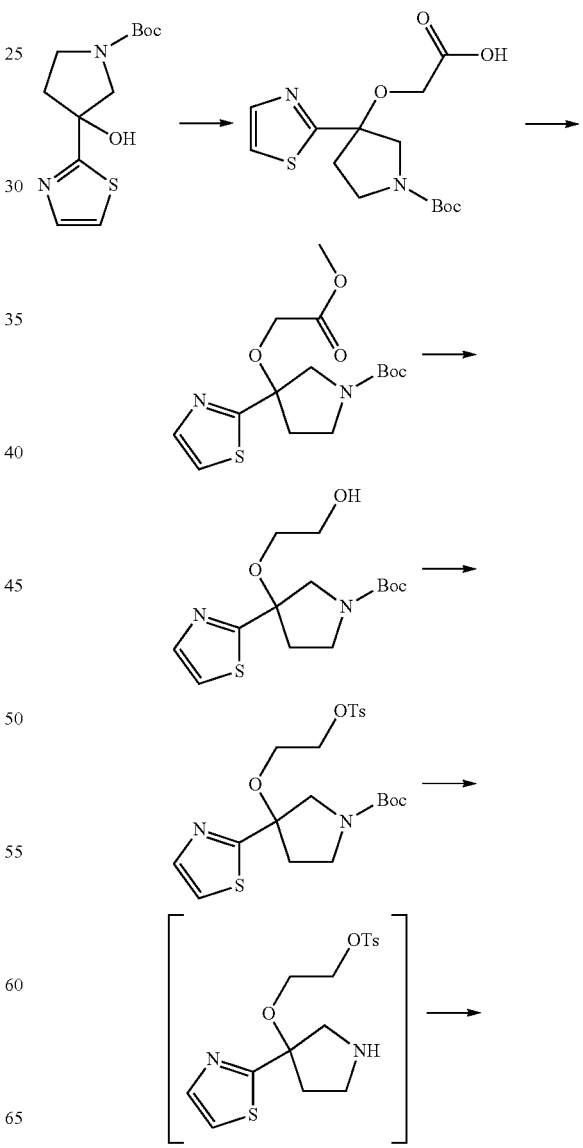

Scheme 13

-continued

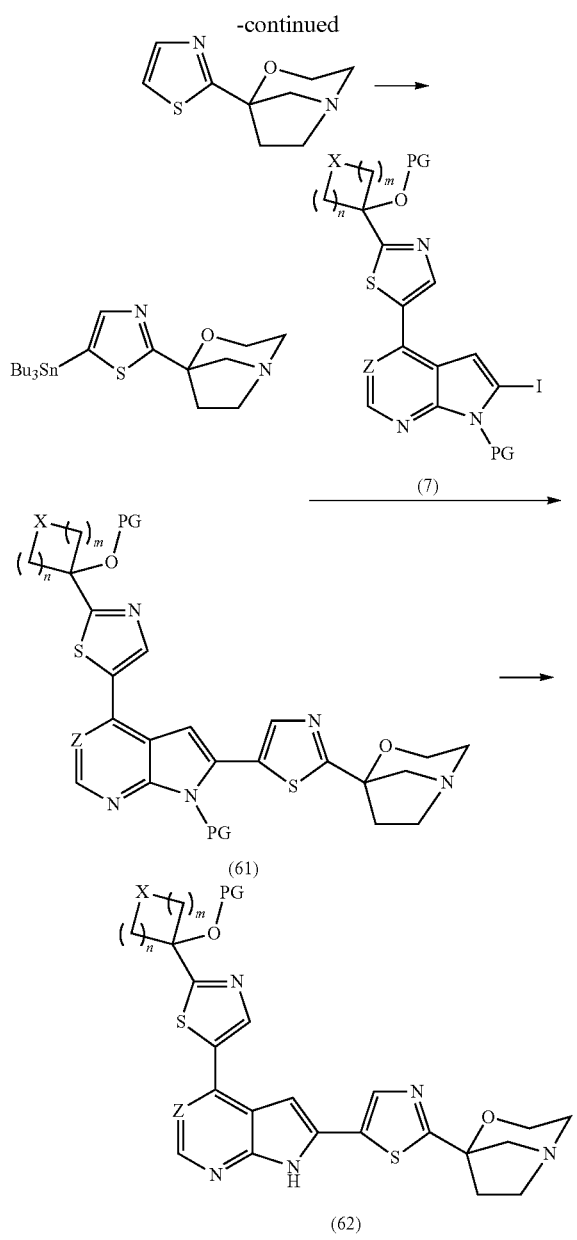

As shown in Scheme 13, tert-butyl 3-hydroxy-3-(thiazol-2-yl)pyrrolidine-1-carboxylate can be reacted with NaH, followed by bromoacetic acid, to provide 2-(1-(tert-butoxycarbonyl)-3-(thiazol-2-yl)pyrrolidin-3-yloxy)acetic acid. The reaction is typically performed in a solvent such as but not limited to N,N-dimethylformamide, and typically requires elevated temperatures. 2-(1-(tert-Butoxycarbonyl)-3-(thiazol-2-yl)pyrrolidin-3-yloxy)acetic acid can then be treated with oxalyl chloride in the presence of N,N-dimethylformamide, followed by methanol, to provide tert-butyl 3-(2-methoxy-2-oxoethoxy)-3-(thiazol-2-yl)pyrrolidine-1-carboxylate. The oxalyl chloride is typically added at low temperature followed by the methanol at room temperature. Additional solvents such as but not limited to dichloromethane may be used. Reduction of tert-butyl 3-(2-methoxy-2-oxoethoxy)-3-(thiazol-2-yl)pyrrolidine-1-carboxylate to tert-butyl 3-(2-hydroxyethoxy)-3-(thiazol-2-yl)pyrrolidine-1-carboxylate can be accomplished at ambient temperature using NaBH$_4$ in a solvent such as but not limited to methanol. The hydroxyl group can be protected by reacting tert-butyl 3-(2-hydroxyethoxy)-3-(thiazol-2-yl)pyrrolidine-1-carboxylate with paratoluenesulfonyl chloride in the presence of 4-dimethylaminopyridine and a base such as but not limited to triethylamine. The reaction is typically performed at ambient temperature in a solvent such as but not limited to dichloromethane. Deprotection of the Boc group with trifluoroacetic acid in dichloromethane followed by the addition of potassium carbonate will provide 5-(thiazol-2-yl)-4-oxa-1-azabicyclo[3.2.1]octane. Lithium diisopropylamide can be added to a cold solution of 5-(thiazol-2-yl)-4-oxa-1-azabicyclo[3.2.1]octane followed by the addition of tributyltin chloride to provide 5-(5-(tributylstannyl)thiazol-2-yl)-4-oxa-1-azabicyclo[3.2.1]octane. The reaction is typically performed at low temperature. Compounds of formula (7) can be reacted with 545-(tributylstannyl)thiazol-2-yl)-4-oxa-1-azabicyclo[3.2.1]octane, using Stille coupling conditions known to those skilled in the art and widely available in the literature, to provide compounds of formula (61). Removal of the final protecting group, PG, can be performed using methods known to those skilled in the art and widely available in the literature, to provide compounds of formula (62), which are representative of the compounds of this invention.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all Aurora-kinase family members are expressed. In yet another aspect, compounds of this invention are expected to have utility in treatment of diseases or conditions during which protein kinases such as any or all KDR (VEGFR2) family members are expressed. In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPB), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Pik) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxy-nucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORE-TAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TRE-ANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-nl, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like

EXAMPLES

Example 1

1-(5-{5-chloro-2-[1-(2-morpholin-4-ylethyl)-1H-pyrazol-4-yl]-1H-pyrrolo[2,3-b]pyridin-4-yl}-1,3-thiazol-2-yl)cyclobutanol Example 1A 1-(thiazol-2-yl)cyclobutanol To a cold (−78° C.) solution of thiazole (6.59 ml, 93 mmol) in tetrahydrofuran (238 mL) was added n-butyllithium (58.0 mL, 93 mmol) dropwise. The reaction was stirred for 15 minutes, and cyclobutanone (5.0 g, 71.3 mmol) was added via syringe. The reaction was stirred for 10 minutes and was then quenched by the addition of saturated aqueous bicarbonate solution. The cold bath was removed, and the reaction was warmed to room temperature. Ethyl acetate was added, and the layers were separated. The aqueous layer was extracted with additional ethyl acetate (2×). The combined organics were dried with anhydrous sodium sulfate, filtered and concentrated under reduced pressure to give the title compound, which was used in the subsequent step without further purification. MS ESI(+) m/z 156 [M+H]$^+$.

Example 1B 2-(1-(methoxymethoxy)cyclobutyl)thiazole

To a cold (0° C.) suspension of sodium hydride (1.07 g, 44.4 mmol) in N,N-dimethylformamide (50 mL) was added a solution of 1-(thiazol-2-yl)cyclobutanol (Example 1A) (5.3 g, 34.1 mmol) in N,N-dimethylformamide (18 mL). After 0.5 hours, chloro(methoxy)methane (3.89 ml, 51.2 mmol) was added, and the reaction was stirred for 16 hours. The reaction was quenched by the addition of ether and water. The layers were separated, and the aqueous layer was extracted with additional ether. The combined organics were dried with anhydrous sodium sulfate, filtered and concentrated. The residue was purified by flash chromatography on silica gel, eluting with a gradient of 0 to 50% ethyl acetate in hexane, to give the title compound. MS ESI(+) m/z 200 [M+H]$^+$.

Example 1C 2-(1-(methoxymethoxy)cyclobutyl)-5-(tributylstannyl)thiazole

To a cold (−78° C.) solution of the 2-(1-(methoxymethoxy)cyclobutyl)thiazole (Example 1B) (5.67 g, 28.5 mmol) in tetrahydrofuran (95 mL) was added a solution of lithium diisopropylamide (34.1 mmol) in tetrahydrofuran (30 mL) dropwise. The solution was stirred at −78° C. for 45 minutes, and tributyltin chloride (9.26 mL, 34.1 mmol) was added dropwise. The cold bath was removed, and the reaction warmed to room temperature. The ambient reaction was then quenched by the addition of saturated aqueous ammonium chloride solution and ether. The layers were separated, and the aqueous layer was extracted with additional ether. The combined organics were washed with water, dried with anhydrous sodium sulfate, filtered and concentrated under reduced pressure to give the title compound, which was used without further purification. MS ESI(+) m/z 490 [M+H]+.

Example 1D 5-chloro-4-iodo-1-tosyl-1H-pyrrolo[2,3-b]pyridine

To an ambient suspension of sodium hydride (0.560 g, 23.34 mmol) in N,N-dimethylformamide (40 mL) was added a solution of 5-chloro-4-iodo-1H-pyrrolo[2,3-b]pyridine (5.0 g, 17.95 mmol) (Example 1E) in N,N-dimethylformamide (10 mL) slowly. The reaction was stirred for 0.5 hours, and a solution of para-toluenesulfonyl chloride (3.59 g, 18.85 mmol) in N,N-dimethylformamide (8 mL) was added. The reaction was stirred for 1 hour and was then quenched by pipetting the reaction portionwise into water (50 mL) with vigorous stirring. The solid was filtered and air-dried to give the title compound as a solid. MS ESI(+) m/z 433 [M+H]+.

Example 1E 5-(5-chloro-1-tosyl-1H-pyrrolo[2,3-b]pyridin-4-yl)-2-(1-(methoxymethoxy)cyclobutyl)thiazole A solution of 5-chloro-4-iodo-1-tosyl-1H-pyrrolo[2,3-b]pyridine (Example 1D) (7.12 g, 16.46 mmol), bis(triphenylphosphine)palladium dichloride (0.809 g, 1.15 mmol), and 2-(1-(methoxymethoxy)cyclobutyl)-5-(tributylstannyl)thiazole (Example 1C) (10.45 g, 21.39 mmol) in N,N-dimethylformamide (54.9 ml) was heated to 70° C. for 1 hour. The reaction was cooled to room temperature and quenched by the addition of an aqueous potassium fluoride solution (19 g in 100 mL water) and ethyl acetate (200 mL). The mixture was stirred vigorously overnight and was then filtered through diatomaceous earth, eluting with ethyl acetate. The layers were separated, and the organic layer was washed with aqueous saturated bicarbonate solution and water. The organic layer was dried with anhydrous sodium sulfate, filtered and concentrated under reduced pressure. The residue was purified by flash chromatography on silica gel, eluting with a gradient of 0 to 35% ethyl acetate in hexane, to afford the title compound. MS ESI(+) m/z 504 [M+H]+.

Example 1F 5-(5-chloro-2-iodo-1-tosyl-1H-pyrrolo[2,3-b]pyridin-4-yl)-2-(1-(methoxymethoxy)cyclobutyl)thiazole To a cold (−78° C.) solution of 5-(5-chloro-1-tosyl-1H-pyrrolo[2,3-b]pyridin-4-yl)-2-(1-(methoxymethoxy)cyclobutyl)thiazole (Example 1E) (5.0 g, 9.92 mmol) in tetrahydrofuran (50 mL) was added a solution of lithium diisopropylamide (13.9 mmol) in tetrahydrofuran (15 mL). The reaction was stirred at −78° C. for 1 hour, and a solution of iodine (3.52 g, 13.89 mmol) in tetrahydrofuran (10 mL) was added. The cold bath was removed, and, after 15 minutes, the reaction was quenched by the addition of saturated aqueous sodium thiosulfate and ethyl acetate. The layers were separated, and the aqueous layer was extracted with additional ethyl acetate (2×). The combined organics were dried with anhydrous sodium sulfate, filtered and concentrated under reduced pressure. The residue was purified by flash chromatography on silica gel, eluting with a gradient of 0 to 30% ethyl acetate in hexane, to give the title compound. MS ESI(+) m/z 586 [M+H]+;

Example 1G 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine To a stirred ambient solution of 5-(5-chloro-2-iodo-1-tosyl-1H-pyrrolo[2,3-b]pyridin-4-yl)-2-(1-(methoxymethoxy)cyclobutyl)thiazole (Example 1F) (200 mg, 0.318 mmol) and 4-(2-(4-(4,4,5,5-tetramethyl-1,3,2-dioxaborolan-2-yl)-1H-pyrazol-1-yl)ethyl)morpholine (127 mg, 0.413 mmol) in N,N-dimethylformamide (0.79 mL) was added saturated aqueous bicarbonate solution (0.79 mL) followed by bis(triphenylphosphine)palladium dichloride (15.60 mg, 0.022 mmol). The mixture was heated to 70° C. for 4 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. The crude material was purified by flash chromatography on silica gel, eluting with a gradient of 20% ethyl acetate in hexane to 100% ethyl acetate with 3% methanol, to afford the title compound. MS ESI(+) m/z 683.52 [M+H]+.

Example 1H 1-(5-(5-chloro-2-(1-(2-morpholino ethyl)-1H-pyrazol-4-yl)-1-tosyl-1H-pyrrolo[2,3-b]pyridin-4-yl)thiazol-2-yl)cyclobutanol A mixture of 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine (Example 1G) (80 mg, 0.117 mmol) in methanol (1.95 mL) and 10% aqueous HCl solution (0.39 mL) was heated to 65° C. for 3 hours and was then concentrated to dryness. The residue was partitioned between ethyl acetate and saturated aqueous bicarbonate solution. The layers were separated, and the aqueous layer was extracted with additional ethyl acetate (2×). The combined organics were dried with anhydrous sodium sulfate, filtered and concentrated to give the title compound. MS ESI (−) m/z 639.52 [M−H]−.

Example 1I 1-(5-{5-chloro-2-[1-(2-morpholin-4-ylethyl)-1H-pyrazol-4-yl]-1H-pyrrolo[2,3-b]pyridin-4-yl}-1,3-thiazol-2-yl)cyclobutanol A solution of 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H) (0.070 g, 0.11 mmol) in methanol (3 mL) and 2N aqueous NaOH (0.55 mL) was heated by microwave irradiation (Biotage, Initiator) to 120° C. for 20 minutes. The reaction was cooled to room temperature, and the pH was adjusted to ~7 with 10% aqueous HCl solution. The resulting solution was purified by reverse phase high performance liquid chromatography (RP HPLC, 19×150 mm Atlantis Prep T3 OBD 5 m column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound as its trifluoroacetic acid salt. ¹H NMR (300 MHz, DMSO-d$_6$) δ ppm 12.44 (bs, 1H), 9.73 (s, 1H), 8.40 (s, 1H), 8.26 (s, 1H), 8.19 (d, J=2.0 Hz, 1H), 6.80 (d, J=2.0 Hz, 1H), 6.68 (s, 1H), 4.59 (br s, 2H), 4.05-3.86 (m, 2H), 3.76-3.57 (m, 6H), 3.26-3.06 (m, 2H), 2.67-2.55 (m, 2H), 2.47-2.34 (m, 2H), 2.07-1.87 (m, 2H); MS ESI(+) m/z 485.1 [M+H]$^+$.

Example 2

1-{5-[5-fluoro-2-(4-piperazin-1-ylphenyl)-1H-pyrrolo[2,3-b]pyridin-4-yl]-1,3-thiazol-2-yl}cyclobutanol Example 2A 5-fluoro-4-iodo-1-tosyl-1H-pyrrolo[2,3-b]pyridine To a stirring suspension of sodium hydride (0.595 g, 24.81 mmol) in N,N-dimethylformamide (74.2 ml) was added a solution of 5-fluoro-4-iodo-1H-pyrrolo[2,3-b]pyridine (5 g, 19.08 mmol, Adesis) in N,N-dimethylformamide (10.60 mL). The mixture was stirred under nitrogen for about 30 minutes. para-Toluenesulfonyl chloride (4.00 g, 20.99 mmol) in N,N-dimethylformamide (10.60 ml) was added, and the reaction stirred at room temperature for about an hour. The reaction was quenched by the slow addition of the reaction mixture to a stirring ice-water solution (about 100 mL). The resulting mixture was filtered, and the solid was collected and dried under vacuum overnight to give the title compound. ¹H NMR (300 MHz, DMSO-d$_6$) δ 8.28 (s, 1H), 8.09 (d, 1H), 7.98 (d, 2H), 7.43 (d, 2H), 6.67 (d, 1H), 2.35 (s, 3H). MS ESI(+) m/z 416.31 [M+H]$^+$.

Example 2B 5-(5-fluoro-1-tosyl-1H-pyrrolo[2,3-b]pyridin-4-yl)-2-(1-(methoxymethoxy)cyclobutyl)thiazole The title compound was prepared as described in Example 1E, except substituting Example 2A for 5-chloro-4-iodo-1-tosyl-1H-pyrrolo[2,3-b]pyridine. MS APCI(+) m/z 488.03 [M+H]$^+$.

Example 2C 5-(5-fluoro-2-iodo-1-tosyl-1H-pyrrolo[2,3-b]pyridin-4-yl)-2-(1-(methoxymethoxy)cyclobutyl)thiazole The title compound was prepared as described in Example 1F, except substituting Example 2B for 5-(5-chloro-1-tosyl-1H-pyrrolo[2,3-b]pyridin-4-yl)-2-(1-(methoxymethoxy)cyclobutyl)thiazole. MS APCI(+) m/z 614.3 [M+H]$^+$.

Example 2D tert-butyl 4-(4-(5-fluoro-4-(2-(1-(methoxymethoxy) cyclobutyl)thiazol-5-yl)-1-tosyl-1H-pyrrolo[2,3-b] pyridin-2-yl)phenyl)piperazine-1-carboxylate The title compound was prepared as described in Example 1G, substituting Example 2C for 5-(5-chloro-2-iodo-1-tosyl-1H-pyrrolo[2,3-b]pyridin-4-yl)-2-(1-(methoxymethoxy)cyclobutyl)thiazole and tert-butyl 4-(4-(4,4,5,5-tetramethyl-1,3,2-dioxaborolan-2-yl)phenyl)piperazine-1-carboxylate for 4-(2-(4-(4,4,5,5-tetramethyl-1,3,2-dioxaborolan-2-yl)-1H-pyrazol-1-yl)ethyl)morpholine. MS APCI(+) m/z 748.6 [M+H]$^+$.

Example 2E 1-(5-(5-fluoro-2-(4-(piperazin-1-yl)phenyl)-1-tosyl-1H-pyrrolo[2,3-b]pyridin-4-yl)thiazol-2-yl)cyclobutanol The title compound was prepared as described in Example 1H, except substituting Example 2D for 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine. MS APCI(+) m/z 604.42 [M+H]$^+$.

Example 2F 1-(5-(5-fluoro-2-(4-(piperazin-1-yl)phenyl)-1H-pyrrolo[2,3-b]pyridin-4-yl)thiazol-2-yl)cyclobutanol The title compound was prepared as described in Example 1I, except substituting Example 2E for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol. ¹H NMR (300 MHz, DMSO-d$_6$) δ 12.29 (s, 1H), 8.48 (s, 1H), 8.21 (d, 1H), 7.89 (d, 2H), 7.13 (s, 1H), 7.01 (d, 2H), 3.18-3.13 (m, 4H), 2.88-2.80 (m, 4H), 2.65-2.57 (m, 2H), 2.45-2.35 (m, 3H), 2.00-1.92 (m, 2H). MS APCI(+) m/z 450.30 [M+H]$^+$.

Example 3

1-(5-{2-[4-(morpholin-4-ylmethyl)phenyl]-1H-pyrrolo[2,3-b]pyridin-4-yl}-1,3-thiazol-2-yl)cyclobutanol Example 3A 4-bromo-1-tosyl-1H-pyrrolo[2,3-b]pyridine The title compound was prepared as described in Example 1D, substituting 4-bromo-1H-pyrrolo[2,3-b]pyridine for 5-chloro-4-iodo-1H-pyrrolo[2,3-b]pyridine. MS ESI(+) m/z 353.08 [M+H]$^+$;

Example 3B 4-bromo-2-iodo-1-tosyl-1H-pyrrolo[2,3-b]pyridine

The title compound was prepared as described in Example 1F, substituting Example 3A for Example 1E. MS ESI(+) m/z 479.2 [M+H]$^+$.

Example 3C 4-(4-(4-bromo-1-tosyl-1H-pyrrolo[2,3-b]pyridin-2-yl)benzyl)morpholine The title compound was prepared as described in Example 1G, substituting 4-(4-(4,4,5,5-tetramethyl-1,3,2-dioxaborolan-2-yl)benzyl)morpholine for 4-(2-(4-(4,4,5,5-tetramethyl-1,3,2-dioxaborolan-2-yl)-1H-pyrazol-1-yl)ethyl)morpholine. MS ESI(+) m/z 528.4 [M+H]$^+$.

Example 3D 1-(5-(tributylstannyl)thiazol-2-yl)cyclobutanol

To a cold (−78° C.) solution of thiazole (1.0 mL, 14.1 mmol) in tetrahydrofuran (70 mL) was added n-butyllithium (11.83 mL, 14.1 mmol, 2.38 M in hexane) dropwise. After 15 minutes, cyclobutanone (1.06 mL, 14.1 mmol) was added in a single portion. The reaction was stirred at −78° C. for 30 minutes, and n-butyllithium (11.83 mL, 14.1 mmol, 2.38 M in hexane) was added dropwise. The reaction was stirred for an additional 20 minutes, after which tributyltin chloride (3.82 mL, 14.1 mmol) was added dropwise. After 10 minutes, the cold reaction was quenched by the addition of saturated aqueous ammonium chloride solution (100 mL) and ethyl acetate (100 mL). The reaction was warmed to ambient temperature. The layers were separated, and the aqueous layer was extracted with additional ethyl acetate (2×100 mL). The combined organics were dried with anhydrous $Na_2SO_4$, filtered, and concentrated. Trituration of the residue with hexane gave the title compound, which was used without further purification. MS ESI(+) m/z 445.3 $[M+H]^+$.

Example 3E 1-(5-(2-(4-(morpholinomethyl)phenyl)-1-tosyl-1H-pyrrolo[2,3-b]pyridin-4-yl)thiazol-2-yl)cyclobutanol The title compound was prepared as described in Example 1E, substituting 4-(4-(4-bromo-1-tosyl-1H-pyrrolo[2,3-b]pyridin-2-yl)benzyl)morpholine (Example 3C) for 5-chloro-4-iodo-1-tosyl-1H-pyrrolo[2,3-b]pyridine (Example 1D) and substituting 1-(5-(tributylstannyl)thiazol-2-yl)cyclobutanol (Example 3D) for 2-(1-(methoxymethoxy)cyclobutyl)-5-(tributylstannyl)thiazole (Example 1C). MS ESI(+) m/z 601.2 $[M+H]^+$.

Example 3F

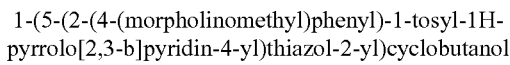
1-(5-(2-(4-(morpholinomethyl)phenyl)-1H-pyrrolo[2,3-b]pyridin-4-yl)thiazol-2-yl)cyclobutanol The title compound was prepared as described in Example 1I, substituting 1-(5-(2-(4-(morpholinomethyl)phenyl)-1-tosyl-1H-pyrrolo[2,3-b]pyridin-4-yl)thiazol-2-yl)cyclobutanol (Example 3E) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). $^1$H NMR (300 MHz, DMSO-$d_6$) δ 12.48 (s, 1H), 9.90 (s, 1H), 8.51 (s, 1H), 8.27 (d, J=5.1 Hz, 1H), 8.17 (d, J=8.3 Hz, 2H), 7.61 (d, J=8.4 Hz, 2H), 7.40 (d, J=2.0 Hz, 1H), 7.34 (d, J=5.0 Hz, 1H), 4.40 (s, 2H), 4.06-3.93 (m, 2H), 3.65-3.54 (m, 2H), 3.40-3.25 (m, 2H), 3.23-3.05 (m, 2H), 2.70-2.55 (m, 2H), 2.46-2.32 (m, 2H), 2.09-1.84 (m, 2H); MS ESI(+) m/z 447.1 $[M+H]^+$.

Example 4

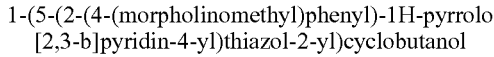
5-chloro-4-{2-[1-(methoxymethoxy)cyclobutyl]-1,3-thiazol-5-yl}-2-[4-(morpholin-4-ylmethyl)phenyl]-1H-pyrrolo[2,3-b]pyridine The title compound was prepared as described in Example 1I, substituting 4-(4-(5-chloro-4-(2-(1-(methoxymethoxy)cyclobutyl)thiazol-5-yl)-1-tosyl-1H-pyrrolo[2,3-b]pyridin-2-yl)benzyl)morpholine (Example 5A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). $^1$H NMR (300 MHz, DMSO-$d_6$) δ 12.58 (bs, 1H), 8.34 (s, 1H), 8.30 (s, 1H), 7.97 (d, 2H), 7.41 (d, 2H), 7.07 (s, 1H), 3.62-3.55 (m, 4H), 3.50 (s, 2H), 3.35 (s, 3H), 2.70-2.55 (m, 4H), 2.41-2.34 (m, 4H), 2.05-1.82 (m, 2H); MS ESI(+) m/z 525.1 $[M+H]^+$.

Example 5

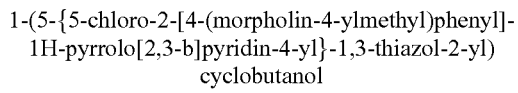
1-(5-{5-chloro-2-[4-(morpholin-4-ylmethyl)phenyl]-1H-pyrrolo[2,3-b]pyridin-4-yl}-1,3-thiazol-2-yl)cyclobutanol Example 5A 4-(4-(5-chloro-4-(2-(1-(methoxymethoxy)cyclobutyl)thiazol-5-yl)-1-tosyl-1H-pyrrolo[2,3-b]pyridin-2-yl)benzyl)morpholine The title compound was prepared as described in Example 1G, substituting 4-(4-(4,4,5,5-tetramethyl-1,3,2-dioxaborolan-2-yl)benzyl)morpholine for 4-(2-(4-(4,4,5,5-tetramethyl-1,3,2-dioxaborolan-2-yl)-1H-pyrazol-1-yl)ethyl)morpholine. MS ESI(+) m/z 679.2 $[M+H]^+$;

Example 5B

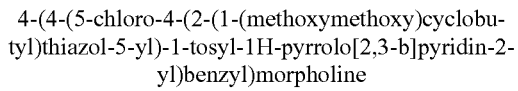
1-(5-(5-chloro-2-(4-(morpholinomethyl)phenyl)-1-tosyl-1H-pyrrolo[2,3-b]pyridin-4-yl)thiazol-2-yl)cyclobutanol The title compound was prepared as described in Example 1H, substituting 4-(4-(5-chloro-4-(2-(1-(methoxymethoxy)cyclobutyl)thiazol-5-yl)-1-tosyl-1H-pyrrolo[2,3-b]pyridin-2-yl)benzyl)morpholine (Example 5A) for Example 1G. MS ESI(+) m/z 635.2 $[M+H]^+$.

Example 5C

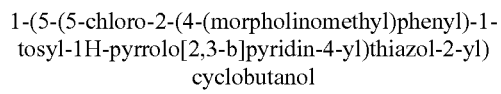
1-(5-(5-chloro-2-(4-(morpholinomethyl)phenyl)-1H-pyrrolo[2,3-b]pyridin-4-yl)thiazol-2-yl)cyclobutanol The title compound was prepared as described in Example 1I, substituting 1-(5-(5-chloro-2-(4-(morpholinomethyl)phenyl)-1-tosyl-1H-pyrrolo[2,3-b]pyridin-4-yl)thiazol-2-yl)cyclobutanol (Example 5B) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). $^1$H NMR (300 MHz, DMSO-$d_6$) δ 12.55 (bs, 1H), 8.32 (s, 1H), 8.25 (s, 1H), 8.00-7.92 (m, 2H), 7.44-7.33 (m, 2H), 7.03 (s, 1H), 6.66 (s, 1H), 3.62-3.55 (m, 4H), 3.50 (s, 2H), 2.70-2.55 (m, 2H), 2.46-2.34 (m, 6H), 2.07-1.89 (m, 2H); MS ESI(+) m/z 481.0 $[M+H]^+$.

Example 6

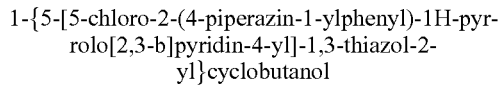
1-{5-[5-chloro-2-(4-piperazin-1-ylphenyl)-1H-pyrrolo[2,3-b]pyridin-4-yl]-1,3-thiazol-2-yl}cyclobutanol Example 6A

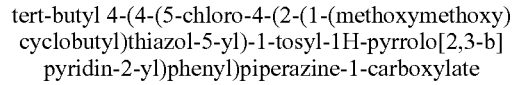
tert-butyl 4-(4-(5-chloro-4-(2-(1-(methoxymethoxy)cyclobutyl)thiazol-5-yl)-1-tosyl-1H-pyrrolo[2,3-b]pyridin-2-yl)phenyl)piperazine-1-carboxylate The title compound was prepared as described in Example 1G, substituting tert-butyl 4-(4-(4,4,5,5-tetramethyl-1,3,2-dioxaborolan-2-yl)phenyl)piperazine-1-carboxylate for 4-(2-(4-(4,4,5,5-tetramethyl-1,3,2-dioxaborolan-2-yl)-1H-pyrazol-1-yl)ethyl)morpholine. MS ESI(+) m/z 764.2 $[M+H]^+$.

Example 6B 1-(5-(5-chloro-2-(4-(piperazin-1-yl)phenyl)-1-tosyl-1H-pyrrolo[2,3-b]pyridin-4-yl)thiazol-2-yl)cyclobutanol The title compound was prepared as described in Example 1H, substituting tert-butyl 4-(4-(5-chloro-4-(2-(1-(methoxymethoxy)cyclobutyl)thiazol-5-yl)-1-tosyl-1H-pyrrolo[2,3-b]pyridin-2-yl)phenyl)piperazine-1-carboxylate (Example 6A) for 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine (Example 1G). MS ESI(+) m/z 620.1 [M+H]$^+$.

Example 6C 1-(5-(5-chloro-2-(4-(piperazin-1-yl)phenyl)-1H-pyrrolo[2,3-b]pyridin-4-yl)thiazol-2-yl)cyclobutanol The title compound was prepared as described in Example 1I, substituting tert-butyl 4-(4-(5-chloro-4-(2-(1-(methoxymethoxy)cyclobutyl)thiazol-5-yl)-1-tosyl-1H-pyrrolo[2,3-b]pyridin-2-yl)phenyl)piperazine-1-carboxylate (Example 6B) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). $^1$H NMR (300 MHz, DMSO-d$_6$) δ 12.36 (bs, 1H), 8.24 (s, 1H), 8.23 (s, 1H), 7.87-7.80 (m, 2H), 7.02-6.95 (m, 2H), 6.86 (s, 1H), 6.65 (s, 1H), 3.21-3.11 (m, 4H), 2.87-2.79 (m, 4H), 2.70-2.56 (m, 2H), 2.46-2.34 (m, 2H), 2.06-1.87 (m, 2H); MS ESI(+) m/z 466.0 [M+H]$^+$.

Example 7

5-chloro-4-[2-(1-methoxycyclobutyl)-1,3-thiazol-5-yl]-2-(4-piperazin-1-ylphenyl)-1H-pyrrolo[2,3-b]pyridine

Example 7A tert-butyl 4-(4-(5-chloro-4-(2-(1-hydroxycyclobutyl)thiazol-5-yl)-1-tosyl-1H-pyrrolo[2,3-b]pyridin-2-yl)phenyl)piperazine-1-carboxylate To an ambient solution of 1-(5-(2-(4-(piperazin-1-yl)phenyl)-1-tosyl-1H-pyrrolo[2,3-b]pyridin-4-yl)thiazol-2-yl)cyclobutanol (Example 6B) (0.100 g, 0.161 mmol) and 4-dimethylaminopyridine (0.001 g, 0.01 mmol) in tetrahydrofuran (2 mL) was added di-tert-butyl dicarbonate (0.056 mL, 0.242 mmol) in a single portion. The reaction was stirred for 3 hours and was then concentrated to dryness. The crude material was purified by flash chromatography on silica gel, eluting with a gradient of 0 to 50% ethyl acetate in hexane, to afford the title compound. MS ESI(+) m/z 720.2 [M+H]$^+$.

Example 7B 5-chloro-4-[2-(1-methoxycyclobutyl)-1,3-thiazol-5-yl]-2-(4-piperazin-1-ylphenyl)-1H-pyrrolo[2,3-b]pyridine To a suspension of sodium hydride (0.002 g, 0.092 mmol) in N,N-dimethylformamide (0.5 mL) was added tert-butyl 4-(4-(5-chloro-4-(2-(1-hydroxycyclobutyl)thiazol-5-yl)-1-tosyl-1H-pyrrolo[2,3-b]pyridin-2-yl)phenyl)piperazine-1-carboxylate (Example 7A) (0.044 g, 0.061 mmol) as a solution in N,N-dimethylformamide (0.5 mL). After 0.5 hours, a solution of iodomethane (0.037 mL, 0.073 mmol, 2 M in tert-butylmethyl ether) was added. The reaction was stirred at ambient temperature for 3 hours and was quenched by the addition of saturated aqueous ammonium chloride solution. The reaction was concentrated to dryness under reduced pressure. The residue, dissolved in methanol (3 mL) and 2N aqueous NaOH (0.31 mL), was heated by microwave irradiation (Biotage, Initiator) to 120° C. for 20 minutes. The reaction was cooled to room temperature and concentrated to dryness under reduced pressure. The residue was dissolved in dichlormethane (2 mL), and trifluoroacetic acid (2 mL) was added. The reaction was stirred at room temperature for 0.5 hours and was concentrated under reduced pressure. The residue was purified by reverse phase high performance liquid chromatography (RP HPLC, 19×150 mm Atlantis Prep T3 OBD 5 m column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound as its trifluoroacetic acid salt. $^1$H NMR (500 MHz, DMSO-d$_6$) δ 12.45 (s, 1H), 8.31-8.27 (m, 2H), 7.95-7.89 (m, 2H), 7.11-7.05 (m, 2H), 6.98-6.94 (m, 1H), 3.47-3.42 (m, 4H), 3.26-3.21 (m, J=8.5 Hz, 4H), 3.23 (s, 3H), 2.54-2.45 (m, 4H), 1.96-1.86 (m, 2H); MS ESI(+) m/z 480.0 [M+H]$^+$.

Example 8

1-(5-{5-chloro-2-[4-(pyrrolidin-1-ylmethyl)phenyl]-1H-pyrrolo[2,3-b]pyridin-4-yl}-1,3-thiazol-2-yl)cyclobutanol

Example 8A 1-(5-(5-chloro-2-iodo-1-tosyl-1H-pyrrolo[2,3-b]pyridin-4-yl)thiazol-2-yl)cyclobutanol To a solution of 5-(5-chloro-2-iodo-1-tosyl-1H-pyrrolo[2,3-b]pyridin-4-yl)-2-(1-(methoxymethoxy)cyclobutyl)thiazole (Example 1F) (1.5 g, 2.381 mmol) in a solvent mixture of tetrahydrofuran (24 mL) and methanol (10 mL) was added 10% aqueous HCl solution (7.24 ml, 23.81 mmol). The reaction was heated to 65° C. for 8 hours and was then cooled to room temperature. The reaction was partitioned between ethyl acetate (50 mL) and water (50 mL), and the layers were separated. The aqueous layer was extracted with additional ethyl acetate (2×50 mL). The combined organics were dried with anhydrous sodium sulfate, filtered and concentrated under reduced pressure to give the title compound, which was used without further purification. MS ESI(+) m/z 586.2 [M+H]$^+$.

Example 8B 4-(5-chloro-4-(2-(1-hydroxycyclobutyl)thiazol-5-yl)-1-tosyl-1H-pyrrolo[2,3-b]pyridin-2-yl)benzaldehyde To a stirred ambient solution of 1-(5-(5-chloro-2-iodo-1-tosyl-1H-pyrrolo[2,3-b]pyridin-4-yl)thiazol-2-yl)cyclobutanol (Example 8A) (2.85 g, 4.86 mmol) and 4-formylphenylboronic acid (1.094 g, 7.30 mmol) in N,N-dimethylformamide (36.5 ml) was added saturated aqueous bicarbonate solution (12.16 ml) followed by bis(triphenylphosphine)palladium dichloride (0.239 g, 0.341 mmol). The mixture was heated to 70° C. for 2 hours, cooled to room temperature, and quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was purified by flash chromatography on silica gel, eluting with a gradient of 0 to 70% ethyl acetate in hexane, to afford the title compound. MS ESI(+) m/z 564.5 [M+H]$^+$.

Example 8C 1-(5-(5-chloro-2-(4-(pyrrolidin-1-ylmethyl)phenyl)-1-tosyl-1H-pyrrolo[2,3-b]pyridin-4-yl)thiazol-2-yl) cyclobutanol To a solution of 4-(5-chloro-4-(2-(1-hydroxycyclobutyl) thiazol-5-yl)-1-tosyl-1H-pyrrolo[2,3-b]pyridin-2-yl)benzaldehyde (Example 8B) (2.10 g, 3.72 mmol) in tetrahydrofuran (33.8 mL) was added sequentially acetic acid (0.426 mL, 7.45 mmol), sodium sulfate (1.058 g, 7.45 mmol), and pyrrolidine (0.466 ml, 5.58 mmol). The reaction was stirred for 0.5 hours at ambient temperature, and sodium triacetoxyborohydride (1.578 g, 7.45 mmol) was added in a single portion. The reaction was stirred for 1 hour and was then quenched by the addition of saturated aqueous sodium bicarbonate solution (20 mL), ethyl acetate (20 mL), and solid sodium bicarbonate. The layers were separated, and the aqueous layer was extracted with addition ethyl acetate (2×). The combined organics were dried with anhydrous sodium sulfate, filtered and concentrated under reduced pressure. The residue was purified by flash chromatography on silica gel, eluting with a gradient of 0 to 10% methanol in dichloromethane with 1% v/v aqueous ammonium hydroxide solution, to give the title compound. MS ESI(+) m/z 619.3 [M+H]$^+$.

Example 8D 1-(5-(5-chloro-2-(4-(pyrrolidin-1-ylmethyl)phenyl)-1H-pyrrolo[2,3-b]pyridin-4-yl)thiazol-2-yl)cyclobutanol A solution of 1-(5-(5-chloro-2-(4-(pyrrolidin-1-ylmethyl) phenyl)-1-tosyl-1H-pyrrolo[2,3-b]pyridin-4-yl)thiazol-2-yl) cyclobutanol (Example 8C) (1.81 g, 2.92 mmol) in methanol (19.49 mL) and aqueous 2N sodium hydroxide (5.85 ml, 11.69 mmol) was heated to 70° C. for 1 hour. The methanol was removed under reduced pressure, and the remaining aqueous layer was diluted with 20 mL water. The aqueous layer was extracted with ethyl acetate (3×20 mL). The combined organics were dried with anhydrous sodium sulfate, filtered and concentrated under reduced pressure. The residue was triturated with a 2:1 methanol:water solution to give the title compound. $^1$H NMR (300 MHz, DMSO-d$_6$) δ 12.55 (s, 1H), 8.32 (s, 1H), 8.26 (s, 1H), 7.98-7.91 (m, 2H), 7.43-7.36 (m, 2H), 7.03 (s, 1H), 6.67 (s, 1H), 3.60 (s, 2H), 2.69-2.55 (m, 2H), 2.47-2.33 (m, 6H), 2.04-1.89 (m, 2H), 1.75-1.66 (m, 4H); MS ESI(+) m/z 465.2 [M+H]$^+$.

Example 9

1-(5-{5-fluoro-2-[1-(2-morpholin-4-ylethyl)-1H-pyrazol-4-yl]-1H-pyrrolo[2,3-b]pyridin-4-yl}-1,3-thiazol-2-yl)cyclobutanol The title compound was prepared as described in Examples 2A-2F, except substituting 4-(2-(4-(4,4,5,5-tetramethyl-1,3,2-dioxaborolan-2-yl)-1H-pyrazol-1-yl)ethyl)morpholine (Boron Molecular) for tert-butyl 4-(4-(4,4,5,5-tetramethyl-1,3,2-dioxaborolan-2-yl)phenyl)piperazine-1-carboxylate in Example 2D. $^1$H NMR (300 MHz, DMSO d$_6$) δ ppm 12.29 (s, 1H), 8.42 (d, 1H), 8.36 (s, 1H), 8.20 (d, 1H), 8.09 (d, 1H), 7.01 (d, 1H), 6.67 (s, 1H), 4.28 (t, 2H), 3.59-3.54 (m, 4H), 2.74 (t, 2H), 2.64-2.55 (m, 2H), 2.46-2.39 (m, 6H), 2.05-1.87 (m, 2H). MS APCI(+) m/z 469.28 [M+H]$^+$.

Example 10

1-(5-{5-fluoro-2-[4-(morpholin-4-ylmethyl)phenyl]-1H-pyrrolo[2,3-b]pyridin-4-yl}-1,3-thiazol-2-yl) cyclobutanol The title compound was prepared as described in Examples 2A-2F, except substituting 4-(4-(4,4,5,5-tetramethyl-1,3,2-dioxaborolan-2-yl)benzyl)morpholine (Aldrich) for tert-butyl 4-(4-(4,4,5,5-tetramethyl-1,3,2-dioxaborolan-2-yl)phenyl)piperazine-1-carboxylate in Example 2D. $^1$H NMR (300 MHz, DMSO d$_6$) δ ppm 12.51 (s, 1H), 8.52 (s, 1H), 8.31 (d, J=3.4, 1H), 8.02 (d, 2H), 7.43 (d, 2H), 7.31 (d, 1H), 6.73 (s, 1H), 3.62-3.58 (m, 4H), 3.53 (s, 2H), 2.66-2.57 (m, 2H), 2.46-2.37 (m, 6H), 2.04-1.92 (m, 2H). MS APCI(+) m/z 465.38 (M+H)$^+$.

Example 11

3-(5-{5-chloro-2-[4-(morpholin-4-ylmethyl)phenyl]-1H-pyrrolo[2,3-b]pyridin-4-yl}-1,3-thiazol-2-yl) oxetan-3-ol Example 11A 2,2-dimethyl-5-(thiazol-2-yl)-1,3-dioxan-5-ol The title compound was prepared as described in Example 1A, substituting 2,2-dimethyl-1,3-dioxan-5-one for cyclobutanone. MS ESI(+) m/z 215.9 [M+H]$^+$;

Example 11B 2-(5-(4-methoxybenzyloxy)-2,2-dimethyl-1,3-dioxan-5-yl)thiazole

To an ambient suspension of sodium hydride (1.136 g, 47.3 mmol) in N,N-dimethylformamide (126 ml) was added 2,2-dimethyl-5-(thiazol-2-yl)-1,3-dioxan-5-ol (Example 11A) (8.15 g, 37.9 mmol) as a solution in N,N-dimethylformamide (20 mL). The reaction was stirred for 30 minutes, and tetrabutylammonium iodide (0.699 g, 1.893 mmol) and 1-(chloromethyl)-4-methoxybenzene (6.42 ml, 47.3 mmol) were sequentially added. The reaction was stirred overnight and then quenched by the addition of saturated aqueous ammonium chloride solution and ethyl acetate. The layers were separated, and the aqueous layer was extracted with additional ethyl acetate (2×). The combined organics were dried with anhydrous sodium sulfate, filtered and concentrated under reduced pressure. The residue was purified by flash chromatography on silica gel, eluting with a gradient of 0 to 40% ethyl acetate in hexane, to give the title product. MS ESI(+) m/z 336.0 [M+H]$^+$.

Example 11C 2-(4-methoxybenzyloxy)-2-(thiazol-2-yl)propane-1,3-diol

To a solution of the 2-(5-(4-methoxybenzyloxy)-2,2-dimethyl-1,3-dioxan-5-yl)thiazole (Example 11B) (8.0 g, 23.85 mmol) in methanol (239 mL) was added copper(II) chloride dihydrate (12.20 g, 71.6 mmol) in a single portion. The mixture was heated to 70° C. for 1 hour. The reaction was cooled to room temperature and concentrated to a volume of ~50 mL under reduced pressure. The solution was diluted with saturated aqueous ammonium chloride solution (100 mL) and ethyl acetate (150 mL). The layers were separated, and the aqueous layer was extracted with additional ethyl acetate (2×100 mL). The combined organics were dried with anhydrous sodium sulfate, filtered and concentrated under reduced pressure to give the title compound. MS ESI(+) m/z 296.3 [M+H]$^+$.

Example 11D 2-(3-(4-methoxybenzyloxy)oxetan-3-yl)thiazole

To a cold (0° C.) solution of 2-(4-methoxybenzyloxy)-2-(thiazol-2-yl)propane-1,3-diol (Example 11C) (4.02 g, 13.61 mmol) in tetrahydrofuran (120 mL) was added n-butyllithium (5.4 mL, 13.6 mmol, 2.5 M solution in hexane) dropwise. After 0.5 hours, a solution of para-toluenesulfonyl chloride (2.59 g, 13.61 mmol) in tetrahydrofuran (16 mL) was added to the suspension. The reaction was stirred for an additional 0.5 hours. Thereafter, n-butyllithium (5.4 mL, 13.6 mmol, 2.5 M solution in hexane) was added to the reacton dropwise, and the reaction was heated to 65° C. for 1 hour. The reaction was cooled to room temperature and quenched by the addition of water and ethyl acetate. The layers were separated, and the aqueous layer was extracted with additional ethyl acetate (2×). The combined organics were dried with anhydrous sodium sulfate, filtered and concentrated. The residue was purified by flash chromatography on silica gel, eluting with a gradient of 0 to 30% ethyl acetate in hexane, to give the title product. MS ESI(+) m/z 278.3 [M+H]$^+$;

Example 11E 2-(3-(4-methoxybenzyloxy)oxetan-3-yl)-5-(tributylstannyl)thiazole

To a cold (−78° C.) solution of the 2-(3-(4-methoxybenzyloxy)oxetan-3-yl)thiazole (Example 11D) (1.8 g, 6.49 mmol) in tetrahydrofuran (11 mL) was added a solution of lithium diisopropylamide (7.79 mmol in 10 mL tetrahydrofuran) dropwise. The solution was stirred at −78° C. for 45 minutes, and tributyltin chloride (2.11 mL, 7.79 mmol) was added dropwise. The cold bath was removed, and the reaction slowly warmed to room temperature. The ambient reaction was then quenched by the addition of saturated aqueous ammonium chloride solution and diethyl ether. The layers were separated, and the aqueous layer was extracted with additional diethyl ether. The combined organics were washed with water, dried with anhydrous sodium sulfate, filtered and concentrated under reduced pressure to give the title compound, which was used without further purification. MS ESI(+) m/z 568.7 [M+H]$^+$.

Example 11F 5-(5-chloro-1-tosyl-1H-pyrrolo[2,3-b]pyridin-4-yl)-2-(3-(4-methoxybenzyloxy)oxetan-3-yl)thiazole The title compound was prepared as described in Example 1E, substituting 2-(3-(4-methoxybenzyloxy)oxetan-3-yl)-5-(tributylstannyl)thiazole (Example 11E) for 2-(1-(methoxymethoxy)cyclobutyl)-5-(tributylstannyl)thiazole (Example 1C). MS ESI(+) m/z 582.5 [M+H]$^+$;

Example 11G 5-(5-chloro-2-iodo-1-tosyl-1H-pyrrolo[2,3-b]pyridin-4-yl)-2-(3-(4-methoxybenzyloxy)oxetan-3-yl)thiazole The title compound was prepared as described in Example 1F, substituting 5-(5-chloro-1-tosyl-1H-pyrrolo[2,3-b]pyridin-4-yl)-2-(3-(4-methoxybenzyloxy)oxetan-3-yl)thiazole (Example 11F) for 5-(5-chloro-1-tosyl-1H-pyrrolo[2,3-b]pyridin-4-yl)-2-(1-(methoxymethoxy)cyclobutyl)thiazole (Example 1E). MS ESI(+) m/z 707.9 [M+H]$^+$.

Example 11H 4-(4-(5-chloro-4-(2-(3-(4-methoxybenzyloxy)oxetan-3-yl)thiazol-5-yl)-1-tosyl-1H-pyrrolo[2,3-b]pyridin-2-yl)benzyl)morpholine To a stirred ambient solution of 5-(5-chloro-2-iodo-1-tosyl-1H-pyrrolo[2,3-b]pyridin-4-yl)-2-(3-(4-methoxybenzyloxy)oxetan-3-yl)thiazole (Example 11G) (200 mg, 0.282 mmol) and 4-(4-(4,4,5,5-tetramethyl-1,3,2-dioxaborolan-2-yl)benzyl)morpholine (120 mg, 0.395 mmol) in N,N-dimethylformamide (2.65 mL) was added saturated aqueous bicarbonate solution (0.883 mL) followed by bis(triphenylphosphine)palladium dichloride (13.88 mg, 0.020 mmol). The mixture was heated to 70° C. for 4 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was purified by flash chromatography on silica gel, eluting with a gradient of 0 to 30% ethyl acetate in hexane, to afford the title compound. MS ESI(+) m/z 757.2 [M+H]$^+$.

Example 11I 3-(5-(5-chloro-2-(4-(morpholinomethyl)phenyl)-1-tosyl-1H-pyrrolo[2,3-b]pyridin-4-yl)thiazol-2-yl)oxetan-3-ol To an ambient solution of 4-(4-(5-chloro-4-(2-(3-(4-methoxybenzyloxy)oxetan-3-yl)thiazol-5-yl)-1-tosyl-1H-pyrrolo[2,3-b]pyridin-2-yl)benzyl)morpholine (Example 11H) (130 mg, 0.172 mmol) in dichloromethane (2.5 mL) was added trifluoroacetic acid (2.5 mL, 32.4 mmol). The reaction was stirred for 0.5 hours and was then concentrated to dryness under reduced pressure. The residue was partitioned between ethyl acetate (5 mL) and saturated aqueous bicarbonate solution (1 mL). The layers were separated, and the organic layer was dried with anhydrous sodium sulfate, filtered and concentrated under reduced pressure. The residue was purified by flash chromatography on silica gel, eluting with a gradient of 0 to 10% methanol in dichloromethane, to give the title compound. MS ESI(+) m/z 637.1 [M+H]$^+$.

Example 11J 3-(5-(5-chloro-2-(4-(morpholinomethyl)phenyl)-1H-pyrrolo[2,3-b]pyridin-4-yl)thiazol-2-yl)oxetan-3-ol The title compound was prepared as described in Example 8D, substituting 3-(5-(5-chloro-2-(4-(morpholinomethyl)

phenyl)-1-tosyl-1H-pyrrolo[2,3-b]pyridin-4-yl)thiazol-2-yl) oxetan-3-ol (Example 11I) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.57 (s, 1H), 8.36 (s, 1H), 8.34 (s, 1H), 7.99-7.92 (m, 2H), 7.44-7.36 (m, 3H), 7.04 (s, 1H), 5.01 (d, J=6.6 Hz, 2H), 4.79 (d, J=6.8 Hz, 2H), 3.61-3.55 (m, 4H), 3.50 (s, 3H), 2.40-2.34 (m, 4H); MS ESI(+) m/z 483.0 [M+H]$^+$.

Example 12

3-(5-{5-chloro-2-[1-(2-morpholin-4-ylethyl)-1H-pyrazol-4-yl]-1H-pyrrolo[2,3-b]pyridin-4-yl}-1,3-thiazol-2-yl)oxetan-3-ol Example 12A 4-(2-(4-(5-chloro-4-(2-(3-(4-methoxybenzyloxy) oxetan-3-yl)thiazol-5-yl)-1-tosyl-1H-pyrrolo[2,3-b] pyridin-2-yl)-1H-pyrazol-1-yl)ethyl)morpholine The title compound was prepared as described in Example 11H, substituting 4-(2-(4-(4,4,5,5-tetramethyl-1,3,2-dioxaborolan-2-yl)-1H-pyrazol-1-yl)ethyl)morpholine for 4-(4-(4,4,5,5-tetramethyl-1,3,2-dioxaborolan-2-yl)benzyl)morpholine. MS ESI(+) m/z 761.2 [M+H]$^+$.

Example 12B 3-(5-(5-chloro-2-(1-(2-morpholinoethyl)-1H-pyrazol-4-yl)-1-tosyl-1H-pyrrolo[2,3-b]pyridin-4-yl)thiazol-2-yl)oxetan-3-ol The title compound was prepared as described in Example 11I, substituting 4-(2-(4-(5-chloro-4-(2-(3-(4-methoxybenzyloxy)oxetan-3-yl)thiazol-5-yl)-1-tosyl-1H-pyrrolo[2,3-b]pyridin-2-yl)-1H-pyrazol-1-yl)ethyl)morpholine (Example 12A) for 4-(4-(5-chloro-4-(2-(3-(4-methoxybenzyloxy)oxetan-3-yl)thiazol-5-yl)-1-tosyl-1H-pyrrolo[2,3-b]pyridin-2-yl)benzyl)morpholine (Example 11H). MS ESI(+) m/z 641.2 [M+H]$^+$.

Example 12C 3-(5-(5-chloro-2-(1-(2-morpholinoethyl)-1H-pyrazol-4-yl)-1H-pyrrolo[2,3-b]pyridin-4-yl)thiazol-2-yl) oxetan-3-ol The title compound was prepared as described in Example 8D, substituting 3-(5-(5-chloro-2-(1-(2-morpholinoethyl)-1H-pyrazol-4-yl)-1-tosyl-1H-pyrrolo[2,3-b]pyridin-4-yl) thiazol-2-yl)oxetan-3-ol (Example 12B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.38 (bs, 1H), 8.34 (s, 1H), 8.29 (s, 1H), 8.25 (s, 1H), 8.06 (s, 1H), 7.46 (bs, 1H), 6.74 (s, 1H), 5.00 (d, J=6.4 Hz, 2H), 4.79 (d, J=6.4 Hz, 2H), 4.30-4.23 (m, 2H), 3.64-3.48 (m, 4H), 2.77-2.69 (m, 2H), 2.45-2.33 (m, 4H); MS ESI(+) m/z 487.1 [M+H]$^+$.

Example 13

1-(5-{5-chloro-2-[1-(1,3-dioxolan-2-ylmethyl)-1H-pyrazol-4-yl]-1H-pyrrolo[2,3-b]pyridin-4-yl}-1,3-thiazol-2-yl)cyclobutanol Example 13A 5-(2-(1((1,3-dioxolan-2-yl)methyl)-1H-pyrazol-4-yl)-5-chloro-1-tosyl-1H-pyrrolo[2,3-b]pyridin-4-yl)-2-(1-(methoxymethoxy)cyclobutyl)thiazole The title compound was prepared as described in Example 1G, substituting 14(1,3-dioxolan-2-yl)methyl)-4-(4,4,5,5-tetramethyl-1,3,2-dioxaborolan-2-yl)-1H-pyrazole for 4-(2-(4-(4,4,5,5-tetramethyl-1,3,2-dioxaborolan-2-yl)-1H-pyrazol-1-yl)ethyl)morpholine. MS ESI(+) m/z 656.1 [M+H]$^+$.

Example 13B 1-(5-(2-(1((1,3-dioxolan-2-yl)methyl)-1H-pyrazol-4-yl)-5-chloro-1-tosyl-1H-pyrrolo[2,3-b]pyridin-4-yl) thiazol-2-yl)cyclobutanol The title compound was prepared as described in Example 1H, substituting 5-(2-(1-(1,3-dioxolan-2-yl)methyl)-1H-pyrazol-4-yl)-5-chloro-1-tosyl-1H-pyrrolo[2,3-b]pyridin-4-yl)-2-(1-(methoxymethoxy)cyclobutyl)thiazole (Example 13A) for 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine (Example 1G). MS ESI(+) m/z 612.1 [M+H]$^+$.

Example 13C 1-(5-(2-(1-((1,3-dioxolan-2-yl)methyl)-1H-pyrazol-4-yl)-5-chloro-1H-pyrrolo[2,3-b]pyridin-4-yl)thiazol-2-yl)cyclobutanol The title compound was prepared as described in Example 8D, substituting 1-(5-(2-(1-((1,3-dioxolan-2-yl)methyl)-1H-pyrazol-4-yl)-5-chloro-1-tosyl-1H-pyrrolo[2,3-b]pyridin-4-yl)thiazol-2-yl)cyclobutanol (Example 13B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.35 (bs, 1H), 8.33 (s, 1H), 8.24 (s, 1H), 8.19 (s, 1H), 8.09 (s, 1H), 6.78 (s, 1H), 6.65 (bs, 1H), 5.19 (t, J=4.1 Hz, 1H), 4.30 (d, J=4.1 Hz, 2H), 3.92-3.78 (m, 4H), 2.69-2.56 (m, 2H), 2.47-2.33 (m, 2H), 2.07-1.87 (m, 2H); MS ESI(+) m/z 458.0 [M+H]$^+$.

Example 14

1-[5-(5-chloro-2-{1-[2-(dimethylamino)ethyl]-1H-pyrazol-4-yl}-1H-pyrrolo[2,3-b]pyridin-4-yl)-1,3-thiazol-2-yl]cyclobutanol Example 14A 5-(2-(1-allyl-1H-pyrazol-4-yl)-5-chloro-1-tosyl-1H-pyrrolo[2,3-b]pyridin-4-yl)-2-(1-(methoxymethoxy) cyclobutyl)thiazole The title compound was prepared as described in Example 1G, substituting 1-allyl-4-(4,4,5,5-tetramethyl-1,3,2-dioxaborolan-2-yl)-1H-pyrazole for 4-(2-(4-(4,4,5,5-tetramethyl-1,3,2-dioxaborolan-2-yl)-1H-pyrazol-1-yl)ethyl)morpholine. MS ESI(+) m/z 610.2 [M+H]+.

Example 14B 3-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)propane-1,2-diol To an ambient solution of 5-(2-(1-allyl-1H-pyrazol-4-yl)-5-chloro-1-tosyl-1H-pyrrolo[2,3-b]pyridin-4-yl)-2-(1-(methoxymethoxy)cyclobutyl)thiazole (Example 14A) (1.5 g, 2.458 mmol) in a solvent mixture of acetone (6.15 mL) and water (2.05 mL) was added potassium osmate (VI) dihydrate (9.06 mg, 0.025 mmol) followed by N-methylmorpholine-N-oxide (0.288 g, 2.458 mmol). The reaction was stirred overnight and was then quenched by the addition of 10% aqueous sodium thiosulfate solution (10 mL) and ethyl acetate (15 mL). The layers were separated, and the aqueous layer was extracted with additional ethyl acetate (2×15 mL). The combined organics were washed with 10% aqueous sodium thiosulfate solution (10 mL), dried with anhydrous sodium sulfate, filtered and concentrated. The residue was purified by flash chromatography on silica gel, eluting with a gradient of 0 to 10% methanol in dichloromethane, to give the title compound. MS ESI(+) m/z 642.2 [M+H]+.

Example 14C 2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)acetaldehyde To an ambient solution of 3-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)propane-1,2-diol (Example 14B) (1.28 g, 1.987 mmol) in a solvent mixture of tetrahydrofuran (14.90 mL) and water (4.97 mL) was added solid sodium periodate (0.638 g, 2.98 mmol) in a single portion. The reaction was stirred at room temperature for 1 hour and was then quenched by the addition of 10% aqueous sodium thiosulfate solution (10 mL) and ethyl acetate (15 mL). The layers were separated, and the aqueous layer was extracted with additional ethyl acetate (2×15 mL). The combined organics were washed once with 10% aqueous sodium thiosulfate solution (10 mL), dried with anhydrous sodium sulfate, filtered and concentrated to give the title compound, which was used in the next step without further purification. MS ESI(−) m/z 610.2 [M−H]−.

Example 14D 2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)-N,N-dimethylethanamine To a solution of 2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)acetaldehyde (14C) (300 mg, 0.490 mmol) in tetrahydrofuran (3.267 mL) was added sequentially acetic acid (0.056 mL, 0.980 mmol), sodium sulfate (139 mg, 0.980 mmol) and dimethylamine (0.368 mL, 0.735 mmol). The reaction was stirred for 0.5 hours at ambient temperature, and sodium triacetoxyborohydride (208 mg, 0.980 mmol) was added in a single portion. The reaction was stirred overnight and then quenched by the addition of saturated aqueous sodium bicarbonate and ethyl acetate. The layers were separated, and the aqueous layer was extracted with addition ethyl acetate (2×). The combined organics were dried with anhydrous sodium sulfate, filtered and concentrated under reduced pressure to give the title compound, which was used in the next step without further purification. MS ESI(+) m/z 641.2 [M+H]+.

Example 14E 1-(5-(5-chloro-2-(1-(2-(dimethylamino)ethyl)-1H-pyrazol-4-yl)-1-tosyl-1H-pyrrolo[2,3-b]pyridin-4-yl)thiazol-2-yl)cyclobutanol The title compound was prepared as described in Example 1H, substituting 2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)-N,N-dimethylethanamine (Example 14D) for 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine (Example 1G). MS ESI(+) m/z 597.1 [M+H]+.

Example 14F 1-(5-(5-chloro-2-(1-(2-(dimethylamino)ethyl)-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1-(2-(dimethylamino)ethyl)-1H-pyrazol-4-yl)-1-tosyl-1H-pyrrolo[2,3-b]pyridin-4-yl)thiazol-2-yl)cyclobutanol (Example 14E) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.33 (bs, 1H), 8.34 (s, 1H), 8.23 (s, 1H), 8.19 (s, 1H), 8.05 (s, 1H), 6.74 (d, J=1.7 Hz, 1H), 6.66 (s, 1H), 4.22 (t, J=6.3 Hz, 2H), 2.76-2.56 (m, 4H), 2.45-2.34 (m, 2H), 2.18 (s, 6H), 2.01-1.97 (m, 2H); MS ESI(+) m/z 443.0 [M+H]+.

Example 15

1-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)cyclobutanol Example 15A 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(1-(methoxymethoxy)cyclobutyl)thiazole The title compound was prepared as described in Example 14D, substituting pyrrolidine for dimethylamine. MS ESI(+) m/z 667.2 [M+H]+.

Example 15B 1-(5-(5-chloro-2-(1-(2-(pyrrolidin-1-yl)ethyl)-1H-pyrazol-4-yl)-1-tosyl-1H-pyrrolo[2,3-b]pyridin-4-yl)thiazol-2-yl)cyclobutanol The title compound was prepared as described in Example 1H, substituting 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(1-(methoxymethoxy)cyclobutyl)thiazole (Example 15A) for 4-(2-(4-(5-chloro-4-(2-(1-(methoxymethoxy)cyclobutyl)

thiazol-5-yl)-1-tosyl-1H-pyrrolo[2,3-b]pyridin-2-yl)-1H-pyrazol-1-yl)ethyl)morpholine (Example 1G). MS ESI(+) m/z 623.2 [M+H]+.

Example 15

1-(5-(5-chloro-2-(1-(2-(pyrrolidin-1-yl)ethyl)-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1-(2-(pyrrolidin-1-yl)ethyl)-1H-pyrazol-4-yl)-1-tosyl-1H-pyrrolo[2,3-b]pyridin-4-yl)thiazol-2-yl)cyclobutanol (Example 15B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.33 (s, 1H), 8.35 (s, 1H), 8.23 (s, 1H), 8.19 (s, 1H), 8.05 (d, J=0.7 Hz, 1H), 6.75 (d, J=2.0 Hz, 1H), 6.65 (s, 1H), 4.24 (t, J=6.4 Hz, 2H), 2.84 (t, J=6.4 Hz, 2H), 2.69-2.56 (m, 2H), 2.47-2.32 (m, 6H), 2.07-1.91 (m, 2H), 1.76-1.58 (m, 4H); MS ESI(+) m/z 469.0 [M+H]+.

Example 16

4-{5-chloro-4-[2-(1-hydroxycyclobutyl)-1,3-thiazol-5-yl]-1H-pyrrolo[2,3-b]pyridin-2-yl}benzoic acid Example 16A 4-(5-chloro-4-(2-(1-(methoxymethoxy)cyclobutyl)thiazol-5-yl)-1-tosyl-1H-pyrrolo[2,3-b]pyridin-2-yl)benzoic acid The title compound was prepared as described in Example 1G, substituting 4-(4,4,5,5-tetramethyl-1,3,2-dioxaborolan-2-yl)benzoic acid for 4-(2-(4-(4,4,5,5-tetramethyl-1,3,2-dioxaborolan-2-yl)-1H-pyrazol-1-yl)ethyl)morpholine. MS ESI(+) m/z 624.1 [M+H]+;

Example 16B 4-(5-chloro-4-(2-(1-hydroxycyclobutyl)thiazol-5-yl)-1-tosyl-1H-pyrrolo[2,3-b]pyridin-2-yl)benzoic acid A solution of 4-(5-chloro-4-(2-(1-(methoxymethoxy)cyclobutyl)thiazol-5-yl)-1-tosyl-1H-pyrrolo[2,3-b]pyridin-2-yl)benzoic acid (Example 16A) (700 mg, 1.122 mmol) in tetrahydrofuran (9.3 mL) and 10% aqueous HCl solution (1.9 mL) was heated to 65° C. for 24 hours. An additional 3 mL 10% aqueous HCl solution and 3 mL methanol were added, and the reaction was heated to 80° C. for 3 hours. The reaction was removed from the heat bath and allowed to slowly cool to room temperature. The reaction was diluted with 5 mL water, and the solid was filtered and air-dried to yield the title compound. MS ESI(+) m/z 580.1 [M+H]+;

Example 16C

4-{5-chloro-4-[2-(1-hydroxycyclobutyl)-1,3-thiazol-5-yl]-1H-pyrrolo[2,3-b]pyridin-2-yl}benzoic acid A solution of 4-(5-chloro-4-(2-(1-hydroxycyclobutyl)thiazol-5-yl)-1-tosyl-1H-pyrrolo[2,3-b]pyridin-2-yl)benzoic acid (Example 16B) (450 mg, 0.776 mmol) in methanol (7.8 mL) and 2N sodium hydroxide solution (2.7 mL, 5.43 mmol) was heated by microwave irradiation (Biotage, Initiator) in a sealed vessel to 105° C. for 7 minutes. The reaction was cooled to room temperature and concentrated to dryness. The residue was suspended in water, and the pH adjusted to ~2 with 10% aqueous HCl solution. The solid was filtered and air-dried to give the title compound. $^1$H NMR (300 MHz, DMSO-$d_6$) δ 12.69 (bs, 1H), 8.37 (s, 1H), 8.28 (s, 1H), 8.09 (d, J=8.4 Hz, 2H), 7.98 (d, J=8.4 Hz, 2H), 7.19 (s, 1H), 6.68 (s, 1H), 2.70-2.58 (m, 2H), 2.47-2.35 (m, 1H), 2.15-1.82 (m, 2H); MS ESI(+) m/z 425.9 [M+H]+.

Example 17

1-{5-[5-chloro-2-(1-{2-[cyclopropyl(methyl)amino]ethyl}-1H-pyrazol-4-yl)-1H-pyrrolo[2,3-b]pyridin-4-yl]-1,3-thiazol-2-yl}cyclobutanol Example 17A N-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)-N-methylcyclopropanamine The title compound was prepared as described in Example 14D, substituting methylcyclopropylamine hydrochloride salt for dimethylamine. MS ESI(+) m/z 667.2 [M+H]+.

Example 17B 1-(5-(5-chloro-2-(1-(2-(cyclopropyl(methyl)amino)ethyl)-1H-pyrazol-4-yl)-1-tosyl-1H-pyrrolo[2,3-b]pyridin-4-yl)thiazol-2-yl)cyclobutanol The title compound was prepared as described in Example 1H, substituting N-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)-N-methylcyclopropanamine (Example 17A) for 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine (Example 1G). MS ESI(+) m/z 623.1 [M+H]+.

Example 17C

1-{5-[5-chloro-2-(1-{2-[cyclopropyl(methyl)amino]ethyl}-1H-pyrazol-4-yl)-1H-pyrrolo[2,3-b]pyridin-4-yl]-1,3-thiazol-2-yl}cyclobutanol The title compound was prepared as described in Example 8D, substituting 1-(5-(5-chloro-2-(1-(2-(cyclopropyl(methyl)amino)ethyl)-1H-pyrazol-4-yl)-1-tosyl-1H-pyrrolo[2,3-b]pyridin-4-yl)thiazol-2-yl)cyclobutanol (Example 17B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (400 MHz, DMSO-$d_6$) δ 12.33 (bs, 1H), 8.32 (s, 1H), 8.23 (s, 1H), 8.19 (s, 1H), 8.06 (s, 1H), 6.75 (d, J=2.0 Hz, 1H), 6.67 (s, 1H), 4.23 (t, J=6.4 Hz, 2H), 2.93 (t, J=6.4 Hz, 2H), 2.67-2.57 (m, 2H), 2.47-2.35 (m, 2H), 2.05-1.90 (m, 2H), 1.76-1.67 (m, 1H), 0.43-0.35 (m, 2H), 0.23-0.16 (m, 2H); MS ESI(+) m/z 469.1 [M+H]+.

Example 18

1-(5-{5-chloro-2-[6-(4-methylpiperazin-1-yl)pyridin-3-yl]-1H-pyrrolo[2,3-b]pyridin-4-yl}-1,3-thiazol-2-yl)cyclobutanol

Example 18A 5-(5-chloro-2-(6-(4-methylpiperazin-1-yl)pyridin-3-yl)-1-(phenylsulfonyl)-1H-pyrrolo[2,3-b]pyridin-4-yl)-2-(1-(methoxymethoxy)cyclobutyl)thiazole The title compound was prepared as described in Example 1G, substituting 1-methyl-4-(5-(4,4,5,5-tetramethyl-1,3,2-dioxaborolan-2-yl)pyridin-2-yl)piperazine for 4-(2-(4-(4,4,5,5-tetramethyl-1,3,2-dioxaborolan-2-yl)-1H-pyrazol-1-yl)ethyl)morpholine. MS ESI(+) m/z 679.2 [M+H]$^+$;

Example 18B 1-(5-(5-chloro-2-(6-(4-methylpiperazin-1-yl)pyridin-3-yl)-1-(phenylsulfonyl)-1H-pyrrolo[2,3-b]pyridin-4-yl)thiazol-2-yl)cyclobutanol The title compound was prepared as described in Example 1H, substituting 5-(5-chloro-2-(6-(4-methylpiperazin-1-yl)pyridin-3-yl)-1-(phenylsulfonyl)-1H-pyrrolo[2,3-b]pyridin-4-yl)-2-(1-(methoxymethoxy)cyclobutyl)thiazole (Example 18A) for 4-(2-(4-(5-chloro-4-(2-(1-(methoxymethoxy)cyclobutyl)thiazol-5-yl)-1-tosyl-1H-pyrrolo[2,3-b]pyridin-2-yl)-1H-pyrazol-1-yl)ethyl)morpholine (Example 1G). MS ESI(−) m/z 633.1 [M−H]$^−$.

Example 18C 1-(5-{5-chloro-2-[6-(4-methylpiperazin-1-yl)pyridin-3-yl]-1H-pyrrolo[2,3-b]pyridin-4-yl}-1,3-thiazol-2-yl)cyclobutanol The title compound was prepared as described in Example 8D, substituting 1-(5-(5-chloro-2-(6-(4-methylpiperazin-1-yl)pyridin-3-yl)-1-(phenylsulfonyl)-1H-pyrrolo[2,3-b]pyridin-4-yl)thiazol-2-yl)cyclobutanol (Example 18B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.46-12.41 (m, 1H), 8.74 (d, J=2.5 Hz, 1H), 8.26 (s, 1H), 8.24 (s, 1H), 8.13 (dd, J=8.9, 2.5 Hz, 1H), 6.96-6.89 (m, 2H), 6.66 (s, 1H), 3.61-3.56 (m, 4H), 2.69-2.57 (m, 2H), 2.44-2.34 (m, 6H), 2.22 (s, 3H), 2.01-1.94 (m, 2H); MS ESI(+) m/z 481.1 [M+H]$^+$.

Example 19

1-[5-(5-chloro-2-{4-[(4-methylpiperazin-1-yl)carbonyl]phenyl}-1H-pyrrolo[2,3-b]pyridin-4-yl)-1,3-thiazol-2-yl]cyclobutanol To a solution of 4-(5-chloro-4-(2-(1-hydroxycyclobutyl)thiazol-5-yl)-1H-pyrrolo[2,3-b]pyridin-2-yl)benzoic acid (Example 16C) (100 mg, 0.235 mmol) in N,N-dimethylformamide (1.17 mL) was added 1-methylpiperazine (78 μl, 0.704 mmol), 4-methylmorpholine (71.2 mg, 0.704 mmol), hydroxybenzotriazole (53.9 mg, 0.352 mmol), and N-(3-dimethylaminopropyl)-N'-ethylcarbodiimide hydrochloride (67.5 mg, 0.352 mmol). The solution was heated to 45° C. for 3 hours. The reaction was cooled to room temperature and diluted with dimethyl sulfoxide (1 mL). The resulting solution was purified by reverse phase high performance liquid chromatography (RP HPLC, 19×150 mm Atlantis Prep T3 OBD 5 m column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound. $^1$H NMR (300 MHz, DMSO-d$_6$) δ 12.67 (bs, 1H), 8.37 (s, 1H), 8.28 (s, 1H), 8.10-8.05 (m, 2H), 7.51-7.44 (m, 2H), 7.17 (s, 1H), 6.68 (s, 1H), 3.76-3.48 (m, 4H), 2.69-2.58 (m, 2H), 2.47-2.25 (m, 6H), 2.20 (s, 3H), 2.05-1.91 (m, 2H); MS ESI(+) m/z 508.1 [M+H]$^+$.

Example 20

5-chloro-4-(2-{3-[(4-methoxybenzyl)oxy]oxetan-3-yl}-1,3-thiazol-5-yl)-2-[1-(2-pyrrolidin-1-ylethyl)-1H-pyrazol-4-yl]-1H-pyrrolo[2,3-b]pyridine

Example 20A 1-(2-(pyrrolidin-1-yl)ethyl)-4-(4,4,5,5-tetramethyl-1,3,2-dioxaborolan-2-yl)-1H-pyrazole To a suspension of sodium hydride (0.272 g, 11.34 mmol) in N,N-dimethylformamide (13 mL) was added 4-(4,4,5,5-tetramethyl-1,3,2-dioxaborolan-2-yl)-1H-pyrazole (1.0 g, 5.15 mmol) and 2-chloroethylpyrrolidine HCl salt (0.964 g, 5.67 mmol) as solutions in N,N-dimethylformamide (2 mL each). The reaction was stirred at room temperature for 0.5 hours and then heated to 65° C. for 3 hours. The reaction was cooled to room temperature and diluted with ethyl acetate (50 mL). Water (50 mL) was added, and the layers were separated. The aqueous layer was extracted with additional ethyl acetate (2×30 mL). The combined organics were washed with water, dried with anhydrous sodium sulfate, filtered and concentrated under reduced pressure to give the title compound, which was used without further purification. MS ESI(+) m/z 292.2 [M+H]$^+$;

Example 20B 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(3-(4-methoxybenzyloxy)oxetan-3-yl)thiazole To a stirred ambient solution of 5-(5-chloro-2-iodo-1-tosyl-1H-pyrrolo[2,3-b]pyridin-4-yl)-2-(3-(4-methoxybenzyloxy)oxetan-3-yl)thiazole (Example 11G) (300 mg, 0.424 mmol) and 1-(2-(pyrrolidin-1-yl)ethyl)-4-(4,4,5,5-tetramethyl-1,3,2-dioxaborolan-2-yl)-1H-pyrazole (Example 20A) (173 mg, 0.593 mmol) in N,N-dimethylformamide (3.97 mL) was added saturated aqueous bicarbonate solution (1.32 mL) followed by bis(triphenylphosphine)palladium dichloride (20.8 mg, 0.030 mmol). The mixture was heated to 70° C. for 4 hours, cooled to room temperature, and then quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was purified by flash chromatography on silica gel, eluting with a gradient of 0 to 10% methanol in dichloromethane, to afford the title compound. MS ESI(+) m/z 745.1 [M+H]$^+$.

Example 20C 5-chloro-4-(2-{3-[(4-methoxybenzyl)oxy]oxetan-3-yl}-1,3-thiazol-5-yl)-2-[1-(2-pyrrolidin-1-ylethyl)-1H-pyrazol-4-yl]-1H-pyrrolo[2,3-b]pyridine The title compound was prepared as described in Example 8D, substituting 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(3-(4-methoxybenzyloxy)oxetan-3-yl)thiazole (Example 20B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.39 (s, 1H), 8.36 (s, 1H), 8.34 (s, 1H), 8.26 (s, 1H), 8.05 (d, J=0.7 Hz, 1H), 7.39-7.32 (m, 2H), 6.97-6.90 (m, 2H), 6.78 (s, 1H), 5.06-4.96 (m, 4H), 4.59 (s, 2H), 4.25 (t, J=6.4 Hz, 2H), 2.89-2.80 (m, 2H), 2.47 (s, 4H), 1.70-1.62 (m, 4H); MS ESI(+) m/z 591.2 [M+H]$^+$.

Example 21

3-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)oxetan-3-ol

Example 21A 3-(5-(5-chloro-2-(1-(2-(pyrrolidin-1-yl)ethyl)-1H-pyrazol-4-yl)-1-tosyl-1H-pyrrolo[2,3-b]pyridin-4-yl)thiazol-2-yl)oxetan-3-ol To an ambient solution of 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(3-(4-methoxybenzyloxy)oxetan-3-yl)thiazole (Example 20B) (160 mg, 0.215 mmol) in dichloromethane (2.5 mL) was added trifluoroacetic acid (2.5 mL, 32.4 mmol). The reaction was stirred for 0.5 hours and then concentrated to dryness under reduced pressure. The residue was partitioned between ethyl acetate (5 mL) and saturated aqueous bicarbonate solution (1 mL). The organic layer was dried with anhydrous sodium sulfate, filtered and concentrated under reduced pressure. The residue was purified by flash chromatography on silica gel, eluting with 0 to 10% methanol in dichloromethane, to give the title compound. MS ESI(+) m/z 625.1 [M+H]$^+$.

Example 21

3-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)oxetan-3-ol The title compound was prepared as described in Example 8D, substituting 3-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)oxetan-3-ol (Example 21A) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.36 (bs, 1H), 8.35 (s, 1H), 8.29 (s, 1H), 8.24 (s, 1H), 8.05 (s, 1H), 7.46 (s, 1H), 6.75 (d, J=1.9 Hz, 1H), 5.00 (d, J=6.4 Hz, 2H), 4.79 (d, J=6.4 Hz, 2H), 4.24 (t, J=6.4 Hz, 2H), 2.84 (t, J=6.4 Hz, 2H), 2.48-2.41 (m, 4H), 1.69-1.64 (m, 4H); MS ESI(+) m/z 471.0 [M+H]$^+$.

Example 22

1-{5-[5-chloro-2-(5-piperidin-3-yl-1,2,4-oxadiazol-3-yl)-1H-pyrrolo[2,3-b]pyridin-4-yl]-1,3-thiazol-2-yl}cyclobutanol

Example 22A 5-chloro-4-(2-(1-(methoxymethoxy)cyclobutyl)thiazol-5-yl)-1-tosyl-1H-pyrrolo[2,3-b]pyridine-2-carbonitrile A nitrogen-sparged solution of Example 1F (0.2 g, 0.318 mmol) in 1-methyl-2-pyrrolidinone (4.5 mL) was treated with zinc cyanide (0.039 g, 0.333 mmol) and tetrakis(triphenylphosphine)palladium (0.022 g, 0.019 mmol). The reaction was heated at 150° C. for 20 minutes in a Biotage Initiator microwave reactor. The reaction was cooled to ambient temperature, treated with saturated aqueous sodium bicarbonate, and extracted with ethyl acetate. The organic layer was washed with water and brine, dried over anhydrous sodium sulfate, filtered, and concentrated. The concentrate was purified by flash chromatography on silica gel, eluting with a gradient of from 0% to 15% ethyl acetate in hexane, to provide the title compound. MS ESI(+) m/z 529.0 [M+H]$^+$.

Example 22B (Z)-5-chloro-N'-hydroxy-4-(2-(1-(methoxymethoxy)cyclobutyl)thiazol-5-yl)-1H-pyrrolo[2,3-b]pyridine-2-carboximidamide A suspension of Example 22A (0.118 g, 0.223 mmol), ethanol (3 mL), water (0.25 mL), hydroxylamine hydrochloride (0.039 g, 0.558 mmol), and triethylamine (0.140 mL, 1.0 mmol) was heated at 80° C. for 30 minutes. The reaction was cooled to ambient temperature, diluted with water (13 mL) and stirred 5 minutes. The suspension was filtered. The solid collected was washed with water and dried in a vacuum oven at 50° C. to provide the title compound. MS ESI(+) m/z 408.0 [M+H]$^+$.

Example 22C (Z)-tert-butyl 3-((amino(5-chloro-4-(2-(1-(methoxymethoxy)cyclobutyl)thiazol-5-yl)-1H-pyrrolo[2,3-b]pyridin-2-yl)methyleneaminooxy)carbonyl)piperidine-1-carboxylate A mixture of Example 22B (0.09 g, 0.221 mmol), 1-(tert-butoxycarbonyl)piperidine-3-carboxylic acid (0.056 g, 0.243 mmol), N-methylmorpholine (0.085 mL, 0.772 mmol), and 1-hydroxybenzotriazole hydrate (0.017 g, 0.110 mmol) in N,N-dimethylformamide (2.5 mL) was treated with N-(3-dimethylaminopropyl)-N'-ethylcarbodiimide hydrochloride (0.063 g, 0.331 mmol), and the reaction was stirred at ambient temperature for 3 hours. The reaction was treated with water (15 mL), and the resulting suspension was stirred for 10 minutes and filtered. The solid collected was washed with water and dried under vacuum. The crude material was purified by flash chromatography on silica gel, eluting with a gradient of from 0% to 40% ethyl acetate in hexane, to provide the title compound. MS ESI(+) m/z 619.2 [M+H]$^+$.

Example 22D tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate A solution of Example 22C (0.084 g, 0.136 mmol) in toluene (3 mL) was heated to 110° C. for 10 hours. The reaction was cooled to ambient temperature and concentrated to give the title compound, which was used without further purification. MS ESI(+) m/z 601.2 [M+H]$^+$.

Example 22E

1-{5-[5-chloro-2-(5-piperidin-3-yl-1,2,4-oxadiazol-3-yl)-1H-pyrrolo[2,3-b]pyridin-4-yl]-1,3-thiazol-2-yl}cyclobutanol A solution of Example 22D (0.085 g, 0.141 mmol) in tetrahydrofuran (1.5 mL) was treated with 10% aqueous HCl solution (0.28 mL, 0.922 mmol), and the reaction was heated at 65° C. for 5 hours. The reaction was concentrated, and the residue was purified by reverse-phase HPLC on a Phenomenex C18 column (3×15 cm, 10 m particle size) eluting with a gradient of 20% to 60% acetonitrile in 0.15% aqueous trifluoroacetic acid to provide the title compound as a trifluoroacetic acid salt. $^1$H NMR (300 MHz, DMSO-d$_6$) ppm 1.73-2.03 (m, 6H), 2.19-2.25 (m, 1H), 2.36-2.45 (m, 2H), 2.55-2.69 (m, 2H), 2.90-3.07 (m, 1H), 3.54-3.75 (m, 3H), 6.72 (bs, 1H), 7.19 (m, 1H), 8.25 (s, 1H), 8.53 (s, 1H), 8.58-8.84 (m, 2H), 13.24 (bs, 1H); MS ESI(+) m/z 457.0 [M+H]$^+$.

Example 23

N$^1$-(4-{5-chloro-4-[2-(1-hydroxycyclobutyl)-1,3-thiazol-5-yl]-1H-pyrrolo[2,3-b]pyridin-2-yl}phenyl)-N$^2$,N$^2$-dimethylglycinamide

Example 23A 4-(5-chloro-4-(2-(1-(methoxymethoxy)cyclobutyl)thiazol-5-yl)-1-tosyl-1H-pyrrolo[2,3-b]pyridin-2-yl)aniline The title compound was prepared as described in Example 1G, substituting 4-(4,4,5,5-tetramethyl-1,3,2-dioxaborolan-2-yl)aniline for 4-(2-(4-(4,4,5,5-tetramethyl-1,3,2-dioxaborolan-2-yl)-1H-pyrazol-1-yl)ethyl)morpholine. MS ESI(+) m/z 595.1 [M+H]$^+$.

Example 23B 4-(5-chloro-4-(2-(1-(methoxymethoxy)cyclobutyl)thiazol-5-yl)-1H-pyrrolo[2,3-b]pyridin-2-yl)aniline The title compound was prepared as described in Example 1I, substituting 4-(5-chloro-4-(2-(1-(methoxymethoxy)cyclobutyl)thiazol-5-yl)-1-tosyl-1H-pyrrolo[2,3-b]pyridin-2-yl)aniline (Example 23A) for 1-(5-(5-chloro-2-(1-(2-morpholinoethyl)-1H-pyrazol-4-yl)-1H-pyrrolo[2,3-b]pyridin-4-yl)thiazol-2-yl)cyclobutanol (Example 1H). MS ESI(+) m/z 441.0 [M+H]$^+$.

Example 23C

N-(4-(5-chloro-4-(2-(1-(methoxymethoxy)cyclobutyl)thiazol-5-yl)-1H-pyrrolo[2,3-b]pyridin-2-yl)phenyl)-2-(dimethylamino)acetamide A solution of 4-(5-chloro-4-(2-(1-(methoxymethoxy)cyclobutyl)thiazol-5-yl)-1H-pyrrolo[2,3-b]pyridin-2-yl)aniline (Example 23B) (20 mg, 0.045 mmol) and dimethyl glycine (5.61 mg, 0.054 mmol) in N,N-dimethylformamide (0.5 mL) was treated with N-(3-dimethylaminopropyl)-N'-ethylcarbodiimide hydrochloride (10.43 mg, 0.054 mmol), and 1-hydroxybenzotriazole hydrate (8.34 mg, 0.054 mmol). The reaction was stirred for 4 hours at ambient temperature. The reaction was treated with 4-(dimethylamino)pyridine (5.50 mg, 0.045 mmol), and the reaction was stirred 4 hours at ambient temperature. The reaction was diluted with ethyl acetate and washed with water, saturated sodium bicarbonate solution, and brine. The organic layer was dried with sodium sulfate, filtered, and concentrated under reduced pressure. The residue was purified by flash chromatography on silica gel, eluting with a gradient of 2 to 10% methanol in dichloromethane, to give the title compound. MS ESI(+) m/z 526.0 [M+H]$^+$.

Example 23D

N-(4-(5-chloro-4-(2-(1-hydroxycyclobutyl)thiazol-5-yl)-1H-pyrrolo[2,3-b]pyridin-2-yl)phenyl)-2-(dimethylamino)acetamide The title compound was prepared as described in Example 22E, substituting N-(4-(5-chloro-4-(2-(1-(methoxymethoxy)cyclobutyl)thiazol-5-yl)-1H-pyrrolo[2,3-b]pyridin-2-yl)phenyl)-2-(dimethylamino)acetamide (Example 23C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-d$_6$) ppm 12.49 (s, 1H) 9.88 (s, 1H) 8.31 (s, 1H) 8.25 (s, 1H) 7.95 (d, 2H) 7.78 (d, 2H) 6.99 (s, 1H) 6.68 (s, 1H) 3.09 (s, 2H) 2.63 (m, 2H) 2.40 (m, 2H) 2.29 (s, 6H) 1.99 (m, 2H); MS ESI(+) m/z 482.0 [M+H]$^+$.

Example 24

1-(5-{5-chloro-2-[3-fluoro-4-(pyrrolidin-1-ylmethyl)phenyl]-1H-pyrrolo[2,3-b]pyridin-4-yl}-1,3-thiazol-2-yl)cyclobutanol The title compound was prepared as described in Examples 30A-30D, except substituting pyrrolidine for 4-fluoropiperidine in Example 30B. $^1$H NMR (300 MHz, DMSO-d$_6$) δ ppm 12.71 (s, 1H), 9.88 (bs, 1H), 8.40 (s, 1H), 8.29 (s, 1H), 8.07 (dd, 1H), 8.00 (dd, 1H), 7.69 (t, 1H), 7.32 (d, 1H), 6.84-6.50 (m, 1H), 4.46 (d, 2H), 3.47 (m, 2H), 3.22-3.10 (m, 2H), 2.69-2.58 (m, 2H), 2.46-2.34 (m, 2H), 2.10-1.85 (m, 6H). MS APCI(+) m/z 483.29 (M+H)$^+$.

Example 25

1-[5-(5-chloro-2-{4-[(dimethylamino)methyl]-3-fluorophenyl}-1H-pyrrolo[2,3-b]pyridin-4-yl)-1,3-thiazol-2-yl]cyclobutanol The title compound was prepared as described in Examples 30A-30D, except substituting dimethylamine for 4-fluoropiperidine in Example 30B. $^1$H NMR (300 MHz, DMSO-d$_6$) δ

Example 26

1-(4-{5-chloro-4-[2-(1-hydroxycyclobutyl)-1,3-thiazol-5-yl]-1H-pyrrolo[2,3-b]pyridin-2-yl}-2-fluorobenzyl)pyrrolidin-3-ol The title compound was prepared as described in Examples 30A-30D, except substituting pyrrolidin-3-ol for 4-fluoropiperidine in Example 30B. $^1$H NMR (300 MHz, DMSO-d$_6$) δ ppm 12.70 (s, 1H), 10.17 (d, 1H), 8.40 (s, 1H), 8.29 (s, 1H), 8.12-7.94 (m, 2H), 7.71 (t, 1H), 7.32 (s, 1H), 6.69 (s, 1H), 5.43 (s, 1H), 4.54-4.40 (m, 3H), 3.64-3.50 (m, 2H), 3.26 (s, 1H), 3.08 (dd, 1H), 2.70-2.58 (m, 2H), 2.44-2.26 (m, 3H), 2.04-1.89 (m, 3H). MS APCI(+) m/z 499.29 (M+H)$^+$.

Example 27

1-[5-(5-chloro-2-{3-fluoro-4-[(3-fluoropyrrolidin-1-yl)methyl]phenyl}-1H-pyrrolo[2,3-b]pyridin-4-yl)-1,3-thiazol-2-yl]cyclobutanol The title compound was prepared as described in Examples 30A-30D, except substituting 3-fluoropyrrolidine for 4-fluoropiperidine in Example 30B. $^1$H NMR (300 MHz, DMSO-d$_6$) δ ppm 12.63 (s, 1H), 8.35 (s, 1H), 8.27 (s, 1H), 7.93-7.82 (m, 2H), 7.49 (t, 1H), 7.18 (s, 1H), 6.87-6.57 (m, 1H), 5.20 (dt, 1H), 3.69 (s, 2H), 2.88-2.59 (m, 6H), 2.41 (s, 3H), 1.98 (dd, 3H). MS APCI(+) m/z 501.33 (M+H)$^+$.

Example 28

1-[5-(5-chloro-2-{3-fluoro-4-[(2-methylpyrrolidin-1-yl)methyl]phenyl}-1H-pyrrolo[2,3-b]pyridin-4-yl)-1,3-thiazol-2-yl]cyclobutanol The title compound was prepared as described in Examples 30A-30D, except substituting 2-methylpyrrolidine for 4-fluoropiperidine in Example 30B. $^1$H NMR (300 MHz, DMSO-d$_6$) δ ppm 12.71 (s, 1H), 9.50-9.34 (m, 1H), 8.40 (s, 1H), 8.29 (s, 1H), 8.09 (d, 1H), 8.00 (d, 1H), 7.71 (t, 1H), 7.32 (s, 1H), 6.81-6.55 (m, 1H), 4.61 (d, 1H), 4.28 (s, 1H), 3.39-3.35 (m, 1H), 3.30-3.16 (m, 2H), 2.62 (s, 2H), 2.43 (d, J=10.4, 2H), 2.27 (s, 1H), 2.06-1.86 (m, 4H), 1.69-1.55 (m, 1H), 1.40 (d, 3H). MS APCI(+) m/z 497.31 (M+H)$^+$.

Example 29

1-{5-[5-chloro-2-(4-{[cyclopropyl(methyl)amino]methyl}-3-fluorophenyl)-1H-pyrrolo[2,3-b]pyridin-4-yl]-1,3-thiazol-2-yl}cyclobutanol The title compound was prepared as described in Examples 30A-30D, except substituting N-methylcyclopropanamine for 4-fluoropiperidine in Example 30B. $^1$H NMR (300 MHz, DMSO-d$_6$) δ ppm 12.70 (s, 1H), 9.32 (s, 1H), 8.40 (s, 1H), 8.29 (s, 1H), 8.06 (d, 1H), 7.98 (d, 1H), 7.72-7.60 (m, 1H), 7.31 (s, 1H), 6.69 (s, 1H), 4.53 (s, 2H), 2.90 (s, 3H), 2.68-2.58 (m, 2H), 2.46-2.33 (m, 3H), 2.03-1.93 (m, 2H), 0.91-0.64 (m, 4H). MS APCI(+) m/z 483.3 (M+H)$^+$.

Example 30

1-[5-(5-chloro-2-{3-fluoro-4-[(4-fluoropiperidin-1-yl)methyl]phenyl}-1H-pyrrolo[2,3-b]pyridin-4-yl)-1,3-thiazol-2-yl]cyclobutanol

Example 30A 4-(5-chloro-4-(2-(1-(methoxymethoxy)cyclobutyl)thiazol-5-yl)-1-tosyl-1H-pyrrolo[2,3-b]pyridin-2-yl)-2-fluorobenzaldehyde To a solution of 5-(5-chloro-2-iodo-1-tosyl-1H-pyrrolo[2,3-b]pyridin-4-yl)-2-(1-(methoxymethoxy)cyclobutyl)thiazole (580 mg, 0.921 mmol) (Example 1F), 3-fluoro-4-formylphenylboronic acid (309 mg, 1.842 mmol), and bis(triphenylphosphine)palladium dichloride (32.3 mg, 0.046 mmol) in N,N-dimethylformamide (12 ml) was added saturated aqueous sodium bicarbonate solution (12 mL). The mixture was heated to 65° C. under an atmosphere of nitrogen for about 90 minutes. The reaction mixture was cooled to room temperature, and diluted with water (about 50 mL) and saturated brine solution (about 25 mL). The aqueous layer was extracted with ethyl acetate (3×30 mL), and the combined organics were washed with brine, dried over anhydrous magnesium sulfate, filtered, and concentrated under reduced pressure. The residue was purified by flash chromatography on silica gel, eluting with a gradient of 0 to 30% ethyl acetate in hexane, to give the title compound. $^1$H NMR (300 MHz, DMSO-d$_6$) δ ppm 10.30 (s, 1H), 8.63-8.60 (m, 1H), 8.23 (s, 1H), 7.95 (t, 1H), 7.81-7.72 (m, 3H), 7.65 (dd, 1H), 7.40 (d, 2H), 7.14 (d, 1H), 4.76 (s, 2H), 2.71-2.54 (m, 2H), 2.35 (s, 3H), 2.01-1.88 (m, 3H). MS APCI(+) m/z 626.42 [M+H]$^+$.

Example 30B 5-(5-chloro-2-(3-fluoro-4-((4-fluoropiperidin-1-yl)methyl)phenyl)-1-tosyl-1H-pyrrolo[2,3-b]pyridin-4-yl)-2-(1-(methoxymethoxy)cyclobutyl)thiazole To a 4 mL reaction vial was added 4-(5-chloro-4-(2-(1-(methoxymethoxy)cyclobutyl)thiazol-5-yl)-1-tosyl-1H-pyrrolo[2,3-b]pyridin-2-yl)-2-fluorobenzaldehyde (Example 30A) (53 mg, 0.085 mmol), 4-fluoropiperidine, hydrochloric acid (35.46 mg, 0.255 mmol), methanol (0.5 ml), dichloromethane (0.5 ml), and a few drops of acetic acid. The reaction mixture was stirred at room temperature for 30 minutes, and sodium triacetoxyborohydride (53.82 mg, 0.255 mmol) was added. The reaction was stirred at room temperature overnight and then carefully quenched by addition of saturated sodium bicarbonate solution (about 400 μL) and dichloromethane (about 1 mL). The organic layer was collected, and the aqueous layer extracted with dichloromethane (2×1 mL). The combined organics were concentrated to give the title compound, which was used without further purification. MS APCI(+) m/z 713.42 [M+H]$^+$.

Example 30C 1-(5-(5-chloro-2-(3-fluoro-4-((4-fluoropiperidin-1-yl)methyl)phenyl)-1-tosyl-1H-pyrrolo[2,3-b]pyridin-4-yl)thiazol-2-yl)cyclobutanol A 4 mL reaction vial was charged with 5-(5-chloro-2-(3-fluoro-4-((4-fluoropiperidin-1-yl)methyl)phenyl)-1-tosyl-1H-pyrrolo[2,3-b]pyridin-4-yl)-2-(1-(methoxymethoxy)cyclobutyl)thiazole (Example 30B) (60.6 mg, 0.085 mmol), methanol (1.0 mL) and 2 normal aqueous hydrochloric acid solution (0.200 ml, 0.658 mmol). The mixture was heated to 60° C. for about 2 hours, and then to 40° C. overnight. The reaction was cooled to room temperature, and the solvent removed under reduced pressure. The residue was partitioned between ethyl acetate and saturated aqueous sodium bicarbonate solution. The layers were separated, and the aqueous layer was extracted with ethyl acetate (2×1 mL). The combined organics were concentrated to give the title compound, which was used without further purification. MS APCI(+) m/z 669.33 [M+H]$^+$.

Example 30D 1-(5-(5-chloro-2-(3-fluoro-4-((4-fluoropiperidin-1-yl)methyl)phenyl)-1H-pyrrolo[2,3-b]pyridin-4-yl)thiazol-2-yl)cyclobutanol In a 2 mL microwave reaction vial, 1-(5-(5-chloro-2-(3-fluoro-4-((4-fluoropiperidin-1-yl)methyl)phenyl)-1-tosyl-1H-pyrrolo[2,3-b]pyridin-4-yl)thiazol-2-yl)cyclobutanol (Example 30C) (42.6 mg, 0.064 mmol) (10032591-524) was dissolved in methanol (1.0 ml). 2 Normal aqueous sodium hydroxide solution (0.318 ml, 0.637 mmol) was added, the vial was sealed, and the mixture was heated via microwave irradiation (Biotage Initiator Microwave Synthesizer) to 120° C. for about 20 minutes. The reaction was cooled to room temperature, and the solvent was removed under reduced pressure. The residue was purified by reverse phase high pressure liquid chromatography (RP HPLC, 19×150 mm Atlantis Prep T3 OBD 5 μm column, eluting with a gradient of 5% B in A to 75% B in A over 25 minutes, wherein A is water containing 0.1% v/v trifluoroacetic acid and B is acetonitrile) to give the title compound as the trifluoroacetic acid salt. $^1$H NMR (300 MHz, DMSO-d$_6$) δ ppm 12.71 (s, 1H), 9.54 (s, 1H), 8.40 (s, 1H), 8.29 (s, 1H), 8.08 (d, 1H), 8.01 (d, 1H), 7.68 (t, 1H), 7.32 (d, 1H), 6.68 (s, 1H), 4.99 (d, 1H), 4.43 (d, 2H), 3.21-3.10 (m, 2H), 2.69-2.58 (m, 2H), 2.44-2.35 (m, 3H), 2.16-2.04 (m, 2H), 2.03-1.92 (m, 3H), 1.92-1.79 (m, 2H). MS APCI(+) m/z 515.28 [M+H]$^+$ Example 31

1-[5-(5-chloro-2-{4-[(4,4-difluoropiperidin-1-yl)methyl]-3-fluorophenyl}-1H-pyrrolo[2,3-b]pyridin-4-yl)-1,3-thiazol-2-yl]cyclobutanol The title compound was prepared as described in Examples 30A-30D, except substituting 4,4-difluoropiperidine for 4-fluoropiperidine in Example 30B. $^1$H NMR (300 MHz, DMSO-d$_6$) δ ppm 12.70 (s, 1H), 10.16-9.35 (m, 1H), 8.39 (s, 1H), 8.29 (s, 1H), 8.02 (dd, 2H), 7.64 (t, 1H), 7.30 (s, 1H), 6.67 (s, 1H), 4.38 (s, 2H), 3.36-3.00 (m, 4H), 2.68-2.60 (m, 2H), 2.45-2.36 (m, 2H), 2.33-2.08 (m, 4H), 2.06-1.89 (m, 2H). MS APCI(+) m/z 533.32 (M+H)$^+$.

Example 32

1-[5-(5-chloro-2-phenyl-1H-pyrrolo[2,3-b]pyridin-4-yl)-1,3-thiazol-2-yl]cyclobutanol To a stirred ambient solution of 1-(5-(5-chloro-2-iodo-1-tosyl-1H-pyrrolo[2,3-b]pyridin-4-yl)thiazol-2-yl)cyclobutanol (Example 8A) (80 mg, 0.137 mmol) and phenylboronic acid (24.97 mg, 0.205 mmol) in N,N-dimethylformamide (2.0 mL) was added saturated aqueous bicarbonate solution (683 μl) followed by bis(triphenylphosphine)palladium dichloride (6.71 mg, 9.56 μmol). The mixture was heated to 70° C. for 4 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was dissolved in a mixture of methanol (2 mL) and 2N aqueous sodium hydroxide solution (341 μl, 0.683 mmol) and heated by microwave irradiation (Biotage, Initiator) to 105° C. for 5 minutes. The reaction was cooled to room temperature, diluted with 1 mL DMSO, and acidified to pH ~5 with 10% aqueous HCl solution. The sample was purified by reverse phase high performance liquid chromatography (RP HPLC, 19×150 mm Atlantis Prep T3 OBD m column, eluting with a gradient of 5% B in A to 75% B in A over 25 minutes, wherein A is water containing 0.1% v/v trifluoroacetic acid and B is acetonitrile containing 0.1% v/v trifluoroacetic acid). The fractions containing the product were diluted with ethyl acetate and washed with saturated aqueous bicarbonate solution. The ethyl acetate solution was dried with anhydrous sodium sulfate, filtered and concentrated under reduced pressure to give the title compound. $^1$H NMR (300 MHz, DMSO-d$_6$) δ 12.58 (bs, 1H), 8.34 (s, 1H), 8.26 (s, 1H), 8.01 (dd, J=7.1, 1.5 Hz, 2H), 7.53-7.43 (m, 2H), 7.43-7.34 (m, 1H), 7.07 (d, J=2.1 Hz, 1H), 6.66 (s, 1H), 2.70-2.57 (m, 2H), 2.46-2.34 (m, 2H), 2.07-1.89 (m, 2H); MS ESI(+) m/z 381.9 [M+H]$^+$.

Example 33

1-{5-[5-chloro-2-(1-methyl-1H-pyrazol-4-yl)-1H-pyrrolo[2,3-b]pyridin-4-yl]-1,3-thiazol-2-yl}cyclobutanol The title compound was prepared as described in Example 32, substituting 1-methyl-4-(4,4,5,5-tetramethyl-1,3,2-dioxaborolan-2-yl)-1H-pyrazole for phenylboronic acid. $^1$H NMR (300 MHz, DMSO-d$_6$) δ 12.34 (bs, 1H), 8.28 (s, 1H), 8.23 (s, 1H), 8.18 (s, 1H), 8.04 (s, 1H), 6.74 (d, J=2.0 Hz, 1H), 6.65 (s, 1H), 3.88 (s, 3H), 2.68-2.55 (m, 2H), 2.44-2.34 (m, 2H), 2.09-1.84 (m, 2H); MS ESI(+) m/z 385.9 [M+H]$^+$.

Example 34

1-[5-(5-chloro-2-pyridin-4-yl-1H-pyrrolo[2,3-b]pyridin-4-yl)-1,3-thiazol-2-yl]cyclobutanol The title compound was prepared as described in Example 32, substituting 4-(4,4,5,5-tetramethyl-1,3,2-dioxaborolan-2-yl)pyridine for phenylboronic acid. $^1$H NMR (300 MHz, DMSO-d$_6$) δ 13.01-12.96 (m, 1H), 8.79-8.72 (m, 2H), 8.48 (s, 1H), 8.32 (s, 1H), 8.25-8.19 (m, 2H), 7.56 (d, J=2.0 Hz, 1H), 6.70 (s, 1H), 2.70-2.52 (m, 2H), 2.46-2.35 (m, 2H), 2.08-1.88 (m, 2H); MS ESI(+) m/z 382.9 [M+H]$^+$.

Example 35

1-(5-{5-chloro-2-[4-(ethylsulfonyl)phenyl]-1H-pyrrolo[2,3-b]pyridin-4-yl}-1,3-thiazol-2-yl)cyclobutanol The title compound was prepared as described in Example 32, substituting 4-(ethylsulfonyl)phenylboronic acid for phenylboronic acid. $^1$H NMR (300 MHz, DMSO-d$_6$) δ 12.84-12.78 (m, 1H), 8.41 (s, 1H), 8.34-8.25 (m, 3H), 8.04-7.88 (m, 2H), 7.32 (d, J=2.1 Hz, 1H), 6.68 (s, 1H), 3.40-3.32 (m, 2H), 2.70-2.57 (m, 2H), 2.45-2.35 (m, 2H), 2.09-1.90 (m, 2H), 1.18-1.08 (m, 3H); MS ESI(+) m/z 474.2 [M+H]$^+$.

Example 36

3-{5-chloro-4-[2-(1-hydroxycyclobutyl)-1,3-thiazol-5-yl]-1H-pyrrolo[2,3-b]pyridin-2-yl}benzoic acid The title compound was prepared as described in Example 32, substituting 3-boronobenzoic acid for phenylboronic acid. $^1$H NMR (300 MHz, DMSO-d$_6$) δ 13.16 (s, 1H), 12.77-12.71 (m, 1H), 8.55 (t, J=1.7 Hz, 1H), 8.36 (s, 1H), 8.29 (s, 1H), 8.25 (, 3H), 7.97-7.90 (m, 2H), 7.61 (t, J=7.8 Hz, 1H), 7.15 (d, J=2.1 Hz, 1H), 6.70 (bs, 1H), 2.70-2.58 (m, 2H), 2.47-2.35 (m, 2H), 2.07-1.89 (m, 2H); MS ESI(+) m/z 425.9 [M+H]$^+$.

Example 37

(4-{5-chloro-4-[2-(1-hydroxycyclobutyl)-1,3-thiazol-5-yl]-1H-pyrrolo[2,3-b]pyridin-2-yl}phenyl)acetic acid The title compound was prepared as described in Example 32, substituting 2-(4-(4,4,5,5-tetramethyl-1,3,2-dioxaborolan-2-yl)phenyl)acetic acid for phenylboronic acid. $^1$H NMR (300 MHz, DMSO-d$_6$) δ 12.59-12.53 (m, 1H), 12.38 (s, 1H), 8.33 (s, 1H), 8.26 (s, 1H), 7.95 (d, J=8.3 Hz, 2H), 7.39-7.32 (m, 2H), 7.04 (d, J=2.1 Hz, 1H), 6.67 (s, 1H), 3.63 (s, 2H), 2.70-2.56 (m, 2H), 2.46-2.34 (m, 2H), 2.07-1.89 (m, 2H); MS ESI(+) m/z 439.9 [M+H]$^+$.

Example 38

(4-{5-chloro-4-[2-(1-hydroxycyclobutyl)-1,3-thiazol-5-yl]-1H-pyrrolo[2,3-b]pyridin-2-yl}-1H-pyrazol-1-yl)acetic acid The title compound was prepared as described in Example 32, substituting ethyl 2-(4-(4,4,5,5-tetramethyl-1,3,2-dioxaborolan-2-yl)-1H-pyrazol-1-yl)acetate for phenylboronic acid. $^1$H NMR (300 MHz, DMSO-d$_6$) δ 13.19 (s, 1H), 12.42-12.37 (m, 1H), 8.32 (s, 1H), 8.24 (s, 1H), 8.20 (s, 1H), 8.10 (d, J=0.7 Hz, 1H), 6.79 (d, J=2.0 Hz, 1H), 6.56 (s, 1H), 5.03 (s, 2H), 2.69-2.56 (m, 2H), 2.47-2.33 (m, 2H), 2.09-1.87 (m, 2H); MS ESI(+) m/z 429.9 [M+H]$^+$.

Example 39

1-(5-{5-chloro-2-[1-(2-hydroxyethyl)-1H-pyrazol-4-yl]-1H-pyrrolo[2,3-b]pyridin-4-yl}-1,3-thiazol-2-yl)cyclobutanol Example 39A 2-(4-(4,4,5,5-tetramethyl-1,3,2-dioxaborolan-2-yl)-1H-pyrazol-1-yl)ethanol 4-(4,4,5,5-Tetramethyl-1,3,2-dioxaborolan-2-yl)-1H-pyrazole (9.66 g, 49.8 mmol), 1,3-dioxolan-2-one (21 g, 238 mmol) and cesium carbonate (16 g, 49.1 mmol) were combined in a 100 mL round bottom flask. The reaction was warmed from room temperature to 100° C. in an oil bath, by which time the carbonate had melted and served as the solvent for the reaction, which remained a slurry. After heating for 3.5 hours, the reaction was cooled to room temperature and was diluted with ethyl acetate, then filtered through diatomaceous earth washing repeatedly with ethyl acetate. The filtrate was concentrated, then purified by chromatography on an Analogix® Intelliflash™ purification system using a SF60-200 g column at a flow rate of 80 mL/minute, eluting as follows: 5 minutes at 20% ethyl acetate/hexanes, then ramped from 40% to 90% ethyl acetate/hexanes over 35 minutes, then 100% ethyl acetate for another 20 minutes, to provide the title compound. MS ESI(+) m/z 239.0 (M+H)$^+$.

Example 39B 1-(5-{5-chloro-2-[1-(2-hydroxyethyl)-1H-pyrazol-4-yl]-1H-pyrrolo[2,3-b]pyridin-4-yl}-1,3-thiazol-2-yl)cyclobutanol The title compound was prepared as described in Example 32, substituting 2-(4-(4,4,5,5-tetramethyl-1,3,2-dioxaborolan-2-yl)-1H-pyrazol-1-yl)ethanol Example 39A for phenylboronic acid. $^1$H NMR (300 MHz, DMSO-d$_6$) δ 12.34 (s, 1H), 8.33 (s, 1H), 8.23 (s, 1H), 8.19 (s, 1H), 8.07 (d, J=0.7 Hz, 1H), 6.76 (d, J=2.0 Hz, 1H), 6.59 (s, 1H), 4.17 (t, J=5.4 Hz, 2H), 3.76 (t, J=5.4 Hz, 2H), 2.68-2.55 (m, 2H), 2.46-2.33 (m, 2H), 2.05-1.87 (m, 2H); MS ESI(-) m/z 414.0 [M+H]$^-$.

Example 40

1-{5-[5-chloro-2-(2-methylphenyl)-1H-pyrrolo[2,3-b]pyridin-4-yl]-1,3-thiazol-2-yl}cyclobutanol The title compound was prepared as described in Example 32, substituting ortho-tolylboronic acid for phenylboronic acid. $^1$H NMR (300 MHz, DMSO-d$_6$) δ 12.33 (s, 1H), 8.36 (s, 1H), 8.24 (s, 1H), 7.60-7.53 (m, 1H), 7.40-7.27 (m, 4H), 6.67-6.63 (m, 2H), 2.67-2.56 (m, 2H), 2.47-2.32 (m, 5H), 2.01-1.89 (m, 2H); MS ESI(+) m/z 396.0 [M+H]$^+$.

Example 41

1-{5-[5-chloro-2-(3-methylphenyl)-1H-pyrrolo[2,3-b]pyridin-4-yl]-1,3-thiazol-2-yl}cyclobutanol The title compound was prepared as described in Example 32, substituting meta-tolylboronic acid for phenylboronic acid. $^1$H NMR (300 MHz, DMSO-d$_6$) δ 12.53 (bs, 1H), 8.33 (s, 1H), 8.26 (s, 1H), 7.87 (bs, 1H), 7.83-7.76 (m, 1H), 7.36 (t, J=7.6 Hz, 1H), 7.24-7.17 (m, 1H), 7.05 (d, J=2.1 Hz, 1H), 6.67 (s, 1H), 2.70-2.58 (m, 2H), 2.44-2.33 (m, 5H), 2.08-1.88 (m, 2H); MS ESI(+) m/z 396.0 [M+H]$^+$.

Example 42

1-{5-[5-chloro-2-(2-methoxyphenyl)-1H-pyrrolo[2,3-b]pyridin-4-yl]-1,3-thiazol-2-yl}cyclobutanol The title compound was prepared as described in Example 32, substituting 2-methoxyphenylboronic acid for phenylboronic acid. $^1$H NMR (300 MHz, DMSO-d$_6$) δ 12.18 (s, 1H), 8.33 (s, 1H), 8.22 (s, 1H), 7.87 (dd, J=7.7, 1.7 Hz, 1H), 7.45-7.35 (m, 1H), 7.22-7.18 (m, 1H), 7.13-7.01 (m, 2H), 6.65 (s, 1H), 3.91 (s, 3H), 2.68-2.57 (m, 2H), 2.47-2.34 (m, 2H), 2.03-1.89 (m, 2H); MS ESI(+) m/z 412.1 [M+H]$^+$.

Example 43

1-{5-[5-chloro-2-(3-methoxyphenyl)-1H-pyrrolo[2,3-b]pyridin-4-yl]-1,3-thiazol-2-yl}cyclobutanol The title compound was prepared as described in Example 32, substituting 3-methoxyphenylboronic acid for phenylboronic acid. $^1$H NMR (300 MHz, DMSO-d$_6$) δ 12.57 (s, 1H), 8.34 (s, 1H), 8.27 (s, 1H), 7.62-7.56 (m, 2H), 7.39 (t, J=8.1 Hz, 1H), 7.10 (d, J=2.1 Hz, 1H), 6.95 (ddd, J=8.2, 2.4, 1.0 Hz, 1H), 6.66 (s, 1H), 3.85 (s, 3H), 2.70-2.57 (m, 2H), 2.47-2.34 (m, 2H), 2.07-1.89 (m, 2H); MS ESI(+) m/z 411.9 [M+H]$^+$.

Example 44

1-{5-[5-chloro-2-(3-fluorophenyl)-1H-pyrrolo[2,3-b]pyridin-4-yl]-1,3-thiazol-2-yl}cyclobutanol The title compound was prepared as described in Example 32, substituting 3-fluorophenylboronic acid for phenylboronic acid. $^1$H NMR (300 MHz, DMSO-d$_6$) δ 12.66-12.60 (m, 1H), 8.37 (s, 1H), 8.28 (s, 1H), 7.91-7.87 (m, 2H), 7.55-7.48 (m, 1H), 7.24-7.18 (m, 2H), 6.65 (s, 1H), 2.69-2.58 (m, 2H), 2.46-2.34 (m, 2H), 2.10-1.88 (m, 2H); MS ESI(+) m/z 399.9 [M+H]$^+$.

Example 45

1-{5-[5-chloro-2-(1,2,3,4-tetrahydro isoquinolin-7-yl)-1H-pyrrolo[2,3-b]pyridin-4-yl]-1,3-thiazol-2-yl}cyclobutanol Example 45A tert-butyl 7-(5-chloro-4-(2-(1-(methoxymethoxy)cyclobutyl)thiazol-5-yl)-1-tosyl-1H-pyrrolo[2,3-b]pyridin-2-yl)-3,4-dihydroisoquinoline-2(1H)-carboxylate A stirring solution of Example 1F (0.1 g, 0.159 mmol) and 2-(tert-butoxycarbonyl)-1,2,3,4-tetrahydroisoquinolin-7-ylboronic acid (0.053 g, 0.191 mmol) in N,N-dimethylformamide (1.4 mL) was treated with saturated aqueous sodium bicarbonate (0.35 mL) followed by bis(triphenylphosphine)palladium(II) chloride (0.008 g, 0.012 mmol). The suspension was heated at 65° C. for 4 hours. The reaction was cooled to ambient temperature, and ethyl acetate and water were added. The layers were separated, and the aqueous layer was extracted with additional ethyl acetate. The combined organic layers were washed with brine, dried over anhydrous sodium sulfate, filtered, and concentrated. The concentrate was purified by flash chromatography on silica gel, eluting with a gradient of from 0% to 25% ethyl acetate in hexane, to provide the title compound. MS ESI(+) m/z 735.2 [M+H]$^+$.

Example 45B 1-(5-(5-chloro-2-(1,2,3,4-tetrahydroisoquinolin-7-yl)-1-tosyl-1H-pyrrolo[2,3-b]pyridin-4-yl)thiazol-2-yl)cyclobutanol A solution of Example 45A (0.09 g, 0.122 mmol) in methanol (0.7 mL) was treated with 10% aqueous HCl solution (0.165 mL), and the reaction was heated at 65° C. for 3 hours. The reaction was cooled to ambient temperature and concentrated. The concentrate was partitioned between ethyl acetate and saturated aqueous sodium bicarbonate. The layers were separated, and the aqueous layer was extracted with additional ethyl acetate (2×). The combined organic layers were dried over anhydrous sodium sulfate, filtered, and concentrated to provide the title compound. ESI(+) m/z 591.1 [M+H]$^+$.

Example 45C

1-{5-[5-chloro-2-(1,2,3,4-tetrahydroisoquinolin-7-yl)-1H-pyrrolo[2,3-b]pyridin-4-yl]-1,3-thiazol-2-yl}cyclobutanol A solution of Example 45B (0.066 g, 0.112 mmol) in methanol (1.8 mL) and 2 N aqueous sodium hydroxide solution (0.279 mL, 0.558 mmol) was heated at 75° C. for 15 minutes. The reaction was cooled to ambient temperature, and the pH adjusted to ~7 with 10% aqueous HCl. The resulting mixture was purified by reverse-phase HPLC on a Phenomenex C18 column (3×15 cm, 10 m particle size) using a gradient of from 20% to 60% acetonitrile in 0.15% aqueous trifluoroacetic acid to provide the title compound as the trifluoroacetic acid salt. $^1$H NMR (300 MHz, methanol-d$_4$) ppm 2.02-2.15 (m, 2H), 2.42-2.53 (m, 2H), 2.71-2.84 (m, 2H), 3.13-3.22 (m, 2H), 3.49-3.59 (m, 2H), 4.44 (s, 2H), 6.95 (s, 1H), 7.34-7.40 (m, 1H), 7.71-7.75 (m, 1H), 7.77-7.83 (m, 1H), 8.15 (s, 1H), 8.30 (s, 1H); ESI(+) m/z 437.0 [M+H]$^+$.

Example 46

1-{5-[5-chloro-2-(3-piperidin-4-yl-1,2,4-oxadiazol-5-yl)-1H-pyrrolo[2,3-b]pyridin-4-yl]-1,3-thiazol-2-yl}cyclobutanol Example 46A methyl 5-chloro-4-(2-(1-(methoxymethoxy)cyclobutyl)thiazol-5-yl)-1-tosyl-1H-pyrrolo[2,3-b]pyridine-2-carboxylate In a 50 ml pressure bottle, a solution of Example 1F (0.15 g, 0.238 mmol) and triethylamine (0.066 ml, 0.476 mmol) in methanol (2 ml) and acetonitrile (2 mL) was treated with [1,1'-bis(diphenylphosphino)ferrocene]dichloropalladium(II) (0.017 g, 0.024 mmol). The mixture was pressurized with carbon monoxide (60 psi), and stirred at 60° C. for 4 hours. The reaction was cooled to ambient temperature and concentrated under reduced pressure. The concentrate was purified by flash chromatography on silica gel, eluting with dichloromethane, to provide the title compound. MS ESI(+) m/z 562.0 [M+H]$^+$.

Example 46B 5-chloro-4-(2-(1-(methoxymethoxy)cyclobutyl)thiazol-5-yl)-1H-pyrrolo[2,3-b]pyridine-2-carboxylic acid A suspension of Example 46A (0.134 g, 0.238 mmol) in methanol (2.5 mL) was treated with 2 M aqueous sodium hydroxide solution (0.714 mL, 1.19 mmol). The reaction was heated at 75° C. for 40 minutes, cooled to ambient temperature, and concentrated under reduced pressure. The residue was suspended in water (2 mL), and the pH adjusted to ~4 with 1 N aqueous HCl solution. The suspension was filtered, and the solid collected was washed with water and dried in a vacuum oven at 60° C. to provide the title compound. ESI(+) m/z 393.9 [M+H]$^+$.

Example 46C (Z)-tert-butyl 4-(N'-hydroxycarbamimidoyl)piperidine-1-carboxylate

A solution of tert-butyl 4-cyanopiperidine-1-carboxylate (0.5 g, 2.378 mmol) in ethanol (12 mL) was treated with hydroxylamine (50% in water, 0.51 mL, 8.32 mmol). The reaction was heated at 80° C. for 1.5 hours. The reaction was cooled to ambient temperature and concentrated under reduced pressure. The concentrate was dried to constant weight in a vacuum oven at 60° C. to provide the title compound. DCI(+) m/z 244.1 [M+H]+.

Example 46D (Z)-tert-butyl 4-(N'-(5-chloro-4-(2-(1-(methoxymethoxy)cyclobutyl)thiazol-5-yl)-1H-pyrrolo[2,3-b]pyridine-2-carbonyloxy)carbamimidoyl)piperidine-1-carboxylate The title compound was prepared as described in Example 22C, substituting Example 46C for Example 22B and Example 46B for 1-(tert-butoxycarbonyl)piperidine-3-carboxylic acid. MS ESI(+) m/z 619.2 [M+H]+.

Example 46E tert-butyl 4-(5-(5-chloro-4-(2-(1-(methoxymethoxy)cyclobutyl)thiazol-5-yl)-1H-pyrrolo[2,3-b]pyridin-2-yl)-1,2,4-oxadiazol-3-yl)piperidine-1-carboxylate A solution of Example 46D (0.66 g, 0.107 mmol) in 1-methyl-2-pyrrolidinone (1.2 mL) was heated at 110° C. for 5 hours. The reaction was cooled to ambient temperature and poured into water (5 mL). The resulting suspension was filtered, and the solid collected was washed with water and dried under vacuum to provide the title compound. MS ESI(+) m/z 601.2 [M+H]+.

Example 46F

1-{5-[5-chloro-2-(3-piperidin-4-yl-1,2,4-oxadiazol-5-yl)-1H-pyrrolo[2,3-b]pyridin-4-yl]-1,3-thiazol-2-yl}cyclobutanol A solution of Example 46E (0.54 g, 0.09 mmol) in tetrahydrofuran (1 mL) was treated with 10% aqueous HCl solution (0.19 mL, 0.629 mmol), and the reaction was heated at 70° C. for 5 hours. The reaction was cooled to ambient temperature and concentrated under reduced pressure. The concentrate was purified by reverse-phase HPLC on a Phenomenex C18 column (3×15 cm, 10 m particle size) using a gradient of 15% to 55% acetonitrile in 0.15% aqueous trifluoroacetic acid to provide the title compound as the trifluoroacetic acid salt. $^1$H NMR (300 MHz, DMSO-$d_6$) ppm 1.90-2.04 (m, 4H), 2.16-2.29 (m, 2H), 2.36-2.47 (m, 2 H), 2.56-2.69 (m, 2H), 3.05-3.16 (m, 2H), 3.26-3.42 (m, 3H), 6.72 (s, 1H), 7.40 (m, 1H), 8.23-8.37 (m, 2H), 8.54-8.65 (m, 2H), 13.54 (bs, 1H); MS ESI(+) m/z 619.2 [M+H]+.

Example 47

1-{5-[5-chloro-2-(1-methyl-1H-pyrazol-4-yl)-3-(pyrrolidin-1-ylmethyl)-1H-pyrrolo[2,3-b]pyridin-4-yl]-1,3-thiazol-2-yl}cyclobutanol Example 47A 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole The title compound was prepared as described in Example 45A substituting 1-methyl-4-(4,4,5,5-tetramethyl-1,3,2-dioxaborolan-2-yl)-1H-pyrazole for 2-(tert-butoxycarbonyl)-1,2,3,4-tetrahydroisoquinolin-7-ylboronic acid. MS ESI(+) m/z 584.1 [M+H]+.

Example 47B 5-(5-chloro-2-(1-methyl-1H-pyrazol-4-yl)-1H-pyrrolo[2,3-b]pyridin-4-yl)-2-(1-(methoxymethoxy)cyclobutyl)thiazole A solution of Example 47A (0.074 g, 0.127 mmol) in methanol (1.5 mL) and 2 M aqueous sodium hydroxide solution (0.317 mL, 0.633 mmol) was heated at 75° C. for 15 minutes. The reaction was cooled to ambient temperature, and the pH adjusted to ~7 with 10% aqueous HCl solution. The resulting suspension was extracted with ethyl acetate. The aqueous layer was extracted with additional ethyl acetate. The combined organic layers were washed with brine, dried over anhydrous sodium sulfate, filtered, and concentrated. The concentrate was purified by flash chromatography on a silica gel column with a gradient of 0% to 3% methanol in dichloromethane to provide the title compound. ESI(+) m/z 429.9 [M+H]+.

Example 47C 5-(5-chloro-2-(1-methyl-1H-pyrazol-4-yl)-3-(pyrrolidin-1-ylmethyl)-1H-pyrrolo[2,3-b]pyridin-4-yl)-2-(1-(methoxymethoxy)cyclobutyl)thiazole A solution of Example 47B (0.034 g, 0.079 mmol) in 0.8 mL acetic acid was treated with formalin (0.035 mL, 0.475 mmol) and pyrrolidine (0.039 mL, 0.475 mmol). The reaction was heated at 75° C. for 1 hour. Additional pyrrolidine (0.163 mL, 1.98 mmol) was added, and the reaction was heated at 75° C. for 6 hours. The reaction was cooled to ambient temperature and concentrated under reduced pressure. The concentrate was dissolved in dichloromethane and washed with saturated aqueous sodium bicarbonate. The aqueous layer was extracted with additional dichloromethane. The combined organic layers were dried over anhydrous sodium sulfate, filtered, and concentrated under reduced pressure to provide the title compound. ESI(+) m/z 513.1 [M+H]+.

Example 47D

1-{5-[5-chloro-2-(1-methyl-1H-pyrazol-4-yl)-3-(pyrrolidin-1-ylmethyl)-1H-pyrrolo[2,3-b]pyridin-4-yl]-1,3-thiazol-2-yl}cyclobutanol A solution of Example 47C (0.04 g, 0.078 mmol) in tetrahydrofuran (0.7 mL) was treated with 10% aqueous HCl solution (0.140 mL). The reaction was heated at 65° C. for 2 hours, cooled to ambient temperature, and concentrated under reduced pressure. The concentrate was purified by reverse-phase HPLC on a Phenomenex C18 column (3×15 cm, 10 m particle size) using a gradient of 15% to 50% acetonitrile in 0.15% aqueous trifluoroacetic acid to provide the title compound as the trifluoroacetic acid salt. $^1$H NMR (300 MHz, methanol-$d_4$) ppm 1.75-1.87 (m, 2H), 1.89-1.99 (m, 2H), 2.04-2.14 (m, 2H), 2.43-2.57 (m, 2H), 2.69-2.84 (m, 4 H), 2.99-3.09 (m, 2H), 4.00 (s, 3H), 4.28 (s, 2H), 7.87 (s, 1H), 7.97 (s, 1H), 8.16 (s, 1H), 8.39 (s, 1H); MS ESI(+) m/z 469.1 [M+H]+.

Example 48

N'-(4-{5-chloro-4-[2-(1-hydroxycyclobutyl)-1,3-thiazol-5-yl]-1H-pyrrolo[2,3-b]pyridin-2-yl}-3-methylphenyl)-N²,N²-dimethylglycinamide

Example 48A 4-(5-chloro-4-(2-(1-(methoxymethoxy)cyclobutyl) thiazol-5-yl)-1-tosyl-1H-pyrrolo[2,3-b]pyridin-2-yl)-3-methylaniline The title compound was prepared as described in Example 1G, substituting 3-methyl-4-(4,4,5,5-tetramethyl-1,3,2-dioxaborolan-2-yl)aniline for 4-(2-(4-(4,4,5,5-tetramethyl-1,3,2-dioxaborolan-2-yl)-1H-pyrazol-1-yl)ethyl)morpholine. MS ESI(+) m/z 609.1 [M+H]⁺.

Example 48B 4-(5-chloro-4-(2-(1-(methoxymethoxy)cyclobutyl) thiazol-5-yl)-1H-pyrrolo[2,3-b]pyridin-2-yl)-3-methylaniline The title compound was prepared as described in Example 1I, substituting 4-(5-chloro-4-(2-(1-(methoxymethoxy)cyclobutyl)thiazol-5-yl)-1-tosyl-1H-pyrrolo[2,3-b]pyridin-2-yl)-3-methylaniline (Example 48A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 455.0 [M+H]⁺.

Example 48C

N-(4-(5-chloro-4-(2-(1-(methoxymethoxy)cyclobutyl)thiazol-5-yl)-1H-pyrrolo[2,3-b]pyridin-2-yl)-3-methylphenyl)-2-(dimethylamino)acetamide The title compound was prepared as described in Example 23C, substituting 4-(5-chloro-4-(2-(1-(methoxymethoxy)cyclobutyl)thiazol-5-yl)-1H-pyrrolo[2,3-b]pyridin-2-yl)-3-methylaniline (Example 48B) for 4-(5-chloro-4-(2-(1-(methoxymethoxy)cyclobutyl)thiazol-5-yl)-1H-pyrrolo[2,3-b]pyridin-2-yl)aniline (Example 23B). MS ESI(+) m/z 540.1 [M+H]⁺.

Example 48D

N-(4-(5-chloro-4-(2-(1-hydroxycyclobutyl)thiazol-5-yl)-1H-pyrrolo[2,3-b]pyridin-2-yl)-3-methylphenyl)-2-(dimethylamino)acetamide The title compound was prepared as described in Example 22E, substituting N-(4-(5-chloro-4-(2-(1-(methoxymethoxy)cyclobutyl)thiazol-5-yl)-1H-pyrrolo[2,3-b]pyridin-2-yl)-3-methylphenyl)-2-(dimethylamino)acetamide (Example 48C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). ¹H NMR (500 MHz, DMSO-d₆) ppm 12.28 (s, 1H) 9.80 (s, 1H), 8.34 (s, 1H) 8.23 (s, 1H) 7.64 (m, 2H) 7.52 (d, 1H) 6.67 (s, 1H) 6.61 (s, 1H) 3.09 (s, 2H) 2.62 (m, 2H) 2.44 (s, 3H) 2.40 (m, 2H) 2.29 (s, 6H) 1.96 (m, 2H); MS ESI(+) m/z 496.1 [M+H]⁺.

Example 49

N¹-(4-{5-chloro-4-[2-(1-hydroxycyclobutyl)-1,3-thiazol-5-yl]-1H-pyrrolo[2,3-b]pyridin-2-yl}-2-methoxyphenyl)-N²,N²-dimethylglycinamide

Example 49A 4-(5-chloro-4-(2-(1-(methoxymethoxy)cyclobutyl) thiazol-5-yl)-1-tosyl-1H-pyrrolo[2,3-b]pyridin-2-yl)-2-methoxyaniline The title compound was prepared as described in Example 1G, substituting 2-methoxy-4-(4,4,5,5-tetramethyl-1,3,2-dioxaborolan-2-yl)aniline for 4-(2-(4-(4,4,5,5-tetramethyl-1,3,2-dioxaborolan-2-yl)-1H-pyrazol-1-yl)ethyl)morpholine. MS ESI(+) m/z 625.1 [M+H]⁺.

Example 49B 4-(5-chloro-4-(2-(1-(methoxymethoxy)cyclobutyl) thiazol-5-yl)-1H-pyrrolo[2,3-b]pyridin-2-yl)-2-methoxyaniline The title compound was prepared as described in Example 1I, substituting 4-(5-chloro-4-(2-(1-(methoxymethoxy)cyclobutyl)thiazol-5-yl)-1-tosyl-1H-pyrrolo[2,3-b]pyridin-2-yl)-2-methoxyaniline (Example 49A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 471.0 [M+H]⁺.

Example 49C

N-(4-(5-chloro-4-(2-(1-(methoxymethoxy)cyclobutyl)thiazol-5-yl)-1H-pyrrolo[2,3-b]pyridin-2-yl)-2-methoxyphenyl)-2-(dimethylamino)acetamide The title compound was prepared as described in Example 23C, substituting 4-(5-chloro-4-(2-(1-(methoxymethoxy)cyclobutyl)thiazol-5-yl)-1-tosyl-1H-pyrrolo[2,3-b]pyridin-2-yl)-2-methoxyaniline (Example 49B) for 4-(5-chloro-4-(2-(1-(methoxymethoxy)cyclobutyl)thiazol-5-yl)-1H-pyrrolo[2,3-b]pyridin-2-yl)aniline (Example 23B). MS ESI(+) m/z 556.1 [M+H]⁺.

Example 49D

N-(4-(5-chloro-4-(2-(1-hydroxycyclobutyl)thiazol-5-yl)-1H-pyrrolo[2,3-b]pyridin-2-yl)-2-methoxyphenyl)-2-(dimethylamino)acetamide The title compound was prepared as described in Example 22E, substituting N-(4-(5-chloro-4-(2-(1-(methoxymethoxy)cyclobutyl)thiazol-5-yl)-1H-pyrrolo[2,3-b]pyridin-2-yl)-2-methoxyphenyl)-2-(dimethylamino)acetamide (Example 49C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). ¹H NMR (500 MHz, DMSO-d₆) ppm 12.54 (s, 1H) 9.53 (s, 1H) 8.31 (m, 2H) 8.27 (s, 1H) 7.70 (d, 1H) 7.61 (dd, 1H) 7.08 (s, 1H) 6.68 (s, 1H) 3.99 (s, 3H) 3.10 (s, 2H) 2.63 (m, 2H) 2.42 (m, 2H) 2.32 (s, 6H) 1.99 (m, 2 H); MS ESI(+) m/z 512.1 [M+H]⁺.

Example 50

1-{5-[5-chloro-2-(1-piperidin-4-yl-1H-pyrazol-4-yl)-1H-pyrrolo[2,3-b]pyridin-4-yl]-1,3-thiazol-2-yl}cyclobutanol

Example 50A tert-butyl 4-(4-(5-chloro-4-(2-(1-hydroxycyclobutyl)thiazol-5-yl)-1-tosyl-1H-pyrrolo[2,3-b]pyridin-2-yl)-1H-pyrazol-1-yl)piperidine-1-carboxylate The title compound was prepared as described in Example 8B, substituting tert-butyl 4-(4-(4,4,5,5-tetramethyl-1,3,2-dioxaborolan-2-yl)-1H-pyrazol-1-yl)piperidine-1-carboxylate for 4-formylphenylboronic acid. MS ESI(+) m/z 709.2 [M+H]$^+$.

Example 50B 1-(5-(5-chloro-2-(1-(piperidin-4-yl)-1H-pyrazol-4-yl)-1-tosyl-1H-pyrrolo[2,3-b]pyridin-4-yl)thiazol-2-yl)cyclobutanol To a solution of tert-butyl 4-(4-(5-chloro-4-(2-(1-hydroxycyclobutyl)thiazol-5-yl)-1-tosyl-1H-pyrrolo[2,3-b]pyridin-2-yl)-1H-pyrazol-1-yl)piperidine-1-carboxylate (Example 50A) (120 mg, 0.169 mmol) in dichloromethane (846 μl) was added trifluoroacetic acid (652 μl, 8.46 mmol). The reaction was stirred for 1 hour and was then concentrated to dryness. The residue was partitioned between ethyl acetate (5 mL) and saturated aqueous bicarbonate solution (1 mL). The organic layer was dried with anhydrous sodium sulfate, filtered and concentrated under reduced pressure to give the title compound, which was used without further purification. MS ESI (+) m/z 609.4 [M+H]$^+$.

Example 50C 1-(5-(5-chloro-2-(1-(piperidin-4-yl)-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1-(piperidin-4-yl)-1H-pyrazol-4-yl)-1-tosyl-1H-pyrrolo[2,3-b]pyridin-4-yl)thiazol-2-yl)cyclobutanol (Example 50B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.33 (s, 1H), 8.42 (s, 1H), 8.23 (s, 1H), 8.18 (s, 1H), 8.08 (d, J=0.7 Hz, 1H), 6.78 (d, J=1.4 Hz, 1H), 6.69 (s, 1H), 4.29-4.15 (m, 1H), 3.10-3.01 (m, 2H), 2.68-2.56 (m, 4H), 2.45-2.34 (m, 2H), 2.04-1.88 (m, 6H), 1.85-1.72 (m, 2H). MS ESI(+) m/z 455.0 [M+H]$^+$.

Example 51

3-{5-chloro-4-[2-(1-hydroxycyclobutyl)-1,3-thiazol-5-yl]-1H-pyrrolo[2,3-b]pyridin-2-yl}benzonitrile To a stirred ambient solution of 1-(5-(5-chloro-2-iodo-1-tosyl-1H-pyrrolo[2,3-b]pyridin-4-yl)thiazol-2-yl)cyclobutanol (Example 8A) (50 mg, 0.085 mmol) and 3-cyanophenylboronic acid (18.8 mg, 0.128 mmol) in N,N-dimethylformamide (2.0 mL) was added saturated aqueous bicarbonate solution (683 μl) followed by bis(triphenylphosphine)palladium dichloride (4.2 mg, 6.0 μmol). The mixture was heated to 70° C. for 4 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was dissolved in methanol (2 mL). Magnesium turnings (20.7 mg, 0.853 mmol) and solid ammonium chloride (18.26 mg, 0.341 mmol) were added, and the mixture stirred vigorously for 16 hours. The reaction was partitioned between ethyl acetate and saturated aqueous bicarbonate solution. The layers were separated, and the aqueous layer was extracted with additional ethyl acetate. The combined organics were dried with anhydrous sodium sulfate, filtered and concentrated under reduced pressure. The residue was purified by reverse phase high performance liquid chromatography (RP HPLC, 19×150 mm Atlantis Prep T3 OBD m column, eluting with a gradient of 5% B in A to 75% B in A over 25 minutes, wherein A is water containing 0.1% v/v trifluoroacetic acid and B is acetonitrile containing 0.1% v/v trifluoroacetic acid). The fractions containing the product were diluted with ethyl acetate and washed with saturated aqueous bicarbonate solution. The ethyl acetate solution was dried with anhydrous sodium sulfate, filtered and concentrated under reduced pressure to give the title compound. $^1$H NMR (500 MHz, DMSO-d$_6$) δ 12.71 (s, 1H), 8.57 (bs, 1H), 8.39 (s, 1H), 8.35 (d, J=8.4 Hz, 1H), 8.30 (s, 1H), 7.83 (d, J=7.7 Hz, 1H), 7.70-7.67 (m, 1H), 7.35 (bs, 1H), 6.70 (s, 2H), 2.68-2.59 (m, 2H), 2.46-2.38 (m, 2H), 2.06-1.89 (m, 2H); MS ESI(+) m/z 406.9 [M+H]$^+$.

Example 52

1-(5-{5-chloro-2-[1-(N,N-dimethylglycyl)-2,3-dihydro-1H-indol-5-yl]-1H-pyrrolo[2,3-b]pyridin-4-yl}-1,3-thiazol-2-yl)cyclobutanol

Example 52A 1-(5-bromoindolin-1-yl)-2-(dimethylamino)ethanone

A solution of 5-bromoindoline (0.5 g, 2.52 mmol), 1-hydroxybenzotriazole hydrate (0.387 g, 2.52 mmol), N-methylmorpholine (1.11 mL, 10.1 mmol) and 2-(dimethylamino)acetic acid (0.299 g, 2.9 mmol) in N,N-dimethylformamide (9.5 mL) was treated with N-(3-dimethylaminopropyl)-N'-ethylcarbodiimide hydrochloride (0.678 g, 3.53 mmol) and the reaction was stirred at ambient temperature for 18 hours. The reaction was diluted with water (100 mL) and extracted with 1:1 ether/ethyl acetate (2×120 mL). The combined organic layers were washed with water (2×80 mL) and brine (2×80 mL), dried over anhydrous sodium sulfate, filtered, and concentrated under reduced pressure. The concentrate was purified by flash chromatography on a silica gel column eluting with a gradient of from 0% to 5% methanol in dichloromethane to provide the title compound. MS DCI (+) m/z 283.0 [M+H]$^+$.

Example 52B 2-(dimethylamino)-1-(5-(4,4,5,5-tetramethyl-1,3,2-dioxaborolan-2-yl)indolin-1-yl)ethanone To a stirring mixture of Example 52A (0.257 g, 0.908 mmol), potassium acetate (0.267 g, 2.72 mmol), and bis(pinacolato)diboron (0.277 g, 1.09 mmol) in dimethyl sulfoxide (3 mL) was added [1,1'-bis(diphenylphosphino)-ferrocene]dichloropalladium(II) complex with dichloromethane (0.059 g, 0.073 mmol) and the reaction was heated at 80° C. for 1 hour. The reaction was cooled to ambient temperature and partitioned between ethyl acetate and water. The aqueous layer was extracted with additional ethyl acetate. The combined organic layers were washed with water and brine, dried over anhydrous sodium sulfate, filtered, and concentrated under reduced pressure. The concentrate was purified by flash chromatography on a silica gel column, eluting with a gradient of 0% to 6% methanol in dichloromethane, to provide the title compound. MS APCI(+) m/z 331.3 [M+H]$^+$.

Example 52C 1-(5-(5-chloro-4-(2-(1-(methoxymethoxy)cyclobutyl)thiazol-5-yl)-1-tosyl-1H-pyrrolo[2,3-b]pyridin-2-yl)indolin-1-yl)-2-(dimethylamino)ethanone The title compound was prepared as described in Example 45A, substituting Example 52B for 2-(tert-butoxycarbonyl)-1,2,3,4-tetrahydroisoquinolin-7-ylboronic acid. MS ESI(+) m/z 706.2 [M+H]$^+$.

Example 52D 1-(5-(5-chloro-4-(2-(1-hydroxycyclobutyl)thiazol-5-yl)-1-tosyl-1H-pyrrolo[2,3-b]pyridin-2-yl)indolin-1-yl)-2-(dimethylamino)ethanone A solution of Example 52C (0.083 g, 0.118 mmol) in tetrahydrofuran (0.8 mL) was treated with 10% aqueous HCl solution (0.25 mL), and the reaction was heated at 65° C. for 4 hours. The reaction was cooled to ambient temperature and concentrated under reduced pressure. The concentrate was partitioned between ethyl acetate and saturated aqueous sodium bicarbonate. The aqueous layer was extracted with additional ethyl acetate. The combined organic layers were washed with brine, dried over anhydrous sodium sulfate, filtered, and concentrated under reduced pressure to provide the title compound. MS ESI(+) m/z 662.2 [M+H]$^+$.

Example 52E 1-(5-{5-chloro-2-[1-(N,N-dimethylglycyl)-2,3-dihydro-1H-indol-5-yl]-1H-pyrrolo[2,3-b]pyridin-4-yl}-1,3-thiazol-2-yl)cyclobutanol The title compound was prepared as described in Example 45C, substituting Example 52D for Example 45B. $^1$H NMR (300 MHz, methanol-d$_4$) ppm 2.02-2.14 (m, 2H), 2.42-2.53 (m, 2H), 2.72-2.82 (m, 2H), 3.03 (s, 6H), 3.29 (m, 2H), 4.13 (m, 2H), 4.34 (s, 2H), 6.89 (s, 1H), 7.70-7.76 (m, 1H), 7.79 (m, 1H) 8.15 (s, 1H), 8.24 (m, 1H) 8.26 (s, 1H); MS ESI(+) m/z 508.1 [M+H]$^+$.

Example 53

1-{5-[5-chloro-2-(2,3-dihydro-1H-indol-5-yl)-1H-pyrrolo[2,3-b]pyridin-4-yl]-1,3-thiazol-2-yl}cyclobutanol The title compound was prepared as described in Example 45C, substituting Example 52D for Example 45B. $^1$H NMR (300 MHz, methanol-d$_4$) ppm 2.02-2.14 (m, 2H), 2.40-2.53 (m, 2H), 2.71-2.81 (m, 2H), 3.30 (m, 2H), 3.82 (m, 2H), 6.94 (s, 1H), 7.34 (m, 1H), 7.82 (m, 1H), 7.90 (bs, 1H), 8.16 (s, 1H), 8.29 (s, 1H); MS ESI(+) m/z 422.9 [M+H]$^+$.

Example 54

3-(5-{5-fluoro-2-[1-(2-pyrrolidin-1-ylethyl)-1H-pyrazol-4-yl]-1H-pyrrolo[2,3-b]pyridin-4-yl}-1,3-thiazol-2-yl)azetidin-3-ol

Example 54A tert-butyl 3-(methoxymethoxy)-3-(5-(tributylstannyl)thiazol-2-yl)azetidine-1-carboxylate The title compound was prepared as described in Examples 1A-1C, except substituting tert-butyl 3-oxoazetidine-1-carboxylate for cyclobutanone in Example 1A. MS APCI(+) m/z 591.43 (M+H)$^+$.

Example 54B tert-butyl 3-(5-(5-fluoro-1-tosyl-1H-pyrrolo[2,3-b]pyridin-4-yl)thiazol-2-yl)-3-(methoxymethoxy)azetidine-1-carboxylate The title compound was prepared as described in Example 1E, except substituting Example 54A for 2-(1-(methoxymethoxy)cyclobutyl)-5-(tributylstannyl)thiazole (Example 1C) and Example 2A for 5-chloro-4-iodo-1-tosyl-1H-pyrrolo[2,3-b]pyridine (Example 1D). $^1$H NMR (300 MHz, CDCl$_3$) δ 8.37 (d, 1H), 8.26 (d, 1H), 8.11-8.03 (m, 2H), 7.88 (d, 1H), 7.30 (d, 2H), 6.88 (d, 1H), 4.88 (s, 2H), 4.45 (q, 4H), 3.48 (s, 3H), 2.39 (s, 3H), 1.47 (s, 9H). MS APCI (+) m/z 589.35 (M+H)$^+$.

Example 54C tert-butyl 3-(5-(5-fluoro-2-iodo-1-tosyl-1H-pyrrolo[2,3-b]pyridin-4-yl)thiazol-2-yl)-3-(methoxymethoxy)azetidine-1-carboxylate The title compound was prepared as described in Example 1F, except substituting Example 54B for 5-(5-chloro-1-tosyl-1H-pyrrolo[2,3-b]pyridin-4-yl)-2-(1-(methoxymethoxy)cyclobutyl)thiazole (Example 1E). MS APCI(+) m/z 715.28 (M+H)$^+$.

Example 54D 3-(5-(5-fluoro-2-(1-(2-(pyrrolidin-1-yl)ethyl)-1H-pyrazol-4-yl)-1H-pyrrolo[2,3-b]pyridin-4-yl)thiazol-2-yl)azetidin-3-ol The title compound was prepared as described in Examples 1G-1I, except substituting Example 54C for 5-(5-chloro-2-iodo-1-tosyl-1H-pyrrolo[2,3-b]pyridin-4-yl)-2-(1-(methoxymethoxy)cyclobutyl)thiazole (Example 1F) and 1-(2-(pyrrolidin-1-yl)ethyl)-4-(4,4,5,5-tetramethyl-1,3,2-dioxaborolan-2-yl)-1H-pyrazole (Example 20A) for -(4,4,5,5-tetramethyl-1,3,2-dioxaborolan-2-yl)-1H-pyrazol-1-yl)ethyl)morpholine in Example 1G. The title compound was isolated as a trifluoroacetic acid salt. $^1$H NMR (300 MHz, DMSO-d$_6$) δ 12.45 (s, 1H), 9.67 (s, 1H), 9.29 (d, 2H), 8.55 (s, 1H), 8.42 (d, 1H), 8.27 (d, 1H), 8.23 (s, 1H), 7.88 (s, 1H), 7.05 (d, 1H), 4.58 (t, 2H), 4.50 (dd, 2H), 4.27-4.20 (m, 2H), 3.71

(d, 2H), 3.58-3.52 (m, 2H), 3.11-3.00 (m, 2H), 2.07-1.94 (m, 2H), 1.93-1.79 (m, 2H); MS APCI(+) m/z 454.42 (M+H)$^+$.

Example 55

1-(5-{5-chloro-2-[3-fluoro-4-(hydroxymethyl)phenyl]-1H-pyrrolo[2,3-b]pyridin-4-yl}-1,3-thiazol-2-yl)cyclobutanol The title compound was prepared as described in Examples 30A-30D and isolated as a by-product. $^1$H NMR (300 MHz, DMSO-d$_6$) δ 12.59 (s, 1H), 8.34 (s, 1H), 8.27 (s, 1H), 7.86 (d, 2H), 7.54 (s, 1H), 7.16 (s, 1H), 6.66 (s, 1H), 5.31 (t, 1H), 4.58 (d, 2H), 2.69-2.58 (m, 2H), 2.46-2.36 (m, 2H), 2.06-1.90 (m, 2H); MS APCI(+) m/z 430.23 (M+H)$^+$.

Example 56

1-(5-{5-chloro-2-[4-(2-pyrrolidin-1-ylethyl)phenyl]-1H-pyrrolo[2,3-b]pyridin-4-yl}-1,3-thiazol-2-yl)cyclobutanol Example 56A 4-bromophenethyl 4-methylbenzenesulfonate A solution of 2-(4-bromophenyl)ethanol (3.48 mL, 24.87 mmol), p-toluenesulfonyl chloride (5.69 g, 29.8 mmol), and 4-(dimethylamino)pyridine (0.304 g, 2.487 mmol) in anhydrous dichloromethane (70 mL) was treated with triethylamine (6.93 mL, 49.7 mmol). The reaction stirred for 16 hours at ambient temperature. The reaction was diluted with ethyl acetate and washed with water and brine. The organic layer dried with sodium sulfate, filtered, and concentrated under reduced pressure. The residue was purified by flash chromatography on silica gel, eluting with a gradient of 10 to 20% ethyl acetate in hexanes, to give the title compound. MS ESI(+) m/z 356.9 [M+H]$^+$.

Example 56B 1-(4-bromophenethyl)pyrrolidine

A solution of 4-bromophenethyl 4-methylbenzenesulfonate (500 mg, 1.407 mmol) from Example 56A in anhydrous acetonitrile (3 mL) was treated with triethylamine (0.589 mL, 4.22 mmol) and pyrrolidine (0.349 mL, 4.22 mmol). The reaction was stirred 16 hours at ambient temperature. The reaction was diluted with ethyl acetate and washed with water, saturated ammonium chloride, and brine. The organic layer was dried with sodium sulfate, filtered, and concentrated under reduced pressure. The residue was purified by flash chromatography on silica gel, eluting with a gradient of 5% methanol in dichloromethane, to give the title compound. MS DCI(+) m/z 254.0 [M+H]$^+$.

Example 56C 1-(4-(4,4,5,5-tetramethyl-1,3,2-dioxaborolan-2-yl)phenethyl)pyrrolidine The title compound was prepared as described in Example 52B, substituting 1-(4-bromophenethyl)pyrrolidine from Example 56B for 1-(5-bromoindolin-1-yl)-2-(dimethylamino)ethanone from Example 52A. MS ESI(+) m/z 302.0 [M+H]$^+$.

Example 56D 5-(5-chloro-2-(4-(2-(pyrrolidin-1-yl)ethyl)phenyl)-1-tosyl-1H-pyrrolo[2,3-b]pyridin-4-yl)-2-(1-(methoxymethoxy)cyclobutyl)thiazole The title compound was prepared as described in Example 1G, substituting 1-4-(4,4,5,5-tetramethyl-1,3,2-dioxaborolan-2-yl)phenethyl)pyrrolidine from Example 56C for 4-(2-(4-(4,4,5,5-tetramethyl-1,3,2-dioxaborolan-2-yl)-1H-pyrazol-1-yl)ethyl)morpholine. MS ESI(+) m/z 677.2 [M+H]$^+$.

Example 56E 1-(5-(5-chloro-2-(4-(2-(pyrrolidin-1-yl)ethyl)phenyl)-1-tosyl-1H-pyrrolo[2,3-b]pyridin-4-yl)thiazol-2-yl)cyclobutanol The title compound was prepared as described in Example 52D, substituting 5-(5-chloro-2-(4-(2-(pyrrolidin-1-yl)ethyl)phenyl)-1-tosyl-1H-pyrrolo[2,3-b]pyridin-4-yl)-2-(1-(methoxymethoxy)cyclobutyl)thiazole from Example 56D for 1-(5-(5-chloro-4-(2-(1-(methoxymethoxy)cyclobutyl)thiazol-5-yl)-1-tosyl-1H-pyrrolo[2,3-b]pyridin-2-yl)indolin-1-yl)-2-(dimethylamino)ethanone from Example 52C. MS ESI (+) m/z 633.1 [M+H]$^+$.

Example 56F 1-(5-(5-chloro-2-(4-(2-(pyrrolidin-1-yl)ethyl)phenyl)-1H-pyrrolo[2,3-b]pyridin-4-yl)thiazol-2-yl)cyclobutanol The title compound was prepared as described in Example 1I, substituting 1-(5-(5-chloro-2-(4-(2-(pyrrolidin-1-yl)ethyl)phenyl)-1-tosyl-1H-pyrrolo[2,3-b]pyridin-4-yl)thiazol-2-yl)cyclobutanol from Example 56E for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol from Example 1H. MS ESI(+) m/z 479.1 [M+H]$^+$. $^1$H NMR (500 MHz, DMSO-d$_6$) ppm 12.57 (s, 1H) 8.33 (s, 1H) 8.26 (s, 1H) 7.98 (d, 2H) 7.39 (d, 2H) 7.06 (m, 1H) 6.70 (s, 1H) 3.10-3.40 (m, 6H) 3.02 (m, 2H) 2.63 (m, 2H) 2.43 (m, 2H) 1.84-2.05 (m, 6H).

Example 57

1-[5-(5-chloro-2-{4-[(4-methyl-1,4-diazepan-1-yl)carbonyl]phenyl}-1H-pyrrolo[2,3-b]pyridin-4-yl)-1,3-thiazol-2-yl]cyclobutanol The title compound was prepared as described in Example 19, substituting 1-methyl-1,4-diazepane for 1-methylpiperazine. $^1$H NMR (300 MHz, DMSO-d$_6$) δ 12.65 (s, 1H), 8.36 (s, 1H), 8.28 (s, 1H), 8.05 (s, 1H), 7.50-7.43 (m, 2H), 7.15 (s, 1H), 6.66 (s, 1H), 3.68-3.57 (m, 2H), 3.46-3.37 (m, 2H), 3.28 (s, 3H), 2.69-2.54 (m, 4H), 2.47-2.34 (m, 2H), 2.31-2.21 (m, 2H), 2.06-1.91 (m, 2H), 1.90-1.70 (m, 2H); MS ESI(+) m/z 522.0 [M+H]$^+$.

Example 58

1-[5-(5-chloro-2-{4-[4-(dimethylamino)piperidin-1-yl]phenyl}-1H-pyrrolo[2,3-b]pyridin-4-yl)-1,3-thiazol-2-yl]cyclobutanol Example 58A 1-(4-bromophenyl)-N,N-dimethylpiperidin-4-amine A solution of triethylamine (0.987 mL, 7.08 mmol) in ethanol (6.2 mL) and methanol (4.2 mL) was treated with 1-(4-bromophenyl)piperidin-4-one (0.9 g, 3.54 mmol) and dimethylamine hydrochloride (0.578 g, 7.08 mmol). Titanium(IV) isopropoxide (2.075 mL, 7.08 mmol) was added and a thick mixture formed. The suspension was stirred at ambient temperature for 18 hours. Sodium borohydride (0.2 g, 5.31 mmol) was then added portion-wise over 5 minutes and the reaction mixture was stirred at ambient temperature for 18 hours. The reaction was quenched with 70 mL 10% aqueous ammonia and the resulting suspension was extracted with 250 mL dichloromethane. The aqueous layer was extracted with 150 mL additional dichloromethane. The combined organic layers were washed with brine, dried over anhydrous sodium sulfate, filtered, and concentrated. The concentrate was purified by flash chromatography on a silica gel column eluting with a gradient of from 0% to 7% methanol in dichloromethane to provide the title compound. MS ESI(+) m/z 284.8 [M+H]$^+$.

Example 58B

N,N-dimethyl-1-(4-(4,4,5,5-tetramethyl-1,3,2-dioxaborolan-2-yl)phenyl)piperidin-4-amine The title compound was prepared as described in Example 52B, substituting Example 58A for Example 52A and 1,4-dioxane for dimethyl sulfoxide. MS ESI(+) m/z 331.0 [M+H]$^+$.

Example 58C 1-(4-(5-chloro-4-(2-(1-(methoxymethoxy)cyclobutyl)thiazol-5-yl)-1-tosyl-1H-pyrrolo[2,3-b]pyridin-2-yl)phenyl)-N,N-dimethylpiperidin-4-amine The title compound was prepared as described in Example 45A, substituting Example 58B for 2-(tert-butoxycarbonyl)-1,2,3,4-tetrahydroisoquinolin-7-ylboronic acid. MS ESI(+) m/z 706.2 [M+H]$^+$.

Example 58D 1-(5-(5-chloro-2-(4-(4-(dimethylamino)piperidin-1-yl)phenyl)-1-tosyl-1H-pyrrolo[2,3-b]pyridin-4-yl)thiazol-2-yl)cyclobutanol The title compound was prepared as described in Example 52D, substituting Example 58C for Example 52C. MS ESI(+) m/z 662.2 [M+H]$^+$.

Example 58E

1-[5-(5-chloro-2-{4-[4-(dimethylamino)piperidin-1-yl]phenyl}-1H-pyrrolo[2,3-b]pyridin-4-yl)-1,3-thiazol-2-yl]cyclobutanol The title compound was prepared as described in Example 45C, substituting Example 58D for Example 45B. $^1$H NMR (300 MHz, DMSO-d$_6$) ppm 1.38-1.53 (m, 2H), 1.78-1.88 (m, 2H), 1.91-2.03 (m, 2H), 2.19 (s, 6H), 2.22-2.28 (m, 1H), 2.34-2.46 (m, 2H), 2.56-2.68 (m, 2H), 2.70-2.81 (m, 2H), 3.78-3.89 (m, 2H), 6.64 (s, 1H), 6.84 (s, 1H), 7.00 (d, 2 H), 7.82 (d, 2H), 8.20-8.26 (m, 2H), 12.35 (s, 1H); MS ESI(+) m/z 508.1 [M+H]$^+$;

Example 59

1-{5-[5-fluoro-2-(1-methyl-1H-pyrazol-4-yl)-1H-pyrrolo[2,3-b]pyridin-4-yl]-1,3-thiazol-2-yl}cyclobutanol Example 59A 1-(5-(5-fluoro-2-iodo-1-tosyl-1H-pyrrolo[2,3-b]pyridin-4-yl)thiazol-2-yl)cyclobutanol The title compound was prepared as described in Example 8A, substituting 5-(5-fluoro-1-tosyl-1H-pyrrolo[2,3-b]pyridin-4-yl)-2-(1-(methoxymethoxy)cyclobutyl)thiazole (Example 2C) for 5-(5-chloro-2-iodo-1-tosyl-1H-pyrrolo[2,3-b]pyridin-4-yl)-2-(1-(methoxymethoxy)cyclobutyl)thiazole (Example 1F). MS ESI(+) m/z 570.0 [M+H]$^+$.

Example 59B 1-(5-(5-fluoro-2-(1-methyl-1H-pyrazol-4-yl)-1-tosyl-1H-pyrrolo[2,3-b]pyridin-4-yl)thiazol-2-yl)cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 59A) (200 mg, 0.351 mmol) and 1-methyl-4-(4,4,5,5-tetramethyl-1,3,2-dioxaborolan-2-yl)-1H-pyrazole (110 mg, 0.527 mmol) in N,N-dimethylformamide (2.63 mL) was added saturated aqueous bicarbonate solution (0.88 mL) followed by bis(triphenylphosphine)palladium dichloride (17.26 mg, 0.025 mmol). The mixture was heated to 70° C. for 4 hours and was quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was purified by flash chromatography on silica gel, eluting with a gradient of 0 to 75% ethyl acetate in hexane, to give the title compound MS ESI(+) m/z 524.1 [M+H]$^+$.

Example 59C

The title compound was prepared as described in Example 1I, substituting 1-(5-(5-fluoro-2-(1-methyl-1H-pyrazol-4-yl)-1-tosyl-1H-pyrrolo[2,3-b]pyridin-4-yl)thiazol-2-yl)cyclobutanol (Example 59B) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). $^1$H NMR (300 MHz, DMSO-d$_6$) δ 12.27 (bs, 1H), 8.41 (d, J=1.0 Hz, 1H), 8.30 (s, 1H), 8.20 (d, J=3.6 Hz, 1H), 8.07 (d, J=0.7 Hz, 1H), 7.01 (s, 1H), 6.65 (s, 1H), 3.90 (s, 3H), 2.67-2.55 (m, 2H), 2.45-2.34 (m, 2H), 2.06-1.86 (m, 2H); MS ESI(+) m/z 369.9 [M+H]$^+$.

Example 60

N$^1$-(4-{5-chloro-4-[2-(1-hydroxycyclobutyl)-1,3-thiazol-5-yl]-1H-pyrrolo[2,3-b]pyridin-2-yl}-3-fluorophenyl)-N$^2$,N$^2$-dimethylglycinamide Example 60A 4-(5-chloro-4-(2-(1-(methoxymethoxy)cyclobutyl)thiazol-5-yl)-1-tosyl-1H-pyrrolo[2,3-b]pyridin-2-yl)-3-fluoroaniline The title compound was prepared as described in Example 1G, substituting 3-fluoro-4-(4,4,5,5-tetramethyl-1,3,2-dioxaborolan-2-yl)aniline for 4-(2-(4-(4,4,5,5-tetramethyl-1,3,2-dioxaborolan-2-yl)-1H-pyrazol-1-yl)ethyl)morpholine. MS ESI(+) m/z 613.1 [M+H]⁺.

Example 60B 4-(5-chloro-4-(2-(1-(methoxymethoxy)cyclobutyl)thiazol-5-yl)-1H-pyrrolo[2,3-b]pyridin-2-yl)-3-fluoroaniline The title compound was prepared as described in Example 1I, substituting 4-(5-chloro-4-(2-(1-(methoxymethoxy)cyclobutyl)thiazol-5-yl)-1-tosyl-1H-pyrrolo[2,3-b]pyridin-2-yl)-3-fluoroaniline (Example 60A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 459.0 [M+H]⁺.

Example 60C

N-(4-(5-chloro-4-(2-(1-(methoxymethoxy)cyclobutyl)thiazol-5-yl)-1H-pyrrolo[2,3-b]pyridin-2-yl)-3-fluorophenyl)-2-(dimethylamino)acetamide A solution of 4-(5-chloro-4-(2-(1-(methoxymethoxy)cyclobutyl)thiazol-5-yl)-1H-pyrrolo[2,3-b]pyridin-2-yl)-3-fluoroaniline (Example 60B) (68 mg, 0.148 mmol) and dimethyl glycine (15.3 mg, 0.148 mmol) in N,N-dimethylformamide (0.5 mL) was treated with O-(7-azabenzotriazol-1-yl)-N,N,N',N'-tetramethyluronium hexafluorophosphate (67.6 mg, 0.178 mmol) and 4-(dimethylamino)pyridine (1.8 mg, 0.015 mmol). The reaction was stirred for 16 hours at ambient temperature. The reaction was treated with more O-(7-azabenzotriazol-1-yl)-N,N,N',N'-tetramethyluronium hexafluorophosphate (67.6 mg, 0.178 mmol) and 4-(dimethylamino)pyridine (18.1 mg, 0.148 mmol), and the reaction was stirred another 16 hours at ambient temperature. The reaction was diluted with ethyl acetate and washed with water, saturated sodium bicarbonate solution, and brine. The organic layer was dried with sodium sulfate, filtered, and concentrated under reduced pressure. The residue was purified by flash chromatography on silica gel, eluting with a gradient of 1 to 5% methanol in dichloromethane, to give the title compound. MS ESI(+) m/z 544.1 [M+H]⁺.

Example 60D

N-(4-(5-chloro-4-(2-(1-hydroxycyclobutyl)thiazol-5-yl)-1H-pyrrolo[2,3-b]pyridin-2-yl)-3-fluorophenyl)-2-(dimethylamino)acetamide The title compound was prepared as described in Example 22E, substituting N-(4-(5-chloro-4-(2-(1-(methoxymethoxy)cyclobutyl)thiazol-5-yl)-1H-pyrrolo[2,3-b]pyridin-2-yl)-3-fluorophenyl)-2-(dimethylamino)acetamide (Example 60C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). ¹H NMR (400 MHz, DMSO-D₆) ppm 12.49 (s, 1H) 10.12 (s, 1H) 8.37 (s, 1H) 8.22 (s, 1H) 7.95 (m, 1H) 7.84 (dd, 1H) 7.59 (dd, 1H) 6.90 (d, 1H) 6.69 (s, 1H) 3.12 (s, 2H) 2.63 (m, 2H) 2.41 (m, 2H) 2.29 (s, 6H) 1.99 (m, 2H); MS ESI(+) m/z 500.1 [M+H]⁺.

Example 61

N¹-(3-chloro-4-{5-chloro-4-[2-(1-hydroxycyclobutyl)-1,3-thiazol-5-yl]-1H-pyrrolo[2,3-b]pyridin-2-yl}phenyl)-N²,N²-dimethylglycinamide Example 61A 3-chloro-4-(5-chloro-4-(2-(1-(methoxymethoxy)cyclobutyl)thiazol-5-yl)-1-tosyl-1H-pyrrolo[2,3-b]pyridin-2-yl)aniline The title compound was prepared as described in Example 1G, substituting 3-chloro-4-(4,4,5,5-tetramethyl-1,3,2-dioxaborolan-2-yl)aniline for 4-(2-(4-(4,4,5,5-tetramethyl-1,3,2-dioxaborolan-2-yl)-1H-pyrazol-1-yl)ethyl)morpholine. MS ESI(+) m/z 629.1 [M+H]⁺.

Example 61B 3-chloro-4-(5-chloro-4-(2-(1-(methoxymethoxy)cyclobutyl)thiazol-5-yl)-1H-pyrrolo[2,3-b]pyridin-2-yl)aniline The title compound was prepared as described in Example 1I, substituting 3-chloro-4-(5-chloro-4-(2-(1-(methoxymethoxy)cyclobutyl)thiazol-5-yl)-1-tosyl-1H-pyrrolo[2,3-b]pyridin-2-yl)aniline (Example 61A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 475.0 [M+H]⁺.

Example 61C

N-(3-chloro-4-(5-chloro-4-(2-(1-(methoxymethoxy)cyclobutyl)thiazol-5-yl)-1H-pyrrolo[2,3-b]pyridin-2-yl)phenyl)-2-(dimethylamino)acetamide The title compound was prepared as described in Example 60C, substituting 3-chloro-4-(5-chloro-4-(2-(1-(methoxymethoxy)cyclobutyl)thiazol-5-yl)-1H-pyrrolo[2,3-b]pyridin-2-yl)aniline (Example 61B) for 4-(5-chloro-4-(2-(1-(methoxymethoxy)cyclobutyl)thiazol-5-yl)-1H-pyrrolo[2,3-b]pyridin-2-yl)-3-fluoroaniline (Example 60B). MS ESI(+) m/z 560.0 [M+H]⁺.

Example 61D

N-(3-chloro-4-(5-chloro-4-(2-(1-hydroxycyclobutyl)thiazol-5-yl)-1H-pyrrolo[2,3-b]pyridin-2-yl)phenyl)-2-(dimethylamino)acetamide The title compound was prepared as described in Example 22E, substituting N-(3-chloro-4-(5-chloro-4-(2-(1-(methoxymethoxy)cyclobutyl)thiazol-5-yl)-1H-pyrrolo[2,3-b]pyridin-2-yl)phenyl)-2-(dimethylamino)acetamide (Example 61C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). ¹H NMR (400 MHz, DMSO-d₆) ppm 12.45 (s, 1H) 10.10 (s, 1H) 8.38 (s, 1H) 8.23 (s, 1H) 8.06 (d, 1H)

7.73 (m, 2H) 6.89 (s, 1H) 6.68 (s, 1H) 3.12 (s, 2H) 2.61 (m, 2H) 2.40 (m, 2H) 2.29 (s, 6H) 1.97 (m, 2H); MS ESI(+) m/z 518.0 [M+H]+.

Example 62

N$^1$-(4-{5-chloro-4-[2-(1-hydroxycyclobutyl)-1,3-thiazol-5-yl]-1H-pyrrolo[2,3-b]pyridin-2-yl}-2-methylphenyl)-N$^2$,N$^2$-dimethylglycinamide

Example 62A 2-methyl-4-(4,4,5,5-tetramethyl-1,3,2-dioxaborolan-2-yl)aniline

The title compound was prepared as described in Example 52B, substituting 4-bromo-2-methylaniline for 1-(5-bromoindolin-1-yl)-2-(dimethylamino)ethanone (Example 52A). MS DCI(+) m/z 234.1 [M+H]+.

Example 62B 4-(5-chloro-4-(2-(1-(methoxymethoxy)cyclobutyl)thiazol-5-yl)-1-tosyl-1H-pyrrolo[2,3-b]pyridin-2-yl)-2-methylaniline The title compound was prepared as described in Example 1G, substituting 2-methyl-4-(4,4,5,5-tetramethyl-1,3,2-dioxaborolan-2-yl)aniline (Example 62A) for 4-(2-(4-(4,4,5,5-tetramethyl-1,3,2-dioxaborolan-2-yl)-1H-pyrazol-1-yl)ethyl)morpholine. MS ESI(+) m/z 609.2 [M+H]+.

Example 62C 4-(5-chloro-4-(2-(1-(methoxymethoxy)cyclobutyl)thiazol-5-yl)-1H-pyrrolo[2,3-b]pyridin-2-yl)-2-methylaniline The title compound was prepared as described in Example 1I, substituting 4-(5-chloro-4-(2-(1-(methoxymethoxy)cyclobutyl)thiazol-5-yl)-1-tosyl-1H-pyrrolo[2,3-b]pyridin-2-yl)-2-methylaniline (Example 62B) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 455.0 [M+H]+.

Example 62D

N-(4-(5-chloro-4-(2-(1-(methoxymethoxy)cyclobutyl)thiazol-5-yl)-1H-pyrrolo[2,3-b]pyridin-2-yl)-2-methylphenyl)-2-(dimethylamino)acetamide The title compound was prepared as described in Example 60C, substituting 4-(5-chloro-4-(2-(1-(methoxymethoxy)cyclobutyl)thiazol-5-yl)-1H-pyrrolo[2,3-b]pyridin-2-yl)-2-methylaniline (Example 62C) for 4-(5-chloro-4-(2-(1-(methoxymethoxy)cyclobutyl)thiazol-5-yl)-1H-pyrrolo[2,3-b]pyridin-2-yl)-3-fluoroaniline (Example 60B). MS ESI(+) m/z 540.1 [M+H]+.

Example 62E

N-(4-(5-chloro-4-(2-(1-hydroxycyclobutyl)thiazol-5-yl)-1H-pyrrolo[2,3-b]pyridin-2-yl)-2-methylphenyl)-2-(dimethylamino)acetamide The title compound was prepared as described in Example 22E, substituting N-(4-(5-chloro-4-(2-(1-(methoxymethoxy)cyclobutyl)thiazol-5-yl)-1H-pyrrolo[2,3-b]pyridin-2-yl)-2-methylphenyl)-2-(dimethylamino)acetamide (Example 62D) for tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (400 MHz, DMSO-d$_6$) ppm 12.49 (s, 1H) 9.42 (s, 1H) 8.31 (s, 1H) 8.25 (s, 1H) 7.92 (s, 1H) 7.83 (s, 2H) 7.02 (d, 1H) 6.67 (s, 1H) 3.10 (s, 2H) 2.64 (m, 2H) 242 (m, 2H) 2.34 (s, 6H) 2.29 (s, 3H) 1.97 (m, 2H); MS ESI(+) m/z 496.0 [M+H]+.

Example 63

N$^1$-(2-chloro-4-{5-chloro-4-[2-(1-hydroxycyclobutyl)-1,3-thiazol-5-yl]-1H-pyrrolo[2,3-b]pyridin-2-yl}phenyl)-N$^2$,N$^2$-dimethylglycinamide

Example 63A 2-chloro-4-(4,4,5,5-tetramethyl-1,3,2-dioxaborolan-2-yl)aniline

The title compound was prepared as described in Example 52B, substituting 4-bromo-2-chloroaniline for 1-(5-bromoindolin-1-yl)-2-(dimethylamino)ethanone (Example 52A). MS DCI(+) m/z 254.1 [M+H]+.

Example 63B 2-chloro-4-(5-chloro-4-(2-(1-(methoxymethoxy)cyclobutyl)thiazol-5-yl)-1-tosyl-1H-pyrrolo[2,3-b]pyridin-2-yl)aniline The title compound was prepared as described in Example 1G, substituting 2-chloro-4-(4,4,5,5-tetramethyl-1,3,2-dioxaborolan-2-yl)aniline (Example 63A) for 4-(2-(4-(4,4,5,5-tetramethyl-1,3,2-dioxaborolan-2-yl)-1H-pyrazol-1-yl)ethyl)morpholine. MS ESI(+) m/z 629.1 [M+H]+.

Example 63C 2-chloro-4-(5-chloro-4-(2-(1-(methoxymethoxy)cyclobutyl)thiazol-5-yl)-1H-pyrrolo[2,3-b]pyridin-2-yl)aniline The title compound was prepared as described in Example 1I, substituting 2-chloro-4-(5-chloro-4-(2-(1-(methoxymethoxy)cyclobutyl)thiazol-5-yl)-1-tosyl-1H-pyrrolo[2,3-b]pyridin-2-yl)aniline (Example 63B) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 475.0 [M+H]+.

Example 63D

N-(2-chloro-4-(5-chloro-4-(2-(1-(methoxymethoxy)cyclobutyl)thiazol-5-yl)-1H-pyrrolo[2,3-b]pyridin-2-yl)phenyl)-2-(dimethylamino)acetamide The title compound was prepared as described in Example 60C, substituting 2-chloro-4-(5-chloro-4-(2-(1-(methoxymethoxy)cyclobutyl)thiazol-5-yl)-1H-pyrrolo[2,3-b]pyridin-2-yl)aniline (Example 63C) for 4-(5-chloro-4-(2-(1-(methoxymethoxy)cyclobutyl)thiazol-5-yl)-1H-pyrrolo[2,3-b]pyridin-2-yl)-3-fluoroaniline (Example 60B). MS ESI(+) m/z 560.1 [M+H]+.

Example 63E

N-(2-chloro-4-(5-chloro-4-(2-(1-hydroxycyclobutyl) thiazol-5-yl)-1H-pyrrolo[2,3-b]pyridin-2-yl)phenyl)-2-(dimethylamino)acetamide The title compound was prepared as described in Example 22E, substituting N-(2-chloro-4-(5-chloro-4-(2-(1-(methoxymethoxy)cyclobutyl)thiazol-5-yl)-1H-pyrrolo[2,3-b]pyridin-2-yl)phenyl)-2-(dimethylamino)acetamide (Example 63D) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (400 MHz, DMSO-d$_6$) ppm 12.59 (s, 1H) 9.86 (s, 1H) 8.33 (s, 1H) 8.29 (s, 1H) 8.27 (s, 1H) 8.26 (d, 1H) 8.00 (dd, 1H) 7.17 (s, 1H) 6.69 (s, 1H) 3.15 (s, 2H) 2.63 (m, 2H) 2.42 (m, 2H) 2.36 (s, 6H) 1.99 (m, 2H); MS ESI(+) m/z 516.1 [M+H]$^+$.

Example 64

N$^1$-(4-{5-chloro-4-[2-(1-hydroxycyclobutyl)-1,3-thiazol-5-yl]-1H-pyrrolo[2,3-b]pyridin-2-yl}-2-fluorophenyl)-N$^2$,N$^2$-dimethylglycinamide

Example 64A 4-(5-chloro-4-(2-(1-(methoxymethoxy)cyclobutyl) thiazol-5-yl)-1-tosyl-1H-pyrrolo[2,3-b]pyridin-2-yl)-2-fluoroaniline The title compound was prepared as described in Example 1G, substituting 2-fluoro-4-(4,4,5,5-tetramethyl-1,3,2-dioxaborolan-2-yl)aniline for 4-(2-(4-(4,4,5,5-tetramethyl-1,3,2-dioxaborolan-2-yl)-1H-pyrazol-1-yl)ethyl)morpholine. MS ESI(+) m/z 613.1 [M+H]$^+$.

Example 64B 4-(5-chloro-4-(2-(1-(methoxymethoxy)cyclobutyl) thiazol-5-yl)-1H-pyrrolo[2,3-b]pyridin-2-yl)-2-fluoro aniline The title compound was prepared as described in Example 1I, substituting 4-(5-chloro-4-(2-(1-(methoxymethoxy)cyclobutyl)thiazol-5-yl)-1-tosyl-1H-pyrrolo[2,3-b]pyridin-2-yl)-2-fluoro aniline (Example 64A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 459.0 [M+H]$^+$.

Example 64C

N-(4-(5-chloro-4-(2-(1-(methoxymethoxy)cyclobutyl)thiazol-5-yl)-1H-pyrrolo[2,3-b]pyridin-2-yl)-2-fluorophenyl)-2-(dimethylamino)acetamide The title compound was prepared as described in Example 60C, substituting 4-(5-chloro-4-(2-(1-(methoxymethoxy)cyclobutyl)thiazol-5-yl)-1H-pyrrolo[2,3-b]pyridin-2-yl)-2-fluoroaniline (Example 64B) for 4-(5-chloro-4-(2-(1-(methoxymethoxy)cyclobutyl)thiazol-5-yl)-1H-pyrrolo[2,3-b]pyridin-2-yl)-3-fluoroaniline (Example 60B). MS ESI(+) m/z 544.1 [M+H]$^+$.

Example 64D

N-(4-(5-chloro-4-(2-(1-hydroxycyclobutyl)thiazol-5-yl)-1H-pyrrolo[2,3-b]pyridin-2-yl)-2-fluorophenyl)-2-(dimethylamino)acetamide The title compound was prepared as described in Example 22E, substituting N-(4-(5-chloro-4-(2-(1-(methoxymethoxy) cyclobutyl)thiazol-5-yl)-1H-pyrrolo[2,3-b]pyridin-2-yl)-2-fluorophenyl)-2-(dimethylamino)acetamide (Example 64C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (400 MHz, DMSO-d$_6$) ppm 12.57 (s, 1H) 9.63 (s, 1H) 8.34 (s, 1H) 8.27 (s, 1H) 8.10 (t, 1H) 8.01 (dd, 1H) 7.85 (dd, 1H) 7.15 (s, 1H) 6.68 (s, 1H) 3.14 (s, 2H) 2.64 (m, 2H) 2.42 (m, 2H) 2.32 (s, 6H) 198 (m, 2H); MS ESI(+) m/z 500.1 [M+H]$^+$.

Example 65

1-[5-(5-fluoro-2-{1-[2-(4-methylpiperazin-1-yl)-2-oxo ethyl]-1H-pyrazol-4-yl}-1H-pyrrolo[2,3-b]pyridin-4-yl)-1,3-thiazol-2-yl]cyclobutanol

Example 65A ethyl 2-(4-(5-fluoro-4-(2-(1-hydroxycyclobutyl)thiazol-5-yl)-1-tosyl-1H-pyrrolo[2,3-b]pyridin-2-yl)-1H-pyrazol-1-yl)acetate To a stirred ambient solution of 1-(5-(5-fluoro-2-iodo-1-tosyl-1H-pyrrolo[2,3-b]pyridin-4-yl)thiazol-2-yl)cyclobutanol (Example 59A) (940 mg, 1.651 mmol) and ethyl 2-(4-(4,4,5,5-tetramethyl-1,3,2-dioxaborolan-2-yl)-1H-pyrazol-1-yl)acetate (694 mg, 2.476 mmol) in N,N-dimethylformamide (11.5 mL) was added saturated aqueous bicarbonate solution (3.83 mL) followed by bis(triphenylphosphine)palladium dichloride (81 mg, 0.116 mmol). The mixture was heated to 70° C. for 4 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was purified by flash chromatography on silica gel, eluting with a gradient of 0 to 95% ethyl acetate in hexane, to give the title compound. MS ESI(+) m/z 596.1 [M+H]$^+$.

Example 65B 2-(4-(5-fluoro-4-(2-(1-hydroxycyclobutyl)thiazol-5-yl)-1H-pyrrolo[2,3-b]pyridin-2-yl)-1H-pyrazol-1-yl) acetic acid A solution of ethyl 2-(4-(5-fluoro-4-(2-(1-hydroxycyclobutyl)thiazol-5-yl)-1-tosyl-1H-pyrrolo[2,3-b]pyridin-2-yl)-1H-pyrazol-1-yl)acetate (Example 65A) (734 mg, 1.232 mmol) in methanol (8.2 mL) and 2N aqueous sodium hydroxide solution (2.16 mL, 4.31 mmol) was heated by microwave irradiation (Biotage, Initiator) in a sealed vessel to 105° C. for 5 minutes. The reaction was cooled to room temperature and concentrated to a volume of 2 mL. The solution was diluted with 10% aqueous HCl. The solid was filtered and air-dried to give the title compound. MS ESI(+) m/z 413.9 [M+H]+.

Example 65C 2-(4-(5-fluoro-4-(2-(1-hydroxycyclobutyl)thiazol-5-yl)-1H-pyrrolo[2,3-b]pyridin-2-yl)-1H-pyrazol-1-yl)-1-(4-methylpiperazin-1-yl)ethanone The title compound was prepared as described in Example 19, substituting 2-(4-(5-fluoro-4-(2-(1-hydroxycyclobutyl)thiazol-5-yl)-1H-pyrrolo[2,3-b]pyridin-2-yl)-1H-pyrazol-1-yl)acetic acid (Example 65B) for 4-(5-chloro-4-(2-(1-hydroxycyclobutyl)thiazol-5-yl)-1H-pyrrolo[2,3-b]pyridin-2-yl)benzoic acid (Example 16C). $^1$H NMR (300 MHz, DMSO-$d_6$) δ 12.30 (bs, 1H), 8.43 (d, J=0.9 Hz, 1H), 8.27 (s, 1H), 8.20 (d, J=3.6 Hz, 0H), 8.10 (s, 1H), 7.05 (s, 1H), 6.66 (s, 1H), 5.21 (s, 2H), 3.55-3.43 (m, 4H), 2.67-2.55 (m, 2H), 2.47-2.24 (m, 6H), 2.20 (s, 3H), 2.06-1.86 (m, 2H); MS ESI(+) m/z 496.1 [M+H]+.

Example 66

2-(4-{5-fluoro-4-[2-(1-hydroxycyclobutyl)-1,3-thiazol-5-yl]-1H-pyrrolo[2,3-b]pyridin-2-yl}-1H-pyrazol-1-yl)-N-(methylsulfonyl)acetamide To a solution of 2-(4-(5-fluoro-4-(2-(1-hydroxycyclobutyl)thiazol-5-yl)-1H-pyrrolo[2,3-b]pyridin-2-yl)-1H-pyrazol-1-yl)acetic acid (Example 65B) (75 mg, 0.181 mmol) in N,N-dimethylformamide (1.0 mL) was added methanesulfonamide (20.7 mg, 0.218 mmol), 4-dimethylaminopyridine (66.5 mg, 0.544 mmol), and N-(3-dimethylaminopropyl)-N'-ethylcarbodiimide hydrochloride (52.2 mg, 0.272 mmol). The solution was heated to 45° C. for 4 hours. The reaction was cooled to room temperature and diluted with dimethyl sulfoxide (1 mL). The resulting solution was purified by reverse phase high performance liquid chromatography (RP HPLC, 19×150 mm Atlantis Prep T3 OBD 5 um column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound. $^1$H NMR (300 MHz, DMSO-$d_6$) δ 12.35 (s, 1H), 12.30-12.18 (m, 1H), 8.43 (s, 1H), 8.35 (s, 1H), 8.22 (d, J=3.6 Hz, 1H), 8.16 (s, 1H), 7.07 (d, J=2.0 Hz, 1H), 6.67 (s, 1H), 5.10 (s, 2H), 3.29 (s, 3H), 2.64-2.56 (m, 2H), 2.46-2.32 (m, 2H), 2.05-1.87 (m, 2H); MS ESI(+) m/z 490.9 [M+H]+.

Example 67

1-[5-(5-chloro-2-{1-[(1-methylpiperidin-4-yl)carbonyl]-1,2,3,6-tetrahydropyridin-4-yl}-1H-pyrrolo[2,3-b]pyridin-4-yl)-1,3-thiazol-2-yl]cyclobutanol A mixture of 1-{5-[5-chloro-2-(1,2,3,6-tetrahydropyridin-4-yl)-1H-pyrrolo[2,3-b]pyridin-4-yl]-1,3-thiazol-2-yl}cyclobutanol (Example 89C) (0.02 g, 0.052 mmol), 1-methylpiperidine-4-carboxylic acid hydrochloride (0.011 g, 0.059 mmol), N-methylmorpholine (0.023 mL, 0.207 mmol), and 1-hydroxybenzotriazole hydrate (0.004 g, 0.026 mmol) in N,N-dimethylformamide (0.75 mL), was treated with N-(3-dimethylaminopropyl)-N'-ethylcarbodiimide hydrochloride (0.015 g, 0.078 mmol), and the reaction was stirred at ambient temperature for 4 hours. The reaction was concentrated under reduced pressure. The concentrate was purified by reverse-phase HPLC on a Phenomenex C18 column (3×15 cm, 10 m particle size) using a gradient of 15% to 55% acetonitrile in 0.15% aqueous trifluoroacetic acid to provide the title compound as a trifluoroacetic acid salt. $^1$H NMR (300 MHz, methanol-$d_4$) ppm 1.91-2.15 (m, 6H), 2.39-2.52 (m, 2H), 2.60 (m, 1H), 2.67-2.77 (m, 3H), 2.89 (s, 3H), 3.01-3.14 (m, 3H), 3.51-3.64 (m, 2H), 3.80-3.88 (m, 2H), 4.29 (m, 1H), 4.39 (m, 1H), 6.46 (m, 1H), 6.56 (m, 1H), 8.09 (s, 1H), 8.26 (s, 1H); MS ESI(+) m/z 512.1 [M+H]+.

Example 68 N'-(4-{5-chloro-4-[2-(1-hydroxycyclobutyl)-1,3-thiazol-5-yl]-1H-pyrrolo[2,3-b]pyridin-2-yl}-3-methoxyphenyl)-N$^2$,N$^2$-dimethylglycinamide

Example 68A 3-methoxy-4-(4,4,5,5-tetramethyl-1,3,2-dioxaborolan-2-yl)aniline The title compound was prepared as described in Example 52B, substituting 4-bromo-3-methoxyaniline for 1-(5-bromoindolin-1-yl)-2-(dimethylamino)ethanone (Example 52A). MS DCI(+) m/z 250.2 [M+H]+.

Example 68B 4-(5-chloro-4-(2-(1-(methoxymethoxy)cyclobutyl)thiazol-5-yl)-1-tosyl-1H-pyrrolo[2,3-b]pyridin-2-yl)-3-methoxyaniline ne The title compound was prepared as described in Example 1G, substituting 3-methoxy-4-(4,4,5,5-tetramethyl-1,3,2-dioxaborolan-2-yl)aniline (Example 68A) for 4-(2-(4-(4,4,5,5-tetramethyl-1,3,2-dioxaborolan-2-yl)-1H-pyrazol-1-yl)ethyl)morpholine. MS ESI(+) m/z 625.1 [M+H]+.

Example 68C 4-(5-chloro-4-(2-(1-(methoxymethoxy)cyclobutyl)thiazol-5-yl)-1H-pyrrolo[2,3-b]pyridin-2-yl)-3-methoxyaniline The title compound was prepared as described in Example 1I, 4-(5-chloro-4-(2-(1-(methoxymethoxy)cyclobutyl)thiazol-5-yl)-1-tosyl-1H-pyrrolo[2,3-b]pyridin-2-yl)-3-methoxyaniline (Example 68B) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). MS ESI(+) m/z 471.0 [M+H]+.

Example 68D

N-(4-(5-chloro-4-(2-(1-(methoxymethoxy)cyclobutyl)thiazol-5-yl)-1H-pyrrolo[2,3-b]pyridin-2-yl)-3-methoxyphenyl)-2-(dimethylamino)acetamide The title compound was prepared as described in Example 60C, substituting 4-(5-chloro-4-(2-(1-(methoxymethoxy)cyclobutyl)thiazol-5-yl)-1H-pyrrolo[2,3-b]pyridin-2-yl)-3-methoxyaniline (Example 68C) for 4-(5-chloro-4-(2-(1-(methoxymethoxy)cyclobutyl)thiazol-5-yl)-1H-pyrrolo[2,3-b]pyridin-2-yl)-3-fluoroaniline (Example 60B). MS ESI(+) m/z 556.1 [M+H]+.

Example 68E

N-(4-(5-chloro-4-(2-(1-hydroxycyclobutyl)thiazol-5-yl)-1H-pyrrolo[2,3-b]pyridin-2-yl)-3-methoxyphenyl)-2-(dimethylamino)acetamide The title compound was prepared as described in Example 22E, substituting N-(4-(5-chloro-4-(2-(1-(methoxymethoxy)cyclobutyl)thiazol-5-yl)-1H-pyrrolo[2,3-b]pyridin-2-yl)-3-methoxyphenyl)-2-(dimethylamino)acetamide (Example 68D) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-$d_6$) ppm 12.10 (s, 1H) 9.89 (s, 1H) 8.30 (s, 1H) 8.22 (s, 1H) 7.81 (d, 1H) 7.61 (d, 1H) 7.44 (dd, 1 H) 6.97 (d, 1H) 6.67 (s, 1H) 3.89 (s, 3H) 3.10 (s, 2H) 2.63 (m, 2H) 2.41 (m, 2H) 2.30 (s, 6H) 1.97 (m, 2H); MS ESI(+) m/z 512.0 [M+H]$^+$.

Example 69

1-(5-{5-chloro-2-[4-(tetrahydrofuran-3-yloxy)phenyl]-1H-pyrrolo[2,3-b]pyridin-4-yl}-1,3-thiazol-2-yl)cyclobutanol

Example 69A 4-(5-chloro-4-(2-(1-(methoxymethoxy)cyclobutyl)thiazol-5-yl)-1-tosyl-1H-pyrrolo[2,3-b]pyridin-2-yl)phenol The title compound was prepared as described in Example 1G, substituting 4-hydroxyphenylboronic acid pinacol ester for 4-(2-(4-(4,4,5,5-tetramethyl-1,3,2-dioxaborolan-2-yl)-1H-pyrazol-1-yl)ethyl)morpholine. MS ESI(+) m/z 596.1 [M+H]$^+$.

Example 69B 5-(5-chloro-2-(4-(tetrahydrofuran-3-yloxy)phenyl)-1-tosyl-1H-pyrrolo[2,3-b]pyridin-4-yl)-2-(1-(methoxymethoxy)cyclobutyl)thiazole A solution of 4-(5-chloro-4-(2-(1-(methoxymethoxy)cyclobutyl)thiazol-5-yl)-1-tosyl-1H-pyrrolo[2,3-b]pyridin-2-yl)phenol (Example 69A) (60 mg, 0.101 mmol), tetrahydrofuran-3-ol (12 mg, 0.131 mmol), and triphenylphosphine (34.3 mg, 0.131 mmol) in anhydrous tetrahydrofuran (1 mL) was treated with diisopropyl azodicarboxylate (0.025 mL, 0.131 mmol). The reaction was stirred for 16 hours at ambient temperature. The reaction treated with more tetrahydrofuran-3-ol (12 mg, 0.131 mmol), diisopropyl azodicarboxylate (0.025 mL, 0.131 mmol) and triphenylphosphine (34.3 mg, 0.131 mmol), and the reaction was warmed to 70° C. for 5 hours. The reaction was cooled, diluted with ethyl acetate, and washed with water and brine. The organic layer dried with sodium sulfate, filtered, and concentrated under reduced pressure. The residue was purified by flash chromatography on silica gel, eluting with a gradient of 30 to 40% ethyl acetate in hexanes, to give the title compound. MS ESI(+) m/z 666.1 [M+H]$^+$.

Example 69C 5-(5-chloro-2-(4-(tetrahydrofuran-3-yloxy)phenyl)-1H-pyrrolo[2,3-b]pyridin-4-yl)-2-(1-(methoxymethoxy)cyclobutyl)thiazole The title compound was prepared as described in Example 47B, substituting 5-(5-chloro-2-(4-(tetrahydrofuran-3-yloxy)phenyl)-1-tosyl-1H-pyrrolo[2,3-b]pyridin-4-yl)-2-(1-(methoxymethoxy)cyclobutyl)thiazole (Example 69B) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). MS ESI(+) m/z 511.0 [M+H]$^+$.

Example 69D 1-(5-(5-chloro-2-(4-(tetrahydro furan-3-yloxy)phenyl)-1H-pyrrolo[2,3-b]pyridin-4-yl)thiazol-2-yl)cyclobutanol The title compound was prepared as described in Example 22E, substituting 5-(5-chloro-2-(4-(tetrahydrofuran-3-yloxy)phenyl)-1H-pyrrolo[2,3-b]pyridin-4-yl)-2-(1-(methoxymethoxy)cyclobutyl)thiazole (Example 69C) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-$d_6$) ppm 12.47 (s, 1H) 8.29 (s, 1H) 8.25 (s, 1H) 7.94 (d, 2H) 7.02 (d, 2H) 6.95 (d, 1H) 6.67 (s, 1H) 5.11 (m, 1H) 3.93-3.75 (m, 4H) 2.63 (m, 2H) 2.41 (m, 2H) 2.26 (m, 1H) 1.97 (m, 3H); MS ESI(+) m/z 468.0 [M+H]$^+$.

Example 70

1-(5-{5-chloro-2-[4-(tetrahydrofuran-2-ylmethoxy)phenyl]-1H-pyrrolo[2,3-b]pyridin-4-yl}-1,3-thiazol-2-yl)cyclobutanol

Example 70A 5-(5-chloro-2-(4-((tetrahydrofuran-2-yl)methoxy)phenyl)-1-tosyl-1H-pyrrolo[2,3-b]pyridin-4-yl)-2-(1-(methoxymethoxy)cyclobutyl)thiazole The title compound was prepared as described in Example 69B, substituting (tetrahydrofuran-2-yl)methanol for tetrahydrofuran-3-ol. MS ESI(+) m/z 680.1 [M+H]$^+$.

Example 70B 5-(5-chloro-2-(4-((tetrahydrofuran-2-yl)methoxy)phenyl)-1H-pyrrolo[2,3-b]pyridin-4-yl)-2-(1-(methoxymethoxy)cyclobutyl)thiazole The title compound was prepared as described in Example 47B, substituting 5-(5-chloro-2-(4-((tetrahydrofuran-2-yl)methoxy)phenyl)-1-tosyl-1H-pyrrolo[2,3-b]pyridin-4-yl)-2-(1-(methoxymethoxy)cyclobutyl)thiazole (Example 70A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). MS ESI(+) m/z 525.0 [M+H]$^+$.

Example 70C 1-(5-(5-chloro-2-(4-((tetrahydro furan-2-yl)methoxy)phenyl)-1H-pyrrolo[2,3-b]pyridin-4-yl)thiazol-2-yl)cyclobutanol The title compound was prepared as described in Example 22E, substituting 5-(5-chloro-2-(4-((tetrahydrofuran-2-yl)

methoxy)phenyl)-1H-pyrrolo[2,3-b]pyridin-4-yl)-2-(1-(methoxymethoxy)cyclobutyl)thiazole (Example 70B) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-$d_6$) ppm 12.45 (s, 1H) 8.29 (s, 1H) 8.25 (s, 1H) 7.94 (d, 2H) 7.04 (d, 2H) 6.94 (d, 1H) 6.66 (s, 1H) 4.17 (m, 1H) 4.00 (m, 2H) 3.79 (m, 1H) 3.69 (m, 1H) 2.63 (m, 2H) 2.41 (m, 2H) 1.80-2.06 (m, 5H) 1.69 (m, 1H); MS ESI(+) m/z 482.0 [M+H]$^+$.

Example 71

1-(5-{5-chloro-2-[4-(1,4-dioxan-2-ylmethoxy)phenyl]-1H-pyrrolo[2,3-b]pyridin-4-yl}-1,3-thiazol-2-yl)cyclobutanol Example 71A 5-(2-(4-((1,4-dioxan-2-yl)methoxy)phenyl)-5-chloro-1-tosyl-1H-pyrrolo[2,3-b]pyridin-4-yl)-2-(1-(methoxymethoxy)cyclobutyl)thiazole The title compound was prepared as described in Example 69B, substituting (1,4-dioxan-2-yl)methanol for tetrahydrofuran-3-ol. MS ESI(+) m/z 696.1 [M+H]$^+$.

Example 71B 5-(2-(4-((1,4-dioxan-2-yl)methoxy)phenyl)-5-chloro-1H-pyrrolo[2,3-b]pyridin-4-yl)-2-(1-(methoxymethoxy)cyclobutyl)thiazole The title compound was prepared as described in Example 47B, substituting 5-(2-(4-((1,4-dioxan-2-yl)methoxy)phenyl)-5-chloro-1-tosyl-1H-pyrrolo[2,3-b]pyridin-4-yl)-2-(1-(methoxymethoxy)cyclobutyl)thiazole (Example 71A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). MS ESI(+) m/z 541.0 [M+H]$^+$.

Example 71C 1-(5-(2-(4-((1,4-dioxan-2-yl)methoxy)phenyl)-5-chloro-1H-pyrrolo[2,3-b]pyridin-4-yl)thiazol-2-yl)cyclobutanol The title compound was prepared as described in Example 22E, substituting 5-(2-(4-((1,4-dioxan-2-yl)methoxy)phenyl)-5-chloro-1H-pyrrolo[2,3-b]pyridin-4-yl)-2-(1-(methoxymethoxy)cyclobutyl)thiazole (Example 71B) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-$d_6$) ppm 12.46 (s, 1H) 8.29 (s, 1H) 8.25 (s, 1H) 7.94 (d, 2H) 7.04 (d, 2H) 6.95 (d, 1H) 6.66 (s, 1H) 4.03 (m, 2H) 3.85 (m, 2H) 3.78 (m, 1H) 3.65 (m, 2H) 3.51 (m, 1H) 3.42 (m, 1H) 2.63 (m, 2H) 2.40 (m, 2H) 1.97 (m, 2H); MS ESI(+) m/z 498.0 [M+H]$^+$.

Example 72

1-[5-(5-chloro-2-{4-[(1-methylpiperidin-4-yl)oxy]phenyl}-1H-pyrrolo[2,3-b]pyridin-4-yl)-1,3-thiazol-2-yl]cyclobutanol Example 72A 5-(5-chloro-2-(4-(1-methylpiperidin-4-yloxy)phenyl)-1-tosyl-1H-pyrrolo[2,3-b]pyridin-4-yl)-2-(1-(methoxymethoxy)cyclobutyl)thiazole The title compound was prepared as described in Example 69B, substituting 1-methylpiperidin-4-ol for tetrahydrofuran-3-ol. MS ESI(+) m/z 693.2 [M+H]$^+$.

Example 72B 5-(5-chloro-2-(4-(1-methylpiperidin-4-yloxy)phenyl)-1H-pyrrolo[2,3-b]pyridin-4-yl)-2-(1-(methoxymethoxy)cyclobutyl)thiazole The title compound was prepared as described in Example 47B, 5-(5-chloro-2-(4-(1-methylpiperidin-4-yloxy)phenyl)-1-tosyl-1H-pyrrolo[2,3-b]pyridin-4-yl)-2-(1-(methoxymethoxy)cyclobutyl)thiazole (Example 72A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). MS ESI(+) m/z 539.0 [M+H]$^+$.

Example 72C 1-(5-(5-chloro-2-(4-(1-methylpiperidin-4-yloxy)phenyl)-1H-pyrrolo[2,3-b]pyridin-4-yl)thiazol-2-yl)cyclobutanol The title compound was prepared as described in Example 22E, substituting 5-(5-chloro-2-(4-(1-methylpiperidin-4-yloxy)phenyl)-1H-pyrrolo[2,3-b]pyridin-4-yl)-2-(1-(methoxymethoxy)cyclobutyl)thiazole (Example 72B) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-$d_6$) ppm 12.46 (s, 1H) 8.28 (s, 1H) 8.24 (s, 1H) 7.92 (d, 2H) 7.04 (d, 2H) 6.93 (d, 1H) 6.68 (s, 1H) 4.47 (m, 1H) 2.63 (m, 4H) 2.41 (m, 2H) 2.23 (m, 2H) 2.20 (s, 3H) 1.96 (m, 4H) 1.66 (m, 2H); MS ESI(+) m/z 495.0 [M+H]$^+$.

Example 73

1-[5-(5-fluoro-2-{1-[2-(4-methyl-1,4-diazepan-1-yl)-2-oxoethyl]-1H-pyrazol-4-yl}-1H-pyrrolo[2,3-b]pyridin-4-yl)-1,3-thiazol-2-yl]cyclobutanol To a solution of 2-(4-(5-fluoro-4-(2-(1-hydroxycyclobutyl)thiazol-5-yl)-1H-pyrrolo[2,3-b]pyridin-2-yl)-1H-pyrazol-1-yl)acetic acid (Example 65B) (100 mg, 0.242 mmol) in N,N-dimethylformamide (783 µl) was added 1-methyl-1,4-diazepane (35.9 mg, 0.314 mmol), 4-methylmorpholine (80 µl, 0.726 mmol), 1-hydroxybenzotriazole hydrate (55.6 mg, 0.363 mmol), and N-(3-dimethylaminopropyl)-N'-ethylcarbodiimide hydrochloride (69.6 mg, 0.363 mmol). The reaction was cooled to room temperature and diluted with dimethyl sulfoxide (1 mL). The resulting solution was purified by reverse phase high performance liquid chromatography (RP HPLC, 19×150 mm Atlantis Prep T3 OBD 5 um column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound. $^1$H NMR (300 MHz, DMSO-$d_6$) δ 12.29 (bs, 1H), 8.43 (s, 1H), 8.29 (s, 1H), 8.20 (d, J=3.6 Hz, 1H), 8.10 (s, 1H), 7.05 (s, 1H), 6.65 (s, 1H), 5.22-5.17 (m, 2H), 3.67-3.41 (m, 4H), 2.67-2.34 (m, 6H), 2.32-2.23 (m, 3H), 2.05-1.71 (m, 4H); MS ESI(+) m/z 510.1 [M+H]$^+$.

Example 74

1-{5-[5-chloro-2-(1,5-dimethyl-1H-pyrazol-4-yl)-1H-pyrrolo[2,3-b]pyridin-4-yl]-1,3-thiazol-2-yl}cyclobutanol

Example 74A 1-(5-(5-chloro-2-(1,5-dimethyl-1H-pyrazol-4-yl)-1-tosyl-1H-pyrrolo[2,3-b]pyridin-4-yl)thiazol-2-yl)cyclobutanol The title compound was prepared as described in Example 8B, substituting 1,5-dimethyl-4-(4,4,5,5-tetramethyl-1,3,2-dioxaborolan-2-yl)-1H-pyrazole for 4-formylphenylboronic acid. MS ESI(+) m/z 554.1 [M+H]$^+$.

Example 74B 1-(5-(5-chloro-2-(1,5-dimethyl-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1,5-dimethyl-1H-pyrazol-4-yl)-1-tosyl-1H-pyrrolo[2,3-b]pyridin-4-yl)thiazol-2-yl)cyclobutanol (Example 74A) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.24 (bs, 1H), 8.26 (s, 1H), 8.23 (s, 1H), 7.89 (s, 1H), 6.65 (s, 1H), 6.50 (s, 1H), 3.81 (s, 3H), 2.69-2.55 (m, 2H), 2.47 (s, 3H), 2.44-2.33 (m, 2H), 2.06-1.88 (m, 2H); MS ESI(+) m/z 400.0 [M+H]$^+$.

Example 75

1-{5-[5-chloro-2-(2,3-dihydro-1,4-benzodioxin-6-yl)-1H-pyrrolo[2,3-b]pyridin-4-yl]-1,3-thiazol-2-yl}cyclobutanol

Example 75A 5-(5-chloro-2-(2,3-dihydrobenzo[b][1,4]dioxin-6-yl)-1-tosyl-1H-pyrrolo[2,3-b]pyridin-4-yl)-2-(1-(methoxymethoxy)cyclobutyl)thiazole The title compound was prepared as described in Example 1G, substituting 2,3-dihydrobenzo[b][1,4]dioxin-6-ylboronic acid for 4-(2-(4-(4,4,5,5-tetramethyl-1,3,2-dioxaborolan-2-yl)-1H-pyrazol-1-yl)ethyl)morpholine. MS ESI(+) m/z 638.1 [M+H]$^+$.

Example 75B 5-(5-chloro-2-(2,3-dihydrobenzo[b][1,4]dioxin-6-yl)-1H-pyrrolo[2,3-b]pyridin-4-yl)-2-(1-(methoxymethoxy)cyclobutyl)thiazole The title compound was prepared as described in Example 47B, substituting 5-(5-chloro-2-(2,3-dihydrobenzo[b][1,4]dioxin-6-yl)-1-tosyl-1H-pyrrolo[2,3-b]pyridin-4-yl)-2-(1-(methoxymethoxy)cyclobutyl)thiazole (Example 75A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). MS ESI(+) m/z 483.1 [M+H]$^+$.

Example 75C 1-(5-(5-chloro-2-(2,3-dihydrobenzo[b][1,4]dioxin-6-yl)-1H-pyrrolo[2,3-b]pyridin-4-yl)thiazol-2-yl)cyclobutanol The title compound was prepared as described in Example 22E, substituting 1-(5-(5-chloro-2-(2,3-dihydrobenzo[b][1,4]dioxin-6-yl)-1H-pyrrolo[2,3-b]pyridin-4-yl)thiazol-2-yl)cyclobutanol (Example 75B) for 1 tert-butyl 3-(3-(5-chloro-4-(2-(1-(methoxymethoxy)cyclobutyl)thiazol-5-yl)-1H-pyrrolo[2,3-b]pyridin-2-yl)-1,2,4-oxadiazol-5-yl)piperidine-1-carboxylate (Example 22D). $^1$H NMR (500 MHz, DMSO-$d_6$) ppm 12.42 (s, 1H) 8.29 (s, 1H) 8.25 (s, 1H) 7.56 (d, 1H) 7.49 (dd, 1H) 6.94 (m, 2H) 6.66 (s, 1H) 4.29 (s, 4H) 2.63 (m, 2H) 2.41 (m, 2H) 1.97 (m, 2H); MS ESI(+) m/z 440.0 [M+H]$^+$.

Example 76

1-[5-(5-chloro-2-{4-[(3,3-difluoropiperidin-1-yl)methyl]-3-fluorophenyl}-1H-pyrrolo[2,3-b]pyridin-4-yl)-1,3-thiazol-2-yl]cyclobutanol The title compound was prepared as described in Examples 30A-30D, substituting 3,3-difluoropiperidine for 4-fluoropiperidine in Example 30B. $^1$H NMR (500 MHz, DMSO-$d_6$) δ 12.61 (s, 1H), 8.35 (s, 1H), 8.27 (s, 1H), 7.89 (d, 1H), 7.85 (d, 1H), 7.47 (t, 1H), 7.18 (s, 1H), 6.69 (s, 1H), 3.66 (s, 2H), 2.70-2.59 (m, 4H), 2.47-2.37 (m, 4H), 2.04-1.92 (m, 2H), 1.91-1.81 (m, 2H), 1.65 (s, 2H); MS APCI(+) m/z 533.33 (M+H)$^+$.

Example 77

4-(4-{5-chloro-4-[2-(1-hydroxycyclobutyl)-1,3-thiazol-5-yl]-1H-pyrrolo[2,3-b]pyridin-2-yl}-2-fluorobenzyl)piperazin-2-one The title compound was prepared as described in Examples 30A-30D, substituting piperazin-2-one for 4-fluoropiperidine in Example 30B. $^1$H NMR (500 MHz, DMSO-$d_6$) δ 12.62 (s, 1H), 8.36 (s, 1H), 8.28 (s, 1H), 7.92 (dd, 1H), 7.86 (dd, 1H), 7.76 (s, 1H), 7.51 (t, 1H), 7.20 (s, 1H), 6.68 (s, 1H), 3.63 (s, 2H), 3.19-3.13 (m, 2H), 2.97 (s, 2H), 2.67-2.57 (m, 4H), 2.47-2.37 (m, 2H), 2.05-1.92 (m, 2H). MS APCI(+) m/z 512.19 (M+H)$^+$.

Example 78

1-{5-[5-chloro-2-(4-{[3-(dimethylamino)pyrrolidin-1-yl]methyl}-3-fluorophenyl)-1H-pyrrolo[2,3-b]pyridin-4-yl]-1,3-thiazol-2-yl}cyclobutanol The title compound was prepared as described in Examples 30A-30D, except substituting N,N-dimethylpyrrolidin-3-amine for 4-fluoropiperidine in Example 30B. $^1$H NMR (500 MHz, DMSO-$d_6$) δ 12.73 (s, 1H), 10.64 (s, 1H), 8.39 (d, 1H), 8.30 (s, 1H), 8.06 (dd, 1H), 7.98 (t, 1H), 7.66 (dd, 1H), 7.32 (dd, 1H), 4.38 (d, 2H), 4.18-4.03 (m, 1H), 3.78-3.29 (m, 4H), 3.09 (s, 3H), 2.84 (s, 3H), 2.68-2.59 (m, 2H), 2.43 (dt, 2H), 2.37 (bs, 1H), 2.31 (bs, 1H), 2.09-1.90 (m, 2H). MS APCI(+) m/z 526.33 (M+H)$^+$.

Example 79

1-{5-[5-chloro-2-(3-fluoro-4-{[4-(trifluoromethyl) piperidin-1-yl]methyl}phenyl)-1H-pyrrolo[2,3-b] pyridin-4-yl]-1,3-thiazol-2-yl}cyclobutanol The title compound was prepared as described in Examples 30A-30D, except substituting 4-(trifluoromethyl)piperidine for 4-fluoropiperidine in Example 30B. $^1$H NMR (500 MHz, DMSO-d$_6$) δ 12.74 (s, 1H), 10.13-9.87 (m, 1H), 8.40 (s, 1H), 8.30 (s, 1H), 8.09 (dd, 1H), 8.02 (dd, 1H), 7.70 (d, 1H), 7.34 (d, 1H), 4.41 (s, 2H), 3.56 (d, 2H), 3.10 (t, 2H), 2.64 (s, 3H), 2.43 (dd, 2H), 2.06 (d, 2H), 2.03-1.93 (m, 2H), 1.82-1.69 (m, 2H). MS APCI(+) m/z 565.31 (M+H)$^+$.

Example 80

1-{5-[5-chloro-2-(3-fluoro-4-{[3-(trifluoromethyl) piperidin-1-yl]methyl}phenyl)-1H-pyrrolo[2,3-b] pyridin-4-yl]-1,3-thiazol-2-yl}cyclobutanol The title compound was prepared as described in Examples 30A-30D, except substituting 3-(trifluoromethyl)piperidine for 4-fluoropiperidine in Example 30B. $^1$H NMR (500 MHz, DMSO-d$_6$) δ 12.74 (s, 1H), 10.37 (bs, 1H), 8.40 (s, 1H), 8.30 (s, 1H), 8.08 (dd, 1H), 8.01 (dd, 1H), 7.70 (t, 1H), 7.34 (d, 1H), 4.46 (dd, 2H), 3.64 (d, 1H), 3.42 (d, 1H), 3.16 (t, 1H), 3.04 (t, 1H), 2.89 (s, 1H), 2.68-2.60 (m, 2H), 2.49-2.38 (m, 2H), 2.07-1.91 (m, 4H), 1.73 (d, 1H), 1.51 (dd, 1H). MS APCI(+) m/z 565.35 (M+H)$^+$.

Example 81

1-[5-(5-chloro-2-{3-fluoro-4-[(2-methylpiperidin-1-yl)methyl]phenyl}-1H-pyrrolo[2,3-b]pyridin-4-yl)-1,3-thiazol-2-yl]cyclobutanol The title compound was prepared as described in Examples 30A-30D, except substituting 2-methylpiperidine for 4-fluoropiperidine in Example 30B. $^1$H NMR (500 MHz, DMSO-d$_6$) δ 12.73 (s, 1H), 9.73-9.28 (m, 1H), 8.40 (s, 1H), 8.30 (s, 1H), 8.09 (dd, 1H), 8.01 (dd, 1H), 7.69 (t, 1H), 7.33 (d, 1H), 4.69 (d, 2H), 4.19 (dd, 1H), 3.38-3.06 (m, 2H), 2.98-2.86 (m, 1H), 2.67-2.59 (m, 2H), 2.46-2.39 (m, 2H), 2.06-1.90 (m, 3H), 1.62 (m, 4H), 1.49 (d, 2H), 1.40 (d, 1H); MS ESI(+) 540.1 (M+H)$^+$.

Example 82

1-(5-{5-chloro-2-[3-fluoro-4-(piperazin-1-ylmethyl) phenyl]-1H-pyrrolo[2,3-b]pyridin-4-yl}-1,3-thiazol-2-yl)cyclobutanol The title compound was prepared as described in Examples 30A-30D, except substituting 1-(piperazin-1-yl)ethanone for 4-fluoropiperidine in Example 30B. $^1$H NMR (500 MHz, DMSO-d$_6$) δ 12.71 (s, 1H), 8.97 (s, 2H), 8.39 (s, 1H), 8.29 (s, 1H), 8.02 (d, 1H), 7.95 (dd, 1H), 7.61 (t, 1H), 7.29 (d, 1H), 4.11 (s, 2H), 3.28 (s, 4H), 3.07 (s, 4H), 2.67-2.60 (m, 2H), 2.48-2.38 (m, 2H), 2.06-1.92 (m, 2H). MS APCI(+) m/z 498.33 (M+H)$^+$.

Example 83

1-[5-(5-chloro-2-{4-[(4-fluoropiperidin-1-yl)methyl] phenyl}-1H-pyrrolo[2,3-b]pyridin-4-yl)-1,3-thiazol-2-yl]cyclobutanol

Example 83A 1-(5-(5-chloro-2-(4-((4-fluoropiperidin-1-yl)methyl) phenyl)-1-tosyl-1H-pyrrolo[2,3-b]pyridin-4-yl)thiazol-2-yl)cyclobutanol The title compound was prepared as described in Example 8C, substituting 4-fluoropiperidine hydrochloride salt for pyrrolidine. MS APCI(+) m/z 651.4 [M+H]$^+$.

Example 83B 1-(5-(5-chloro-2-(4-((4-fluoropiperidin-1-yl)methyl) phenyl)-1H-pyrrolo[2,3-b]pyridin-4-yl)thiazol-2-yl) cyclobutanol The title compound was prepared as described in Example 8D, substituting 1-(5-(5-chloro-2-(4-((4-fluoropiperidin-1-yl)methyl)phenyl)-1-tosyl-1H-pyrrolo[2,3-b]pyridin-4-yl) thiazol-2-yl)cyclobutanol (Example 83A) for 1-(5-(5-chloro-2-(4-(pyrrolidin-1-ylmethyl)phenyl)-1-tosyl-1H-pyrrolo[2, 3-b]pyridin-4-yl)thiazol-2-yl)cyclobutanol (Example 8C). $^1$H NMR (300 MHz, DMSO-d$_6$) δ 12.55 (bs, 1H), 8.32 (s, 1H), 8.26 (s, 1H), 7.99-7.92 (m, 2H), 7.43-7.35 (m, 2H), 7.03 (s, 1H), 6.66 (s, 1H), 4.81-4.55 (m, 1H), 3.51 (bs, 2H), 2.69-2.24 (m, 8H), 2.04-1.66 (m, 6H); MS ESI(+) m/z 497.0 [M+H]$^+$.

Example 84

1-(5-{5-chloro-2-[1-(pyridin-2-ylmethyl)-1H-pyrazol-4-yl]-1H-pyrrolo[2,3-b]pyridin-4-yl}-1,3-thiazol-2-yl)cyclobutanol

Example 84A 2-((4-(4,4,5,5-tetramethyl-1,3,2-dioxaborolan-2-yl)-1H-pyrazol-1-yl)methyl)pyridine To a suspension of sodium hydride (0.096 ml, 5.15 mmol) in N,N-dimethylformamide (8.59 ml) was added 4-(4,4,5,5-tetramethyl-1,3,2-dioxaborolan-2-yl)-1H-pyrazole (0.5 g, 2.58 mmol). After 0.5 hours, 2-chloromethylpyridine hydrochloride salt (0.423 g, 2.58 mmol), and tetrabutylammonium iodide (0.095 g, 0.258 mmol) were added as solution in N,N-dimethylformamide (2 mL). The reaction was cooled to room temperature and diluted with ethyl acetate (10 mL). Water (10 mL) was added, and the layers were separated. The aqueous layer was extracted with additional ethyl acetate (2×30 mL). The combined organics were washed with water, dried with anhydrous sodium sulfate, filtered and concentrated under reduced pressure to give the title compound, which was used without further purification. MS ESI(+) m/z 285.9 [M+H]$^+$.

Example 84B 1-(5-(5-chloro-2-(1-(pyridin-2-ylmethyl)-1H-pyrazol-4-yl)-1-tosyl-1H-pyrrolo[2,3-b]pyridin-4-yl)thiazol-2-yl)cyclobutanol The title compound was prepared as described in Example 8B, substituting 2-((4-(4,4,5,5-tetramethyl-1,3,2-dioxaborolan-2-yl)-1H-pyrazol-1-yl)methyl)pyridine (Example 84A) for 4-formylphenylboronic acid. MS ESI(+) m/z 617.1 [M+H]+.

Example 84C 1-(5-(5-chloro-2-(1-(pyridin-2-ylmethyl)-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1-(pyridin-2-ylmethyl)-1H-pyrazol-4-yl)-1-tosyl-1H-pyrrolo[2,3-b]pyridin-4-yl)thiazol-2-yl)cyclobutanol (Example 84B) 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.36 (bs, 1H), 8.55 (dd, J=5.0, 1.6 Hz, 1H), 8.45 (s, 1H), 8.23 (s, 1H), 8.19 (s, 1H), 8.13 (s, 1H), 7.83-7.77 (m, 1H), 7.34 (ddd, J=7.5, 4.8, 0.9 Hz, 1H), 7.18 (d, J=7.8 Hz, 1H), 6.80 (s, 1H), 6.65 (s, 1H), 5.48 (s, 2H), 2.67-2.55 (m, 2H), 2.44-2.32 (m, 2H), 2.06-1.86 (m, 2H); MS ESI(+) m/z 463.0 [M+H]+.

Example 85

1-(5-{5-chloro-2-[1-(pyridin-3-ylmethyl)-1H-pyrazol-4-yl]-1H-pyrrolo[2,3-b]pyridin-4-yl}-1,3-thiazol-2-yl)cyclobutanol

Example 85A 3-((4-(4,4,5,5-tetramethyl-1,3,2-dioxaborolan-2-yl)-1H-pyrazol-1-yl)methyl)pyridine The title compound was prepared as described in Example 84A, substituting 3-chloromethylpyridine hydrochloride salt for 2-chloromethylpyridine hydrochloride salt. MS ESI(+) m/z 285.9 [M+H]+.

Example 85B 1-(5-(5-chloro-2-(1-(pyridin-3-ylmethyl)-1H-pyrazol-4-yl)-1-tosyl-1H-pyrrolo[2,3-b]pyridin-4-yl)thiazol-2-yl)cyclobutanol The title compound was prepared as described in Example 8B, substituting 3-((4-(4,4,5,5-tetramethyl-1,3,2-dioxaborolan-2-yl)-1H-pyrazol-1-yl)methyl)pyridine (Example 85A) for 4-formylphenylboronic acid. MS ESI(+) m/z 617.1 [M+H]+.

Example 85C 1-(5-(5-chloro-2-(1-(pyridin-3-ylmethyl)-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1-(pyridin-3-ylmethyl)-1H-pyrazol-4-yl)-1-tosyl-1H-pyrrolo[2,3-b]pyridin-4-yl)thiazol-2-yl)cyclobutanol (Example 85B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.34 (bs, 1H), 8.58-8.56 (m, 1H), 8.53 (dd, J=4.8, 1.6 Hz, 1H), 8.44 (s, 1H), 8.23 (s, 1H), 8.18 (s, 1H), 8.12 (d, J=0.7 Hz, 1H), 7.73-7.67 (m, 1H), 7.40 (ddd, J=7.8, 4.8, 0.9 Hz, 1H), 6.77 (s, 1H), 6.64 (s, 1H), 5.44 (s, 2H), 2.66-2.56 (m, 2H), 2.45-2.33 (m, 2H), 2.03-1.90 (m, 2H); MS ESI(+) m/z 463.0 [M+H]+.

Example 86

1-(5-{5-chloro-2-[1-(pyridin-4-ylmethyl)-1H-pyrazol-4-yl]-1H-pyrrolo[2,3-b]pyridin-4-yl}-1,3-thiazol-2-yl)cyclobutanol

Example 86A 4-((4-(4,4,5,5-tetramethyl-1,3,2-dioxaborolan-2-yl)-1H-pyrazol-1-yl)methyl)pyridine The title compound was prepared as described in Example 84A, substituting 3-chloromethylpyridine hydrochloride salt for 2-chloromethylpyridine hydrochloride salt. MS ESI(+) m/z 285.9 [M+H]+.

Example 86B 1-(5-(5-chloro-2-(1-(pyridin-4-ylmethyl)-1H-pyrazol-4-yl)-1-tosyl-1H-pyrrolo[2,3-b]pyridin-4-yl)thiazol-2-yl)cyclobutanol The title compound was prepared as described in Example 8B, substituting 4-((4-(4,4,5,5-tetramethyl-1,3,2-dioxaborolan-2-yl)-1H-pyrazol-1-yl)methyl)pyridine (Example 86A) for 4-formylphenylboronic acid. MS ESI(+) m/z 617.1 [M+H]+.

Example 86C 1-(5-(5-chloro-2-(1-(pyridin-4-ylmethyl)-1H-pyrazol-4-yl)-1H-pyrrolo[2,3-b]pyridin-4-yl)thiazol-2-yl)cyclobutanol The title compound was prepared as described in Example 8D, substituting 1-(5-(5-chloro-2-(1-(pyridin-4-ylmethyl)-1H-pyrazol-4-yl)-1-tosyl-1H-pyrrolo[2,3-b]pyridin-4-yl)thiazol-2-yl)cyclobutanol (Example 86B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.37 (bs, 1H), 8.58-8.52 (m, 2H), 8.46 (d, J=0.7 Hz, 1H), 8.24 (s, 1H), 8.19 (s, 1H), 8.16 (d, J=0.5 Hz, 1H), 7.22-7.16 (m, 2H), 6.80 (s, 1H), 6.65 (s, 1H), 5.47 (s, 2H), 2.67-2.56 (m, 2H), 2.47-2.33 (m, 2H), 2.00-1.97 (m, 2H); MS ESI(+) m/z 463.0 [M+H]+.

Example 87

1-[5-(5-chloro-2-pyrazolo[1,5-a]pyridin-3-yl-1H-pyrrolo[2,3-b]pyridin-4-yl)-1,3-thiazol-2-yl]cyclobutanol

Example 87A 1-(5-(5-chloro-2-(pyrazolo[1,5-a]pyridin-3-yl)-1-tosyl-1H-pyrrolo[2,3-b]pyridin-4-yl)thiazol-2-yl)cyclobutanol The title compound was prepared as described in Example 8B, substituting 3-(4,4,5,5-tetramethyl-1,3,2-dioxaborolan-2-yl)pyrazolo[1,5-a]pyridine for 4-formylphenylboronic acid. MS ESI(+) m/z 576.1 [M+H]+.

Example 87B 1-(5-(5-chloro-2-(pyrazolo[1,5-a]pyridin-3-yl)-1H-pyrrolo[2,3-b]pyridin-4-yl)thiazol-2-yl)cyclobutanol The title compound was prepared as described in Example 8D, substituting 1-(5-(5-chloro-2-(pyrazolo[1,5-a]pyridin-3-yl)-1-tosyl-1H-pyrrolo[2,3-b]pyridin-4-yl)thiazol-2-yl)cyclobutanol (Example 87A) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-$d_6$) δ 12.45 (s, 1H), 8.75-8.68 (m, 1H), 8.52 (d, J=2.3 Hz, 1H), 8.36-8.26 (m, 1H), 8.21 (s, 1H), 8.12-8.04 (m, 1H), 7.40-7.31 (m, 1H), 7.01-6.88 (m, 1H), 6.74 (bs, 1H), 6.54 (s, 1H), 2.70-2.58 (m, 2H), 2.46-2.33 (m, 2H), 2.03-1.89 (m, 2H); MS ESI(+) m/z 421.9 [M+H]$^+$.

Example 88

3-[5-(5-fluoro-1H-pyrrolo[2,3-b]pyridin-4-yl)-1,3-thiazol-2-yl]azetidin-3-ol

The title compound was prepared as described in Examples 1D-1E and 1H-1I, except substituting 5-fluoro-4-iodo-1H-pyrrolo[2,3-b]pyridine for 5-chloro-4-iodo-1H-pyrrolo[2,3-b]pyridine in Example 1D and Example 54A for 2-(1-(methoxymethoxy)cyclobutyl)-5-(tributylstannyl)thiazole in Example 1E. $^1$H NMR (300 MHz, DMSO-$d_6$) δ 12.16 (s, 1H), 9.46 (s, 1H), 9.32 (s, 1H), 8.54 (s, 1H), 8.37 (d, 1H), 7.76-7.73 (m, 1H), 6.82 (dd, 1H), 4.55-4.48 (m, 2H), 4.28-4.21 (m, 2H); MS APCI(+) m/z 291.12 (M+H)$^+$.

Example 89

1-{5-[5-chloro-2-(1,2,3,6-tetrahydropyridin-4-yl)-1H-pyrrolo[2,3-b]pyridin-4-yl]-1,3-thiazol-2-yl}cyclobutanol

Example 89A tert-butyl 4-(5-chloro-4-(2-(1-(methoxymethoxy)cyclobutyl)thiazol-5-yl)-1-tosyl-1H-pyrrolo[2,3-b]pyridin-2-yl)-5,6-dihydropyridine-1(2H)-carboxylate The title compound was prepared as described in Example 45A, substituting tert-butyl 4-(4,4,5,5-tetramethyl-1,3,2-dioxaborolan-2-yl)-5,6-dihydropyridine-1(2H)-carboxylate for 2-(tert-butoxycarbonyl)-1,2,3,4-tetrahydroisoquinolin-7-ylboronic acid. MS ESI(+) m/z 685.2 [M+H]$^+$.

Example 89B 1-(5-(5-chloro-2-(1,2,3,6-tetrahydropyridin-4-yl)-1-tosyl-1H-pyrrolo[2,3-b]pyridin-4-yl)thiazol-2-yl)cyclobutanol A mixture of tert-butyl 4-(5-chloro-4-(2-(1-(methoxymethoxy)cyclobutyl)thiazol-5-yl)-1-tosyl-1H-pyrrolo[2,3-b]pyridin-2-yl)-5,6-dihydropyridine-1(2H)-carboxylate (Example 89A) (0.1 g, 0.146 mmol) in methanol (0.7 mL) and tetrahydrofuran (0.25 mL) was treated with 10% aqueous HCl solution (0.165 mL), and the reaction was heated at 65° C. for 5 hours. The reaction was cooled to ambient temperature and concentrated to dryness. The residue was partitioned between dichloromethane and saturated aqueous sodium bicarbonate. The layers were separated, and the aqueous layer was extracted with additional dichloromethane. The combined organic layers were dried over anhydrous sodium sulfate, filtered, and concentrated. The concentrate was purified by flash chromatography on a silica gel column, eluting with a gradient of 0% to 5% methanol in dichloromethane, to provide the title compound. MS ESI(+) m/z 541.0 [M+H]$^+$.

Example 89C

1-{5-[5-chloro-2-(1,2,3,6-tetrahydropyridin-4-yl)-1H-pyrrolo[2,3-b]pyridin-4-yl]-1,3-thiazol-2-yl}cyclobutanol The title compound was prepared as described in Example 45C, substituting Example 89B for Example 45B. $^1$H NMR (300 MHz, DMSO-$d_6$) ppm 1.89-2.04 (m, 2H), 2.32-2.45 (m, 5H), 2.55-2.67 (m, 2H), 2.84-2.93 (m, 2H), 3.40 (m, 2H), 6.47 (s, 1H), 6.60 (m, 1H), 6.64 (s, 1H), 8.17 (s, 1H), 8.27 (s, 1H), 12.12 (bs, 1H); MS ESI(+) m/z 387.0 [M+H]$^+$;

Example 90

1-{5-[5-fluoro-2-(3,4,5-trimethoxyphenyl)-1H-pyrrolo[2,3-b]pyridin-4-yl]-1,3-thiazol-2-yl}cyclobutanol

Example 90A 1-(5-(5-fluoro-1-tosyl-2-(3,4,5-trimethoxyphenyl)-1H-pyrrolo[2,3-b]pyridin-4-yl)thiazol-2-yl)cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 59A) (200 mg, 0.351 mmol) and 3,4,5-trimethoxy phenylboronic acid (112 mg, 0.527 mmol) in N,N-dimethylformamide (2630 μl) was added saturated aqueous bicarbonate solution (880 μl) followed by bis(triphenylphosphine)palladium dichloride (17.26 mg, 0.025 mmol). The mixture was heated to 70° C. for 4 hours and was quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with a gradient of 0 to 100% ethyl acetate in hexane, to give the title compound. MS ESI(+) m/z 610.2 [M+H]$^+$.

Example 90B

1-{5-[5-fluoro-2-(3,4,5-trimethoxyphenyl)-1H-pyrrolo[2,3-b]pyridin-4-yl]-1,3-thiazol-2-yl}cyclobutanol 1-(5-(5-fluoro-1-tosyl-2-(3,4,5-trimethoxyphenyl)-1H-pyrrolo[2,3-b]pyridin-4-yl)thiazol-2-yl)cyclobutanol (Example 90A) (103 mg, 0.169 mmol) in methanol (2.50 mL) and 2N aqueous sodium hydroxide solution (830 μL) was heated by microwave irradiation (Biotage, Initiator) to 120° C. for 30 minutes. The reaction was cooled to room temperature, and the pH was adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v ammonium acetate and B is acetonitrile) to give the title compound. $^1$H NMR (300 MHz, DMSO-$d_6$) δ ppm 12.48 (bs, 1H), 8.80 (s, 1H), 8.29 (d, J=2.0 Hz, 1H), 8.37 (m, 3H), 6.69 (s, 1H), 3.91 (s, 6H), 3.71 (s, 3H), 2.64-2.55 (m, 2H), 2.45-2.35 (m, 2H), 2.05-1.92 (m, 2H); MS ESI(+) m/z 456.1 [M+H]$^+$.

Example 91

1-(5-{5-fluoro-2-[3-(methylsulfonyl)phenyl]-1H-pyrrolo[2,3-b]pyridin-4-yl}-1,3-thiazol-2-yl)cyclobutanol

Example 91A 1-(5-(5-fluoro-2-(3-(methylsulfonyl)phenyl)-1-tosyl-1H-pyrrolo[2,3-b]pyridin-4-yl)thiazol-2-yl)cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 59A) (200 mg, 0.351 mmol) and 3-(methylsulfonyl)phenyl boronic acid (105 mg, 0.527 mmol) in N,N-dimethylformamide (2.63 mL) was added saturated aqueous bicarbonate solution (880 µL) followed by bis(triphenylphosphine)palladium dichloride (17.26 mg, 0.025 mmol). The mixture was heated to 70° C. for 4 hours and was quenched by the addition of water and dichloromethane. The layers were separated, and the aqueous layer was extracted with additional dichloromethane. The combined organics were dried with anhydrous magnesium sulfate, filtered and concentrated under reduced pressure. The residue was purified by flash chromatography on silica gel, eluting with a gradient of 0 to 100% ethyl acetate in hexane, to give the title compound MS ESI(+) m/z 598.1 [M+H]$^+$.

Example 91B 1-(5-(5-fluoro-2-(3-(methylsulfonyl)phenyl)-1H-pyrrolo[2,3-b]pyridin-4-yl)thiazol-2-yl)cyclobutanol A solution of 1-(5-(5-fluoro-2-(3-(methylsulfonyl)phenyl)-1-tosyl-1H-pyrrolo[2,3-b]pyridin-4-yl)thiazol-2-yl)cyclobutanol (Example 91A) (94.2 mg, 0.158 mmol) in methanol (2.500 mL) and 2N sodium hydroxide solution (833 µL) was heated by microwave irradiation (Biotage, Initiator) to 120° C. for 30 minutes. The reaction was cooled to room temperature, and the pH adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v ammonium acetate and B is acetonitrile) to give the title compound. $^1$H NMR (300 MHz, DMSO-d$_6$) δ ppm 12.73 (b s, 1H), 8.60 (b s, 1H), 8.57 (s, 1H), 8.39 (d, J=8.85 Hz, 1H), 8.38 (d, J=3.51 Hz, 1H), 7.91 (d, J=7.78 Hz, 1H), 7.78 (t, 1H), 7.56 (s, 1H), 3.33 (s, 3H), 2.64-2.59 (m, 2H), 2.45-2.37 (m, 2H), 2.03-1.93 (m, 2H); MS ESI(+) m/z 443.9 [M+H]$^+$.

Example 92

1-[5-(5-fluoro-2-quinolin-6-yl-1H-pyrrolo[2,3-b]pyridin-4-yl)-1,3-thiazol-2-yl]cyclobutanol

Example 92A 1-(5-(5-fluoro-2-(quinolin-6-yl)-1-tosyl-1H-pyrrolo[2,3-b]pyridin-4-yl)thiazol-2-yl)cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 59A) (200 mg, 0.351 mmol) and quinoline-6-boronic acid (91 mg, 0.527 mmol) in N,N-dimethylformamide (2.63 mL) was added saturated aqueous bicarbonate solution (880 µL) followed by bis(triphenylphosphine)palladium dichloride (17.26 mg, 0.025 mmol). The mixture was heated to 70° C. for 16 hours and was quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with a gradient of 0 to 100% ethyl acetate in hexane, to give the title compound. MS ESI(+) m/z 571.1 [M+H]$^+$.

Example 92B 3-(5-(5-fluoro-2-(quinolin-6-yl)-1H-pyrrolo[2,3-b]pyridin-4-yl)thiazol-2-yl)pentan-3-ol A solution of 1-(5-(5-fluoro-2-(quinolin-6-yl)-1-tosyl-1H-pyrrolo[2,3-b]pyridin-4-yl)thiazol-2-yl)cyclobutanol (Example 92A) (86.9 mg, 0.152 mmol) in methanol (2.5 mL) and 2N sodium hydroxide solution (833 µL) was heated by microwave irradiation (Biotage, Initiator) to 120° C. for 30 minutes. The reaction was cooled to room temperature, and the pH adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v ammonium acetate and B is acetonitrile) to give the title compound. $^1$H NMR (300 MHz, DMSO-d$_6$) δ ppm 12.48 (bs, 1H), 8.92 (d of d, J=5.8 Hz, 1H), 8.68 (m, 1H), 8.57 (s, 1H), 8.48 (d, J=8.85 Hz, 1H), 8.38 (d, J=9.46 Hz, 1H), 6.36 (d, J=3.51 Hz, 1H), 8.10 (d, J=8.85 Hz, 1H), 7.59 (d of d, 8.24 and 4.12 Hz, 1H), 7.56 (s, 1H), 6.72 (s, 1H), 2.66-2.60 (m, 2H), 2.45-2.36 (m, 2H), 2.05-1.92 (m, 2H); MS ESI(+) m/z 417.0 [M+H]$^+$.

Example 93

1-{5-[5-fluoro-2-(5-methoxy-1H-indol-3-yl)-1H-pyrrolo[2,3-b]pyridin-4-yl]-1,3-thiazol-2-yl}cyclobutanol

Example 93A tert-butyl 5-methoxy-3-(4,4,5,5-tetramethyl-1,3,2-dioxaborolan-2-yl)-1H-indole-1-carboxylate To 1,1'bis(diphenylphosphino)ferrocene-palladium(II) dichloride dichloromethane complex (0.449 g, 0.55 mmol), potassium acetate (1.805 g, 18.39 mmol), and bis(pinacolato)diboron (2.57 g, 10.12 mmol) under an atmosphere of nitrogen was added methylsulfoxide (46.0 mL), followed by tert-butyl 3-bromo-5-methoxy-1H-indole-1-carboxylate (3.0 g, 9.20 mmol), and the reaction was stirred at 80° C. over night. The reaction was cooled to room temperature and quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with hexanes, to give the title compound. MS DCI(+) m/z 374.1 [M+H]$^+$.

Example 93B tert-butyl 3-(5-fluoro-4-(2-(1-hydroxycyclobutyl) thiazol-5-yl)-1-tosyl-1H-pyrrolo[2,3-b]pyridin-2-yl)-5-methoxy-1H-indole-1-carboxylate To a stirred ambient solution of 1-(5-(5-fluoro-2-iodo-1-tosyl-1H-pyrrolo[2,3-b]pyridin-4-yl)thiazol-2-yl)cyclobutanol (Example 59A) (200 mg, 0.351 mmol) and tert-butyl 5-methoxy-3-(4,4,5,5-tetramethyl-1,3,2-dioxaborolan-2-yl)-1H-indole-1-carboxylate (Example 93A) (262 mg, 0.702 mmol) in N,N-dimethylformamide (2.63 mL) was added saturated aqueous bicarbonate solution (880 μL) followed by bis(triphenylphosphine)palladium dichloride (17.26 mg, 0.025 mmol). The mixture was heated to 70° C. for 3 hours and was quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with a gradient of 0 to 100% ethyl acetate in hexane, to give the title compound. MS ESI(+) m/z 689.3 [M+H]$^+$.

Example 93C 1-(5-(5-fluoro-2-(5-methoxy-1H-indol-3-yl)-1H-pyrrolo[2,3-b]pyridin-4-yl)thiazol-2-yl)cyclobutanol A solution of tert-butyl 3-(5-fluoro-4-(2-(1-hydroxycyclobutyl)thiazol-5-yl)-1-tosyl-1H-pyrrolo[2,3-b]pyridin-2-yl)-5-methoxy-1H-indole-1-carboxylate (Example 93B) (140 mg, 0.203 mmol) in methanol (2.00 mL) and 2N sodium hydroxide solution (670 μL) was heated by microwave irradiation (Biotage, Initiator) to 120° C. for 30 minutes. The reaction was cooled to room temperature, and the pH adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v ammonium acetate and B is acetonitrile) to give the title compound. $^1$H NMR (300 MHz, DMSO-$d_6$) δ ppm 12.19 (bs, 1H), 11.52 (s, 1H), 8.48 (s, 1H), 8.21 (d, J=2.0 Hz, 1H), 8.04 (d, J=2.0 Hz, 1H), 7.46 (d, J=2.0 Hz, 1H), 7.41 (d, J=3.51 Hz, 1H), 7.01 (s, 1H), 6.89 (d, J=3.51 Hz, 1H), 6.68 (s, 1H), 3.87 (s, 3H), 2.64-2.55 (m, 2H), 2.45-2.35 (m, 2H), 2.05-1.92 (m, 2H); MS ESI(+) m/z 435.0 [M+H]$^+$.

Example 94

3-[5-(5-fluoro-2-pyridin-4-yl-1H-pyrrolo[2,3-b]pyridin-4-yl)-1,3-thiazol-2-yl]azetidin-3-ol The title compound was prepared as described in Examples 1D-1I, except substituting 5-fluoro-4-iodo-1H-pyrrolo[2,3-b]pyridine for 5-chloro-4-iodo-1H-pyrrolo[2,3-b]pyridine in Example 1D, Example 54A for 2-(1-(methoxymethoxy)cyclobutyl)-5-(tributylstannyl)thiazole in Example 1E, and 4-(4,4,5,5-tetramethyl-1,3,2-dioxaborolan-2-yl)pyridine for 4-(2-(4-(4,4,5,5-tetramethyl-1,3,2-dioxaborolan-2-yl)-1H-pyrazol-1-yl)ethyl)morpholine in Example 1G. $^1$H NMR (500 MHz, DMSO-$d_6$) δ 13.02 (s, 1H), 9.46 (s, 1H), 9.32 (s, 1H), 8.80 (d, 2H), 8.73 (s, 1H), 8.51 (d, 1H), 8.26 (d, 2H), 7.82 (d, 1H), 4.57-4.48 (m, 2H), 4.30-4.23 (m, 2H); MS APCI (+) m/z 368.23 (M+H)$^+$.

Example 95

3-{5-[5-fluoro-2-(1-methyl-1H-pyrazol-4-yl)-1H-pyrrolo[2,3-b]pyridin-4-yl]-1,3-thiazol-2-yl}azetidin-3-ol The title compound was prepared as described in Examples 1D-1I, except substituting 5-fluoro-4-iodo-1H-pyrrolo[2,3-b]pyridine for 5-chloro-4-iodo-1H-pyrrolo[2,3-b]pyridine in Example 1D, Example 54A for 2-(1-(methoxymethoxy)cyclobutyl)-5-(tributylstannyl)thiazole in Example 1E, and 1-methyl-4-(4,4,5,5-tetramethyl-1,3,2-dioxaborolan-2-yl)-1H-pyrazole for 4-(2-(4-(4,4,5,5-tetramethyl-1,3,2-dioxaborolan-2-yl)-1H-pyrazol-1-yl)ethyl)morpholine in Example 1G. $^1$H NMR (500 MHz, DMSO-$d_6$) δ 12.37 (s, 1H), 9.40 (s, 1H), 9.28 (s, 1H), 8.56 (s, 1H), 8.30 (s, 1H), 8.24 (d, 1H), 8.08 (s, 1H), 7.01 (d, 1H), 4.52 (s, 2H), 4.24 (s, 2H), 3.91 (s, 3H); MS APCI(+) m/z 371.20 (M+H)$^+$.

Example 96

3-(5-{2-[4-(ethylsulfonyl)phenyl]-5-fluoro-1H-pyrrolo[2,3-b]pyridin-4-yl}-1,3-thiazol-2-yl)azetidin-3-ol The title compound was prepared as described in Examples 1D-1I, except substituting 5-fluoro-4-iodo-1H-pyrrolo[2,3-b]pyridine for 5-chloro-4-iodo-1H-pyrrolo[2,3-b]pyridine in Example 1D, Example 54A for 2-(1-(methoxymethoxy)cyclobutyl)-5-(tributylstannyl)thiazole in Example 1E, and 4-(ethylsulfonyl)phenylboronic acid for 4-(2-(4-(4,4,5,5-tetramethyl-1,3,2-dioxaborolan-2-yl)-1H-pyrazol-1-yl)ethyl)morpholine in Example 1G. $^1$H NMR (500 MHz, DMSO-$d_6$) δ 12.84 (s, 1H), 9.46 (s, 1H), 9.32 (s, 1H), 8.71 (s, 1H), 8.44 (d, 1H), 8.34 (d, 2H), 7.99 (d, 2H), 7.59 (d, 1H), 4.53 (s, 2H), 4.26 (s, 2H), 3.37 (q, 2H), 1.15 (t, 3H); MS APCI(+) m/z 458.78 (M+H)$^+$

Example 97

3-(5-{5-fluoro-2-[3-fluoro-4-(morpholin-4-ylmethyl) phenyl]-1H-pyrrolo[2,3-b]pyridin-4-yl}-1,3-thiazol-2-yl)azetidin-3-ol The title compound was prepared as described in Examples 1D-1I, except substituting 5-fluoro-4-iodo-1H-pyrrolo[2,3-b]pyridine for 5-chloro-4-iodo-1H-pyrrolo[2,3-b]pyridine in Example 1D, Example 54A for 2-(1-(methoxymethoxy)cyclobutyl)-5-(tributylstannyl)thiazole in Example 1E, and 4-(2-fluoro-4-(4,4,5,5-tetramethyl-1,3,2-dioxaborolan-2-yl)benzyl)morpholine for 4-(2-(4-(4,4,5,5-tetramethyl-1,3,2-dioxaborolan-2-yl)-1H-pyrazol-1-yl)ethyl)morpholine in Example 1G. $^1$H NMR (400 MHz, DMSO-$d_6$) δ 2.74 (s, 1H), 9.53-9.46 (m, 1H), 9.39-9.31 (m, 1H), 8.70 (s, 1H), 8.42 (d, 1H), 8.11 (d, 1H), 8.04 (d, 1H), 7.71 (t, 1H), 7.59 (s, 1H), 4.53 (m, 2H), 4.44 (s, 2H), 4.26 (m, 2H), 3.92 (bs, 4H), 3.29 (bs, 4H); MS APCI(+) m/z 484.88 (M+H)$^+$

Example 98

3-[5-(5-fluoro-2-phenyl-1H-pyrrolo[2,3-b]pyridin-4-yl)-1,3-thiazol-2-yl]azetidin-3-ol The title compound was prepared as described in Examples 1D-1I, except substituting 5-fluoro-4-iodo-1H-pyrrolo[2,3-b]pyridine for 5-chloro-4-iodo-1H-pyrrolo[2,3-b]pyridine in Example 1D, Example 54A for 2-(1-(methoxymethoxy)cyclobutyl)-5-(tributylstannyl)thiazole in Example 1E, and 4,4, 5,5-tetramethyl-2-phenyl-1,3,2-dioxaborolane for 4-(2-(4-(4,4,5,5-tetramethyl-1,3,2-dioxaborolan-2-yl)-1H-pyrazol-1-yl)ethyl)morpholine in Example 1G. $^1$H NMR (400 MHz, DMSO-$d_6$) δ 12.60 (s, 1H), 9.42 (s, 1H), 9.30 (s, 1H), 8.67 (s, 1H), 8.36 (d, 1H), 8.06 (d, 2H), 7.51 (t, 2H), 7.41 (t, 1H), 7.34 (d, 1H), 4.52 (d, 2H), 4.25 (s, 2H); MS APCI (+) m/z 367.23 (M+H)$^+$.

Example 101

3-[5-(2-{4-[(3,3-difluoropiperidin-1-yl)methyl]phenyl}-5-fluoro-1H-pyrrolo[2,3-b]pyridin-4-yl)-1,3-thiazol-2-yl]azetidin-3-ol Example 101A tert-butyl 3-(5-(5-fluoro-2-(4-formylphenyl)-1-tosyl-1H-pyrrolo[2,3-b]pyridin-4-yl)thiazol-2-yl)-3-(methoxymethoxy)azetidine-1-carboxylate The title compound was prepared as described in Example 1G, except substituting Example 54C for 5-(5-chloro-2-iodo-1-tosyl-1H-pyrrolo[2,3-b]pyridin-4-yl)-2-(1-(methoxymethoxy)cyclobutyl)thiazole and 4-formylphenylboronic acid for 4-(2-(4-(4,4,5,5-tetramethyl-1,3,2-dioxaborolan-2-yl)-1H-pyrazol-1-yl)ethyl)morpholine. MS APCI(+) m/z 693.41 (M+H)$^+$.

Example 101B 3-(5-(2-(4-((3,3-difluoropiperidin-1-yl)methyl)phenyl)-5-fluoro-1H-pyrrolo[2,3-b]pyridin-4-yl)thiazol-2-yl)azetidin-3-ol The title compound was prepared as described in Examples 30B-30D except substituting Example 101A for 4-(5-chloro-4-(2-(1-(methoxymethoxy)cyclobutyl)thiazol-5-yl)-1-tosyl-1H-pyrrolo[2,3-b]pyridin-2-yl)-2-fluorobenzaldehyde (Example 30A) and 3,3-difluoropiperidine for 4-fluoropiperidine in Example 30B. The title compound was isolated as a TFA salt. $^1$H NMR (500 MHz, DMSO-$d_6$) δ 12.64 (s, 1H), 9.34 (bs, 1H), 9.25 (bs, 1H), 8.67 (s, 1H), 8.37 (d, 1H), 8.09 (d, 2H), 7.89 (bs, 1H), 7.54 (s, 2H), 7.38 (s, 1H), 4.57-4.48 (m, 2H), 4.27-4.20 (m, 2H), 3.96 (s, 2H), 3.14-2.95 (m, 2H), 2.91-2.67 (m, 2H), 2.03-1.97 (m, 2H), 1.80 (bs, 2H). MS APCI(+) m/z 500.30 (M+H)$^+$.

Example 102

3-[5-(5-fluoro-2-{4-[(2-methylpyrrolidin-1-yl)methyl]phenyl}-1H-pyrrolo[2,3-b]pyridin-4-yl)-1,3-thiazol-2-yl]azetidin-3-ol The title compound was prepared as described in Examples 30B-30D, except substituting Example 101A for 4-(5-chloro-4-(2-(1-(methoxymethoxy)cyclobutyl)thiazol-5-yl)-1-tosyl-1H-pyrrolo[2,3-b]pyridin-2-yl)-2-fluorobenzaldehyde (Example 30A) and 2-methylpyrrolidine for 4-fluoropiperidine in Example 30B. The title compound was isolated as a TFA salt. $^1$H NMR (500 MHz, DMSO-$d_6$) δ 12.68 (s, 1H), 9.62 (s, 1H), 9.40 (s, 1H), 9.29 (s, 1H), 8.68 (s, 1H), 8.39 (d, 1H), 8.16 (d, 2H), 7.94 (s, 1H), 7.66 (d, 2H), 7.44 (s, 1H), 4.58 (dd, 1H), 4.55-4.48 (m, 2H), 4.27-4.23 (m, 2H), 4.22-4.19 (m, 1H), 2.28-2.22 (m, 1H), 2.03-1.93 (m, 2H), 1.91-1.83 (m, 1H), 1.69-1.56 (m, 1H), 1.36 (d, 3H), 1.24 (s, 2H); MS APCI(+) m/z 464.26 (M+H)$^+$.

Example 103

3-[5-(5-fluoro-1H-pyrrolo[2,3-b]pyridin-4-yl)-1,3-thiazol-2-yl]-1-methylazetidin-3-ol Example 103A 3-(5-(5-fluoro-1-tosyl-1H-pyrrolo[2,3-b]pyridin-4-yl)thiazol-2-yl)azetidin-3-ol A flask was charged with tert-butyl 3-(5-(5-fluoro-1-tosyl-1H-pyrrolo[2,3-b]pyridin-4-yl)thiazol-2-yl)-3-(methoxymethoxy)azetidine-1-carboxylate (Example 54B) (500 mg, 0.849 mmol), methanol (6.5 mL) and aqueous 2 molar HCl solution (2.58 mL, 8.49 mmol). The reaction mixture was heated to 60° C. for 5 hours, then 35° C. overnight. The reaction mixture was cooled to room temperature and diluted with saturated aqueous brine solution and ethyl acetate. The layers were separated, and the aqueous layer extracted with ethyl acetate (3×20 mL). The organic layers were combined and concentrated. The remaining solid was triturated with water (pH approximately 10). The solids were collected by vacuum filtration, washed with water, and dried at low temperature in a vacuum oven to give the title compound. $^1$H NMR (300 MHz, DMSO-$d_6$) δ 8.50 (d, 1H), 8.40 (s, 1H), 8.10 (d, 1H), 8.01 (d, 2H), 7.44 (d, 2H), 7.14 (d, 1H), 7.06 (s, 1H), 3.96 (d, 2H), 3.71 (d, 2H), 2.35 (s, 3H); MS APCI(+) m/z 445.22 (M+H)$^+$.

Example 103B 3-(5-(5-fluoro-1-tosyl-1H-pyrrolo[2,3-b]pyridin-4-yl)thiazol-2-yl)-1-methylazetidin-3-ol A round-bottomed flask equipped with a reflux condenser was charged with 3-(5-(5-fluoro-1-tosyl-1H-pyrrolo[2,3-b]pyridin-4-yl)thiazol-2-yl)azetidin-3-ol (100 mg, 0.225 mmol) (Example 103A), paraformaldehyde (33.8 mg, 1.125 mmol), dichloroethane (2.5 mL), and acetic acid (0.064 mL, 1.125 mmol). Sodium cyanoborohydride (0.059 ml, 1.125 mmol) was added in three portions, and the mixture heated to 90° C. for 1 hour. The reaction mixture was slowly cooled to room temperature, and then to 0° C. in an ice-bath. Saturated sodium bicarbonate solution was added, and the mixture stirred vigorously for about an hour. The layers were separated, and the aqueous layer was extracted with dichloromethane (3×10 mL). The combined organic layers were dried over anhydrous MgSO$_4$, filtered, and concentrated to give the title compound. MS APCI(+) m/z 459.24 (M+H)$^+$.

Example 103C

3-[5-(5-fluoro-1H-pyrrolo[2,3-b]pyridin-4-yl)-1,3-thiazol-2-yl]-1-methylazetidin-3-ol A 5 mL microwave reaction vial was charged with 3-(5-(5-fluoro-1-tosyl-1H-pyrrolo[2,3-b]pyridin-4-yl)thiazol-2-yl)-1-methylazetidin-3-ol (Example 103B) (124 mg, 0.216 mmol), tetrahydrofuran (2.1 mL), isopropyl alcohol (0.50 mL) and aqueous 2 molar sodium hydroxide solution (1.08 mL, 2.163 mmol). The vial was sealed, and the reaction heated to 110° C. for 15 minutes by microwave irradiation (Biotage Initiator Microwave Synthesizer). The reaction was cooled to room temperature, and the solvents were removed under reduced pressure. The crude residue was dissolved into 1:1 methyl sulfoxide:methanol and purified by reverse phase high pressure liquid chromatography (RP HPLC, 19×150 mm Atlantis Prep T3 OBD 5 µm column, eluting with a gradient of 5% B in A to 75% B in A over 25 minutes, wherein A is water containing 0.1% v/v trifluoroacetic acid and B is acetonitrile) to give the title compound as a trifluoroacetic acid salt. $^1$H NMR (300 MHz, DMSO-$d_6$) δ 12.14 (s, 1H), 10.48-10.09 (m, 1H), 8.54 (s, 1H), 8.37 (d, 1H), 7.88 (d, 1H), 7.77-7.71 (m, 1H), 6.81 (dd, 1H), 4.79 (d, 1H), 4.49 (s, 2H), 4.27 (d, 1H), 3.02 (s, 3H). MS APCI(+) m/z 305.17 (M+H)$^+$.

Example 104

1-(5-{5-chloro-2-[1-(1,4-dioxan-2-ylcarbonyl)-1,2,3,6-tetrahydropyridin-4-yl]-1H-pyrrolo[2,3-b]pyridin-4-yl}-1,3-thiazol-2-yl)cyclobutanol The title compound was prepared as described in Example 67, substituting 1,4-dioxane-2-carboxylic acid for 1-methylpiperidine-4-carboxylic acid hydrochloride. $^1$H NMR (300 MHz, DMSO-$d_6$) ppm 1.88-2.03 (m, 2H), 2.33-2.46 (m, 3H), 2.55-2.68 (m, 4H), 3.58-3.84 (m, 7H), 4.01-4.25 (m, 1H), 4.27-4.48 (m, 2H), 6.57 (m, 2H), 6.65 (s, 1H), 8.19 (s, 1H), 8.31 (s, 1H), 12.23 (m, 1H); MS ESI(+) m/z 501.5 [M+H]$^+$;

Example 105

1-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)cyclobutanol The title compound was prepared as described in Example 67, substituting 2-(dimethylamino)acetic acid for 1-methylpiperidine-4-carboxylic acid hydrochloride. $^1$H NMR (300 MHz, DMSO-$d_6$) ppm 1.88-2.06 (m, 2H), 2.34-2.46 (m, 3H), 2.55-2.69 (m, 4H), 2.83 (d, 6H), 3.74 (m, 1H), 4.14 (m, 1H), 4.24 (m, 1H), 4.27-4.39 (m, 2H), 6.62 (m, 3H), 8.19 (s, 1H), 8.32 (s, 1H), 9.53 (bs, 1H), 12.29 (bs, 1H); MS ESI(+) m/z 472.6 [M+H]$^+$.

Example 106

1-{5-[5-fluoro-2-(5-methoxy-1-methyl-1H-indol-3-yl)-1H-pyrrolo[2,3-b]pyridin-4-yl]-1,3-thiazol-2-yl}cyclobutanol Example 106A 3-bromo-5-methoxy-1-methyl-1H-indole To an ambient solution of 5-methoxy-1H-indole (5 g, 34.0 mmol) in N,N-dimethylformamide (100 mL) was added a solution of bromine (1.75 mL, 34.0 mmol) in N,N-dimethylformamide (25 mL). The mixture was stirred for about 15 minutes. The mixture was cooled to about 0° C., and NaH (3.26 g, 82 mmol) was added in portions over 15 minutes. The mixture was stirred for 15 minutes, and then iodomethane (2.55 mL, 40.8 mmol) was added. The bath was removed and the slurry was warmed to room temperature. After about 45 minutes, the solvents were removed under reduced pressure, and the mixture was partitioned between dichloromethane (50 mL) and water (100 mL). The layers were separated, and the aqueous layer was extracted with dichloromethane (2×25 mL). The combined organics were dried over magnesium sulfate, filtered and concentrated under reduced pressure. The residue was purified by chromatography on silica gel, eluting with dichloromethane, to give the title compound. LCMS ESI(+) m/z 332.9 [M+H]$^+$.

Example 106B 5-methoxy-1-methyl-3-(4,4,5,5-tetramethyl-1,3,2-dioxaborolan-2-yl)-1H-indole A mixture of 3-bromo-5-methoxy-1-methyl-1H-indole (8.16 g, 34 mmol), potassium acetate (8.68 g, 88 mmol), 4,4,4',4',5,5,5',5'-octamethyl-2,2'-bi(1,3,2-dioxaborolane) (10.36 g, 40.8 mmol), and [1,1'-bis(diphenylphosphino)ferrocene]dichloropalladium(II) dichloromethane (2.221 g, 2.72 mmol) in N,N-dimethylformamide (125 mL) was heated to about 85° C. for about 14 hours. The mixture was cooled and concentrated under reduced pressure. The material was diluted with water (150 mL), and the slurry extracted with diethyl ether (3×100 mL) and ethyl acetate (3×100 mL). The combined organics were dried over magnesium sulfate, filtered and concentrated under reduced pressure. The residue was purified by flash chromatography on silica gel, eluting with dichloromethane, to give the title compound. LCMS ESI(+) m/z 470.1 [M+H]$^+$.

Example 106C 1-(5-(5-fluoro-2-(5-methoxy-1-methyl-1H-indol-3-yl)-1-tosyl-1H-pyrrolo[2,3-b]pyridin-4-yl)thiazol-2-yl)cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 59A) (200 mg, 0.351 mmol) and 5-methoxy-1-methyl-3-(4,4,5,5-tetramethyl-1,3,2-dioxaborolan-2-yl)-1H-indole (Example 106B) (160 mg, 0.557 mmol) in N,N-dimethylformamide (3.21 mL) was added saturated aqueous bicarbonate solution (1.07 mL) followed by bis(triphenylphosphine) palladium dichloride (21.06 mg, 0.030 mmol). The mixture was heated to 70° C. for 2 hours and was quenched by the addition of water and dichloromethane. The layers were separated, and the aqueous layer was extracted with additional dichloromethane. The combined organics were dried with anhydrous magnesium sulfate, filtered and concentrated under reduced pressure. The residue was purified by flash chromatography on silica gel, eluting with a gradient of 0 to 100% ethyl acetate in hexane, to give the title compound. LCMS TFA(+) m/z 602.99 [M+H]$^+$.

Example 106D 1-(5-(5-fluoro-2-(5-methoxy-1-methyl-1H-indol-3-yl)-1H-pyrrolo[2,3-b]pyridin-4-yl)thiazol-2-yl)cyclobutanol 2,2,2-trifluoroacetate A solution of 1-(5-(5-fluoro-2-(5-methoxy-1-methyl-1H-indol-3-yl)-1-tosyl-1H-pyrrolo[2,3-b]pyridin-4-yl)thiazol-2-yl)cyclobutanol (Example 106C) (81.6 mg, 0.135 mmol) in methanol (2.0 mL) and 2N sodium hydroxide solution (670 µL) was heated by microwave irradiation (Biotage, Initiator) to 120° C. for 30 minutes. The reaction was cooled to room temperature, and the pH was adjusted to ~3 with 10% HCl solution. The resulting solution was purified by reverse phase high performance liquid chromatography (RP HPLC, eluting with a gradient of 5% B in A to 75% B in A over 25 minutes, wherein A is water containing 0.1% v/v trifluoroacetic acid and B is acetonitrile) to give the title compound. $^1$H NMR (300 MHz, DMSO-$d_6$) δ ppm 12.19 (bs, 1H), 8.46 (s, 1H), 8.19 (s, 1H), 7.98 (s, 1H), 7.46 (d, J=3.51 Hz, 2H), 6.99 (s, 1H), 6.94 (d, J=3.51 Hz, 1H), 3.87 (s, 3H), 3.84 (s, 3H), 2.64-2.55 (m, 2H), 2.45-2.35 (m, 2H), 2.05-1.92 (m, 2H); MS ESI(+) m/z 449.4 [M+H]+.

Example 107

1-{5-[2-(5-fluoro-1-methyl-1H-indol-3-yl)-1H-pyrrolo[2,3-b]pyridin-4-yl]-1,3-thiazol-2-yl}cyclobutanol

Example 107A 5-fluoro-1-methyl-3-(4,4,5,5-tetramethyl-1,3,2-dioxaborolan-2-yl)-1H-indole A solution of 5-fluoro-3-iodo-1-methyl-1H-indole (11.5 g, 41.8 mmol) in dioxane (200 mL) was treated with triethyl amine (27 mL, 194 mmol) and [1,1'-bis(diphenylphosphino)ferrocene]dichloropalladium(II) dichloromethane (1.707 g, 2.090 mmol). 4,4,5,5-Tetramethyl-1,3,2-dioxaborolane (39.4 mL, 272 mmol) was added carefully to the reaction (gas evolution was observed). The mixture was heated to 100° C. for 30 minutes, cooled, and diluted with about 250 mL ethyl acetate. The precipitate was filtered and washed with ethyl acetate (100 mL). The filtrate was concentrated under reduced pressure. The residue was purifed on silica gel, eluting with 8:2 heptane:ethyl acetate, to give the title compound. MS ESI(+) m/z 276.0 (M+H)+.

Example 107B 5-(2-iodo-1-tosyl-1H-pyrrolo[2,3-b]pyridin-4-yl)-2-(1-(methoxymethoxy)cyclobutyl) thiazole 1-(5-(2-iodo-1-tosyl-1H-pyrrolo[2,3-b]pyridin-4-yl)thiazol-2-yl)cyclobutanol The title compound was prepared as described in Examples 1E-1F, substituting 4-bromo-1-tosyl-1H-pyrrolo[2,3-b]pyridine for 5-chloro-4-iodo-1-tosyl-1H-pyrrolo[2,3-b]pyridine (Example 1D) in Example 1E. MS ESI(+) m/z 614.0 [M+H]+.

Example 107C 1-(5-(2-iodo-1-tosyl-1H-pyrrolo[2,3-b]pyridin-4-yl)thiazol-2-yl)cyclobutanol To a solution of 5-(2-iodo-1-tosyl-1H-pyrrolo[2,3-b]pyridin-4-yl)-2-(1-(methoxymethoxy)cyclobutyl) thiazole (Example 107B) (1.273 g, 2.138 mmol) in methanol (10.8 mL) and tetrahydrofuran (10.8 mL) was added 10% aqueous hydrochloric acid solution (6.61 mL, 21.38 mmol). The reaction mixture was heated to 65° C. for 3 hours. The reaction was partitioned between ethyl acetate (50 mL) and water (50 mL). The layers separated, and the aqueous layer was extracted with additional ethyl acetate (2×50 mL). The combined organics were dried over anhydrous magnesium sulfate, filtered and concentrated under reduced pressure to give the title compound. MS APCI(+) m/z 552.54 (M+H)+.

Example 107D 1-(5-(2-(5-fluoro-1-methyl-1H-indol-3-yl)-1-tosyl-1H-pyrrolo[2,3-b]pyridin-4-yl)thiazol-2-yl)cyclobutanol To a stirred ambient solution of 1-(5-(2-iodo-1-tosyl-1H-pyrrolo[2,3-b]pyridin-4-yl)thiazol-2-yl)cyclobutanol (Example 107C) (150 mg, 0.272 mmol) and 5-fluoro-1-methyl-3-(4,4,5,5-tetramethyl-1,3,2-dioxaborolan-2-yl)-1H-indole (Example 107A) (112 mg, 0.408 mmol) in N,N-dimethylformamide (2.04 mL) was added saturated aqueous bicarbonate solution (680 µL) followed by bis(triphenylphosphine) palladium dichloride (13.37 mg, 0.019 mmol). The mixture was heated to 70° C. for 3 hours and was quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with a gradient of 0 to 100% ethyl acetate in hexane, to give the title compound LCMS APCI(+) m/z 602.99 [M+H]+.

Example 107E 1-(5-(2-(5-fluoro-1-methyl-1H-indol-3-yl)-1H-pyrrolo[2,3-b]pyridin-4-yl)thiazol-2-yl)cyclobutanol A solution of 1-(5-(2-(5-fluoro-1-methyl-1H-indol-3-yl)-1-tosyl-1H-pyrrolo[2,3-b]pyridin-4-yl)thiazol-2-yl)cyclobutanol (Example 107D) in methanol (2.0 mL) and 2N sodium hydroxide solution (700 µL) was heated by microwave irradiation (Biotage, Initiator) to 120° C. for 30 minutes. The reaction was cooled to room temperature, and the pH adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v trifluoroacetic acid and B is acetonitrile) to give the title compound. $^1$H NMR (300 MHz, DMSO-$d_6$) δ ppm 12.14 (s, 1H), 8.54 (s, 1H), 8.16 (d, J=5.2 Hz, 1H), 8.09 (s, 1H), 7.87 (d of d, J=10.08 & 2.4 Hz, 1H), 7.58 (d of d, J=8.95 & 4.5 Hz, 1H), 7.27 (d, J=5.2 Hz, 1H), 7.14 (t, 1H), 6.99 (s, 1H), 3.88 (s, 3H), 2.64-2.55 (m, 2H), 2.45-2.35 (m, 2H), 2.05-1.92 (m, 2H); MS ESI(+) m/z 419.5 [M+H]+.

Example 108

3-(5-{5-chloro-2-[4-(pyrrolidin-1-ylmethyl)phenyl]-1H-pyrrolo[2,3-b]pyridin-4-yl}-1,3-thiazol-2-yl)oxetan-3-ol

Example 108A 4-(5-chloro-4-(2-(3-(4-methoxybenzyloxy)oxetan-3-yl)thiazol-5-yl)-1-tosyl-1H-pyrrolo[2,3-b]pyridin-2-yl)benzaldehyde The title compound was prepared as described in Example 20B, substituting 4-formylphenylboronic acid for 1-(2-(pyrrolidin-1-yl)ethyl)-4-(4,4,5,5-tetramethyl-1,3,2-dioxaborolan-2-yl)-1H-pyrazole (Example 20A). MS ESI(+) m/z 686.4 [M+H]+.

Example 108B 5-(5-chloro-2-(4-(pyrrolidin-1-ylmethyl)phenyl)-1-tosyl-1H-pyrrolo[2,3-b]pyridin-4-yl)-2-(3-(4-methoxybenzyloxy)oxetan-3-yl)thiazole The title compound was prepared as described in Example 8C, substituting 4-(5-chloro-4-(2-(3-(4-methoxybenzyloxy)oxetan-3-yl)thiazol-5-yl)-1-tosyl-1H-pyrrolo[2,3-b]pyridin-2-yl)benzaldehyde (Example 108A) for 4-(5-chloro-4-(2-(1- hydroxycyclobutyl)thiazol-5-yl)-1-tosyl-1H-pyrrolo[2,3-b]pyridin-2-yl)benzaldehyde (Example 8B). MS ESI(+) m/z 741.1 [M+H]$^+$.

Example 108C 3-(5-(5-chloro-2-(4-(pyrrolidin-1-ylmethyl)phenyl)-1-tosyl-1H-pyrrolo[2,3-b]pyridin-4-yl)thiazol-2-yl)oxetan-3-ol The title compound was prepared as described in Example 21A, substituting 5-(5-chloro-2-(4-(pyrrolidin-1-ylmethyl)phenyl)-1-tosyl-1H-pyrrolo[2,3-b]pyridin-4-yl)-2-(3-(4-methoxybenzyloxy)oxetan-3-yl)thiazole (Example 108B) for 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(3-(4-methoxybenzyloxy)oxetan-3-yl)thiazole (Example 20B). MS ESI (+) m/z 621.1 [M+H]$^+$.

Example 108D 3-(5-(5-chloro-2-(4-(pyrrolidin-1-ylmethyl)phenyl)-1H-pyrrolo[2,3-b]pyridin-4-yl)thiazol-2-yl)oxetan-3-ol The title compound was prepared as described in Example 8D, substituting 3-(5-(5-chloro-2-(4-(pyrrolidin-1-ylmethyl)phenyl)-1-tosyl-1H-pyrrolo[2,3-b]pyridin-4-yl)thiazol-2-yl)oxetan-3-ol (Example 108C) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.57 (s, 1H), 8.36 (s, 1H), 8.33 (s, 1H), 7.93 (s, 2H), 7.46 (s, 1H), 7.43-7.36 (m, 2H), 7.03 (s, 1H), 5.01-4.98 (m, 2H), 4.83-4.76 (m, 2H), 3.60 (s, 2H), 2.47-2.41 (m, 4H), 1.73-1.67 (m, 4H); MS ESI(+) m/z 467.5 [M+H]$^+$.

Example 109

3-{5-[5-chloro-2-(1-methyl-1H-pyrazol-4-yl)-1H-pyrrolo[2,3-b]pyridin-4-yl]-1,3-thiazol-2-yl}oxetan-3-ol

Example 109A 5-(5-chloro-2-(1-methyl-1H-pyrazol-4-yl)-1-tosyl-1H-pyrrolo[2,3-b]pyridin-4-yl)-2-(3-(4-methoxybenzyloxy)oxetan-3-yl)thiazole The title compound was prepared as described in Example 20B, substituting 1-methyl-4-(4,4,5,5-tetramethyl-1,3,2-dioxaborolan-2-yl)-1H-pyrazole for 1-(2-(pyrrolidin-1-yl)ethyl)-4-(4,4,5,5-tetramethyl-1,3,2-dioxaborolan-2-yl)-1H-pyrazole (Example 20A). MS ESI(+) m/z 662.5 [M+H]$^+$.

Example 109B 3-(5-(5-chloro-2-(1-methyl-1H-pyrazol-4-yl)-1-tosyl-1H-pyrrolo[2,3-b]pyridin-4-yl)thiazol-2-yl)oxetan-3-ol The title compound was prepared as described in Example 21A, substituting 5-(5-chloro-2-(1-methyl-1H-pyrazol-4-yl)-1-tosyl-1H-pyrrolo[2,3-b]pyridin-4-yl)-2-(3-(4-methoxybenzyloxy)oxetan-3-yl)thiazole (Example 109A) for 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(3-(4-methoxybenzyloxy)oxetan-3-yl)thiazole (Example 20B). MS ESI (+) m/z 542.1 [M+H]$^+$.

Example 109C 3-(5-(5-chloro-2-(1-methyl-1H-pyrazol-4-yl)-1H-pyrrolo[2,3-b]pyridin-4-yl)thiazol-2-yl)oxetan-3-ol The title compound was prepared as described in Example 8D, substituting 3-(5-(5-chloro-2-(1-methyl-1H-pyrazol-4-yl)-1-tosyl-1H-pyrrolo[2,3-b]pyridin-4-yl)thiazol-2-yl)oxetan-3-ol (Example 109B) for 1-(5-(5-chloro-2-(4-(pyrrolidin-1-ylmethyl)phenyl)-1-tosyl-1H-pyrrolo[2,3-b]pyridin-4-yl)thiazol-2-yl)cyclobutanol (Example 8C). $^1$H NMR (300 MHz, DMSO-d$_6$) δ 12.36 (s, 1H), 8.29 (s, 1H), 8.27 (s, 1H), 8.25 (s, 1H), 8.04 (d, J=0.7 Hz, 1H), 7.45 (bs, 1H), 6.74 (d, J=2.0 Hz, 1H), 5.00 (dd, J=6.3, 0.8 Hz, 2H), 4.79 (dd, J=6.3, 0.8 Hz, 2H), 3.89 (s, 3H); MS ESI(+) m/z 388.6 [M+H]$^+$.

Example 110

1-(5-{2-[3-(methylsulfonyl)phenyl]-1H-pyrrolo[2,3-b]pyridin-4-yl}-1,3-thiazol-2-yl)cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 107C) (150 mg, 0.272 mmol) and 3-methylsulfonyl phenylboronic acid (54.4 mg, 0.272 mmol) in N,N-dimethylformamide (2.04 mL) was added saturated aqueous bicarbonate solution (680 μL) followed by bis(triphenylphosphine) palladium dichloride (13.37 mg, 0.019 mmol). The mixture was heated to 70° C. for 3 hours and was quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with a gradient of 0 to 100% ethyl acetate in hexane, to give the title compound. A solution of the residue in methanol (2.0 mL) and 2N sodium hydroxide solution (700 μL) was heated by microwave irradiation (Biotage, Initiator) to 120° C. for 30 minutes. The reaction was cooled to room temperature, and the pH adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v trifluoroacetic acid and B is acetonitrile) to give the title compound. $^1$H NMR (300 MHz, DMSO-d$_6$) δ ppm 12.60 (s, 1H), 8.58 (s, 1H), 8.53 (s, 1H), 8.37 (d, J=7.93 Hz, 1H), 8.28 (d, J=5.04 Hz, 1H), 7.88 (d, J=6.71 Hz, 1H), 7.75 (t, J=7.78 Hz, 3H), 7.51 (s, 1H), 7.32 (d, J=5.04 Hz, 1H), 3.32 (s, 3H), 2.64-2.55 (m, 2H), 2.45-2.35 (m, 2H), 2.05-1.92 (m, 2H); MS ESI(+) m/z 426.7 [M+H]+.

Example 111

1-{5-[2-(1-methyl-1H-pyrazol-4-yl)-1H-pyrrolo[2,3-b]pyridin-4-yl]-1,3-thiazol-2-yl}cyclobutanol To a stirred ambient solution of 1-(5-(5-fluoro-2-iodo-1-tosyl-1H-pyrrolo[2,3-b]pyridin-4-yl)thiazol-2-yl)cyclobutanol (Example 107C) (150 mg, 0.272 mmol) and 1-methyl-4-(4,4,5,5-tetramethyl-1,3,2-dioxaborolan-2-yl)-1H-pyrazole (85 mg, 0.408 mmol) in N,N-dimethylformamide (2.04 mL) was added saturated aqueous bicarbonate solution (680 μL) followed by bis(triphenylphosphine) palladium dichloride (13.37 mg, 0.019 mmol). The mixture was heated to 70° C. for 1.5 hours and was quenched by the addition of water and dichloromethane. The layers were separated, and the aqueous layer was extracted with additional dichloromethane. The combined organics were dried with anhydrous magnesium sulfate, filtered and concentrated under reduced pressure to give crude product. The residue was purified by flash chromatography on silica gel, eluting with a gradient of 0 to 100% ethyl acetate in hexane. A solution of the crude material in methanol (2.0 mL) and 2N aqueous sodium hydroxide solution (700 μL) was heated by microwave irradiation (Biotage, Initiator) to 120° C. for 30 minutes. The reaction was cooled to room temperature, and the pH adjusted to ~3 with 10% aqueous HCl solution. The resulting solution was purified by reverse phase high performance liquid chromatography (RP HPLC, eluting with a gradient of 5% B in A to 75% B in A over 25 minutes, wherein A is water containing 0.1% v/v trifluoroacetic acid and B is acetonitrile) to give the title compound. $^1$H NMR (300 MHz, DMSO-d$_6$) δ ppm 12.48 (bs, 1H), 8.43 (s, 1H), 8.31 (s, 1H), 8.18 (d, J=5.1 Hz, 1H), 8.10 (s, 1H), 7.32 (d, J=5.1 Hz, 1H), 3.93 (s, 3H), 2.64-2.55 (m, 2H), 2.45-2.35 (m, 2H), 2.05-1.92 (m, 2H); MS ESI(+) m/z 352.7 [M+H]$^+$.

Example 112

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N-(4-methoxybenzyl)amine Example 112A N-cyclobutylidene-1-(4-methoxyphenyl)methanamine A solution of (4-methoxyphenyl)methanamine (9.26 mL, 71.3 mmol) and cyclobutanone (5.35 mL, 71.3 mmol) in anhydrous ethyl ether (70 mL) was treated with activated 4 angstrom molecular sieves (2.5 g). The mixture was stirred vigorously for 16 hours at ambient temperature. The reaction mixture was filtered, and the sieves were washed with ethyl ether. The filtrate was concentrated under reduced pressure with no heat. The title compound was stored under nitrogen and used without further purification. MS DCI(+) m/z 190.3 [M+H]$^+$.

Example 112B

N-(4-methoxybenzyl)-1-(thiazol-2-yl)cyclobutanamine

A solution of thiazole (2.253 mL, 31.7 mmol) in anhydrous tetrahydrofuran (30 mL) at –78° C. was treated dropwise with 2.5M n-butyllithium in hexane (12.68 mL, 31.7 mmol) via an additional funnel while maintaining the reaction temperature below –70° C. The lithium species was stirred for about 10 minutes and added dropwise via cannula to a –78° C. solution of N-cyclobutylidene-1-(4-methoxyphenyl)methanamine (5.0 g, 26.4 mmol) and boron trifluoride diethyl etherate (6.70 mL, 52.8 mmol) in 4.0 molar anhydrous tetrahydrofuran in anhydrous toluene (100 mL). The reaction was stirred and allowed to warm to ambient temperature over 30 minutes. The reaction was quenched with saturated ammonium chloride, and product was extracted with ethyl acetate. The organics were washed with water and brine, dried over anhydrous sodium sulfate, filtered and concentrated under reduced pressure. The residue was purified by flash chromatography on silica gel, eluting with a gradient of 10% to 20% ethyl acetate in hexanes, to provide the title compound. MS DCI(+) m/z 275.1 [M+H]$^+$.

Example 112C

N-(4-methoxybenzyl)-1-(5-(tributylstannyl)thiazol-2-yl)cyclobutanamine

A freshly prepared solution of lithium diisopropylamide (12.83 mmol) in anhydrous tetrahydrofuran (15 mL) at –10° C. was added dropwise via cannula over 20 minutes to a –78° C. solution of N-(4-methoxybenzyl)-1-(thiazol-2-yl)cyclobutanamine (1.6 g, 5.83 mmol) (Example 112B) in anhydrous tetrahydrofuran (45 mL). The temperature was maintained below –70° C. during the addition, and after the addition, the reaction was stirred 45 minutes at –78° C. Tributyltin chloride (1.89 mL, 7.00 mmol) was then added dropwise. The cold bath was removed, and the reaction was allowed to warm to ambient temperature over 20 minutes. The reaction was quenched with saturated ammonium chloride, and the product was extracted with ethyl acetate. The combined extracts were washed with water and brine, dried over anhydrous sodium sulfate, filtered, and concentrated under reduced pressure. The residue was purified by flash chromatography on silica gel, eluting with a gradient of 10% to 20% ethyl acetate in hexanes, to provide the title compound. MS ESI(+) m/z 565.1 [M+H]$^+$.

Example 112D 1-(5-(5-chloro-2-(1-methyl-1H-pyrazol-4-yl)-1-tosyl-1H-pyrrolo[2,3-b]pyridin-4-yl)thiazol-2-yl)-N-(4-methoxybenzyl)cyclobutanamine A solution of 4,5-dichloro-2-(1-methyl-1H-pyrazol-4-yl)-1-tosyl-1H-pyrrolo[2,3-b]pyridine (Example 113C) (1.3 g, 3.09 mmol) and N-(4-methoxybenzyl)-1-(5-(tributylstannyl)thiazol-2-yl)cyclobutanamine (Example 112C) (2.45 g, 4.35 mmol) in anhydrous N,N-dimethylformamide (10 mL) was degassed for about 15 minutes under nitrogen. Bis(triphenylphosphine)palladium(II) dichloride (0.108 g, 0.154 mmol) was added to the degassed solution, and reaction was put under nitrogen, sealed, and heated to 100° C. for 16 hours. The reaction was cooled and diluted with ethyl acetate and water. The layers were separated, and organic layer was washed with water and brine, dried over anhydrous sodium sulfate, filtered, and concentrated. The residue was purified by flash chromatography on silica gel, eluting with a gradient of 40% to 50% ethyl acetate in hexanes, to provide the title compound. MS ESI(+) m/z 659.1 [M+H]$^+$.

Example 112E 1-(5-(5-chloro-2-(1-methyl-1H-pyrazol-4-yl)-1H-pyrrolo[2,3-b]pyridin-4-yl)thiazol-2-yl)-N-(4-methoxybenzyl)cyclobutanamine The title compound was prepared as described in Example 47B, substituting 1-(5-(5-chloro-2-(1-methyl-1H-pyrazol-4-yl)-1-tosyl-1H-pyrrolo[2,3-b]pyridin-4-yl)thiazol-2-yl)-N-(4-methoxybenzyl)cyclobutanamine (Example 112D) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (500 MHz, DMSO-D$_6$) ppm 12.34 (s, 1H) 8.25 (s, 1H) 8.23 (s, 1H) 8.17 (s, 1H) 8.02 (s, 1H) 7.62 (m, 1H) 7.32 (d, 2H) 6.87 (d, 2H) 6.75 (s, 1H)

3.89 (s, 3H) 3.71 (s, 3 H) 3.53 (d, 2H) 2.53 (m, 2H) 2.42 (m, 2H) 1.99 (m, 2H); MS ESI(+) m/z 505.0 [M+H]$^+$.

Example 113

4,5-dichloro-2-iodo-1-tosyl-1H-pyrrolo[2,3-b]pyridine

Example 113A 4,5-dichloro-1-tosyl-1H-pyrrolo[2,3-b]pyridine

To a cold (0° C.) suspension of sodium hydride (60% dispersion in mineral oil, 0.556 g, 13.9 mmol) in N,N-dimethylformamide (20 mL) was added a solution of the 5-chloro-4-chloro-1H-pyrrolo[2,3-b]pyridine (2 g, 10.69 mmol) in N,N-dimethylformamide (10 mL) slowly over 5 minutes. The reaction was allowed to stir at ambient temperature for 0.5 hours, and was again cooled to 0° C. A solution of para-toluenesulfonyl chloride (2.14 g, 11.23 mmol) in N,N-dimethylformamide (5 mL) was added, and the reaction was stirred at ambient temperature for 1.5 hours. The reaction was poured into 60 mL water cooled in an ice bath. The suspension was filtered. The solid was collected and purified by flash chromatography on a silica gel, eluting with a gradient of 30% to 100% dichloromethane in hexane, to provide the title compound. MS ESI(+) m/z 340.8 [M+H]$^+$.

Example 113B 4,5-dichloro-2-(1-methyl-1H-pyrazol-4-yl)-1-tosyl-1H-pyrrolo[2,3-b]pyridine To a cold (−78° C.) solution of Example 113A (1 g, 2.93 mmol) in tetrahydrofuran (25 mL) was added a solution of lithium diisopropylamide (4.40 mmol) in tetrahydrofuran (15 mL) dropwise over 10 minutes. The reaction was stirred at −78° C. for 50 minutes, and a solution of iodine (1.2 g, 4.69 mmol) in tetrahydrofuran (6 mL) was added dropwise over 5 minutes. The resulting solution was stirred at −78° C. for 15 minutes. The reaction was quenched by slowly pouring the mixture into a stirring solution of saturated aqueous sodium thiosulfate (40 mL) cooled to 0° C. in an ice bath. The quenched reaction mixture was extracted with ethyl acetate (150 mL). The aqueous layer was extracted with additional ethyl acetate (60 mL). The combined organic layers were washed with brine (50 mL), dried over anhydrous sodium sulfate, filtered, and concentrated. The concentrate was purified by flash chromatography on silica gel, eluting with a gradient of 0% to 30% ethyl acetate in hexane, to provide the title compound. MS ESI(+) m/z 467.3 [M+H]$^+$.

Example 113C 4,5-dichloro-2-(1-methyl-1H-pyrazol-4-yl)-1-tosyl-1H-pyrrolo[2,3-b]pyridine A solution of Example 113B (3.0 g, 6.42 mmol) and 1-methyl-4-(4,4,5,5-tetramethyl-1,3,2-dioxaborolan-2-yl)-1H-pyrazole (1.670 g, 8.03 mmol) in N,N-dimethylformamide (50 mL) was degassed via nitrogen sparge for 15 minutes. The reaction was treated with saturated aqueous sodium bicarbonate (12.5 mL) and bis(triphenylphosphine)palladium(II) chloride (0.406 g, 0.578 mmol), and the mixture was heated to 63° C. for 16 hours. The reaction was cooled to ambient temperature and partitioned between dichloromethane and water. The aqueous layer was extracted with additional dichloromethane. The combined organic layers were washed with water and brine, dried with anhydrous sodium sulfate, filtered, and concentrated under reduced pressure. The concentrate was purified by flash chromatography on a silica gel column, eluting with a gradient of 0% to 40% ethyl acetate in hexane, to provide the title compound. MS ESI(+) m/z 421.4 [M+H]$^+$.

Example 113D 4,5-dichloro-2-(1-methyl-1H-pyrazol-4-yl)-1H-pyrrolo[2,3-b]pyridine A suspension of Example 113C (0.35 g, 0.831 mmol) in methanol (9.2 mL) was treated with 2 N aqueous sodium hydroxide solution (2.08 mL, 4.15 mmol), and the reaction was heated to 70° C. for 10 minutes. The reaction was cooled to ambient temperature, and the pH was adjusted to pH ~7 with 10% aqueous HCl solution. The neutralized mixture was treated with water (12 mL), and the resulting suspension was cooled to 0° C. and filtered. The solid was collected, washed with water, and dried in a vacuum oven at 60° C. to provide the title compound. MS ESI(+) m/z 267.6 [M+H]$^+$.

Example 113E 4,5-dichloro-2-(1-methyl-1H-pyrazol-4-yl)-1-((2-(trimethylsilyl)ethoxy)methyl)-1H-pyrrolo[2,3-b]pyridine A solution of Example 113D (0.17 g, 0.636 mmol) in N,N-dimethylformamide (3.5 mL) was cooled to 0° C. in an ice bath, and sodium hydride (60% dispersion in mineral oil, 0.031 g, 0.776 mmol) was added. The reaction mixture was stirred 30 minutes, cooled to −42° C., and (2-(chloromethoxy)ethyl)trimethylsilane (0.146 mL, 0.827 mol) was added dropwise over 3 minutes. The reaction was stirred at −42° C. for 1 hour and was quenched with saturated aqueous ammonium chloride (3 mL). The mixture was partitioned between water and ethyl acetate. The organic layer was washed with water and brine, dried over anhydrous sodium sulfate, filtered, and concentrated under reduced pressure. The concentrate was purified by flash chromatography on a silica gel column, eluting with a gradient of 0% to 25% ethyl acetae in hexane, to provide the title compound. MS ESI(+) m/z 397.2 [M+H]$^+$.

Example 113F 4-(4-bromo-1H-pyrazol-1-yl)-5-chloro-2-(1-methyl-1H-pyrazol-4-yl)-1-((2-(trimethylsilyl)ethoxy)methyl)-1H-pyrrolo[2,3-b]pyridine A solution of Example 113E (0.194 g, 0.488 mmol) and 4-bromo-1H-pyrazole (0.115 g, 0.781 mmol) in 1-methyl-2-pyrrolidinone (0.8 mL) was treated with potassium carbonate (0.169 g, 1.22 mmol), and the reaction was heated at 150° C. for 2.5 hours. The reaction was cooled to ambient temperature, and partitioned between water and ethyl acetate. The organic layer was washed with water and brine, dried over anhydrous sodium sulfate, filtered, and concentrated under reduced pressure. The concentrate was purified by flash chromatography on a silica gel column, eluting with a gradient of 0% to 1% methanol in dichloromethane, to provide the title compound. MS ESI(+) m/z 509.0 [M+H]$^+$.

Example 113G 1-(1-(5-chloro-2-(1-methyl-1H-pyrazol-4-yl)-1-((2-(trimethylsilyl)ethoxy)methyl)-1H-pyrrolo[2,3-b]pyridin-4-yl)-1H-pyrazol-4-yl)cyclobutanol A −78° C. solution of Example 113F (75 mgs, 0.148 mmol) in tetrahydrofuran (2.1 mL) was treated with n-butyllithium (2.45 M in hexanes, 0.121 mL, 0.295 mmol) dropwise over 3 minutes, and the reaction was stirred for 2 minutes. Cyclobutanone (0.022 mL, 0.295 mmol) was added, and the reaction was stirred for 1 hour at −78° C. The reaction was quenched by the addition of saturated aqueous ammonium chloride. The mixture was extracted with ethyl acetate. The organic layer was washed with brine, dried over anhydrous sodium sulfate, filtered, and concentrated under reduced pressure. The concentrate was purified by flash chromatography on a silica gel column, eluting with a gradient of 0% to 4% methanol in dichloromethane, to provide the title compound. MS ESI(+) m/z 499.2 [M+H]$^+$.

Example 113H 4,5-dichloro-2-iodo-1-tosyl-1H-pyrrolo[2,3-b]pyridine

A solution of Example 113G (0.026 g, 0.052 mmol) and ethylenediamine (0.038 mL, 0.573 mmol) in tetrahydrofuran (0.65 mL) was treated with tetrabutylammonium fluoride (1 M in tetrahydrofuran, 1.3 mL, 1.3 mmol), and the reaction was heated at 75° C. for 2.5 hours. The reaction was concentrated under reduced pressure, and the residue was treated with water (3 mL). The suspension was stirred for 10 minutes and filtered. The solid was collected, washed with water (0.5 mL), and dried under vacuum. The crude solid was purified by flash chromatography on a silica gel column, eluting with a gradient of 0% to 3% methanol in dichloromethane, to provide the title compound. $^1$H NMR (300 MHz, DMSO-d$_6$) ppm 1.63-1.88 (m, 2H), 2.28-2.39 (m, 4H), 3.88 (s, 3H), 5.53 (s, 1H), 6.56 (s, 1H), 7.90 (s, 1H), 8.01 (s, 1H), 8.18 (s, 1H), 8.26 (s, 1H), 8.28 (s, 1H), 12.39 (bs, 1H); MS ESI(+) m/z 369.1 [M+H]$^+$.

Example 114

5-chloro-4-[2-(1-fluorocyclobutyl)-1,3-thiazol-5-yl]-2-[1-(2-morpholin-4-ylethyl)-1H-pyrazol-4-yl]-1H-pyrrolo[2,3-b]pyridine

Example 114A 5-(5-chloro-2-iodo-1-tosyl-1H-pyrrolo[2,3-b]pyridin-4-yl)-2-(1-fluorocyclobutyl)thiazole To a cold (0° C.) solution of 1-(5-(5-chloro-2-iodo-1-tosyl-1H-pyrrolo[2,3-b]pyridin-4-yl)thiazol-2-yl)cyclobutanol (Example 8A) (330 mg, 0.563 mmol) in dichloromethane (6 mL) and dioxane (6 mL) was added diethylaminosulfur trifluoride (0.149 mL, 1.127 mmol) in a single portion via syringe. The reaction was stirred at 0° C. for 2 hours and was then quenched by the addition of saturated sodium bicarbonate solution and ethyl acetate. The layers were separated, and the aqueous layer was extracted with additional ethyl acetate (2×). The combined organics were dried with anhydrous sodium sulfate, filtered, and concentrated under reduced pressure. The residue was purified by flash chromatography on silica gel, eluting with a gradient of hexane to 25% ethyl acetate in hexane, to give the title compound. $^1$H NMR (300 MHz, DMSO-d$_6$) 8.51 (s, 1H), 8.24 (d, J=2.8 Hz, 1H), 7.97 (d, J=8.4 Hz, 2H), 7.47 (d, J=8.0 Hz, 2H), 7.24 (s, 1H), 2.80-2.63 (m, 4H), 2.37 (s, 3H), 2.09-1.96 (m, 1H), 1.94-1.85 (m, 1H).

Example 114B 4-(2-(4-(5-chloro-4-(2-(1-fluorocyclobutyl)thiazol-5-yl)-1-tosyl-1H-pyrrolo[2,3-b]pyridin-2-yl)-1H-pyrazol-1-yl)ethyl)morpholine To a stirred ambient solution of 5-(5-chloro-2-iodo-1-tosyl-1H-pyrrolo[2,3-b]pyridin-4-yl)-2-(1-fluorocyclobutyl)thiazole (Example 114A) (60 mg, 0.102 mmol) and 4-(2-(4-(4,4,5,5-tetramethyl-1,3,2-dioxaborolan-2-yl)-1H-pyrazol-1-yl)ethyl)morpholine (37.6 mg, 0.122 mmol) in N,N-dimethylformamide (0.765 mL) was added saturated aqueous bicarbonate solution (0.765 mL) followed by bis(triphenylphosphine)palladium dichloride (5.01 mg, 7.14 µmol). The mixture was heated to 70° C. for 4 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. MS ESI(+) m/z 641.2 [M+H]$^+$.

Example 114C

A solution of 4-(2-(4-(5-chloro-4-(2-(1-fluorocyclobutyl)thiazol-5-yl)-1-tosyl-1H-pyrrolo[2,3-b]pyridin-2-yl)-1H-pyrazol-1-yl)ethyl)morpholine (Example 114B) (60 mg, 0.094 mmol) in methanol (3 mL) and 2N aqueous sodium hydroxide solution (0.164 mL, 0.328 mmol) was heated by microwave irradiation (Biotage, Initiator) in a sealed vessel to 105° C. for 5 minutes. The reaction was concentrated to dryness, and the residue was dissolved in 1.5 mL of 1:1 methyl sulfoxide:methanol solution. The resulting solution was purified by reverse phase high performance liquid chromatography (RP HPLC, 19×150 mm Atlantis Prep T3 OBD 5 m column, eluting with a gradient of 5% B in A to 75% B in A over 25 minutes, wherein A is water containing 0.1% v/v trifluoroacetic acid and B is acetonitrile containing 0.1% v/v trifluoroacetic acid). The fractions containing the product were diluted with ethyl acetate and saturated aqueous sodium bicarbonate solution. The layers were separated, and the organic layer was dried with anhydrous sodium sulfate, filtered and concentrated under reduced pressure to give the title compound. $^1$H NMR (300 MHz, DMSO-d$_6$) δ 12.41 (s, 1H), 8.35 (s, 1H), 8.32 (d, J=2.8 Hz, 1H), 8.26 (s, 1H), 8.07 (s, 1H), 6.78 (s, 1H), 4.27 (t, J=6.4 Hz, 2H), 3.59-3.52 (m, 4H), 2.84-2.67 (m, 6H), 2.47-2.38 (m, 4H), 2.14-1.86 (m, 2H); MS ESI(+) m/z 487.3 [M+H]$^+$.

Example 115

5-chloro-4-[2-(1-fluorocyclobutyl)-1,3-thiazol-5-yl]-2-[4-(morpholin-4-ylmethyl)phenyl]-1H-pyrrolo[2,3-b]pyridine

Example 115A 4-(4-(5-chloro-4-(2-(1-fluorocyclobutyl)thiazol-5-yl)-1-tosyl-1H-pyrrolo[2,3-b]pyridin-2-yl)benzyl)morpholine The title compound was prepared as described in Example 114B, substituting 4-(4-(4,4,5,5-tetramethyl-1,3,2-dioxaborolan-2-yl)benzyl)morpholine for 4-(2-(4-(4,4,5,5-tetramethyl-1,3,2-dioxaborolan-2-yl)-1H-pyrazol-1-yl)ethyl)morpholine. MS ESI(+) m/z 637.1 [M+H]+.

Example 115B

4-(4-(5-chloro-4-(2-(1-fluorocyclobutyl)thiazol-5-yl)-1H-pyrrolo[2,3-b]pyridin-2-yl)benzyl)morpholine The title compound was prepared as described in Example 1I, substituting 4-(4-(5-chloro-4-(2-(1-fluorocyclobutyl)thiazol-5-yl)-1-tosyl-1H-pyrrolo[2,3-b]pyridin-2-yl)benzyl)morpholine (Example 115A) for 1-(5-(5-chloro-2-(1-(2-morpholinoethyl)-1H-pyrazol-4-yl)-1-tosyl-1H-pyrrolo[2,3-b]pyridin-4-yl)thiazol-2-yl)cyclobutanol (Example 1H). $^1$H NMR (300 MHz, DMSO-$d_6$) δ 12.72 (s, 1H), 8.43-8.37 (m, 2H), 8.18-8.09 (m, 2H), 7.65-7.56 (m, 2H), 7.21 (bs, 1H), 4.05-3.92 (m, 2H), 3.70-3.56 (m, 2H), 3.22-3.05 (m, 4H), 2.85-2.71 (m, 4H), 2.17-1.98 (m, 1H), 2.00-1.83 (m, 1H); MS ESI(+) m/z 483.1 [M+H]+.

Example 116

5-chloro-4-[2-(1-fluorocyclobutyl)-1,3-thiazol-5-yl]-2-[1-(2-pyrrolidin-1-ylethyl)-1H-pyrazol-4-yl]-1H-pyrrolo[2,3-b]pyridine

Example 116A

5-(5-chloro-2-(1-(2-(pyrrolidin-1-yl)ethyl)-1H-pyrazol-4-yl)-1-tosyl-1H-pyrrolo[2,3-b]pyridin-4-yl)-2-(1-fluorocyclobutyl)thiazole The title compound was prepared as described in Example 114B, substituting 1-(2-(pyrrolidin-1-yl)ethyl)-4-(4,4,5,5-tetramethyl-1,3,2-dioxaborolan-2-yl)-1H-pyrazole (Example 20A) for 4-(2-(4-(4,4,5,5-tetramethyl-1,3,2-dioxaborolan-2-yl)-1H-pyrazol-1-yl)ethyl)morpholine. MS ESI(+) m/z 625.2 [M+H]+.

Example 116B

5-(5-chloro-2-(1-(2-(pyrrolidin-1-yl)ethyl)-1H-pyrazol-4-yl)-1H-pyrrolo[2,3-b]pyridin-4-yl)-2-(1-fluorocyclobutyl)thiazole The title compound was prepared as described in Example 114C, substituting 5-(5-chloro-2-(1-(2-(pyrrolidin-1-yl)ethyl)-1H-pyrazol-4-yl)-1-tosyl-1H-pyrrolo[2,3-b]pyridin-4-yl)-2-(1-fluorocyclobutyl)thiazole (Example 116A) for 4-(4-(5-chloro-4-(2-(1-fluorocyclobutyl)thiazol-5-yl)-1-tosyl-1H-pyrrolo[2,3-b]pyridin-2-yl)-1H-pyrazol-1-yl)ethyl)morpholine (Example 114B). $^1$H NMR (300 MHz, DMSO-$d_6$) δ 12.39 (bs, 1H), 8.36 (s, 1H), 8.32 (d, J=2.8 Hz, 1H), 8.26 (s, 1H), 8.07 (s, 1H), 6.78 (s, 1H), 4.24 (t, J=6.4 Hz, 2H), 2.88-2.66 (m, 6H), 2.45 (d, 4H), 2.12-1.85 (m, 2H), 1.75-1.58 (m, 4H); MS ESI(+) m/z 471.3 [M+H]+.

Example 117

3-{5-[5-chloro-2-(1-methyl-1H-pyrazol-4-yl)-1H-pyrrolo[2,3-b]pyridin-4-yl]-1,3-thiazol-2-yl}-1-methylpyrrolidin-3-ol

Example 117A tert-butyl 3-(methoxymethoxy)-3-(5-(tributylstannyl)thiazol-2-yl)pyrrolidine-1-carboxylate The title compound was prepared as described in Examples 1A-1C, except substituting tert-butyl 3-oxopyrrolidine-1-carboxylate for cyclobutanone in Example 1A. MS APCI(+) m/z 604.5 (M+H)+.

Example 117B tert-butyl 3-(5-(5-chloro-1-tosyl-1H-pyrrolo[2,3-b]pyridin-4-yl)thiazol-2-yl)-3-(methoxymethoxy)pyrrolidine-1-carboxylate The title compound was prepared as described in Example 1E, substituting tert-butyl 3-(methoxymethoxy)-3-(5-(tributylstannyl)thiazol-2-yl)pyrrolidine-1-carboxylate (Example 117A) for 2-(1-(methoxymethoxy)cyclobutyl)-5-(tributylstannyl)thiazole (Example 1C). MS ESI(+) m/z 618.9 (M+H)+.

Example 117C tert-butyl 3-(5-(5-chloro-2-iodo-1-tosyl-1H-pyrrolo[2,3-b]pyridin-4-yl)thiazol-2-yl)-3-(methoxymethoxy)pyrrolidine-1-carboxylate The title compound was prepared as described in Example 1F, substituting tert-butyl 3-(5-(5-chloro-1-tosyl-1H-pyrrolo[2,3-b]pyridin-4-yl)thiazol-2-yl)-3-(methoxymethoxy)pyrrolidine-1-carboxylate (Example 117B) for 5-(5-chloro-1-tosyl-1H-pyrrolo[2,3-b]pyridin-4-yl)-2-(1-(methoxymethoxy)cyclobutyl)thiazole (Example 1E). MS ESI(+) m/z 695.4 (M-tBu+H)+.

Example 117D

3-(5-(5-chloro-2-iodo-1-tosyl-1H-pyrrolo[2,3-b]pyridin-4-yl)thiazol-2-yl)pyrrolidin-3-ol The title compound was prepared as described in Example 8A, substituting tert-butyl 3-(5-(5-chloro-2-iodo-1-tosyl-1H-pyrrolo[2,3-b]pyridin-4-yl)thiazol-2-yl)-3-(methoxymethoxy)pyrrolidine-1-carboxylate (Example 117C) for 5-(5-chloro-2-iodo-1-tosyl-1H-pyrrolo[2,3-b]pyridin-4-yl)-2-(1-(methoxymethoxy)cyclobutyl)thiazole (Example 1F). MS APCI(+) m/z 601.2 (M+H)+.

Example 117E

3-(5-(5-chloro-2-iodo-1-tosyl-1H-pyrrolo[2,3-b]pyridin-4-yl)thiazol-2-yl)-1-methylpyrrolidin-3-ol To an ambient solution of 3-(5-(5-chloro-2-iodo-1-tosyl-1H-pyrrolo[2,3-b]pyridin-4-yl)thiazol-2-yl)pyrrolidin-3-ol (Example 117D) (410 mg, 0.682 mmol) in tetrahydrofuran (10 mL) was added formaldehyde (0.254 mL, 3.41 mmol, 37 wt % in water) and acetic acid (0.195 mL, 3.41 mmol). The reaction was stirred at room temperature for 20 minutes, and sodium triacetoxyborohydride (0.723 g, 3.41 mmol) was added in a single portion. The reaction was stirred at room temperature for 1 hour and was quenched by the addition of water and chloroform. The layers were separated, and the aqueous layer was extracted with additional chloroform (2×). The combined organics were dried with anhydrous sodium sulfate, filtered, and concentrated under reduced pressure. The residue was purifed by flash column chromatography on silica gel, wluting with a gradient of 0 to 8% methanol (containing 1% v/v ammonium hydroxide) in dichloromethane, to give the title compound. MS APCI(+) m/z 614.9 (M+H)$^+$.

Example 117F

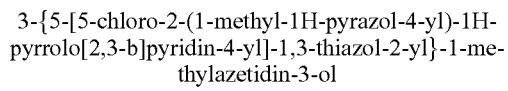

3-{5-[5-chloro-2-(1-methyl-1H-pyrazol-4-yl)-1H-pyrrolo[2,3-b]pyridin-4-yl]-1,3-thiazol-2-yl}-1-methylazetidin-3-ol The title compound was prepared as described in Example 32, substituting 1-methyl-4-(4,4,5,5-tetramethyl-1,3,2-dioxaborolan-2-yl)-1H-pyrazole for phenylboronic acid, and 3-(5-(5-chloro-2-iodo-1-tosyl-1H-pyrrolo[2,3-b]pyridin-4-yl)thiazol-2-yl)-1-methylpyrrolidin-3-ol (Example 117E) for 1-(5-(5-chloro-2-iodo-1-tosyl-1H-pyrrolo[2,3-b]pyridin-4-yl)thiazol-2-yl)cyclobutanol (Example 8A). $^1$H NMR (500 MHz, DMSO-D6) ppm 2.16 (d, J=6.41 Hz, 1H) 2.34 (s, 3H) 2.62 (d, J=6.41 Hz, 1H) 2.85-3.05 (m, 4H) 3.89 (s, 3H) 6.46 (s, 1H) 6.74 (d, J=2.14 Hz, 1H) 8.04 (s, 1H) 8.17 (s, 1H) 8.24 (s, 1H) 8.28 (s, 1H) 12.35 (s, 1H); MS ESI(+) m/z 415 (M+H)$^+$.

Example 118

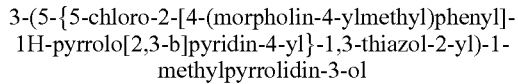

3-(5-{5-chloro-2-[4-(morpholin-4-ylmethyl)phenyl]-1H-pyrrolo[2,3-b]pyridin-4-yl}-1,3-thiazol-2-yl)-1-methylpyrrolidin-3-ol The title compound was prepared as described in Example 32, substituting 4-(4-(4,4,5,5-tetramethyl-1,3,2-dioxaborolan-2-yl)benzyl)morpholine for phenylboronic acid, and 3-(5-(5-chloro-2-iodo-1-tosyl-1H-pyrrolo[2,3-b]pyridin-4-yl)thiazol-2-yl)-1-methylpyrrolidin-3-ol (Example 117E) for 1-(5-(5-chloro-2-iodo-1-tosyl-1H-pyrrolo[2,3-b]pyridin-4-yl)thiazol-2-yl)cyclobutanol (Example 8A). $^1$H NMR (400 MHz, DMSO-D6) ppm 2.16 (d, J=6.41 Hz, 1H) 2.33 (s, 3H) 2.34-2.42 (m, 4H) 2.61 (d, J=6.71 Hz, 1H) 2.80-3.12 (m, 4H) 3.50 (s, 2H) 3.58 (s, 4H) 6.46 (s, 1H) 7.03 (s, 1H) 7.40 (d, J=7.93 Hz, 2H) 7.96 (d, J=7.93 Hz, 2H) 8.24 (s, 1H) 8.33 (s, 1H) 12.57 (s, 1H); MS ESI(+) m/z 511 (M+H)$^+$.

Example 120

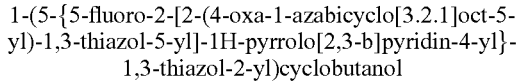

1-(5-{5-fluoro-2-[2-(4-oxa-1-azabicyclo[3.2.1]oct-5-yl)-1,3-thiazol-5-yl]-1H-pyrrolo[2,3-b]pyridin-4-yl}-1,3-thiazol-2-yl)cyclobutanol Example 120A

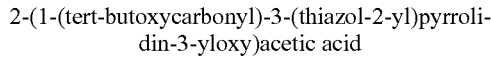

2-(1-(tert-butoxycarbonyl)-3-(thiazol-2-yl)pyrrolidin-3-yloxy)acetic acid

To an ambient suspension of NaH (5.40 g, 135 mmol) in N,N-dimethylformamide (50 mL) was added dropwise a solution of tert-butyl 3-hydroxy-3-(thiazol-2-yl)pyrrolidine-1-carboxylate (7.30 g, 27 mmol) in N,N-dimethylformamide (20 mL). After 30 minutes, bromoacetic acid (7.50 g, 54.0 mmol) in N,N-dimethylformamide (20 mL) was added dropwise. The solution was stirred at room temperature for 16 hours and then heated to 50° C. for 3 hours. The reaction was cooled to room temperature and was quenched by the addition of water. The solution was basicified to pH 10 by the addition of 2.5 M NaOH solution. The aqueous layer was extracted with ether, and the organics discarded. The aqueous layer was acidified to pH 1 with 6 M HCl solution, and then extracted with ethyl acetate (2×). The combined organics were washed with water, brine, dried over sodium sulfate, filtered, and concentrated under reduced pressure to give the product. MS ESI(+) m/z 329.3 [M+H]$^+$.

Example 120B

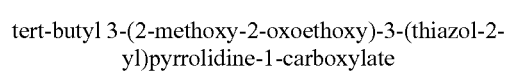

tert-butyl 3-(2-methoxy-2-oxoethoxy)-3-(thiazol-2-yl)pyrrolidine-1-carboxylate

To a cooled (0° C.) solution of 2-(1-(tert-butoxycarbonyl)-3-(thiazol-2-yl)pyrrolidin-3-yloxy)acetic acid (7.5 g, 22.84 mmol) in dichloromethane (150 mL) was added N,N-dimethylformamide (1 mL) followed by dropwise addition of oxalyl chloride (1.999 mL, 22.84 mmol). The cold bath was then removed, and the reaction was stirred for 4 hours. Methanol (30 mL) was added to the ambient reaction, and the reaction was stirred for an additional 0.5 hours. The reaction was concentrated under reduced pressure. The residue was purified by flash chromatography on silica gel, eluting with a gradient of 0 to 50% ethyl acetate in hexane, to give the product. MS ESI(+) m/z 342.8 [M+H]$^+$.

Example 120C

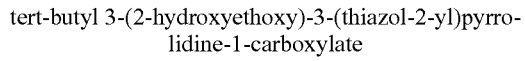

tert-butyl 3-(2-hydroxyethoxy)-3-(thiazol-2-yl)pyrrolidine-1-carboxylate

To an ambient solution of tert-butyl 3-(2-methoxy-2-oxoethoxy)-3-(thiazol-2-yl)pyrrolidine-1-carboxylate (2.05 g, 5.99 mmol) in methanol (29.9 ml) was added NaBH$_4$ (0.680 g, 17.96 mmol). The reaction was stirred for 1 hour and was then quenched by the addition of water (20 mL) and ethyl acetate (20 mL). The layers were separated, and the aqueous layer was extracted with additional ethyl acetate (2×20 mL). The combined organic layers were dried with anhydrous Na$_2$SO$_4$, filtered, and concentrated under reduced pressure to give the title compound, which was used in the subsequent step without further purification. MS ESI(+) m/z 314.9 [M+H]$^+$.

Example 120D

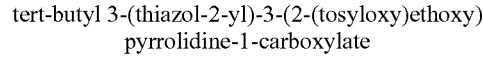

tert-butyl 3-(thiazol-2-yl)-3-(2-(tosyloxy)ethoxy)pyrrolidine-1-carboxylate

To an ambient solution of tert-butyl 3-(2-hydroxyethoxy)-3-(thiazol-2-yl)pyrrolidine-1-carboxylate (1.92 g, 6.11 mmol) in dichloromethane (20 mL) was added triethylamine (1.70 mL, 12.21 mmol), 4-dimethylaminopyridine (0.075 g, 0.611 mmol), and para-toluenesulfonyl chloride (1.28 g, 6.72 mmol). The reaction was stirred for 16 hours and was quenched by the addition of saturated ammonium chloride solution. The layers were separated, and the aqueous layer was extracted with additional dichloromethane. The combined organics were dried with anhydrous sodium sulfate, filtered and concentrated under reduced pressure to give the product, which was used without further purification. MS ESI(+) m/z 468.8 [M+H]$^+$.

Example 120E 5-(thiazol-2-yl)-4-oxa-1-azabicyclo[3.2.1]octane

To an ambient solution of tert-butyl 3-(thiazol-2-yl)-3-(2-(tosyloxy)ethoxy)pyrrolidine-1-carboxylate (2.3 g, 4.91 mmol) in dichloromethane (24.54 ml) was added trifluoroacetic acid (0.378 mL, 4.91 mmol). The reaction was stirred for 2 hours and was then concentrated under reduced pressure. The residue was dissolved in dichloromethane (10 mL), and the solution was added slowly to an ambient mixture of potassium carbonate (6.78 g, 49.1 mmol) in dichloromethane (50 mL). The mixture was heated to 50° C. for 1 hour and then cooled to room temperature. The reaction was diluted with water (100 mL). The layers were separated, and the aqueous layer was extracted with additional dichloromethane (2×). The combined organics were dried with anhydrous sodium sulfate, filtered and dried under reduced pressure, to give the title compound, which was used without further purification. MS ESI(+) m/z 197.1 [M+H]$^+$.

Example 120F 5-(5-(tributylstannyl)thiazol-2-yl)-4-oxa-1-azabicyclo[3.2.1]octane To a cold (−78° C.) solution of the 5-(thiazol-2-yl)-4-oxa-1-azabicyclo[3.2.1]octane (632 mg, 3.22 mmol) in tetrahydrofuran (11 mL) was added a solution of lithium diisopropylamide (7.79 mmol in 10 mL tetrahydrofuran) dropwise. The solution was stirred at −78° C. for 45 minutes, and tributyltin chloride (1.05 mL, 3.86 mmol) was added dropwise. The cold bath was removed, and the reaction allowed to warm to room temperature. The ambient reaction was then quenched by the addition of saturated aqueous ammonium chloride solution and diethyl ether. The layers were separated, and the aqueous layer was extracted with additional diethyl ether. The combined organics were washed with water, dried with anhydrous sodium sulfate, filtered and concentrated under reduced pressure to give the title compound, which was used without further purification. MS ESI(+) m/z 487.4 [M+H]$^+$.

Example 120G 1-(5-(2-(2-(4-oxa-1-azabicyclo[3.2.1]octan-5-yl)thiazol-5-yl)-5-fluoro-1-tosyl-1H-pyrrolo[2,3-b]pyridin-4-yl)thiazol-2-yl)cyclobutanol A solution of 1-(5-(5-fluoro-2-iodo-1-tosyl-1H-pyrrolo[2,3-b]pyridin-4-yl)thiazol-2-yl)cyclobutanol (150 mg, 0.263 mmol), 5-(5-(tributylstannyl)thiazol-2-yl)-4-oxa-1-azabicyclo[3.2.1]octane (192 mg, 0.395 mmol), and bis(triphenylphosphine)palladium dichloride (0.013 g, 0.025 mmol) in N,N-dimethylformamide (1.8 mL) was heated to 70° C. for 2 hours. The reaction was quenched by the addition of an aqueous potassium fluoride solution (1.0 g in 2.5 mL water) and ethyl acetate (5 mL). The mixture was stirred vigorously overnight and was then filtered through diatomaceous earth, eluting with ethyl acetate. The layers were separated, and the organic layer was washed with aqueous saturated sodium bicarbonate and water. The organic layer was dried with anhydrous sodium sulfate, filtered and concentrated under reduced pressure to give the title compound, which was used without further purification. MS ESI(+) m/z 638.2 [M+H]$^+$.

Example 120H 1-(5-(2-(2-(4-oxa-1-azabicyclo[3.2.1]octan-5-yl)thiazol-5-yl)-5-fluoro-1H-pyrrolo[2,3-b]pyridin-4-yl)thiazol-2-yl)cyclobutanol A solution of 1-(5-(2-(2-(4-oxa-1-azabicyclo[3.2.1]octan-5-yl)thiazol-5-yl)-5-fluoro-1-tosyl-1H-pyrrolo[2,3-b]pyridin-4-yl)thiazol-2-yl)cyclobutanol (70 mg, 0.110 mmol) in methanol (1.1 mL) and 2N NaOH solution (274 μL, 0.549 mmol) was heated by microwave irradiation (Biotage, Initiator) in a sealed vessel to 105° C. for 5 minutes. The reaction was concentrated to dryness, and the residue was dissolved in 1.5 mL of 1:1 methylsulfoxide:methanol solution. The resulting solution was purified by reverse phase high performance liquid chromatography (RP HPLC, 19×150 mm Atlantis Prep T3 OBD 5 m column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound as a trifluoroacetic acid salt. $^1$H NMR (300 MHz, DMSO-d$_6$) δ 12.75 (s, 1H), 10.66 (s, 1H), 8.49 (s, 1H), 8.45 (s, 1H), 8.36 (d, J=3.5 Hz, 1H), 7.24 (d, J=2.0 Hz, 1H), 6.68 (s, 1H), 4.41-4.20 (m, 2H), 3.91-3.47 (m, 6H), 2.80-2.55 (m, 4H), 2.47-2.35 (m, 2H), 2.05-1.87 (m, 2H); MS ESI(+) m/z 484.4 [M+H]$^+$.

Example 121

1-{5-[5-chloro-2-(1-methyl-1H-pyrazol-4-yl)-1H-pyrrolo[2,3-b]pyridin-4-yl]-1,3-thiazol-2-yl}cyclobutanamine

Example 121A 1-(5-(5-chloro-2-(1-methyl-1H-pyrazol-4-yl)-1-tosyl-1H-pyrrolo[2,3-b]pyridin-4-yl)thiazol-2-yl)cyclobutanamine A solution of 1-(5-(5-chloro-2-(1-methyl-1H-pyrazol-4-yl)-1-tosyl-1H-pyrrolo[2,3-b]pyridin-4-yl)thiazol-2-yl)-N-(4-methoxybenzyl)cyclobutanamine (500 mg, 0.758 mmol) (Example 112D) in anhydrous dichloromethane (20 mL) and water (1.0 mL) was treated with 2,3-dichloro-5,6-dicyano-1,4-benzoquinone (224 mg, 0.986 mmol) and stirred for 20 minutes at ambient temperature. Additional 2,3-dichloro-5,6-dicyano-1,4-benzoquinone (50 mg, 0.220 mmol) was added to the mixture, and the reaction stirred one hour at ambient temperature. The reaction was quenched with saturated sodium bicarbonate, and layers were separated. The organic layer was washed with brine, dried over anhydrous sodium sulfate, filtered, and concentrated under reduced pressure. The residue was purified by flash chromatography on silica gel, eluting with a gradient of 100% ethyl acetate to 5% methanol in ethyl acetate, to provide the title compound. MS ESI(+) m/z 539.1 [M+H]$^+$.

Example 121B 1-(5-(5-chloro-2-(1-methyl-1H-pyrazol-4-yl)-1H-pyrrolo[2,3-b]pyridin-4-yl)thiazol-2-yl)cyclobutanamine The title compound was prepared as described in Example 47B, substituting 1-(5-(5-chloro-2-(1-methyl-1H-pyrazol-4-yl)-1-tosyl-1H-pyrrolo[2,3-b]pyridin-4-yl)thiazol-2-yl)cyclobutanamine (Example 121A) for 5-(5-chloro-2-(1-methyl-1H-pyrazol-4-yl)-1-tosyl-1H-pyrrolo[2,3-b]pyridin-4- yl)-2-(1-(methoxymethoxy)cyclobutyl)thiazole (Example 47A). $^1$H NMR (400 MHz, DMSO-d$_6$) ppm 12.33 (s, 1H) 8.27 (s, 1H) 8.23 (s, 1H) 8.16 (s, 1H) 8.04 (s, 1H) 6.74 (s, 1H) 3.89 (s, 3H) 2.83 (bs, 2H) 2.63 (m, 2H) 2.21 (m, 2H) 1.99 (m, 2H); MS ESI(+) m/z 385.1 [M+H]$^+$.

Example 122

N-(1-{5-[5-chloro-2-(1-methyl-1H-pyrazol-4-yl)-1H-pyrrolo[2,3-b]pyridin-4-yl]-1,3-thiazol-2-0yl}cyclobutyl)acetamide A mixture of 1-(5-(5-chloro-2-(1-methyl-1H-pyrazol-4-yl)-1H-pyrrolo[2,3-b]pyridin-4-yl)thiazol-2-yl)cyclobutanamine (30 mg, 0.078 mmol) (Example 121B) in anhydrous tetrahydrofuran (1 mL) was treated with triethylamine (0.013 ml, 0.094 mmol) and acetyl chloride (6.10 µL, 0.086 mmol). The reaction mixture was stirred at ambient temperature for about 4 hours. The reaction was diluted with water and brine, and extracted with dichloromethane. The extracts were combined and concentrated under reduced pressure. The residue was purified by flash chromatography on silica gel, eluting with a gradient of 2% to 8% methanol in dichloromethane, to provide the title compound. $^1$H NMR (500 MHz, DMSO-d$_6$) ppm 12.35 (s, 1H) 8.97 (s, 1H) 8.27 (s, 1H) 8.23 (s, 1H) 8.17 (s, 1H) 8.05 (s, 1H) 6.75 (s, 1H) 3.89 (s, 3H) 2.73 (m, 2H) 2.48 (m, 2H) 2.05 (m, 2H) 1.91 (s, 3H); MS ESI(+) m/z 427.4 [M+H]$^+$.

Example 123

N-(1-{5-[5-chloro-2-(1-methyl-1H-pyrazol-4-yl)-1H-pyrrolo[2,3-b]pyridin-4-yl]-1,3-thiazol-2-yl}cyclobutyl)benzamide The title compound was prepared as described in Example 122, substituting benzoyl chloride for acetyl chloride. $^1$H NMR (500 MHz, DMSO-d$_6$) ppm 12.34 (s, 1H) 9.47 (s, 1H) 8.26 (s, 1H) 8.21 (d, 2H) 8.03 (s, 1H) 7.92 (m, 2H) 7.57 (m, 1H) 7.50 (t, 2H) 6.75 (d, 1H) 3.89 (s, 3H) 2.83 (m, 2H) 2.70 (m, 2H) 2.11 (m, 2H); MS ESI(+) m/z 489.4 [M+H]$^+$.

Example 124

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N'-ethylurea A mixture of 1-(5-(5-chloro-2-(1-methyl-1H-pyrazol-4-yl)-1H-pyrrolo[2,3-b]pyridin-4-yl)thiazol-2-yl)cyclobutanamine (30 mg, 0.078 mmol) (Example 121B) in anhydrous tetrahydrofuran (1 mL) was treated with ethyl isocyanate (6.79 µL, 0.086 mmol), and the reaction mixture was stirred at ambient temperature for about 4 hours. The reaction was diluted with water and brine, and extracted with dichloromethane. The extracts were combined and concentrated under reduced pressure. The residue was purified by flash chromatography on silica gel, eluting with a gradient of 2% to 8% methanol in dichloromethane, to provide the title compound. MS ESI(+) m/z 456.2 [M+H]$^+$. $^1$H NMR (500 MHz, DMSO-d$_6$) ppm 12.34 (s, 1H) 8.26 (s, 1H) 8.22 (s, 1H) 8.16 (s, 1H) 8.03 (s, 1H) 7.06 (s, 1H) 6.75 (d, 1H) 5.93 (t, 1H) 3.89 (s, 3H) 3.01 (dd, 2H) 2.70 (m, 2H) 2.40 (m, 2H) 2.05 (m, 2H) 0.99 (t, 3H).

Example 125

N-(1-{5-[5-chloro-2-(1-methyl-1H-pyrazol-4-yl)-1H-pyrrolo[2,3-b]pyridin-4-yl]-1,3-thiazol-2-yl}cyclobutyl)methanesulfonamide The title compound was prepared as described in Example 122, substituting methanesulfonyl chloride for acetyl chloride. $^1$H NMR (500 MHz, DMSO-D$_6$) ppm 12.37 (s, 1H) 8.40 (s, 1H) 8.27 (s, 1H) 8.25 (s, 1H) 8.20 (s, 1H) 8.04 (s, 1H) 6.75 (d, 1H) 3.89 (s, 3H) 2.93 (s, 3H) 2.67 (m, 4H) 2.04 (m, 2H); MS ESI(+) m/z 463.4 [M+H]$^+$.

Example 126

3-{5-[5-chloro-2-(1-methyl-1H-pyrazol-4-yl)-1H-pyrrolo[2,3-b]pyridin-4-yl]-1,3-thiazol-2-yl}-1-methylazetidin-3-ol Example 126A 3-(5-(5-chloro-2-iodo-1-tosyl-1H-pyrrolo[2,3-b]pyridin-4-yl)thiazol-2-yl)-1-methylazetidin-3-ol The title compound was prepared as described in Examples 117B-117E, substituting tert-butyl 3-(methoxymethoxy)-3-(5-(tributylstannyl)thiazol-2-yl)azetidine-1-carboxylate (Example 54A) for tert-butyl 3-(methoxymethoxy)-3-(5-(tributylstannyl)thiazol-2-yl)pyrrolidine-1-carboxylate (Example 117A). MS ESI(+) m/z 401.3 (M+H)$^+$.

Example 126B

3-{5-[5-chloro-2-(1-methyl-1H-pyrazol-4-yl)-1H-pyrrolo[2,3-b]pyridin-4-yl]-1,3-thiazol-2-yl}-1-methylazetidin-3-ol The title compound was prepared as described in Example 32, substituting 1-methyl-4-(4,4,5,5-tetramethyl-1,3,2-dioxaborolan-2-yl)-1H-pyrazole for phenylboronic acid, and 3-(5-(5-chloro-2-iodo-1-tosyl-1H-pyrrolo[2,3-b]pyridin-4-yl)thiazol-2-yl)-1-methylazetidin-3-ol (Example 126A) for 1-(5-(5-chloro-2-iodo-1-tosyl-1H-pyrrolo[2,3-b]pyridin-4-yl)thiazol-2-yl)cyclobutanol (Example 8A). $^1$H NMR (500 MHz, DMSO-d$_6$) ppm 2.40 (s, 3H) 3.52 (d, J=7.93 Hz, 2H) 3.75 (d, J=7.93 Hz, 2H) 3.89 (s, 3H) 6.74 (d, J=1.83 Hz, 1H) 7.03 (s, 1H) 8.04 (s, 1H) 8.23 (d, J=9.76 Hz, 2H) 8.27 (s, 1H) 12.36 (s, 1H); MS ESI(+) m/z 401 (M+H)$^+$.

Example 127

3-(5-{5-chloro-2-[4-(morpholin-4-ylmethyl)phenyl]-1H-pyrrolo[2,3-b]pyridin-4-yl}-1,3-thiazol-2-yl)-1-methylazetidin-3-ol The title compound was prepared as described in Example 32, substituting 4-(4-(4,4,5,5-tetramethyl-1,3,2-dioxaborolan-2-yl)benzyl)morpholine for phenylboronic acid, and 3-(5-(5-chloro-2-iodo-1-tosyl-1H-pyrrolo[2,3-b]pyridin-4-yl)thiazol-2-yl)-1-methylazetidin-3-ol (Example 126A) for 1-(5-(5-chloro-2-iodo-1-tosyl-1H-pyrrolo[2,3-b]pyridin-4-yl)thiazol-2-yl)cyclobutanol (Example 8A). $^1$H NMR (500 MHz, DMSO-D6) ppm 2.27-2.44 (m, 7H) 3.44-3.52 (m, 4H) 3.53-3.63 (m, J=4.27 Hz, 4H) 3.72 (d, J=7.63 Hz, 2H) 7.02 (d, J=16.48 Hz, 2H) 7.40 (d, J=8.24 Hz, 2H) 7.96 (d, J=7.93 Hz, 2H) 8.31 (d, J=24.11 Hz, 2H) 12.58 (s, 1H); MS ESI(+) m/z 496 (M+H)$^+$.

Example 128

1-(1-{5-chloro-2-[4-(pyrrolidin-1-ylmethyl)phenyl]-1H-pyrrolo[2,3-b]pyridin-4-yl}-1H-pyrazol-4-yl)cyclobutanol

Example 128A 1-(4-(4,4,5,5-tetramethyl-1,3,2-dioxaborolan-2-yl)benzyl)pyrrolidine A suspension of 2-(4-(bromomethyl)phenyl)-4,4,5,5-tetramethyl-1,3,2-dioxaborolane (5.18 g, 17.44 mmol), potassium carbonate (2.89 g, 20.93 mmol) and N,N-dimethylformamide (75 mL) was treated with pyrrolidine (1.875 mL, 22.67 mmol), and the reaction was heated to 80° C. for 1 hour. The reaction was cooled to ambient temperature, diluted with ether (115 mL), and filtered. The filtrate was concentrated to dryness to provide the title compound. MS ESI(+) m/z 288.2 [M+H]$^+$.

Example 128B 4,5-dichloro-2-(4-(pyrrolidin-1-ylmethyl)phenyl)-1-tosyl-1H-pyrrolo[2,3-b]pyridine The title compound was prepared as described in Example 113C, substituting Example 128A for 1-methyl-4-(4,4,5,5-tetramethyl-1,3,2-dioxaborolan-2-yl)-1H-pyrazole. MS ESI(+) m/z 500.2 [M+H]$^+$.

Example 128C 4,5-dichloro-2-(4-(pyrrolidin-1-ylmethyl)phenyl)-1H-pyrrolo[2,3-b]pyridine The title compound was prepared as described in Example 113D, substituting Example 128B for Example 113C. MS ESI(+) m/z 346.1 [M+H]$^+$.

Example 128D 4,5-dichloro-2-(4-(pyrrolidin-1-ylmethyl)phenyl)-1-((2-(trimethylsilyl)ethoxy)methyl)-1H-pyrrolo[2,3-b]pyridine The title compound was prepared as described in Example 113E, substituting Example 128C for Example 113D. MS ESI(+) m/z 476.3 [M+H]$^+$.

Example 128E 4-(4-bromo-1H-pyrazol-1-yl)-5-chloro-2-(4-(pyrrolidin-1-ylmethyl)phenyl)-1-((2-(trimethylsilyl)ethoxy)methyl)-1H-pyrrolo[2,3-b]pyridine The title compound was prepared as described in Example 113F, substituting Example 128D for Example 113E. MS ESI(+) m/z 588.2 [M+H]$^+$.

Example 128F (1-(5-chloro-2-(4-(pyrrolidin-1-ylmethyl)phenyl)-1-((2-(trimethylsilyl)ethoxy)methyl)-1H-pyrrolo[2,3-b]pyridin-4-yl)-1H-pyrazol-4-yl)cyclobutanol The title compound was prepared as described in Example 113G, substituting Example 128E for Example 113F. MS ESI(+) m/z 578.4 [M+H]$^+$.

Example 128G 1-(1-{5-chloro-2-[4-(pyrrolidin-1-ylmethyl)phenyl]-1H-pyrrolo[2,3-b]pyridin-4-yl}-1H-pyrazol-4-yl)cyclobutanol The title compound was prepared as described in Example 113H, substituting Example 128F for Example 113G. $^1$H NMR (300 MHz, DMSO-d$_6$) ppm 1.71 (m, 4H), 1.81 (m, 2H), 2.26-2.38 (m, 4H), 2.46 (m, 4H), 3.61 (s, 2H), 5.54 (s, 1H), 6.87 (m, 1H), 7.40 (d, 2H), 7.89 (d, 2H), 7.94 (s, 1H), 8.24 (s, 1H) 8.37 (s, 1H) 12.59 (m, 1H); MS ESI(+) m/z 448.3 [M+H]$^+$;

Example 129

N-(1-{5-[5-chloro-2-(1-methyl-1H-pyrazol-4-yl)-1H-pyrrolo[2,3-b]pyridin-4-yl]-1,3-thiazol-2-yl}cyclobutyl)urea

Example 129A 1-(1-(5-(5-chloro-2-(1-methyl-1H-pyrazol-4-yl)-1-tosyl-1H-pyrrolo[2,3-b]pyridin-4-yl)thiazol-2-yl)cyclobutyl)urea A mixture of 1-(5-(5-chloro-2-(1-methyl-1H-pyrazol-4-yl)-1-tosyl-1H-pyrrolo[2,3-b]pyridin-4-yl)thiazol-2-yl)cyclobutanamine (40 mg, 0.074 mmol) (Example 121A) in anhydrous tetrahydrofuran (1 mL) was treated with trimethylsilyl isocyanate (0.049 ml, 0.371 mmol), and the reaction mixture was heated to 70° C. for 5 hours. Additional trimethylsilyl isocyanate (0.025 ml, 0.185 mmol) was added, and the reaction solution was heated for 16 hours at 70° C. The reaction was cooled, diluted with water, and extracted with dichloromethane. The organic extracts were combined and concentrated under reduced pressure. The residue was purified by flash chromatography on silica gel, eluting with 5% methanol in dichloromethane, to provide the title compound. MS ESI(+) m/z 582.3 [M+H]$^+$.

Example 129B 1-(1-(5-(5-chloro-2-(1-methyl-1H-pyrazol-4-yl)-1H-pyrrolo[2,3-b]pyridin-4-yl)thiazol-2-yl)cyclobutyl)urea The title compound was prepared as described in Example 47B, substituting 1-(1-(5-(5-chloro-2-(1-methyl-1H-pyrazol-4-yl)-1-tosyl-1H-pyrrolo[2,3-b]pyridin-4-yl)thiazol-2-yl)cyclobutyl)urea (Example 129A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (400 MHz, DMSO-d$_6$) ppm 12.33 (s, 1H) 8.25 (s, 1H) 8.21 (s, 1H) 8.15 (s, 1H) 8.03 (s, 1H) 7.17 (s, 1H) 6.74 (s, 1H) 5.62 (s, 2H) 3.88 (s, 3H) 2.69 (m, 2H) 2.39 (m, 2H) 1.04 (m, 2H); MS ESI(+) m/z 428.3 [M+H]$^+$.

Example 130

N'-(1-{5-[5-chloro-2-(1-methyl-1H-pyrazol-4-yl)-1H-pyrrolo[2,3-b]pyridin-4-yl]-1,3-thiazol-2-yl}cyclobutyl)-N,N-dimethylurea

Example 130A 3-(1-(5-(5-chloro-2-(1-methyl-1H-pyrazol-4-yl)-1-tosyl-1H-pyrrolo[2,3-b]pyridin-4-yl)thiazol-2-yl)cyclobutyl)-1,1-dimethylurea A mixture of 1-(5-(5-chloro-2-(1-methyl-1H-pyrazol-4-yl)-1-tosyl-1H-pyrrolo[2,3-b]pyridin-4-yl)thiazol-2-yl)cyclobutanamine (40 mg, 0.074 mmol) (Example 121A) in anhydrous tetrahydrofuran (1 mL) was treated with triethylamine (0.014 ml, 0.104 mmol) and dimethylcarbamoyl chloride (8.18 µl, 0.089 mmol), and the reaction mixture was heated to 70° C. for 16 hours. Additional dimethylcarbamoyl chloride (4.09 µl, 0.044 mmol) and triethylamine (0.007 ml, 0.052 mmol) were added, and reaction solution heated for another 16 hours at 70° C. The reaction was cooled, diluted with water, and extracted with dichloromethane. The extracts were combined and concentrated under reduced pressure. The residue was purified by flash chromatography on silica gel, eluting with a gradient of 2 to 5% methanol in dichloromethane, to provide the title compound. MS ESI(+) m/z 610.3 [M+H]$^+$.

Example 130B 3-(1-(5-(5-chloro-2-(1-methyl-1H-pyrazol-4-yl)-1H-pyrrolo[2,3-b]pyridin-4-yl)thiazol-2-yl)cyclobutyl)-1,1-dimethylurea The title compound was prepared as described in Example 47B, substituting 3-(1-(5-(5-chloro-2-(1-methyl-1H-pyrazol-4-yl)-1-tosyl-1H-pyrrolo[2,3-b]pyridin-4-yl)thiazol-2-yl)cyclobutyl)-1,1-dimethylurea (Example 130A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (400 MHz, DMSO-d$_6$) ppm 12.34 (s, 1H) 8.27 (s, 1H) 8.22 (s, 1H) 8.14 (s, 1H) 8.04 (s, 1H) 7.24 (s, 1H) 6.75 (s, 1H) 3.89 (s, 3H) 2.83 (s, 6H) 2.69 (m, 2H) 2.54 (m, 2 H) 2.03 (m, 2H); MS ESI(+) m/z 456.2 [M+H]$^+$.

Example 131

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N,N-dimethylamine Example 131A 1-(5-(5-chloro-2-(1-methyl-1H-pyrazol-4-yl)-1-tosyl-1H-pyrrolo[2,3-b]pyridin-4-yl)thiazol-2-yl)-N,N-dimethylcyclobutanamine A solution of 1-(5-(5-chloro-2-(1-methyl-1H-pyrazol-4-yl)-1-tosyl-1H-pyrrolo[2,3-b]pyridin-4-yl)thiazol-2-yl)cyclobutanamine (Example 121A) (20 mg, 0.037 mmol) in 37% aqueous formaldehyde (0.5 mL, 18.15 mmol) was treated with formic acid (0.014 mL, 0.371 mmol). The reaction was heated to 85° C. for 1 hour. The reaction was quenched with saturated sodium bicarbonate, and extracted with dichloromethane. The extracts were concentrated to provide the title compound, which was used without further purification. MS ESI(+) m/z 567.3 [M+H]$^+$.

Example 131B 1-(5-(5-chloro-2-(1-methyl-1H-pyrazol-4-yl)-1H-pyrrolo[2,3-b]pyridin-4-yl)thiazol-2-yl)-N,N-dimethylcyclobutanamine The title compound was prepared as described in Example 47B, substituting 1-(5-(5-chloro-2-(1-methyl-1H-pyrazol-4-yl)-1-tosyl-1H-pyrrolo[2,3-b]pyridin-4-yl)thiazol-2-yl)-N,N-dimethylcyclobutanamine (Example 131A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (500 MHz, DMSO-d$_6$) ppm 12.34 (s, 1H) 8.27 (s, 1H) 8.23 (m, 2H) 8.04 (s, 1H) 6.76 (d, 1H) 3.88 (s, 3H) 2.42 (m, 4H) 2.16 (s, 6H) 1.80 (m, 2H); MS ESI(+) m/z 413.1 [M+H]$^+$.

Example 132

3-{5-[5-chloro-2-(1-methyl-1H-pyrazol-4-yl)-1H-pyrrolo[2,3-b]pyridin-4-yl]-1,3-thiazol-2-yl}-1-ethylpyrrolidin-3-ol Example 132A 3-(5-(5-chloro-2-iodo-1-tosyl-1H-pyrrolo[2,3-b]pyridin-4-yl)thiazol-2-yl)-1-ethylpyrrolidin-3-ol The title compound was prepared as described in Example 117E, substituting acetaldehyde for formaldehyde. MS ESI (+) m/z 629.2 [M+H]$^+$.

Example 132B

3-{5-[5-chloro-2-(1-methyl-1H-pyrazol-4-yl)-1H-pyrrolo[2,3-b]pyridin-4-yl]-1,3-thiazol-2-yl}-1-ethylpyrrolidin-3-ol The title compound was prepared as described in Example 32, substituting 1-methyl-4-(4,4,5,5-tetramethyl-1,3,2-dioxaborolan-2-yl)-1H-pyrazole for phenylboronic acid, and 3-(5-(5-chloro-2-iodo-1-tosyl-1H-pyrrolo[2,3-b]pyridin-4-yl)thiazol-2-yl)-1-ethylpyrrolidin-3-ol (Example 132A) for 1-(5-(5-chloro-2-iodo-1-tosyl-1H-pyrrolo[2,3-b]pyridin-4-yl)thiazol-2-yl)cyclobutanol (Example 8A). $^1$H NMR (500 MHz, DMSO-d$_6$) ppm 1.05 (s, 3H) 2.13 (s, 1H) 2.50-2.60 (m, 2H) 2.61-2.72 (m, 1H) 2.98 (s, 4H) 3.87 (s, 3H) 6.45 (s, 1H) 6.72 (s, 1H) 8.03 (s, 1H) 8.15 (s, 1H) 8.22 (s, 1H) 8.26 (s, 1H) 12.34 (s, 1H); MS ESI(+) m/z 429 (M+H)$^+$.

Example 133

1-acetyl-3-(5-{5-chloro-2-[4-(morpholin-4-ylmethyl)phenyl]-1H-pyrrolo[2,3-b]pyridin-4-yl}-1,3-thiazol-2-yl)pyrrolidin-3-ol Example 133A 1-(3-(5-(5-chloro-2-iodo-1-tosyl-1H-pyrrolo[2,3-b]pyridin-4-yl)thiazol-2-yl)-3-hydroxypyrrolidin-1-yl)ethanone To an ambient solution of 3-(5-(5-chloro-2-iodo-1-tosyl-1H-pyrrolo[2,3-b]pyridin-4-yl)thiazol-2-yl)pyrrolidin-3-ol (Example 117D) (180 mg, 0.300 mmol) in N,N-dimethylformamide (10 mL) was added acetic acid (36 mg, 0.599 mmol), triethylamine (0.125 mL, 0.899 mmol), and O-(7-azabenzotriazol-1-yl)-N,N,N'N'-tetramethyluronium hexafluorophosphate (137 mg, 0.359 mmol). The reaction was stirred at room temperature for 3 hours and was quenched by the addition of water and ethyl acetate. The layers were separated, and the aqueous layer was extracted with additional ethyl acetate (2×). The combined organics were dried with anhydrous sodium sulfate, filtered, and concentrated under reduced pressure. The residue was purifed by flash column chromatography on silica gel, eluting with a gradient of 0 to 5% methanol in dichloromethane, to give the title compound. MS ESI(+) m/z 643.3 (M+H)$^+$.

Example 133B 1-acetyl-3-(5-{5-chloro-2-[4-(morpholin-4-ylmethyl)phenyl]-1H-pyrrolo[2,3-b]pyridin-4-yl}-1,3-thiazol-2-yl)pyrrolidin-3-ol The title compound was prepared as described in Example 32, substituting 4-(4-(4,4,5,5-tetramethyl-1,3,2-dioxaborolan-2-yl)benzyl)morpholine for phenylboronic acid, and 1-(3-(5-(5-chloro-2-iodo-1-tosyl-1H-pyrrolo[2,3-b]pyridin-4-yl)thiazol-2-yl)-3-hydroxypyrrolidin-1-yl)ethanone (Example 133A) for 1-(5-(5-chloro-2-iodo-1-tosyl-1H-pyrrolo[2,3-b]pyridin-4-yl)thiazol-2-yl)cyclobutanol (Example 8A). $^1$H NMR (400 MHz, DMSO-d$_6$) ppm 2.02 (s, 3H) 2.18-2.34 (m, 2H) 2.48-2.54 (m, 4H) 3.50 (s, 2H) 3.55-3.63 (m, 4H) 3.64-3.86 (m, 4H) 6.74 (d, J=25.33 Hz, 1H) 7.04 (d, J=5.49 Hz, 1H) 7.40 (d, J=7.93 Hz, 2H) 7.91-8.00 (m, 2H) 8.32 (dd, J=19.38, 1.98 Hz, 2H) 12.59 (s, 1H); MS ESI(+) m/z 538.4 (M+H)$^+$.

Example 134

3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol 1,1-dioxide

Example 134A

3-{5-[5-chloro-1-[(4-methylphenyl)sulfonyl]-2-(1-methyl-1H-pyrazol-4-yl)-1H-pyrrolo[2,3-b]pyridin-4-yl]-1,3-thiazol-2-yl}tetrahydrothiophene-3-ol 1,1-dioxide A solution of Example 144B (0.026 g, 0.045 mmol) and dichloromethane (0.8 mL) was cooled to 0° C., and 3-chloroperoxybenzoic acid (70%, 0.031 g, 0.127 mmol) was added in 3 portions over 2 minutes. The reaction was stirred at 0° C. for 5 minutes, and then at ambient temperature for 75 minutes. The reaction was partitioned between saturated aqueous sodium bicarbonate and dichloromethane. The aqueous layer was extracted with additional dichloromethane. The combined organic layers were dried over anhydrous sodium sulfate, filtered, and concentrated under reduced pressure. The concentrate was purified by flash chromatography on a silica gel column, eluting with a gradient of from 0% to 1% methanol in dichloromethane, to provide the title compound. MS ESI(+) m/z 604.4 [M+H]$^+$.

Example 134B

3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol 1,1-dioxide The title compound was prepared as described in Example 45C, substituting Example 134A for Example 45B. $^1$H NMR (300 MHz, methanol-d$_4$) ppm 2.60-2.67 (m, 1H), 2.82-2.88 (m, 1H), 3.46-3.56 (m, 3H), 3.84 (m, 1H), 3.95 (s, 3H), 6.66 (s, 1H), 7.93 (s, 1H), 8.07 (s, 1H), 8.16 (s, 1H), 8.21 (s, 1H); MS ESI(+) m/z 450.6 [M+H]$^+$.

Example 135

N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N'-phenylurea The title compound was prepared as described in Example 124, substituting phenyl isocyanate for ethyl isocyanate. $^1$H NMR (500 MHz, DMSO-d$_6$) ppm 12.34 (s, 1H) 8.60 (s, 1H) 8.24 (s, 1H) 8.22 (s, 1H) 8.20 (s, 1H) 8.02 (s, 1H) 7.38 (m, 3H) 7.21 (t, 2H) 6.90 (t, 1H) 6.76 (d, 1H) 3.89 (s, 3H) 2.77 (m, 2H) 2.48 (m, 2H) 2.11 (m, 2H); MS ESI(+) m/z 504.2 [M+H]$^+$.

Example 136

N-benzyl-N'-(1-{5-[5-chloro-2-(1-methyl-1H-pyrazol-4-yl)-1H-pyrrolo[2,3-b]pyridin-4-yl]-1,3-thiazol-2-yl}cyclobutyl)urea The title compound was prepared as described in Example 124, substituting benzyl isocyanate for ethyl isocyanate. $^1$H NMR (500 MHz, DMSO-D$_6$) ppm 12.35 (s, 1H) 8.25 (s, 1H) 8.24 (s, 1H) 8.19 (s, 1H) 8.03 (s, 1H) 7.27 (m, 4H) 7.23 (s, 1H) 7.18 (m, 1H) 6.77 (s, 1H) 6.48 (t, 1H) 4.23 (d, 2H) 3.89 (s, 3H) 2.72 (m, 2H) 2.42 (m, 2H) 2.07 (m, 2H); MS ESI(+) m/z 518.2 [M+H]$^+$.

Example 137

3-(5-{5-chloro-2-[3-(pyrrolidin-1-ylmethyl)phenyl]-1H-pyrrolo[2,3-b]pyridin-4-yl}-1,3-thiazol-2-yl)-1-methylpyrrolidin-3-ol The title compound was prepared as described in Example 32, substituting 1-(3-(4,4,5,5-tetramethyl-1,3,2-dioxaborolan-2-yl)benzyl)pyrrolidine for phenylboronic acid, and 3-(5-(5-chloro-2-iodo-1-tosyl-1H-pyrrolo[2,3-b]pyridin-4-yl)thiazol-2-yl)-1-methylpyrrolidin-3-ol (Example 117E) for 1-(5-(5-chloro-2-iodo-1-tosyl-1H-pyrrolo[2,3-b]pyridin-4-yl)thiazol-2-yl)cyclobutanol (Example 8A). $^1$H NMR (500 MHz, DMSO-d$_6$) ppm 1.70 (s, 4H) 2.06-2.24 (m, 1H) 2.33 (s, 3H) 2.39-2.48 (m, 4H) 2.56-2.68 (m, 1H) 2.81-3.11 (m, 4H) 3.63 (s, 2H) 6.46 (s, 1H) 7.04 (s, 1H) 7.33 (d, J=7.32 Hz, 1H) 7.42 (t, J=7.78 Hz, 1H) 7.87 (d, J=7.93 Hz, 1 H) 7.92 (s, 1H) 8.25 (s, 1H) 8.33 (s, 1H) 12.58 (s, 1H); MS ESI(+) m/z 494.3 [M+H]$^+$.

Example 138

1-{3-[5-chloro-2-(1-methyl-1H-pyrazol-4-yl)-1H-pyrrolo[2,3-b]pyridin-4-yl]-1,2,4-oxadiazol-5-yl}cyclobutanol

Example 138A 5-chloro-2-(1-methyl-1H-pyrazol-4-yl)-1-tosyl-1H-pyrrolo[2,3-b]pyridine-4-carbonitrile A solution in a microwave vial of 4,5-dichloro-2-(1-methyl-1H-pyrazol-4-yl)-1-tosyl-1H-pyrrolo[2,3-b]pyridine (Example 113C) (300 mg, 0.712 mmol) in anhydrous N,N-dimethylformamide (4 mL) was degassed by nitrogen sparge for about 20 minutes. The solution was treated with zinc cyanide (167 mg, 1.424 mmol) and tetrakis(triphenylphosphine)palladium (82 mg, 0.071 mmol). The reaction was degassed and back-filled with nitrogen, and heated in a Biotage Initiator microwave for 60 minutes at 160° C. The reaction was treated with additional zinc cyanide (83 mg, 0.712 mmol) and tetrakis(triphenylphosphine)palladium (41 mg, 0.035 mmol), and heated to 160° C. for 30 minutes by microwave irradiation. The reaction was diluted with water and ethyl acetate, and the layers were separated. The organic layer was washed with water and brine, dried over anhydrous sodium sulfate, filtered, and concentrated. The residue was purified by flash chromatography on silica gel, eluting with a gradient of 25 to 40% ethyl acetate in hexanes, to provide the title compound. MS ESI(+) m/z 412.4 [M+H]+.

Example 138B (Z)-5-chloro-N'-hydroxy-2-(1-methyl-1H-pyrazol-4-yl)-1-tosyl-1H-pyrrolo[2,3-b]pyridine-4-carboximidamide A solution of 5-chloro-2-(1-methyl-1H-pyrazol-4-yl)-1-tosyl-1H-pyrrolo[2,3-b]pyridine-4-carbonitrile (Example 138A (160 mg, 0.388 mmol)) in ethanol (4 mL) and water (0.33 mL) was treated with hydroxylamine hydrochloride (54.0 mg, 0.777 mmol) and triethylamine (0.271 mL, 1.942 mmol). The reaction vessel was sealed, and the reaction mixture was heated for 30 minutes at 80° C. Additional hydroxylamine hydrochloride (10.0 mg, 0.143 mmol) added, and the reaction heated for 1 hour at 80° C. The reaction was cooled, diluted with water, and extracted with dichloromethane. The combined organics were dried over anhydrous sodium sulfate, filtered, and concentrated under reduced pressure. The residue was purified by flash chromatography on silica gel, eluting with a gradient of 50 to 70% ethyl acetate in hexanes, to provide the title compound. MS ESI(+) m/z 445.4 [M+H]+.

Example 138C (Z)-5-chloro-N'-(1-hydroxycyclobutanecarbonyloxy)-2-(1-methyl-1H-pyrazol-4-yl)-1-tosyl-1H-pyrrolo[2,3-b]pyridine-4-carboximidamide A solution of (Z)-5-chloro-N'-hydroxy-2-(1-methyl-1H-pyrazol-4-yl)-1-tosyl-1H-pyrrolo[2,3-b]pyridine-4-carboximidamide (Example 138B) (44 mg, 0.099 mmol), 1-hydroxycyclobutanecarboxylic acid (12.63 mg, 0.109 mmol), 1-hydroxybenzotriazole hydrate (7.57 mg, 0.049 mmol), and 4-methylmorpholine (0.038 mL, 0.346 mmol) in anhydrous dimethylformamide (1 mL) was treated with N-(3-dimethylaminopropyl)-N'-ethylcarbodiimide hydrochloride (28.4 mg, 0.148 mmol). The reaction was stirred for 3 hours at ambient temperature. The reaction was diluted with ethyl acetate and washed with water and brine. The organic layer was dried over anhydrous sodium sulfate, filtered, and concentrated to provide the title compound. MS ESI(+) m/z 542.9 [M+H]+.

Example 138D 1-(3-(5-chloro-2-(1-methyl-1H-pyrazol-4-yl)-1-tosyl-1H-pyrrolo[2,3-b]pyridin-4-yl)-1,2,4-oxadiazol-5-yl)cyclobutanol A mixture of (Z)-5-chloro-N'-(1-hydroxycyclobutanecarbonyloxy)-2-(1-methyl-1H-pyrazol-4-yl)-1-tosyl-1H-pyrrolo[2,3-b]pyridine-4-carboximidamide (Example 138C) (53.8 mg, 0.099 mmol) in anhydrous toluene (1 mL) was heated for 4 hours at 110° C. under nitrogen. The reaction was concentrated under reduced pressure, and the residue was purified by flash chromatography on silica gel, eluting with a gradient of 40 to 50% ethyl acetate in hexanes, to provide the title compound. MS ESI(+) m/z 525.4 [M+H]+.

Example 138E 1-(3-(5-chloro-2-(1-methyl-1H-pyrazol-4-yl)-1H-pyrrolo[2,3-b]pyridin-4-yl)-1,2,4-oxadiazol-5-yl)cyclobutanol The title compound was prepared as described in Example 47B, substituting 1-(3-(5-chloro-2-(1-methyl-1H-pyrazol-4-yl)-1-tosyl-1H-pyrrolo[2,3-b]pyridin-4-yl)-1,2,4-oxadiazol-5-yl)cyclobutanol (Example 138D) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (500 MHz, DMSO-d$_6$) ppm 12.49 (s, 1H) 8.32 (s, 1H) 8.29 (s, 1H) 8.04 (s, 1H) 6.78 (s, 1H) 6.67 (s, 1H) 3.90 (s, 3H) 2.70 (m, 2H) 2.44 (m, 2H) 1.84-2.01 (m, 2H); MS ESI(+) m/z 371.5 [M+H]+.

Example 139

3-(5-{5-chloro-2-[4-(pyrrolidin-1-ylmethyl)phenyl]-1H-pyrrolo[2,3-b]pyridin-4-yl}-1,3-thiazol-2-yl)-1-methylpyrrolidin-3-ol The title compound was prepared as described in Example 32, substituting 1-(4-(4,4,5,5-tetramethyl-1,3,2-dioxaborolan-2-yl)benzyl)pyrrolidine (Example 128A) for phenylboronic acid, and 3-(5-(5-chloro-2-iodo-1-tosyl-1H-pyrrolo[2,3-b]pyridin-4-yl)thiazol-2-yl)-1-methylpyrrolidin-3-ol (Example 117E) for 1-(5-(5-chloro-2-iodo-1-tosyl-1H-pyrrolo[2,3-b]pyridin-4-yl)thiazol-2-yl)cyclobutanol (Example 8A). $^1$H NMR (500 MHz, DMSO-d$_6$) ppm 1.70 (s, 4H) 1.99-2.24 (m, 1H) 2.33 (s, 3H) 2.44 (s, 4H) 2.61 (d, J=6.41 Hz, 1H) 2.83-3.09 (m, 4H) 3.60 (s, 2H) 6.46 (s, 1H) 7.02 (s, 1H) 7.39 (d, J=7.93 Hz, 2H) 7.94 (d, J=8.24 Hz, 2 H) 8.24 (s, 1H) 8.33 (s, 1H) 12.56 (s, 1H); MS ESI(+) m/z 494 (M+H)+.

Example 140

3-(5-{5-chloro-2-[4-(pyrrolidin-1-ylmethyl)phenyl]-1H-pyrrolo[2,3-b]pyridin-4-yl}-1,3-thiazol-2-yl)-1-methylazetidin-3-ol The title compound was prepared as described in Example 32, substituting 1-(4-(4,4,5,5-tetramethyl-1,3,2-dioxaborolan-2-yl)benzyl)pyrrolidine (Example 128A) for phenylboronic acid, and 3-(5-(5-chloro-2-iodo-1-tosyl-1H-pyrrolo[2,3-b]pyridin-4-yl)thiazol-2-yl)-1-methylazetidin-3-ol (Example 126A) for 1-(5-(5-chloro-2-iodo-1-tosyl-1H-pyrrolo[2,3-b]pyridin-4-yl)thiazol-2-yl)cyclobutanol (Example 8A). $^1$H NMR (400 MHz, DMSO-d$_6$) ppm 1.71 (s, 4H) 2.38 (s, 3H) 2.45 (s, 4H) 3.45-3.55 (m, 2H) 3.61 (s, 2H) 3.72 (d, J=7.93 Hz, 2H) 7.02 (d, J=7.63 Hz, 2 H) 7.40 (d, J=8.24 Hz, 2H) 7.94 (d, J=8.24 Hz, 2H) 8.29 (s, 1H) 8.33 (s, 1H) 12.57 (s, 1H); MS ESI(+) m/z 480 (M+H)+.

Example 141

3-(5-{5-chloro-2-[3-(pyrrolidin-1-ylmethyl)phenyl]-1H-pyrrolo[2,3-b]pyridin-4-yl}-1,3-thiazol-2-yl)-1-methylazetidin-3-ol The title compound was prepared as described in Example 32, substituting 1-(3-(4,4,5,5-tetramethyl-1,3,2-dioxaborolan-2-yl)benzyl)pyrrolidine for phenylboronic acid, and 3-(5-(5-chloro-2-iodo-1-tosyl-1H-pyrrolo[2,3-b]pyridin-4-yl)thiazol-2-yl)-1-methylazetidin-3-ol (Example 126A) for 1-(5-(5-chloro-2-iodo-1-tosyl-1H-pyrrolo[2,3-b]pyridin-4-yl)thiazol-2-yl)cyclobutanol (Example 8A). $^1$H NMR (400 MHz, DMSO-d$_6$) ppm 1.71 (s, 4H) 2.38 (s, 3 H) 2.47 (s, 4H) 3.49 (d, J=8.24 Hz, 2H) 3.64 (s, 2H) 3.72 (d, J=7.93 Hz, 2H) 6.90-7.11 (m, 2 H) 7.33 (d, J=7.63 Hz, 1H) 7.42 (t, J=7.63 Hz, 1H) 7.88 (d, J=7.93 Hz, 1H) 7.93 (s, 1H) 8.32 (d, J=16.48 Hz, 2H) 12.60 (s, 1H); MS ESI(+) m/z 480 (M+H)+.

Example 142

3-[5-(5-chloro-1H-pyrrolo[2,3-b]pyridin-4-yl)-1,3-thiazol-2-yl]-1-methylpyrrolidin-3-ol The title compound was prepared as described in Examples 103A-103C, substituting tert-butyl 3-(methoxymethoxy)-3-(5-(tributylstannyl)thiazol-2-yl)pyrrolidine-1-carboxylate (Example 117B) for tert-butyl 3-(5-(5-fluoro-1-tosyl-1H-pyrrolo[2,3-b]pyridin-4-yl)thiazol-2-yl)-3-(methoxymethoxy)azetidine-1-carboxylate (Example 54B) in Example 103A. $^1$H NMR (300 MHz, DMSO-$d_6$) ppm 2.07-2.20 (m, 1H) 2.34 (s, 3H) 2.57-2.70 (m, 1H) 2.78-3.08 (m, 4H) 6.44 (s, 1H) 6.55 (dd, J=3.39, 2.03 Hz, 1H) 7.56-7.69 (m, 1H) 8.15 (s, 1H) 8.35 (s, 1H) 12.11 (s, 1H); MS ESI(+) m/z 335 (M+H)$^+$.

Example 143

1-(5-{5-chloro-2-[4-(pyrrolidin-1-ylmethyl)phenyl]-1H-pyrrolo[2,3-b]pyridin-4-yl}pyridin-2-yl)cyclobutanol

Example 143A 1-(5-(tributylstannyl)pyridin-2-yl)cyclobutanol

To a cold (−10° C.) solution of 5-bromo-2-iodopyridine (3.0 g, 10.57 mmol) in tetrahydrofuran (35 mL) was added isopropylmagnesium chloride (5.55 ml, 11.10 mmol, 2 M solution in tetrahydrofuran) dropwise over 10 minutes. The reaction was allowed to warm to 0° C. over 1 hour and then cooled to −10° C. Cyclobutanone (0.792 ml, 10.57 mmol) was added dropwise, and the reaction was warmed to 15° C. over 1 hour to give a homogenous solution. The reaction was cooled to −78° C. (precipitate formed). The reaction was warmed to ~0° C. and diluted with an additional 50 mL tetrahydrofuran to dissolve the precipitate. The reaction was cooled to −78° C., and n-butyllithium (4.23 ml, 10.57 mmol, 2.5 M in hexane) was added dropwise. The reaction was stirred for 0.5 hours, and tributyltin chloride (2.87 mL, 10.57 mmol) was added dropwise. The reaction was stirred at −78° C. for 15 minutes, and was then quenched by the dropwise addition of saturated aqueous sodium bicarbonate solution. The layers were separated, and the aqueous layer was extracted with ethyl acetate (3×30 mL). The combined organic layers were washed with water, brine, dried with anhydrous sodium sulfate, filtered and concentrated under reduced pressure. The residue was purified by chromatography on silica gel, eluting with a gradient of 0 to 10% ethyl acetate in hexane, to give the title compound. MS ESI(+) m/z 440.2 [M+H]$^+$.

Example 143B 1-(5-(5-chloro-2-(4-(pyrrolidin-1-ylmethyl)phenyl)-1H-pyrrolo[2,3-b]pyridin-4-yl)pyridin-2-yl)cyclobutanol A solution of 4,5-dichloro-2-(4-(pyrrolidin-1-ylmethyl)phenyl)-1-tosyl-1H-pyrrolo[2,3-b]pyridine (198 mg, 0.396 mmol) (Example 128B), 1-(5-(tributylstannyl)pyridin-2-yl)cyclobutanol (Example 143A) (260 mg, 0.593 mmol), and bis(triphenylphosphine)palladium dichloride (19.43 mg, 0.028 mmol) in N,N-dimethylformamide (1.318 mL) was heated to 100° C. for 16 hours. The reaction was cooled to room temperature and quenched by the addition of an aqueous potassium fluoride solution (3 g potassium fluoride in 6 mL water) and ethyl acetate (10 mL). The mixture was stirred vigorously for 16 hours and filtered through diatomaceous earth, eluting with ethyl acetate. The eluent was washed with aqueous saturated sodium bicarbonate solution, dried with anhydrous sodium sulfate, filtered and concentrated under reduced pressure. The residue was dissolved in a solvent mixture of 2 N aqueous sodium hydroxide solution (1.0 mL) and methanol (3 mL). The solution was heated to 105° C. by microwave irradiation (Biotage, Initiator) for 5 minutes. The reaction was cooled to room temperature and diluted with dimethyl sulfoxide (1 mL). The resulting solution was purified by reverse phase high performance liquid chromatography (RP HPLC, 19×150 mm Atlantis Prep T3 OBD 5 m column, eluting with a gradient of 5% B in A to 75% B in A over 25 minutes, wherein A is water containing 0.1% v/v trifluoroacetic acid and B is acetonitrile containing 0.1% v/v trifluoroacetic acid) to give the title compound. $^1$H NMR (300 MHz, DMSO-$d_6$) δ 12.50 (bs, 1H), 8.77 (dd, J=2.3, 0.8 Hz, 1H), 8.34 (s, 1H), 8.02 (dd, J=8.1, 2.3 Hz, 1H), 7.94-7.86 (m, 2H), 7.78 (dd, J=8.1, 0.8 Hz, 1H), 7.40-7.33 (m, 2H), 6.72 (s, 1H), 5.86 (s, 1H), 3.59 (s, 2H), 2.74-2.61 (m, 2H), 2.46-2.39 (m, 4H), 2.35-2.22 (m, 2H), 2.05-1.82 (m, 2H), 1.78-1.61 (m, 4H); MS ESI(+) m/z 459.2 [M+H]$^+$.

Example 144

3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol

Example 144A 5-(5-chloro-2-(1-methyl-1H-pyrazol-4-yl)-1-tosyl-1H-pyrrolo[2,3-b]pyridin-4-yl)thiazole A solution of Example 113C (0.148 g, 0.351 mmol) and 5-(tributylstannyl)thiazole (0.184 g, 0.492 mmol), in N,N-dimethylformamide (1.3 mL) was degassed via nitrogen sparge for 5 minutes. The reaction was treated with bis(triphenylphosphine)palladium (II) chloride (0.025 g, 0.35 mmol) and heated at 100° C. for 6 hours. The reaction was cooled to ambient temperature, treated with water (20 mL) and extracted with ethyl acetate (80 mL). The aqueous layer was extracted with additional ethyl acetate (40 mL). The combined organic layers were washed with water (2×25 mL) and brine (25 mL), dried over anhydrous sodium sulfate, filtered, and concentrated under reduced pressure. The concentrate was purified by flash chromatography on a silica gel column, eluting with a gradient of from 0% to 50% ethyl acetae in hexanes, to provide the title compound as an off-white solid. MS ESI(+) m/z 470.2 [M+H]$^+$.

Example 144B 3-(5-(5-chloro-2-(1-methyl-1H-pyrazol-4-yl)-1-tosyl-1H-pyrrolo[2,3-b]pyridin-4-yl)thiazol-2-yl)tetrahydrothiophen-3-ol A solution of Example 144A (0.095 g, 0.202 mmol) in tetrahydrofuran (2.5 mL) was cooled to −78° C. and treated with n-butyllithium (2.45 M in hexanes, 0.173 mL, 0.424 mmol) dropwise over 5 minutes. The reaction was stirred at −78° C. for 20 minutes, and dihydrothiophen-3(2H)-one (0.033 mL, 0.384 mmol) was added. The reaction was stirred 60 minutes at −78° C. and was quenched by addition of saturated aqueous sodium bicarbonate solution. The mixture was allowed to warm to ambient temperature and was extracted with ethyl acetate. The organic layer was washed with brine, dried over anhydrous sodium sulfate, filtered, and concentrated under reduced pressure. The concentrate was purified by flash chromatography on a silica gel column, eluting with 1% methanol in dichloromethane, to provide the title compound. MS ESI(+) m/z 572.3 [M+H]+.

Example 144C

3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol The title compound was prepared as described in Example 45C, substituting Example 144B for Example 45B. $^1$H NMR (300 MHz, methanol-$d_4$) ppm 2.39-2.44 (m, 1H), 2.52-2.58 (m, 1H), 3.04-3.12 (m, 2H), 3.19-3.25 (m, 1H), 3.54 (m, 1H) 3.94 (s, 3H), 6.66 (s, 1H), 7.93 (s, 1H), 8.07 (s, 1H), 8.11 (s, 1H), 8.20 (s, 1H); MS ESI(+) m/z 418.6 [M+H]+.

Example 145

3-(1-{5-chloro-2-[4-(pyrrolidin-1-ylmethyl)phenyl]-1H-pyrrolo[2,3-b]pyridin-4-yl}-1H-pyrazol-4-yl)oxetan-3-ol Example 145A 3-(1-(5-chloro-2-(4-(pyrrolidin-1-ylmethyl)phenyl)-1-((2-(trimethylsilyl)ethoxy)methyl)-1H-pyrrolo[2,3-b]pyridin-4-yl)-1H-pyrazol-4-yl)oxetan-3-ol The title compound was prepared as described in Example 113G, substituting Example 128E for Example 113F and oxetan-3-one for cyclobutanone. MS ESI(+) m/z 580.1 [M+H]+.

Example 145B 3-(1-{5-chloro-2-[4-(pyrrolidin-1-ylmethyl)phenyl]-1H-pyrrolo[2,3-b]pyridin-4-yl}-1H-pyrazol-4-yl)oxetan-3-ol The title compound was prepared as described in Example 113H, substituting Example 145A for Example 113G. $^1$H NMR (300 MHz, methanol-$d_4$) ppm 1.97-2.08 (m, 2H), 2.14-2.25 (m, 2H), 3.15-3.28 (m, 2H), 3.47-3.58 (m, 2H), 4.42 (s, 2H), 4.85-4.94 (m, 4H), 6.96 (s, 1H), 7.61 (d, 2H), 7.98 (d, 2H), 8.06 (s, 1H), 8.32 (s, 1H), 8.38 (s, 1H); MS ESI(+) m/z 450.0 [M+H]+.

Example 146

3-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)oxetan-3-ol Example 146A tert-butyl 4-(4,5-dichloro-1-tosyl-1H-pyrrolo[2,3-b]pyridin-2-yl)-5,6-dihydropyridine-1(2H)-carboxylate The title compound was prepared as described in Example 113C, substituting tert-butyl 4-(4,4,5,5-tetramethyl-1,3,2-dioxaborolan-2-yl)-5,6-dihydropyridine-1(2H)-carboxylate for 1-methyl-4-(4,4,5,5-tetramethyl-1,3,2-dioxaborolan-2-yl)-1H-pyrazole. MS ESI(+) m/z 522.5 [M+H]+.

Example 146B tert-butyl 4-(5-chloro-4-(2-(3-(4-methoxybenzyloxy)oxetan-3-yl)thiazol-5-yl)-1-tosyl-1H-pyrrolo[2,3-b]pyridin-2-yl)-5,6-dihydropyridine-1(2H)-carboxylate The title compound was prepared as described in Example 144A, substituting Example 146A for Example 113C and Example 11E for 5-(tributylstannyl)thiazole. MS ESI(+) m/z 763.2 [M+H]+.

Example 146C 3-(5-(5-chloro-2-(1,2,3,6-tetrahydropyridin-4-yl)-1-tosyl-1H-pyrrolo[2,3-b]pyridin-4-yl)thiazol-2-yl)oxetan-3-ol The title compound was prepared as described in Example 11I, substituting Example 146B for Example 11H. MS ESI(+) m/z 543.0 [M+H]+.

Example 146D 1-(4-(5-chloro-4-(2-(3-hydroxyoxetan-3-yl)thiazol-5-yl)-1-tosyl-1H-pyrrolo[2,3-b]pyridin-2-yl)-5,6-dihydropyridin-1(2H)-yl)-2-(dimethylamino)ethanone A solution of Example 146C (0.048 g, 0.088 mmol), 2-(dimethylamino)acetic acid (0.011 g, 0.102 mmol), N-methylmorpholine (0.019 mL, 0.177 mmol), and 1-hydroxybenzotriazole hydrate (0.007 g, 0.044 mmol) in N,N-dimethylformamide (1 mL) was treated with N-(3-dimethylaminopropyl)-N'-ethylcarbodiimide hydrochloride (0.025 g, 0.133 mmol), and the reaction was stirred at ambient temperature for 6 hours. The reaction was partitioned between ethyl acetate and water. The aqueous layer was extracted with additional ethyl acetate. The combined organic layers were washed with water and brine, dried over anhydrous sodium sulfate, filtered, and concentrated under reduced pressure. The material was used directly in the next step without further purification. MS APCI(+) m/z 627.4 [M+H]+.

Example 146E 3-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)oxetan-3-ol The title compound was prepared as described in Example 89C, substituting Example 146D for Example 89B. $^1$H NMR (300 MHz, DMSO-$d_6$) ppm 2.18 (s, 6H), 2.54-2.64 (m, 2H), 3.12 (m, 2H), 3.61-3.76 (m, 2H), 4.15 (m, 1H) 4.35 (m, 1H), 4.78 (m, 2H), 4.99 (m, 2 H), 6.57 (m, 2H), 7.45 (bs, 1H), 8.29 (s, 1H), 8.32 (s, 1H), 12.25 (bs, 1H); MS ESI(+) m/z 474.3 [M+H]+.

Example 147

3-(5-{5-chloro-2-[1-(1-methyl-L-prolyl)-1,2,3,6-tetrahydropyridin-4-yl]-1H-pyrrolo[2,3-b]pyridin-4-yl}-1,3-thiazol-2-yl) oxetan-3-ol

Example 147A (S)-(4-(5-chloro-4-(2-(3-hydroxyoxetan-3-yl)thiazol-5-yl)-1-tosyl-1H-pyrrolo[2,3-b]pyridin-2-yl)-5,6-dihydropyridin-1(2H)-yl)(1-methylpyrrolidin-2-yl)methanone The title compound was prepared as described in Example 146D, substituting N-methyl-L-proline for 2-(dimethylamino)acetic acid. MS ESI(+) m/z 653.9 [M+H]$^+$.

Example 147B 3-(5-{5-chloro-2-[1-(1-methyl-L-prolyl)-1,2,3,6-tetrahydropyridin-4-yl]-1H-pyrrolo[2,3-b]pyridin-4-yl}-1,3-thiazol-2-yl)oxetan-3-ol The title compound was prepared as described in Example 89C, substituting Example 147A for Example 89B. $^1$H NMR (300 MHz, methanol-d$_4$) ppm 1.74-1.93 (m, 3H), 2.26-2.36 (m, 5H), 2.55-2.67 (m, 2H), 3.08 (m, 1H), 3.26 (m, 1H), 3.84 (m, 2H), 4.29 (m, 1H), 4.37 (m, 1H), 4.87 (m, 2H), 5.13 (m, 2H), 6.45 (m, 1H), 6.55 (m, 1H), 8.19 (s, 1H), 8.26 (s, 1H); MS ESI(+) m/z 500.4 [M+H]$^+$.

Example 148

2-[4-{5-chloro-4-[2-(3-hydroxyoxetan-3-yl)-1,3-thiazol-5-yl]-1H-pyrrolo[2,3-b]pyridin-2-yl}-3,6-dihydropyridin-1(2H)-yl]-N,N-dimethylacetamide

Example 148A 2-(4-(5-chloro-4-(2-(3-hydroxyoxetan-3-yl)thiazol-5-yl)-1-tosyl-1H-pyrrolo[2,3-b]pyridin-2-yl)-5,6-dihydropyridin-1(2H)-yl)-N,N-dimethylacetamide A solution of Example 146C (0.047 g, 0.087 mmol), 2-chloro-N,N-dimethylacetamide (0.011 g, 0.091 mmol) and triethylamine (0.029 mL, 0.208 mmol) in 1-methyl-2-pyrrolidinone (0.8 mL) was heated to 75° C. for 1 hour. The reaction was cooled to ambient temperature and partitioned between water and ethyl acetate. The aqueous layer was extracted with additional ethyl acetate. The combined organic layers were washed with water (2×) and brine, dried over anhydrous sodium sulfate, filtered, and concentrated. The residue was taken directly to the next step without further purification. MS ESI(+) m/z 628.2 [M+H]$^+$.

Example 148B

2-[4-{5-chloro-4-[2-(3-hydroxyoxetan-3-yl)-1,3-thiazol-5-yl]-1H-pyrrolo[2,3-b]pyridin-2-yl}-3,6-dihydropyridin-1(2H)-yl]-N,N-dimethylacetamide The title compound was prepared as described in Example 89C, substituting Example 148A for Example 89B. $^1$H NMR (300 MHz, DMSO-d$_6$) ppm 2.49 (m, 2H), 2.71 (m, 2H), 2.82 (s, 3H), 3.02 (s, 3H), 3.21 (m, 2H), 3.27 (m, 2H) 4.77 (m, 2H), 4.99 (m, 2H), 6.51 (s, 1H), 6.53 (m, 1H), 7.45 (bs, 1H), 8.28 (s, 1H), 8.29 (s, 1H), 12.15 (bs, 1H); MS ESI(+) m/z 474.2 [M+H]$^+$.

Example 149

3-[5-(5-chloro-2-{1-[(1,1-dioxidotetrahydrothien-3-yl)carbonyl]-1,2,3,6-tetrahydropyridin-4-yl}-1H-pyrrolo[2,3-b]pyridin-4-yl)-1,3-thiazol-2-yl]oxetan-3-ol

Example 149A 3-(5-{5-chloro-2-{1-[(1,1-dioxidotetrahydrothien-3-yl)carbonyl]-1,2,3,6-tetrahydropyridin-4-yl}-1-[(4-methylphenyl)sulfonyl]-1H-pyrrolo[2,3-b]pyridin-4-yl}-1,3-thiazol-2-yl)oxetan-3-ol The title compound was prepared as described in Example 146D, substituting 1,1-dioxo-tetrahydrothiophene-3-carboxylic acid for 2-(dimethylamino)acetic acid. MS ESI(+) m/z 689.1 [M+H]$^+$.

Example 149B

3-[5-(5-chloro-2-{1-[(1,1-dioxidotetrahydrothien-3-yl)carbonyl]-1,2,3,6-tetrahydropyridin-4-yl}-1H-pyrrolo[2,3-b]pyridin-4-yl)-1,3-thiazol-2-yl]oxetan-3-ol The title compound was prepared as described in Example 89C, substituting Example 149A for Example 89B. $^1$H NMR (300 MHz, methanol-d$_4$) ppm 2.20-2.33 (m, 1H), 2.40-2.53 (m, 1H), 2.60 (m, 1H), 2.69 (m, 1H), 3.09-3.18 (m, 1H), 3.22-3.37 (m, 3H), 3.77-3.89 (m, 3H), 4.29 (m, 1H), 4.37 (m, 1H), 4.88 (m, 2H), 5.12 (m, 2H), 6.45 (m, 1H), 6.56 (m, 1H), 8.19 (s, 1H), 8.26 (s, 1H); MS ESI(+) m/z 535.4 [M+H]$^+$.

Example 150

3-[5-(5-chloro-2-{1-[(1-methylpyrrolidin-3-yl)carbonyl]-1,2,3,6-tetrahydropyridin-4-yl}-1H-pyrrolo[2,3-b]pyridin-4-yl)-1,3-thiazol-2-yl]oxetan-3-ol

Example 150A (4-(5-chloro-4-(2-(3-hydroxyoxetan-3-yl)thiazol-5-yl)-1-tosyl-1H-pyrrolo[2,3-b]pyridin-2-yl)-5,6-dihydropyridin-1(2H)-yl)(1-methylpyrrolidin-3-yl)methanone The title compound was prepared as described in Example 146D, substituting 1-methylpyrrolidine-3-carboxylic acid for 2-(dimethylamino)acetic acid. MS ESI(+) m/z 654.2 [M+H]$^+$.

Example 150B

3-[5-(5-chloro-2-{1-[(1-methylpyrrolidin-3-yl)carbonyl]-1,2,3,6-tetrahydropyridin-4-yl}-1H-pyrrolo[2,3-b]pyridin-4-yl)-1,3-thiazol-2-yl]oxetan-3-ol The title compound was prepared as described in Example 89C, substituting Example 150A for Example 89B. $^1$H NMR (300 MHz, methanol-d$_4$) ppm 1.98-2.23 (m, 2H), 2.38 (s, 3H), 2.45-2.82 (m, 6H), 2.90-3.00 (m, 1H), 3.76-3.86 (m, 2H), 4.27 (m, 1H), 4.32 (m, 1H), 4.88 (m, 2H), 5.13 (m, 2H), 6.45 (m, 1H), 6.55 (m, 1H), 8.19 (s, 1H), 8.26 (s, 1H); MS ESI(+) m/z 500.3 [M+H]$^+$.

Example 151

3-(5-{5-chloro-2-[4-(pyrrolidin-1-ylmethyl)phenyl]-1H-pyrrolo[2,3-b]pyridin-4-yl}-1,3-thiazol-2-yl)tetrahydrothiophene-3-ol 1,1-dioxide

Example 151A 1-(1-(5-chloro-2-(1-methyl-1H-pyrazol-4-yl)-1H-pyrrolo[2,3-b]pyridin-4-yl)-1H-pyrazol-4-yl)cyclobutanol The title compound was prepared as described in Example 144A, substituting Example 128B for Example 113C. MS ESI(+) m/z 549.1 [M+H]$^+$.

Example 151B 3-(5-(5-chloro-2-(4-(pyrrolidin-1-ylmethyl)phenyl)-1-tosyl-1H-pyrrolo[2,3-b]pyridin-4-yl)thiazol-2-yl)tetrahydrothiophen-3-ol The title compound was prepared as described in Example 144B, substituting Example 151A for Example 144A. MS ESI(+) m/z 651.1 [M+H]$^+$.

Example 151C 3-(5-{5-chloro-1-[(4-methylphenyl)sulfonyl]-2-[4-(pyrrolidin-1-ylmethyl)phenyl]-1H-pyrrolo[2,3-b]pyridin-4-yl}-1,3-thiazol-2-yl)tetrahydrothiophene-3-ol 1,1-dioxide A solution of Example 151B (0.045 g, 0.069 mmol) in dichloromethane (1.1 mL) was cooled to 0° C. and m-chloroperoxybenzoic acid (70%, 0.034 g, 0.139 mmol) was added in 3 portions over 5 minutes at 0° C. The reaction was stirred at 0° C. for 90 minutes. The reaction was treated with saturated aqueous sodium bicarbonate solution and extracted with dichloromethane. The aqueous layer was extracted with additional dichloromethane. The combined organic layers were dried over anhydrous sodium sulfate, filtered, and concentrated under reduced pressure. The concentrate was purified by flash chromatography on a silica gel column, eluting with a gradient of 0% to 12% methanol in dichloromethane, to provide the title compound. MS ESI(+) m/z 683.0 [M+H]$^+$.

Example 151D 3-(5-{5-chloro-2-[4-(pyrrolidin-1-ylmethyl)phenyl]-1H-pyrrolo[2,3-b]pyridin-4-yl}-1,3-thiazol-2-yl)tetrahydrothiophene-3-ol-1,1-dioxide The title compound was prepared as described in Example 89C, substituting Example 151C for Example 89B. $^1$H NMR (300 MHz, methanol-d$_4$) ppm 2.06 (m, 2H), 2.30 (m, 2H), 2.60-2.72 (m, 1H), 2.84-2.96 (m, 1H), 3.16-3.28 (m, 4H), 3.48-3.60 (m, 2H), 3.77-3.85 (m, 2H), 4.51 (s, 2H), 6.98 (s, 1H), 7.70 (m, 2H), 7.91 (m, 2H), 8.16 (s, 1H), 8.31 (s, 1H); MS ESI(+) m/z 529.0 [M+H]$^+$.

Example 152

N-[3-(5-{5-chloro-2-[4-(pyrrolidin-1-ylmethyl)phenyl]-1H-pyrrolo[2,3-b]pyridin-4-yl}-1,3-thiazol-2-yl)oxetan-3-yl]-N'-phenylurea The title compound was prepared as described in Example 124, substituting phenyl isocyanate for ethyl isocyanate and 3-(2-(5-chloro-2-(4-(pyrrolidin-1-ylmethyl)phenyl)-1H-pyrrolo[2,3-b]pyridin-4-yl)thiazol-5-yl)oxetan-3-amine (Example 157C) for 1-(5-(5-chloro-2-(1-methyl-1H-pyrazol-4-yl)-1H-pyrrolo[2,3-b]pyridin-4-yl)thiazol-2-yl)cyclobutanamine (Example 121B). $^1$H NMR (400 MHz, DMSO-d$_6$) ppm 12.58 (s, 1H) 8.94 (s, 1H) 8.37 (s, 1H) 8.33 (s, 1H) 7.92 (d, 2H) 7.84 (s, 1H) 7.40 (m, 4H) 7.23 (t, 2H) 7.04 (s, 1H) 6.93 (t, 1H) 5.06 (d, 2 H) 4.88 (d, 2H) 3.65 (s, 2H) 2.50 (m, 4H) 1.72 (m, 4H); MS ESI(+) m/z 585.1 [M+H]$^+$.

Example 153

3-{5-[5-chloro-2-(1-methyl-1H-pyrazol-4-yl)-1H-pyrrolo[2,3-b]pyridin-4-yl]-1,3-thiazol-2-yl}oxetan-3-amine

Example 153A 1-(4-methoxyphenyl)-N-(oxetan-3-ylidene)methanamine

The title compound was prepared as described in Example 112A, substituting oxetan-3-one for cyclobutanone. MS DCI (+) m/z 192.3 [M+H]$^+$.

Example 153B

N-(4-methoxybenzyl)-3-(thiazol-2-yl)oxetan-3-amine

The title compound was prepared as described in Example 112B, substituting 1-(4-methoxyphenyl)-N-(oxetan-3-ylidene)methanamine (Example 153A) for N-cyclobutylidene-1-(4-methoxyphenyl)methanamine (Example 112A). MS DCI(+) m/z 277.1 [M+H]$^+$.

Example 153C

N-(4-methoxybenzyl)-3-(5-(tributylstannyl)thiazol-2-yl)oxetan-3-amine

The title compound was prepared as described in Example 112C, substituting N-(4-methoxybenzyl)-3-(thiazol-2-yl)oxetan-3-amine (Example 153B) for N-(4-methoxybenzyl)-1-(thiazol-2-yl)cyclobutanamine (Example 112B). MS ESI(+) m/z 567.1 [M+H]$^+$.

Example 153D 3-(2-(5-chloro-2-(1-methyl-1H-pyrazol-4-yl)-1-tosyl-1H-pyrrolo[2,3-b]pyridin-4-yl)thiazol-5-yl)-N-(4-methoxybenzyl)oxetan-3-amine The title compound was prepared as described in Example 112D, substituting N-(4-methoxybenzyl)-3-(5-(tributylstannyl)thiazol-2-yl)oxetan-3-amine (Example 153C) for N-(4-

163 methoxybenzyl)-1-(5-(tributylstannyl)thiazol-2-yl)cyclobutanamine (Example 112C). MS ESI(+) m/z 661.2 [M+H]$^+$.

Example 153E 3-(2-(5-chloro-2-(1-methyl-1H-pyrazol-4-yl)-1-tosyl-1H-pyrrolo[2,3-b]pyridin-4-yl)thiazol-5-yl)oxetan-3-amine The title compound was prepared as described in Example 121A, substituting 3-(2-(5-chloro-2-(1-methyl-1H-pyrazol-4-yl)-1-tosyl-1H-pyrrolo[2,3-b]pyridin-4-yl)thiazol-5-yl)-N-(4-methoxybenzyl)oxetan-3-amine (Example 153D) for 1-(5-(5-chloro-2-(1-methyl-1H-pyrazol-4-yl)-1-tosyl-1H-pyrrolo[2,3-b]pyridin-4-yl)thiazol-2-yl)-N-(4-methoxybenzyl)cyclobutanamine (Example 112D). MS ESI(+) m/z 541.1 [M+H]$^+$.

Example 153F 3-(2-(5-chloro-2-(1-methyl-1H-pyrazol-4-yl)-1H-pyrrolo[2,3-b]pyridin-4-yl)thiazol-5-yl)oxetan-3-amine The title compound was prepared as described in Example 47B, substituting 3-(2-(5-chloro-2-(1-methyl-1H-pyrazol-4-yl)-1-tosyl-1H-pyrrolo[2,3-b]pyridin-4-yl)thiazol-5-yl)oxetan-3-amine (Example 153E) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (400 MHz, DMSO-d$_6$) ppm 12.36 (s, 1H) 8.27 (m, 2H) 8.24 (s, 1H) 8.04 (s, 1H) 6.74 (s, 1H) 4.96 (d, 2H) 4.65 (d, 2H) 3.89 (s, 3H) 3.24 (s, 2H); MS ESI(+) m/z 387.1 [M+H]$^+$.

Example 154

N-(3-{5-[5-chloro-2-(1-methyl-1H-pyrazol-4-yl)-1H-pyrrolo[2,3-b]pyridin-4-yl]-1,3-thiazol-2-yl}oxetan-3-yl)acetamide The title compound was prepared as described in Example 122, substituting 3-(2-(5-chloro-2-(1-methyl-1H-pyrazol-4-yl)-1H-pyrrolo[2,3-b]pyridin-4-yl)thiazol-5-yl)oxetan-3-amine (Example 153F) for 1-(5-(5-chloro-2-(1-methyl-1H-pyrazol-4-yl)-1H-pyrrolo[2,3-b]pyridin-4-yl)thiazol-2-yl)cyclobutanamine (Example 121B). $^1$H NMR (400 MHz, DMSO-d$_6$) ppm 12.38 (s, 1H) 9.50 (s, 1H) 8.27 (s, 2H) 8.24 (s, 1H) 8.05 (s, 1H) 6.75 (d, 1H) 5.03 (d, 2H) 4.83 (d, 2H) 3.89 (s, 3H) 1.98 (s, 3H); MS ESI(+) m/z 429.1 [M+H]$^+$.

Example 155

N-(3-{5-[5-chloro-2-(1-methyl-1H-pyrazol-4-yl)-1H-pyrrolo[2,3-b]pyridin-4-yl]-1,3-thiazol-2-yl}oxetan-3-yl)-N'-phenylurea The title compound was prepared as described in Example 124, substituting phenyl isocyanate for ethyl isocyanate and 3-(2-(5-chloro-2-(1-methyl-1H-pyrazol-4-yl)-1H-pyrrolo[2,3-b]pyridin-4-yl)thiazol-5-yl)oxetan-3-amine (Example 153F) for 1-(5-(5-chloro-2-(1-methyl-1H-pyrazol-4-yl)-1H-pyrrolo[2,3-b]pyridin-4-yl)thiazol-2-yl)cyclobutanamine (Example 121B). $^1$H NMR (400 MHz, DMSO-d$_6$) ppm 12.37 (s, 1H) 8.93 (s, 1H) 8.29 (s, 1H) 8.24 (s, 1H) 8.23 (s, 1H) 8.02 (s, 1H) 7.81 (s, 1H) 7.40 (d, 2H) 7.23 (t, 2H) 6.93 (t, 1H) 6.76 (d, 1H) 5.04 (d, 2H) 4.88 (d, 2H) 3.89 (s, 3H); MS ESI(+) m/z 506.2 [M+H]$^+$.

164

Example 156

N-(3-{5-[5-chloro-2-(1-methyl-1H-pyrazol-4-yl)-1H-pyrrolo[2,3-b]pyridin-4-yl]-1,3-thiazol-2-yl}oxetan-3-yl)urea Example 156A 1-(3-(2-(5-chloro-2-(1-methyl-1H-pyrazol-4-yl)-1-tosyl-1H-pyrrolo[2,3-b]pyridin-4-yl)thiazol-5-yl)oxetan-3-yl)urea The title compound was prepared as described in Example 129A, substituting 3-(2-(5-chloro-2-(1-methyl-1H-pyrazol-4-yl)-1-tosyl-1H-pyrrolo[2,3-b]pyridin-4-yl)thiazol-5-yl)oxetan-3-amine (Example 153E) for 1-(5-(5-chloro-2-(1-methyl-1H-pyrazol-4-yl)-1-tosyl-1H-pyrrolo[2,3-b]pyridin-4-yl)thiazol-2-yl)cyclobutanamine (Example 121A). MS ESI (+) m/z 584.4 [M+H]$^+$.

Example 156B 1-(3-(2-(5-chloro-2-(1-methyl-1H-pyrazol-4-yl)-1H-pyrrolo[2,3-b]pyridin-4-yl)thiazol-5-yl)oxetan-3-yl)urea The title compound was prepared as described in Example 47B, substituting 1-(3-(2-(5-chloro-2-(1-methyl-1H-pyrazol-4-yl)-1-tosyl-1H-pyrrolo[2,3-b]pyridin-4-yl)thiazol-5-yl)oxetan-3-yl)urea (Example 156A) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (400 MHz, DMSO-d$_6$) ppm 12.37 (s, 1H) 8.27 (s, 1H) 8.26 (s, 1H) 8.24 (s, 1H) 8.04 (s, 1H) 7.65 (s, 1H) 6.76 (s, 1H) 5.92 (s, 2H) 4.99 (d, 2H) 4.78 (d, 2H) 3.89 (s, 3H); MS ESI(+) m/z 430.2 [M+H]$^+$.

Example 157

3-(5-{5-chloro-2-[4-(pyrrolidin-1-ylmethyl)phenyl]-1H-pyrrolo[2,3-b]pyridin-4-yl}-1,3-thiazol-2-yl)oxetan-3-amine Example 157A 3-(2-(5-chloro-2-(4-(pyrrolidin-1-ylmethyl)phenyl)-1-tosyl-1H-pyrrolo[2,3-b]pyridin-4-yl)thiazol-5-yl)-N-(4-methoxybenzyl)oxetan-3-amine The title compound was prepared as described in Example 112D, substituting N-(4-methoxybenzyl)-3-(5-(tributylstannyl)thiazol-2-yl)oxetan-3-amine (Example 153C) for N-(4-methoxybenzyl)-1-(5-(tributylstannyl)thiazol-2-yl)cyclobutanamine from Example 112C and 4,5-dichloro-2-(4-(pyrrolidin-1-ylmethyl)phenyl)-1-tosyl-1H-pyrrolo[2,3-b]pyridine (Example 128B) for 4,5-dichloro-2-(1-methyl-1H-pyrazol-4-yl)-1-tosyl-1H-pyrrolo[2,3-b]pyridine from Example 113C. MS ESI(+) m/z 740.2 [M+H]$^+$.

Example 157B 3-(2-(5-chloro-2-(4-(pyrrolidin-1-ylmethyl)phenyl)-1-tosyl-1H-pyrrolo[2,3-b]pyridin-4-yl)thiazol-5-yl)oxetan-3-amine The title compound was prepared as described in Example 121A, substituting 3-(2-(5-chloro-2-(4-(pyrrolidin-1-ylmethyl)phenyl)-1-tosyl-1H-pyrrolo[2,3-b]pyridin-4-yl)thiazol-5-yl)-N-(4-methoxybenzyl)oxetan-3-amine (Example 157A) for 1-(5-(5-chloro-2-(1-methyl-1H-pyrazol-4-yl)-1-tosyl-1H-pyrrolo[2,3-b]pyridin-4-yl)thiazol-2-yl)-N-(4-methoxybenzyl)cyclobutanamine (Example 112D). MS ESI(+) m/z 620.1 [M+H]$^+$.

Example 157C 3-(2-(5-chloro-2-(4-(pyrrolidin-1-ylmethyl)phenyl)-1H-pyrrolo[2,3-b]pyridin-4-yl)thiazol-5-yl)oxetan-3-amine The title compound was prepared as described in Example 47B, substituting 3-(2-(5-chloro-2-(4-(pyrrolidin-1-ylmethyl)phenyl)-1-tosyl-1H-pyrrolo[2,3-b]pyridin-4-yl)thiazol-5-yl)oxetan-3-amine (Example 157B) for 5-(5-chloro-2-(1-methyl-1H-pyrazol-4-yl)-1-tosyl-1H-pyrrolo[2,3-b]pyridin-4-yl)-2-(1-(methoxymethoxy)cyclobutyl)thiazole (Example 47A). $^1$H NMR (400 MHz, DMSO-d$_6$) ppm 12.57 (s, 1H) 8.33 (d, 2H) 7.94 (d, 2H) 7.41 (d, 2H) 7.04 (d, 1H) 4.98 (d, 2H) 4.66 (d, 2H) 3.63 (s, 2H) 3.27 (m, 2H) 2.50 (m, 4H) 1.77 (m, 4H); MS ESI(+) m/z 466.0 [M+H]$^+$.

Example 158

N-[3-(5-{5-chloro-2-[4-(pyrrolidin-1-ylmethyl)phenyl]-1H-pyrrolo[2,3-b]pyridin-4-yl}-1,3-thiazol-2-yl)oxetan-3-yl]acetamide The title compound was prepared as described in Example 122, substituting 3-(2-(5-chloro-2-(4-(pyrrolidin-1-ylmethyl)phenyl)-1H-pyrrolo[2,3-b]pyridin-4-yl)thiazol-5-yl)oxetan-3-amine (Example 157C) for 1-(5-(5-chloro-2-(1-methyl-1H-pyrazol-4-yl)-1H-pyrrolo[2,3-b]pyridin-4-yl)thiazol-2-yl)cyclobutanamine (Example 121B). $^1$H NMR (400 MHz, DMSO-d$_6$) ppm 12.63 (s, 1H) 9.55 (s, 1H) 8.35 (d, 2H) 8.01 (d, 2H) 7.52 (d, 2H) 7.10 (s, 1H) 5.05 (d, 2H) 4.84 (d, 2H) 3.89 (bs, 2H) 2.75 (m, 4H) 1.98 (s, 3H) 1.81 (m, 4H); MS ESI(+) m/z 508.1 [M+H]$^+$.

Example 159

1-(5-{5-chloro-2-[(1E)-3-pyrrolidin-1-ylprop-1-enyl]-1H-pyrrolo[2,3-b]pyridin-4-yl}-1,3-thiazol-2-yl)cyclobutanol Example 159A (E)-1-(3-(4,4,5,5-tetramethyl-1,3,2-dioxaborolan-2-yl)allyl)pyrrolidine A solution of (E)-2-(3-chloroprop-1-enyl)-4,4,5,5-tetramethyl-1,3,2-dioxaborolane (1 g, 4.94 mmol) in acetonitrile (10 mL) was treated with potassium carbonate (1.366 g, 9.88 mmol) and pyrrolidine (0.531 mL, 6.42 mmol). The suspension was stirred at ambient temperature for 20 hours. The reaction mixture was filtered and the filtrate was concentrated on a rotary evaporator to provide the title compound. MS ESI(+) m/z 238.2 [M+H]$^+$.

Example 159B (E)-5-(5-chloro-2-(3-(pyrrolidin-1-yl)prop-1-enyl)-1-tosyl-1H-pyrrolo[2,3-b]pyridin-4-yl)-2-(1-(methoxymethoxy)cyclobutyl)thiazole The title compound was prepared as described in Example 45A substituting Example 159A for 2-(tert-butoxycarbonyl)-1,2,3,4-tetrahydroisoquinolin-7-ylboronic acid. MS ESI(+) m/z 613.1 [M+H]$^+$.

Example 159C (E)-1-(5-(5-chloro-2-(3-(pyrrolidin-1-yl)prop-1-enyl)-1-tosyl-1H-pyrrolo[2,3-b]pyridin-4-yl)thiazol-2-yl)cyclobutanol The title compound was prepared as described in Example 52D, substituting Example 159B for Example 52C. MS ESI (+) m/z 569.0 [M+H]$^+$.

Example 159D 1-(5-{5-chloro-2-[(1E)-3-pyrrolidin-1-ylprop-1-enyl]-1H-pyrrolo[2,3-b]pyridin-4-yl}-1,3-thiazol-2-yl)cyclobutanol The title compound was prepared as described in Example 45C, substituting Example 159C for Example 45B. $^1$H NMR (300 MHz, methanol-d$_4$) ppm 2.00-2.09 (m, 2H), 2.15-2.24 (m, 2H), 2.40-2.51 (m, 3H), 2.69-2.79 (m, 3H), 3.16-3.20 (m, 2H), 3.63-3.68 (m, 2 H), 4.03 (d, 2H), 6.38-6.50 (m, 1H), 6.73 (s, 1H), 6.94 (d, 1H), 8.11 (s, 1H), 8.32 (s, 1H); MS ESI(+) m/z 415.0 [M+H]$^+$.

Example 160

1-{5-[6-(1-methyl-1H-pyrazol-4-yl)-7H-pyrrolo[2,3-d]pyrimidin-4-yl]-1,3-thiazol-2-yl}cyclobutanol Example 160A 4-chloro-7-tosyl-7H-pyrrolo[2,3-d]pyrimidine The title compound was prepared as described in Example 1D, substituting 4-chloro-7H-pyrrolo[2,3-d]pyrimidine for 5-chloro-4-iodo-1H-pyrrolo[2,3-b]pyridine. MS ESI(+) m/z 308.5 [M+H]$^+$.

Example 160B 2-(1-(methoxymethoxy)cyclobutyl)-5-(7-tosyl-7H-pyrrolo[2,3-d]pyrimidin-4-yl)thiazole The title compound was prepared as described in Example 1E, substituting 4-chloro-7-tosyl-7H-pyrrolo[2,3-d]pyrimidine (Example 160A) for 5-chloro-4-iodo-1-tosyl-1H-pyrrolo[2,3-b]pyridine (Example 1D). MS ESI(+) m/z 471.0 [M+H]$^+$.

Example 160C 5-(6-iodo-7-tosyl-7H-pyrrolo[2,3-d]pyrimidin-4-yl)-2-(1-(methoxymethoxy)cyclobutyl)thiazole The title compound was prepared as described in Example 1E, substituting 241-(methoxymethoxy)cyclobutyl)-5-(7-tosyl-7H-pyrrolo[2,3-d]pyrimidin-4-yl)thiazole (Example 160B) for 5-(5-chloro-1-tosyl-1H-pyrrolo[2,3-b]pyridin-4-yl)-2-(1-(methoxymethoxy)cyclobutyl)thiazole (Example 1E). MS ESI(+) m/z 597.0 [M+H]$^+$.

Example 160D

1-{5-[6-(1-methyl-1H-pyrazol-4-yl)-7H-pyrrolo[2,3-d]pyrimidin-4-yl]-1,3-thiazol-2-yl}cyclobutanol To a stirred ambient solution of 5-(6-iodo-7-tosyl-7H-pyrrolo[2,3-d]pyrimidin-4-yl)-2-(1-(methoxymethoxy)cyclobutyl)thiazole (Example 160C) (60 mg, 0.10 mmol) and 1-methyl-4-(4,4,5,5-tetramethyl-1,3,2-dioxaborolan-2-yl)-1H-pyrazole (25.0 mg, 0.120 mmol) in N,N-dimethylformamide (2.0 mL) was added saturated aqueous bicarbonate solution (1.0 mL) followed by bis(triphenylphosphine)palladium dichloride (7.02 mg, 10.0 µmol). The mixture was heated to 70° C. for 3 hours and was then quenched by the addition of water and ethyl acetate. The layers were separated, and the aqueous layer was extracted with additional ethyl acetate. The combined organics were dried with anhydrous sodium sulfate, filtered and concentrated under reduced pressure. The residue was dissolved in methanol (1 mL), and 4 molar aqueous HCl solution (0.5 mL) was added. The reaction was heated to 60° C. for 2 hours and was then cooled to room temperature. 4 Normal aqueous sodium hydroxide solution (1 mL) was added, and the reaction heated to 80° C. for 1 hour. The reaction was cooled to room temperature, and the pH adjusted to ~7 with 10% aqueous HCl solution. The aqueous layer was extracted with ethyl acetate (3×). The combined organics were dried with anhydrous sodium sulfate, filtered and concentrated under reduced pressure. The solid was triturated with diethyl ether to give the title compound. $^1$H NMR (500 MHz, DMSO-d$_6$) ppm 1.76-2.08 (m, 2H) 2.31-2.45 (m, 2H) 2.54-2.66 (m, 2H) 3.93 (s, 3H) 6.62 (s, 1H) 7.24 (s, 1H) 8.11 (s, 1H) 8.29 (s, 1H) 8.65 (s, 1H) 8.69 (s, 1H) 12.58 (s, 1H); MS ESI(+) m/z 353 (M+H)$^+$.

Example 161

1-[5-(6-{4-[(4-methylpiperazin-1-yl)carbonyl]phenyl}-7H-pyrrolo[2,3-d]pyrimidin-4-yl)-1,3-thiazol-2-yl]cyclobutanol The title compound was prepared as described in Example 160D, substituting (4-methylpiperazin-1-yl)(4-(4,4,5,5-tetramethyl-1,3,2-dioxaborolan-2-yl)phenyl)methanone for 1-methyl-4-(4,4,5,5-tetramethyl-1,3,2-dioxaborolan-2-yl)-1H-pyrazole. $^1$H NMR (300 MHz, DMSO-d$_6$) ppm 1.88-2.04 (m, 2H) 2.29 (s, 3H) 2.31-2.46 (m, 6H) 2.57 (d, J=7.46 Hz, 4H) 3.55 (s, 2H) 6.63 (s, 1H) 7.55 (d, J=8.14 Hz, 2H) 7.71 (s, 1H) 8.19 (d, J=8.14 Hz, 2H) 8.75 (s, 1H) 8.88 (s, 1H) 12.88 (s, 1H); MS ESI(+) m/z 475 (M+H)$^+$.

Example 162

1-(5-{6-[4-(4-methylpiperazin-1-yl)phenyl]-7H-pyrrolo[2,3-d]pyrimidin-4-yl}-1,3-thiazol-2-yl)cyclobutanol The title compound was prepared as described in Example 160D, substituting 4-(4-methylpiperazin-1-yl)phenylboronic acid for 1-methyl-4-(4,4,5,5-tetramethyl-1,3,2-dioxaborolan-2-yl)-1H-pyrazole. $^1$H NMR (300 MHz, DMSO-d$_6$) ppm 1.81-2.04 (m, 2H) 2.12-2.28 (m, 3H) 2.28-2.45 (m, 4H) 2.54-2.67 (m, 2H) 3.04-3.30 (m, 6H) 6.60 (s, 1H) 7.06 (d, J=8.72 Hz, 2H) 7.39 (s, 1H) 7.95 (d, J=8.72 Hz, 2H) 8.65 (s, 1H) 8.80 (s, 1H) 12.57 (s, 1H); MS ESI(+) m/z 447 (M+H)$^+$.

Example 163

1-{5-[6-(4-morpholin-4-ylphenyl)-7H-pyrrolo[2,3-d]pyrimidin-4-yl]-1,3-thiazol-2-yl}cyclobutanol The title compound was prepared as described in Example 160D, substituting 4-morpholinophenylboronic acid for 1-methyl-4-(4,4,5,5-tetramethyl-1,3,2-dioxaborolan-2-yl)-1H-pyrazole. $^1$H NMR (300 MHz, DMSO-D6) ppm 1.85-2.05 (m, 2H) 2.26-2.46 (m, 2H) 2.53-2.69 (m, 2H) 3.12-3.27 (m, 4H) 3.58-3.86 (m, 4H) 6.59 (s, 1H) 7.07 (d, J=8.82 Hz, 2H) 7.41 (d, J=1.70 Hz, 1H) 7.98 (d, J=9.16 Hz, 2H) 8.66 (s, 1H) 8.80 (s, 1H) 12.58 (s, 1H); MS ESI(+) m/z 434 (M+H)$^+$.

Example 164

1-(5-{6-[4-(morpholin-4-ylmethyl)phenyl]-7H-pyrrolo[2,3-d]pyrimidin-4-yl}-1,3-thiazol-2-yl)cyclobutanol The title compound was prepared as described in Example 160D, substituting 4-(4-(4,4,5,5-tetramethyl-1,3,2-dioxaborolan-2-yl)benzyl)morpholine for 1-methyl-4-(4,4,5,5-tetramethyl-1,3,2-dioxaborolan-2-yl)-1H-pyrazole. $^1$H NMR (300 MHz, DMSO-d$_6$) ppm 1.79-2.18 (m, 2H) 2.29-2.46 (m, 6H) 2.53-2.75 (m, 2H) 3.53 (s, 2H) 3.56-3.75 (m, 4H) 6.62 (s, 1H) 7.45 (d, J=8.33 Hz, 2H) 7.58 (s, 1H) 8.06 (d, J=7.93 Hz, 2H) 8.72 (s, 1H) 8.85 (s, 1H) 12.77 (s, 1H); MS ESI(+) m/z 448 (M+H)$^+$.

Example 165

This example describes the assays that may be used to identify compounds having kinase activity.

To determine Aurora B activity of representative compounds of the invention, Active Aurora B enzyme (recombinant residues 1-344) and INCENP (recombinant GST fusion protein (Upstate)) were incubated in wells of a 384 well plate with biotinylted histone H3 peptide residues 1-21 (Upstate), 1 mM ATP, and various concentrations of inhibitors in a HEPES buffer, pH 7.4 containing MgCl$_2$, sodium othrovanadate, and Triton X-100. After 1 hour, the reaction was stopped with EDTA and anti-phospho-histone H3 Europium Cryptate (Cis-Bio) and SA-APC (Phycolink, Prozyme) were added to detect the phosphopeptide. The amount of phosphorylation was determined by the time-resolved fluorescence ratio of signals at 665 nm and 615 nm. The IC$_{50}$'s were calculated by an exponential fit of the inhibition values with the inhibitor concentrations using Assay Explorer software.

To determine Aurora A and C activity of representative compounds of the invention, Active Aurora A or C enzyme was incubated in wells of a 384 well plate with biotinylated STK substrate-2 (Upstate), 1 mM ATP, and various concentrations of inhibitors in a Hepes buffer, pH 7.4 containing MgCl$_2$, sodium othrovanadate, and Triton X-100. After 1 hour, the reaction was stopped with EDTA and anti-phospho- STK antibody Europium Cryptate (Upstate) and SA-XL665 (Upstate) were added to detect the phosphopeptide. The amount of phosphorylation was determined by the time-resolved fluorescence ratio of signals at 665 nm and 615 nm. The $IC_{50}$s were calculated by an exponential fit of the inhibition values with the inhibitor concentrations using Assay Explorer software.

To determine the activity of the various kinases, a homogenous time-resolved fluorescence (HTRF) in vitro kinase assay was used. (Mathis, G., *HTRF(R) Technology*. J Biomol Screen, 1999. 4(6): p. 309-314; Alfred J. Kolb, Paul V. Kaplita, David J. Hayes, Young-Whan Park, Christine Pernell, John S. Major and Gerard Mathis, *Drug Discovery Today*, 1998, 3, 333-342.)

For example for KDR, 7 ng/well of purified enzyme (His6-KDR 789-1354, MW 63 kD) was mixed with 0.5 μM N-biotinylated substrate (Biotin-Ahx-AEEEYFFLA-amide (SEQ. ID. 1)), various concentrations of inhibitor in reaction buffer (50 mM HEPES, pH 7.1, 10 mM $MgCl_2$, 2 mM $MnCl_2$, 0.1% BSA and 1 mM DTT, 40 L final volume), ATP (1 mM final conc.) in a black 384-well plate. After 60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphsophotyrosine mAb PT66-K Europium kryptate) was added to the reaction mixture. The quenched reaction was allowed to stand at room temperature for 3 hours and was then read in a time-resolved fluorescence detector (InVision, Perkin-Elmer) at 620 nm and 665 nm sequentially with excitation. The ratio between the signal of 620 nm and 665 nm was used in the calculation of the $IC_{50}$.

To determine the induction of polyploidy in H1299 cells (Human Non-Small Cell Lung Carcinoma), NCI-H1299 were seeded (4K/well) into 96-well culture plates (tissue culture grade, black, flat-clear bottom) and incubated overnight to produce cell-to-plate adherance Inhibitors at varying concentrations were added into duplicate wells containing cells and culture media (RPMI 1640, 10% fetal calf serum) and incubated at 37 C for 48 hours. The plates were then washed with PBS and the adherent cells fixed by incubating with 3% formalin for 1 hour. After washing four times with PBS, the cells were then stained with Hoechst and subjected to fluorescent (360 i/460e) microscopic high content analysis to determine the effect of inhibitors on nuclear size. Polyploid cells (≥4N) were defined as those having nuclear area >750 μ2. Potency was expressed as the concentration of inhibitor necessary to induce polyploidy in 15% of cells (EC15) and was calculated from least squares analysis of the log dose-response.

Compounds of the present invention assessed by the above-described assays were found to have kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. A compound having formula I

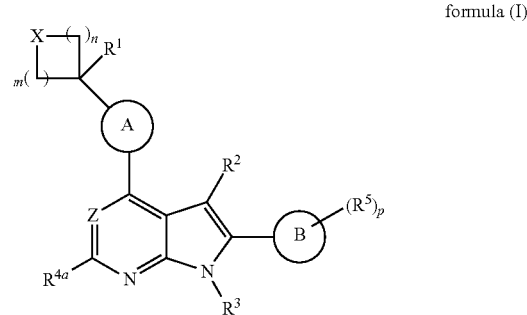

formula (I)

wherein
A is heteroaryl,
B is aryl, heteroaryl, heterocycloalkenyl, or —CH=CH—;
X is —$CH_2$—, —$NR^8$—, —O—, —S—, —S(O)—, or —$SO_2$—;
Z is C—$R^{4b}$;
m is 0, 1, or 2;
n is 1 or 2;
p is 0, 1, 2, 3, or 4;
$R^1$ is halogen, —$OR^9$, or —$NR^{10}R^{11}$;
$R^2$ and $R^3$ are independently hydrogen or $C_{1-8}$-alkyl, wherein the $C_{1-8}$ alkyl is optionally substituted with aryl, heterocyclyl, $C_{3-8}$-cycloalkyl, halogen, cyano, hydroxy, $C_{1-4}$-alkoxy, —$NH_2$, —NH($C_{1-4}$-alkyl), or —N($C_{1-4}$-alkyl)$_2$;
$R^{4a}$ and $R^{4b}$ are independently hydrogen, nitro, halogen, cyano, $C_{1-4}$-alkyl, $C_{1-4}$-haloalkyl, —$OR^a$, —$NR^bR^c$; —C(O)$OR^a$, —C(O)$NR^bR^c$, —$NR^bC(O)R^c$, —NHC(O)$NHR^b$, or —$NHSO_2R^a$;
$R^5$ is $R^6$, nitro, halogen, cyano, $C_{1-4}$-haloalkyl, $OR^d$, —C(O)$R^d$, —C(O)$OR^d$, —OC(O)$R^d$, —$NR^eR^f$, —$NR^eC(O)R^d$, —NHC(O)$NHR^e$, —$NHSO_2R^e$, —C(O)$NR^eR^f$, —$SR^e$, —S(O)$R^e$, —$SO_2R^e$, or —$SO_2NR^cNR^d$;
$R^6$ is $C_{1-8}$-alkyl, aryl, or heterocyclyl, wherein the $R^6$ $C_{1-8}$-alkyl substituent is optionally substituted with one or more substituents selected from the group consisting of $R^7$, halogen, cyano, nitro, —$OR^g$, —C(O)$R^g$, —C(O)$OR^g$, —OC(O)$R^g$, —$NR^hR^i$, —$NR^hC(O)R^g$, —NHC(O)$NHR^h$, and —C(O)$NR^hR^i$; and wherein the $R^6$ aryl or heterocyclyl substituents are optionally substituted with one or more substituents independently selected from the group consisting of $C_{1-8}$-alkyl, aryl, heterocyclyl, halogen, cyano, nitro, $C_{1-4}$-haloalkyl, —$OR^j$, —C(O)$R^j$, —C(O)$OR^j$, —OC(O)$R^j$, —$NR^kR^l$, —$NR^kC(O)R^j$, —NHC(O)$NHR^k$, —$NHSO_2R^j$, —C(O)$NR^kR^l$, —$SR^j$, —S(O)$R^j$, —$SO_2R^j$, and —$SO_2NR^kNR^l$;
$R^7$ is cycloalkyl, aryl, heteroaryl, or heterocycloalkyl, wherein the cycloalkyl, aryl, heteroaryl, or heterocycloalkyl are optionally substituted with $C_{1-8}$-alkyl, halogen, cyano, nitro, $C_{1-4}$-haloalkyl, —$OR^j$, —C(O)$R^j$, —C(O)$OR^j$, —OC(O)$R^j$, —$NR^kR^l$, —$NR^kC(O)R^j$, —NHC(O)$NHR^k$, —$NHSO_2R^j$, —C(O)$NR^kR^l$, —$SR^j$, —S(O)$R^j$, —$SO_2R^j$, or —$SO_2NR^kNR^l$,
$R^8$ is hydrogen, $C_{1-8}$-alkyl, or —C(O)$C_{1-8}$-alkyl;
$R^9$ is hydrogen, $C_{1-8}$-alkyl, phenyl, or benzyl, wherein the $C_{1-8}$-alkyl is optionally substituted with —$OC_{1-8}$-alkyl, —C(O)$C_{1-8}$-alkyl, —C(O)$OC_{1-8}$-alkyl, or —OC(O)

$C_{1-8}$-alkyl, and wherein $R^9$ phenyl or benzyl ring is optionally substituted with —$OC_{1-8}$-alkyl, —$C(O)C_{1-8}$-alkyl, —$C(O)OC_{1-8}$-alkyl, or —$OC(O)C_{1-8}$-alkyl;

$R^{10}$ is hydrogen or $C_{1-8}$-alkyl;

$R^{11}$ is hydrogen, $C_{1-8}$-alkyl, —$C(O)R^m$, —$C(O)NH_2$, —$C(O)NHR^m$, —$C(O)NR^mR^n$, or —$S(O)_2R^m$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-Cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^k$ and $R^l$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$;

$R^m$ and $R^n$, at each occurrence, are independently selected from the group consisting of hydrogen, $C_{1-8}$-alkyl, phenyl, and benzyl;

or a pharmaceutically acceptable salt thereof.

2. The compound of claim 1, wherein A is thiazolyl, pyridinyl, or pyrrolyl.

3. The compound of claim 1, wherein X is —$CH_2$— or —$NR^8$— and m is 1 and n is 1.

4. The compound of claim 1, wherein $R^2$ is hydrogen.

5. The compound of claim 1, wherein B is phenyl, pyridyl, tetrahydropyridyl, pyrimidinyl, pyridazinyl, pyrrolyl, imidazyl, pyrazolyl, triazolyl, furanyl, thiophenyl, oxazolyl, isoxazolyl, thiazolyl, isothiazolyl, oxadiazolyl, or isothiazolyl.

6. The compound according to claim 1, wherein B is indolyl, isoindolyl, indazolyl, isoindazoyl, quinolinyl, benzoxazolyl, benzofuranyl, benzothiophenyl, benzothiazolyl, benzimidazolyl, benzotriazolyl, 1,2,3,4-tetrahydroquinoline, 1,2,3,4-tetrahydroisoquinoline, isoindolinyl, indolinyl, or pyrazolo[1,5-a]pyridine.

7. The compound according to claim 5, wherein B is pyridinyl, tetrahydropyridinyl, pyrazolyl, or phenyl.

8. The compound of claim 1, wherein $R^3$ is hydrogen.

9. The compound of claim 1, wherein $R^{4a}$ and $R^{4b}$ are each independently hydrogen, hydroxy, nitro, halogen, cyano, trifluoromethyl, trifluoromethoxy, or $C_{1-4}$-alkyl.

10. The compound of claim 9, wherein $R^{4a}$ is hydrogen and $R^{4b}$ is halogen.

11. The compound of claim 1, wherein $R^1$ is —OH or —$NH_2$.

12. The compound of claim 1, wherein $R^1$ is fluoro.

13. The compound of claim 5, wherein B is substituted with $R^5$ and p is 1, wherein $R^5$ is $C_{1-8}$-alkyl, wherein the $C_{1-8}$-alkyl is optionally substituted one or two substituents independently selected from the group consisting of $R^7$, —$OR^g$, —$C(O)OR^g$, —$NR^hR^i$, —$NR^hC(O)R^9$, and —$C(O)NR^hR^i$, wherein $R^7$ is heterocycloalkyl is optionally substituted with $C_{1-8}$-alkyl, $C_{1-4}$-haloalkyl, halogen, —$OR^j$, or —$NR^kR^l$, wherein $R^g$, $R^h$, $R^i$, $R^j$, $R^k$, and $R^l$ are independently selected from the group consisting of hydrogen, $C_{1-8}$-alkyl, aryl, and $C_{3-8}$-cycloalkyl.

14. The compound of claim 5, wherein B is substituted with $R^5$ and p is 1, wherein $R^5$ is heterocycloalkyl, wherein the heterocycloalkyl is optionally substituted with $C_{1-8}$-alkyl, $C_{1-4}$-haloalkyl, halogen, —$OR^j$, or —$NR^kR^l$, wherein $R^j$, $R^k$, and $R^l$ are independently selected from the group consisting of hydrogen, $C_{1-8}$-alkyl, aryl, and $C_{3-8}$-cycloalkyl.

15. The compound of claim 5, wherein B is substituted with $R^5$ and p is 1, 2, or 3, and $R^5$ is selected from the group consisting of halogen, $C_{1-4}$-haloalkyl, $OR^d$, —$C(O)OR^d$, —$NR^eC(O)R^d$, —$NHSO_2R^e$, —$C(O)NR^eR^f$, —$SO_2R^c$, and —$SO_2NR^cNR^d$; $R^d$, $R^e$, and $R^f$ are independently selected from the group consisting of hydrogen, $C_{1-8}$-alkyl, aryl, and $C_{3-8}$-cycloalkyl, wherein the $C_{1-8}$-alkyl, aryl, and $C_{3-8}$-cycloalkyl are optionally substituted with one or more substituents independently selected from the group consisting of aryl, heterocyclyl, $C_{3-8}$-cycloalkyl, halogen, cyano, hydroxy, $C_{1-8}$-alkoxy, —$NH_2$, —$NH(C_{1-8}$-alkyl), and —$N(C_{1-8}$-alkyl)$_2$.

16. The compound of claim 1 of formula (I), selected from the group consisting of 1-(5-{5-chloro-2-[1-(2-morpholin-4-ylethyl)-1H-pyrazol-4-yl]-1H-pyrrolo[2,3-b]pyridin-4-yl}-1,3-thiazol-2-yl)cyclobutanol;
1-{5-[5-fluoro-2-(4-piperazin-1-ylphenyl)-1H-pyrrolo[2,3-b]pyridin-4-yl]-1,3-thiazol-2-yl}cyclobutanol;
1-(5-{2-[4-(morpholin-4-ylmethyl)phenyl]-1H-pyrrolo[2,3-b]pyridin-4-yl}-1,3-thiazol-2-yl)cyclobutanol;
5-chloro-4-{2-[1-(methoxymethoxy)cyclobutyl]-1,3-thiazol-5-yl}-2-[4-(morpholin-4-ylmethyl)phenyl]-1H-pyrrolo[2,3-b]pyridine;
1-(5-{5-chloro-2-[4-(morpholin-4-ylmethyl)phenyl]-1H-pyrrolo[2,3-b]pyridin-4-yl}-1,3-thiazol-2-yl)cyclobutanol;
1-{5-[5-chloro-2-(4-piperazin-1-ylphenyl)-1H-pyrrolo[2,3-b]pyridin-4-yl]-1,3-thiazol-2-yl}cyclobutanol;
5-chloro-4-[2-(1-methoxycyclobutyl)-1,3-thiazol-5-yl]-2-(4-piperazin-1-ylphenyl)-1H-pyrrolo[2,3-b]pyridine;
1-(5-{5-chloro-2-[4-(pyrrolidin-1-ylmethyl)phenyl]-1H-pyrrolo[2,3-b]pyridin-4-yl}-1,3-thiazol-2-yl)cyclobutanol;
1-(5-{5-fluoro-2-[1-(2-morpholin-4-ylethyl)-1H-pyrazol-4-yl]-1H-pyrrolo[2,3-b]pyridin-4-yl}-1,3-thiazol-2-yl)cyclobutanol;
1-(5-{5-fluoro-2-[4-(morpholin-4-ylmethyl)phenyl]-1H-pyrrolo[2,3-b]pyridin-4-yl}-1,3-thiazol-2-yl)cyclobutanol;
3-(5-{5-chloro-2-[4-(morpholin-4-ylmethyl)phenyl]-1H-pyrrolo[2,3-b]pyridin-4-yl}-1,3-thiazol-2-yl)oxetan-3-ol;
3-(5-{5-chloro-2-[1-(2-morpholin-4-ylethyl)-1H-pyrazol-4-yl]-1H-pyrrolo[2,3-b]pyridin-4-yl}-1,3-thiazol-2-yl)oxetan-3-ol;
1-(5-{5-chloro-2-[1-(1,3-dioxolan-2-ylmethyl)-1H-pyrazol-4-yl]-1H-pyrrolo[2,3-b]pyridin-4-yl}-1,3-thiazol-2-yl)cyclobutanol;
1-[5-(5-chloro-2-{1-[2-(dimethylamino)ethyl]-1H-pyrazol-4-yl}-1H-pyrrolo[2,3-b]pyridin-4-yl)-1,3-thiazol-2-yl]cyclobutanol;
1-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)cyclobutanol;
4-{5-chloro-4-[2-(1-hydroxycyclobutyl)-1,3-thiazol-5-yl]-1H-pyrrolo[2,3-b]pyridin-2-yl}benzoic acid;
1-{5-[5-chloro-2-(1-{2-[cyclopropyl(methyl)amino]ethyl}-1H-pyrazol-4-yl)-1H-pyrrolo[2,3-b]pyridin-4-yl]-1,3-thiazol-2-yl}cyclobutanol;
1-(5-{5-chloro-2-[6-(4-methylpiperazin-1-yl)pyridin-3-yl]-1H-pyrrolo[2,3-b]pyridin-4-yl}-1,3-thiazol-2-yl)cyclobutanol;
1-[5-(5-chloro-2-{4-[(4-methylpiperazin-1-yl)carbonyl]phenyl}-1H-pyrrolo[2,3-b]pyridin-4-yl)-1,3-thiazol-2-yl]cyclobutanol;
5-chloro-4-(2-{3-[(4-methoxybenzyl)oxy]oxetan-3-yl}-1,3-thiazol-5-yl)-2-[1-(2-pyrrolidin-1-ylethyl)-1H-pyrazol-4-yl]-1H-pyrrolo[2,3-b]pyridine;
3-(5-{5-chloro-2-[1-(2-pyrrolidin-1-ylethyl)-1H-pyrazol-4-yl]-1H-pyrrolo[2,3-b]pyridin-4-yl}-1,3-thiazol-2-yl)oxetan-3-ol;
1-{5-[5-chloro-2-(5-piperidin-3-yl-1,2,4-oxadiazol-3-yl)-1H-pyrrolo[2,3-b]pyridin-4-yl]-1,3-thiazol-2-yl}cyclobutanol;
N~1~-(4-{5-chloro-4-[2-(1-hydroxycyclobutyl)-1,3-thiazol-5-yl]-1H-pyrrolo[2,3-b]pyridin-2-yl}phenyl)-N~2~,N~2~-dimethylglycinamide;
1-(5-{5-chloro-2-[3-fluoro-4-(pyrrolidin-1-ylmethyl)phenyl]-1H-pyrrolo[2,3-b]pyridin-4-yl}-1,3-thiazol-2-yl)cyclobutanol;
1-[5-(5-chloro-2-{4-[(dimethylamino)methyl]-3-fluorophenyl}-1H-pyrrolo[2,3-b]pyridin-4-yl)-1,3-thiazol-2-yl]cyclobutanol;
1-(4-{5-chloro-4-[2-(1-hydroxycyclobutyl)-1,3-thiazol-5-yl]-1H-pyrrolo[2,3-b]pyridin-2-yl}-2-fluorobenzyl)pyrrolidin-3-ol;
1-[5-(5-chloro-2-{3-fluoro-4-[(3-fluoropyrrolidin-1-yl)methyl]phenyl}-1H-pyrrolo[2,3-b]pyridin-4-yl)-1,3-thiazol-2-yl]cyclobutanol;
1-[5-(5-chloro-2-{3-fluoro-4-[(2-methylpyrrolidin-1-yl)methyl]phenyl}-1H-pyrrolo[2,3-b]pyridin-4-yl)-1,3-thiazol-2-yl]cyclobutanol;
1-{5-[5-chloro-2-(4-{[cyclopropyl(methyl)amino]methyl}-3-fluorophenyl)-1H-pyrrolo[2,3-b]pyridin-4-yl]-1,3-thiazol-2-yl}cyclobutanol;
1-[5-(5-chloro-2-{3-fluoro-4-[(4-fluoropiperidin-1-yl)methyl]phenyl}-1H-pyrrolo[2,3-b]pyridin-4-yl)-1,3-thiazol-2-yl]cyclobutanol;
1-[5-(5-chloro-2-{4-[(4,4-difluoropiperidin-1-yl)methyl]-3-fluorophenyl}-1H-pyrrolo[2,3-b]pyridin-4-yl)-1,3-thiazol-2-yl]cyclobutanol;
1-[5-(5-chloro-2-phenyl-1H-pyrrolo[2,3-b]pyridin-4-yl)-1,3-thiazol-2-yl]cyclobutanol;
1-{5-[5-chloro-2-(1-methyl-1H-pyrazol-4-yl)-1H-pyrrolo[2,3-b]pyridin-4-yl]-1,3-thiazol-2-yl}cyclobutanol;
1-[5-(5-chloro-2-pyridin-4-yl-1H-pyrrolo[2,3-b]pyridin-4-yl)-1,3-thiazol-2-yl]cyclobutanol;
1-(5-{5-chloro-2-[4-(ethylsulfonyl)phenyl]-1H-pyrrolo[2,3-b]pyridin-4-yl}-1,3-thiazol-2-yl)cyclobutanol;
3-{5-chloro-4-[2-(1-hydroxycyclobutyl)-1,3-thiazol-5-yl]-1H-pyrrolo[2,3-b]pyridin-2-yl}benzoic acid;
(4-{5-chloro-4-[2-(1-hydroxycyclobutyl)-1,3-thiazol-5-yl]-1H-pyrrolo[2,3-b]pyridin-2-yl}phenyl)acetic acid;
(4-{5-chloro-4-[2-(1-hydroxycyclobutyl)-1,3-thiazol-5-yl]-1H-pyrrolo[2,3-b]pyridin-2-yl}-1H-pyrazol-1-yl)acetic acid;
1-(5-{5-chloro-2-[1-(2-hydroxyethyl)-1H-pyrazol-4-yl]-1H-pyrrolo[2,3-b]pyridin-4-yl}-1,3-thiazol-2-yl)cyclobutanol;
1-{5-[5-chloro-2-(2-methylphenyl)-1H-pyrrolo[2,3-b]pyridin-4-yl]-1,3-thiazol-2-yl}cyclobutanol;
1-{5-[5-chloro-2-(3-methylphenyl)-1H-pyrrolo[2,3-b]pyridin-4-yl]-1,3-thiazol-2-yl}cyclobutanol;
1-{5-[5-chloro-2-(2-methoxyphenyl)-1H-pyrrolo[2,3-b]pyridin-4-yl]-1,3-thiazol-2-yl}cyclobutanol;
1-{5-[5-chloro-2-(3-methoxyphenyl)-1H-pyrrolo[2,3-b]pyridin-4-yl]-1,3-thiazol-2-yl}cyclobutanol;
1-{5-[5-chloro-2-(3-fluorophenyl)-1H-pyrrolo[2,3-b]pyridin-4-yl]-1,3-thiazol-2-yl}cyclobutanol;
1-{5-[5-chloro-2-(1,2,3,4-tetrahydroisoquinolin-7-yl)-1H-pyrrolo[2,3-b]pyridin-4-yl]-1,3-thiazol-2-yl}cyclobutanol;
1-{5-[5-chloro-2-(3-piperidin-4-yl-1,2,4-oxadiazol-5-yl)-1H-pyrrolo[2,3-b]pyridin-4-yl]-1,3-thiazol-2-yl}cyclobutanol;
1-{5-[5-chloro-2-(1-methyl-1H-pyrazol-4-yl)-3-(pyrrolidin-1-ylmethyl)-1H-pyrrolo[2,3-b]pyridin-4-yl]-1,3-thiazol-2-yl}cyclobutanol;

N~1~-(4-{5-chloro-4-[2-(1-hydroxycyclobutyl)-1,3-thiazol-5-yl]-1H-pyrrolo[2,3-b]pyridin-2-yl}-3-methylphenyl)-N~2~,N~2~-dimethylglycinamide;

N~1~-(4-{5-chloro-4-[2-(1-hydroxycyclobutyl)-1,3-thiazol-5-yl]-1H-pyrrolo[2,3-b]pyridin-2-yl}-2-methoxyphenyl)-N~2~,N~2~-dimethylglycinamide;

1-{5-[5-chloro-2-(1-piperidin-4-yl-1H-pyrazol-4-yl)-1H-pyrrolo[2,3-b]pyridin-4-yl]-1,3-thiazol-2-yl}cyclobutanol;

3-{5-chloro-4-[2-(1-hydroxycyclobutyl)-1,3-thiazol-5-yl]-1H-pyrrolo[2,3-b]pyridin-2-yl}benzonitrile;

1-(5-{5-chloro-2-[1-(N,N-dimethylglycyl)-2,3-dihydro-1H-indol-5-yl]-1H-pyrrolo[2,3-b]pyridin-4-yl}-1,3-thiazol-2-yl)cyclobutanol;

1-{5-[5-chloro-2-(2,3-dihydro-1H-indol-5-yl)-1H-pyrrolo[2,3-b]pyridin-4-yl]-1,3-thiazol-2-yl}cyclobutanol;

3-(5-{5-fluoro-2-[1-(2-pyrrolidin-1-ylethyl)-1H-pyrazol-4-yl]-1H-pyrrolo[2,3-b]pyridin-4-yl}-1,3-thiazol-2-yl)azetidin-3-ol;

1-(5-{5-chloro-2-[3-fluoro-4-(hydroxymethyl)phenyl]-1H-pyrrolo[2,3-b]pyridin-4-yl}-1,3-thiazol-2-yl)cyclobutanol;

1-(5-{5-chloro-2-[4-(2-pyrrolidin-1-ylethyl)phenyl]-1H-pyrrolo[2,3-b]pyridin-4-yl}-1,3-thiazol-2-yl)cyclobutanol;

1-[5-(5-chloro-2-{4-[(4-methyl-1,4-diazepan-1-yl)carbonyl]phenyl}-1H-pyrrolo[2,3-b]pyridin-4-yl)-1,3-thiazol-2-yl]cyclobutanol;

1-[5-(5-chloro-2-{4-[4-(dimethylamino)piperidin-1-yl]phenyl}-1H-pyrrolo[2,3-b]pyridin-4-yl)-1,3-thiazol-2-yl]cyclobutanol;

1-{5-[5-fluoro-2-(1-methyl-1H-pyrazol-4-yl)-1H-pyrrolo[2,3-b]pyridin-4-yl]-1,3-thiazol-2-yl}cyclobutanol;

N~1~-(4-{5-chloro-4-[2-(1-hydroxycyclobutyl)-1,3-thiazol-5-yl]-1H-pyrrolo[2,3-b]pyridin-2-yl}-3-fluorophenyl)-N~2~,N~2~-dimethylglycinamide;

N~1~-(3-chloro-4-{5-chloro-4-[2-(1-hydroxycyclobutyl)-1,3-thiazol-5-yl]-1H-pyrrolo[2,3-b]pyridin-2-yl}phenyl)-N~2~,N~2~-dimethylglycinamide;

N~1~-(4-{5-chloro-4-[2-(1-hydroxycyclobutyl)-1,3-thiazol-5-yl]-1H-pyrrolo[2,3-b]pyridin-2-yl}-2-methylphenyl)-N~2~,N~2~-dimethylglycinamide;

N~1~-(2-chloro-4-{5-chloro-4-[2-(1-hydroxycyclobutyl)-1,3-thiazol-5-yl]-1H-pyrrolo[2,3-b]pyridin-2-yl}phenyl)-N~2~,N~2~-dimethylglycinamide;

N~1~-(4-{5-chloro-4-[2-(1-hydroxycyclobutyl)-1,3-thiazol-5-yl]-1H-pyrrolo[2,3-b]pyridin-2-yl}-2-fluorophenyl)-N~2~,N~2~-dimethylglycinamide;

1-[5-(5-fluoro-2-{1-[2-(4-methylpiperazin-1-yl)-2-oxoethyl]-1H-pyrazol-4-yl}-1H-pyrrolo[2,3-b]pyridin-4-yl)-1,3-thiazol-2-yl]cyclobutanol;

2-(4-{5-fluoro-4-[2-(1-hydroxycyclobutyl)-1,3-thiazol-5-yl]-1H-pyrrolo[2,3-b]pyridin-2-yl}-1H-pyrazol-1-yl)-N-(methylsulfonyl)acetamide;

1-[5-(5-chloro-2-{1-[(1-methylpiperidin-4-yl)carbonyl]-1,2,3,6-tetrahydropyridin-4-yl}-1H-pyrrolo[2,3-b]pyridin-4-yl)-1,3-thiazol-2-yl]cyclobutanol;

N~1~-(4-{5-chloro-4-[2-(1-hydroxycyclobutyl)-1,3-thiazol-5-yl]-1H-pyrrolo[2,3-b]pyridin-2-yl}-3-methoxyphenyl)-N~2~,N~2~-dimethylglycinamide;

1-(5-{5-chloro-2-[4-(tetrahydrofuran-3-yloxy)phenyl]-1H-pyrrolo[2,3-b]pyridin-4-yl}-1,3-thiazol-2-yl)cyclobutanol;

1-(5-{5-chloro-2-[4-(tetrahydrofuran-2-ylmethoxy)phenyl]-1H-pyrrolo[2,3-b]pyridin-4-yl}-1,3-thiazol-2-yl)cyclobutanol;

1-(5-{5-chloro-2-[4-(1,4-dioxan-2-ylmethoxy)phenyl]-1H-pyrrolo[2,3-b]pyridin-4-yl}-1,3-thiazol-2-yl)cyclobutanol;

1-[5-(5-chloro-2-{4-[(1-methylpiperidin-4-yl)oxy]phenyl}-1H-pyrrolo[2,3-b]pyridin-4-yl)-1,3-thiazol-2-yl]cyclobutanol;

1-[5-(5-fluoro-2-{1-[2-(4-methyl-1,4-diazepan-1-yl)-2-oxoethyl]-1H-pyrazol-4-yl}-1H-pyrrolo[2,3-b]pyridin-4-yl)-1,3-thiazol-2-yl]cyclobutanol;

1-{5-[5-chloro-2-(1,5-dimethyl-1H-pyrazol-4-yl)-1H-pyrrolo[2,3-b]pyridin-4-yl]-1,3-thiazol-2-yl}cyclobutanol;

1-{5-[5-chloro-2-(2,3-dihydro-1,4-benzodioxin-6-yl)-1H-pyrrolo[2,3-b]pyridin-4-yl]-1,3-thiazol-2-yl}cyclobutanol;

1-[5-(5-chloro-2-{4-[(3,3-difluoropiperidin-1-yl)methyl]-3-fluorophenyl}-1H-pyrrolo[2,3-b]pyridin-4-yl)-1,3-thiazol-2-yl]cyclobutanol;

4-(4-{5-chloro-4-[2-(1-hydroxycyclobutyl)-1,3-thiazol-5-yl]-1H-pyrrolo[2,3-b]pyridin-2-yl}-2-fluorobenzyl)piperazin-2-one;

1-{5-[5-chloro-2-(4-{[3-(dimethylamino)pyrrolidin-1-yl]methyl}-3-fluorophenyl)-1H-pyrrolo[2,3-b]pyridin-4-yl]-1,3-thiazol-2-yl}cyclobutanol;

1-{5-[5-chloro-2-(3-fluoro-4-{[4-(trifluoromethyl)piperidin-1-yl]methyl}phenyl)-1H-pyrrolo[2,3-b]pyridin-4-yl]-1,3-thiazol-2-yl}cyclobutanol;

1-{5-[5-chloro-2-(3-fluoro-4-{[3-(trifluoromethyl)piperidin-1-yl]methyl}phenyl)-1H-pyrrolo[2,3-b]pyridin-4-yl]-1,3-thiazol-2-yl}cyclobutanol;

1-[5-(5-chloro-2-{3-fluoro-4-[(2-methylpiperidin-1-yl)methyl]phenyl}-1H-pyrrolo[2,3-b]pyridin-4-yl)-1,3-thiazol-2-yl]cyclobutanol;

1-(5-{5-chloro-2-[3-fluoro-4-(piperazin-1-ylmethyl)phenyl]-1H-pyrrolo[2,3-b]pyridin-4-yl}-1,3-thiazol-2-yl)cyclobutanol;

1-[5-(5-chloro-2-{4-[(4-fluoropiperidin-1-yl)methyl]phenyl}-1H-pyrrolo[2,3-b]pyridin-4-yl)-1,3-thiazol-2-yl]cyclobutanol;

1-(5-{5-chloro-2-[1-(pyridin-2-ylmethyl)-1H-pyrazol-4-yl]-1H-pyrrolo[2,3-b]pyridin-4-yl}-1,3-thiazol-2-yl)cyclobutanol;

1-(5-{5-chloro-2-[1-(pyridin-3-ylmethyl)-1H-pyrazol-4-yl]-1H-pyrrolo[2,3-b]pyridin-4-yl}-1,3-thiazol-2-yl)cyclobutanol;

1-(5-{5-chloro-2-[1-(pyridin-4-ylmethyl)-1H-pyrazol-4-yl]-1H-pyrrolo[2,3-b]pyridin-4-yl}-1,3-thiazol-2-yl)cyclobutanol;

1-[5-(5-chloro-2-pyrazolo[1,5-a]pyridin-3-yl-1H-pyrrolo[2,3-b]pyridin-4-yl)-1,3-thiazol-2-yl]cyclobutanol;

3-[5-(5-fluoro-1H-pyrrolo[2,3-b]pyridin-4-yl)-1,3-thiazol-2-yl]azetidin-3-ol;

1-{5-[5-chloro-2-(1,2,3,6-tetrahydropyridin-4-yl)-1H-pyrrolo[2,3-b]pyridin-4-yl]-1,3-thiazol-2-yl}cyclobutanol;

1-{5-[5-fluoro-2-(3,4,5-trimethoxyphenyl)-1H-pyrrolo[2,3-b]pyridin-4-yl]-1,3-thiazol-2-yl}cyclobutanol;

1-(5-{5-fluoro-2-[3-(methylsulfonyl)phenyl]-1H-pyrrolo[2,3-b]pyridin-4-yl}-1,3-thiazol-2-yl)cyclobutanol;

1-[5-(5-fluoro-2-quinolin-6-yl-1H-pyrrolo[2,3-b]pyridin-4-yl)-1,3-thiazol-2-yl]cyclobutanol;

1-{5-[5-fluoro-2-(5-methoxy-1H-indol-3-yl)-1H-pyrrolo[2,3-b]pyridin-4-yl]-1,3-thiazol-2-yl}cyclobutanol;

3-[5-(5-fluoro-2-pyridin-4-yl-1H-pyrrolo[2,3-b]pyridin-4-yl)-1,3-thiazol-2-yl]azetidin-3-ol;

3-{5-[5-fluoro-2-(1-methyl-1H-pyrazol-4-yl)-1H-pyrrolo[2,3-b]pyridin-4-yl]-1,3-thiazol-2-yl}azetidin-3-ol;

3-(5-{2-[4-(ethylsulfonyl)phenyl]-5-fluoro-1H-pyrrolo[2,3-b]pyridin-4-yl}-1,3-thiazol-2-yl)azetidin-3-ol;
3-(5-{5-fluoro-2-[3-fluoro-4-(morpholin-4-ylmethyl)phenyl]-1H-pyrrolo[2,3-b]pyridin-4-yl}-1,3-thiazol-2-yl)azetidin-3-ol;
3-[5-(5-fluoro-2-phenyl-1H-pyrrolo[2,3-b]pyridin-4-yl)-1,3-thiazol-2-yl]azetidin-3-ol;
3-[5-(2-{4-[(3,3-difluoropiperidin-1-yl)methyl]phenyl}-5-fluoro-1H-pyrrolo[2,3-b]pyridin-4-yl)-1,3-thiazol-2-yl]azetidin-3-ol;
3-[5-(5-fluoro-2-{4-[(2-methylpyrrolidin-1-yl)methyl]phenyl}-1H-pyrrolo[2,3-b]pyridin-4-yl)-1,3-thiazol-2-yl]azetidin-3-ol;
3-[5-(5-fluoro-1H-pyrrolo[2,3-b]pyridin-4-yl)-1,3-thiazol-2-yl]-1-methylazetidin-3-ol;
1-(5-{5-chloro-2-[1-(1,4-dioxan-2-ylcarbonyl)-1,2,3,6-tetrahydropyridin-4-yl]-1H-pyrrolo[2,3-b]pyridin-4-yl}-1,3-thiazol-2-yl)cyclobutanol;
1-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)cyclobutanol;
1-{5-[5-fluoro-2-(5-methoxy-1-methyl-1H-indol-3-yl)-1H-pyrrolo[2,3-b]pyridin-4-yl]-1,3-thiazol-2-yl}cyclobutanol;
1-{5-[2-(5-fluoro-1-methyl-1H-indol-3-yl)-1H-pyrrolo[2,3-b]pyridin-4-yl]-1,3-thiazol-2-yl}cyclobutanol;
3-(5-{5-chloro-2-[4-(pyrrolidin-1-ylmethyl)phenyl]-1H-pyrrolo[2,3-b]pyridin-4-yl}-1,3-thiazol-2-yl)oxetan-3-ol;
3-{5-[5-chloro-2-(1-methyl-1H-pyrazol-4-yl)-1H-pyrrolo[2,3-b]pyridin-4-yl]-1,3-thiazol-2-yl}oxetan-3-ol;
1-(5-{2-[3-(methylsulfonyl)phenyl]-1H-pyrrolo[2,3-b]pyridin-4-yl}-1,3-thiazol-2-yl)cyclobutanol;
1-{5-[2-(1-methyl-1H-pyrazol-4-yl)-1H-pyrrolo[2,3-b]pyridin-4-yl]-1,3-thiazol-2-yl}cyclobutanol;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N-(4-methoxybenzyl)amine;
1-{1-[5-chloro-2-(1-methyl-1H-pyrazol-4-yl)-1H-pyrrolo[2,3-b]pyridin-4-yl]-1H-pyrazol-4-yl}cyclobutanol;
5-chloro-4-[2-(1-fluorocyclobutyl)-1,3-thiazol-5-yl]-2-[1-(2-morpholin-4-ylethyl)-1H-pyrazol-4-yl]-1H-pyrrolo[2,3-b]pyridine;
5-chloro-4-[2-(1-fluorocyclobutyl)-1,3-thiazol-5-yl]-2-[4-(morpholin-4-ylmethyl)phenyl]-1H-pyrrolo[2,3-b]pyridine;
5-chloro-4-[2-(1-fluorocyclobutyl)-1,3-thiazol-5-yl]-2-[1-(2-pyrrolidin-1-ylethyl)-1H-pyrazol-4-yl]-1H-pyrrolo[2,3-b]pyridine;
3-{5-[5-chloro-2-(1-methyl-1H-pyrazol-4-yl)-1H-pyrrolo[2,3-b]pyridin-4-yl]-1,3-thiazol-2-yl}-1-methylpyrrolidin-3-ol;
3-(5-{5-chloro-2-[4-(morpholin-4-ylmethyl)phenyl]-1H-pyrrolo[2,3-b]pyridin-4-yl}-1,3-thiazol-2-yl)-1-methylpyrrolidin-3-ol;
1-(5-{5-fluoro-2-[2-(4-oxa-1-azabicyclo[3.2.1]oct-5-yl)-1,3-thiazol-5-yl]-1H-pyrrolo[2,3-b]pyridin-4-yl}-1,3-thiazol-2-yl)cyclobutanol;
1-{5-[5-chloro-2-(1-methyl-1H-pyrazol-4-yl)-1H-pyrrolo[2,3-b]pyridin-4-yl]-1,3-thiazol-2-yl}cyclobutanamine;
N-(1-{5-[5-chloro-2-(1-methyl-1H-pyrazol-4-yl)-1H-pyrrolo[2,3-b]pyridin-4-yl]-1,3-thiazol-2-Oyl}cyclobutyl)acetamide;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)benzamide;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N'-ethylurea;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)methanesulfonamide;
3-{5-[5-chloro-2-(1-methyl-1H-pyrazol-4-yl)-1H-pyrrolo[2,3-b]pyridin-4-yl]-1,3-thiazol-2-yl}-1-methylazetidin-3-ol;
3-(5-{5-chloro-2-[4-(morpholin-4-ylmethyl)phenyl]-1H-pyrrolo[2,3-b]pyridin-4-yl}-1,3-thiazol-2-yl)-1-methylazetidin-3-ol;
1-(1-{5-chloro-2-[4-(pyrrolidin-1-ylmethyl)phenyl]-1H-pyrrolo[2,3-b]pyridin-4-yl}-1H-pyrazol-4-yl)cyclobutanol;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)urea;
N'-(1-{5-[5-chloro-2-(1-methyl-1H-pyrazol-4-yl)-1H-pyrrolo[2,3-b]pyridin-4-yl]-1,3-thiazol-2-yl}cyclobutyl)-N,N-dimethylurea;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N,N-dimethylamine;
3-{5-[5-chloro-2-(1-methyl-1H-pyrazol-4-yl)-1H-pyrrolo[2,3-b]pyridin-4-yl]-1,3-thiazol-2-yl}-1-ethylpyrrolidin-3-ol;
1-acetyl-3-(5-{5-chloro-2-[4-(morpholin-4-ylmethyl)phenyl]-1H-pyrrolo[2,3-b]pyridin-4-yl}-1,3-thiazol-2-yl)pyrrolidin-3-ol;
3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol 1,1-dioxide;
N-(1-{5-[5-chloro-2-(1-methyl-1H-pyrazol-4-yl)-1H-pyrrolo[2,3-b]pyridin-4-yl]-1,3-thiazol-2-yl}cyclobutyl)-N'-phenylurea;
N-benzyl-N'-(1-{5-[5-chloro-2-(1-methyl-1H-pyrazol-4-yl)-1H-pyrrolo[2,3-b]pyridin-4-yl]-1,3-thiazol-2-yl}cyclobutyl)urea;
3-(5-{5-chloro-2-[3-(pyrrolidin-1-ylmethyl)phenyl]-1H-pyrrolo[2,3-b]pyridin-4-yl}-1,3-thiazol-2-yl)-1-methylpyrrolidin-3-ol;
1-{3-[5-chloro-2-(1-methyl-1H-pyrazol-4-yl)-1H-pyrrolo[2,3-b]pyridin-4-yl]-1,2,4-oxadiazol-5-yl}cyclobutanol;
3-(5-{5-chloro-2-[4-(pyrrolidin-1-ylmethyl)phenyl]-1H-pyrrolo[2,3-b]pyridin-4-yl}-1,3-thiazol-2-yl)-1-methylpyrrolidin-3-ol;
3-(5-{5-chloro-2-[4-(pyrrolidin-1-ylmethyl)phenyl]-1H-pyrrolo[2,3-b]pyridin-4-yl}-1,3-thiazol-2-yl)-1-methylazetidin-3-ol;
3-(5-{5-chloro-2-[3-(pyrrolidin-1-ylmethyl)phenyl]-1H-pyrrolo[2,3-b]pyridin-4-yl}-1,3-thiazol-2-yl)-1-methylazetidin-3-ol;
3-[5-(5-chloro-1H-pyrrolo[2,3-b]pyridin-4-yl)-1,3-thiazol-2-yl]-1-methylpyrrolidin-3-ol;
1-(5-{5-chloro-2-[4-(pyrrolidin-1-ylmethyl)phenyl]-1H-pyrrolo[2,3-b]pyridin-4-yl}pyridin-2-yl)cyclobutanol;
3-{5-[5-chloro-2-(1-methyl-1H-pyrazol-4-yl)-1H-pyrrolo[2,3-b]pyridin-4-yl]-1,3-thiazol-2-yl}tetrahydrothiophene-3-ol;
3-(1-{5-chloro-2-[4-(pyrrolidin-1-ylmethyl)phenyl]-1H-pyrrolo[2,3-b]pyridin-4-yl}-1H-pyrazol-4-yl)oxetan-3-ol;
3-(5-{5-chloro-2-[1-(N,N-dimethylglycyl)-1,2,3,6-tetrahydropyridin-4-yl]-1H-pyrrolo[2,3-b]pyridin-4-yl}-1,3-thiazol-2-yl)oxetan-3-ol;

3-(5-{5-chloro-2-[1-(1-methyl-L-prolyl)-1,2,3,6-tetrahydropyridin-4-yl]-1H-pyrrolo[2,3-b]pyridin-4-yl}-1,3-thiazol-2-yl)oxetan-3-ol;

2-[4-{5-chloro-4-[2-(3-hydroxyoxetan-3-yl)-1,3-thiazol-5-yl]-1H-pyrrolo[2,3-b]pyridin-2-yl}-3,6-dihydropyridin-1(2H)-yl]-N,N-dimethylacetamide;

3-[5-(5-chloro-2-{1-[(1,1-dioxidotetrahydrothien-3-yl)carbonyl]-1,2,3,6-tetrahydropyridin-4-yl}-1H-pyrrolo[2,3-b]pyridin-4-yl)-1,3-thiazol-2-yl]oxetan-3-ol;

3-[5-(5-chloro-2-{1-[(1-methylpyrrolidin-3-yl)carbonyl]-1,2,3,6-tetrahydropyridin-4-yl}-1H-pyrrolo[2,3-b]pyridin-4-yl)-1,3-thiazol-2-yl]oxetan-3-ol;

3-(5-{5-chloro-2-[4-(pyrrolidin-1-ylmethyl)phenyl]-1H-pyrrolo[2,3-b]pyridin-4-yl}-1,3-thiazol-2-yl)tetrahydrothiophene-3-ol 1,1-dioxide;

N-[3-(2-{5-chloro-2-[4-(pyrrolidin-1-ylmethyl)phenyl]-1H-pyrrolo[2,3-b]pyridin-4-yl}-1,3-thiazol-5-yl)oxetan-3-yl]-N'-phenylurea;

3-{2-[5-chloro-2-(1-methyl-1H-pyrazol-4-yl)-1H-pyrrolo[2,3-b]pyridin-4-yl]-1,3-thiazol-5-yl}oxetan-3-amine;

N-(3-{2-[5-chloro-2-(1-methyl-1H-pyrazol-4-yl)-1H-pyrrolo[2,3-b]pyridin-4-yl]-1,3-thiazol-5-yl}oxetan-3-yl)acetamide;

N-(3-{2-[5-chloro-2-(1-methyl-1H-pyrazol-4-yl)-1H-pyrrolo[2,3-b]pyridin-4-yl]-1,3-thiazol-5-yl}oxetan-3-yl)-N'-phenylurea;

N-(3-{2-[5-chloro-2-(1-methyl-1H-pyrazol-4-yl)-1H-pyrrolo[2,3-b]pyridin-4-yl]-1,3-thiazol-5-yl}oxetan-3-yl)urea;

3-(2-{5-chloro-2-[4-(pyrrolidin-1-ylmethyl)phenyl]-1H-pyrrolo[2,3-b]pyridin-4-yl}-1,3-thiazol-5-yl)oxetan-3-amine;

N-[3-(2-{5-chloro-2-[4-(pyrrolidin-1-ylmethyl)phenyl]-1H-pyrrolo[2,3-b]pyridin-4-yl}-1,3-thiazol-5-yl)oxetan-3-yl]acetamide;

1-(5-{5-chloro-2-[(1E)-3-pyrrolidin-1-ylprop-1-enyl]-1H-pyrrolo[2,3-b]pyridin-4-yl}-1,3-thiazol-2-yl)cyclobutanol, or a pharmaceutically acceptable salt thereof.

17. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

PATENT NO. : 8,691,810 B2  
APPLICATION NO. : 13/106076  
DATED : April 8, 2014  
INVENTOR(S) : Michaelides et al.

Page 1 of 1

It is certified that error appears in the above-identified patent and that said Letters Patent is hereby corrected as shown below:

In the Claims

Column 170, line 62, claim 1: "$NHSO_2R^1$," to read as --$NHSO_2R^l$,--

Column 171, line 42, claim 1: "$C_{3-8}$-Cycloalkyl," to read as --$C_{3-8}$-cycloalkyl,--

Column 172, line 51, claim 13: "-$NR^hC(O)R^9$," to read as -- -$NR^hC(O)R^g$,--

Column 177, line 64, claim 16: "2-0yl}" to read as --2-yl}--

Column 180, line 14, claim 16: "acetamide;" to read as --acetamide; and--

Signed and Sealed this  
Twenty-fourth Day of February, 2015

Michelle K. Lee  
*Deputy Director of the United States Patent and Trademark Office*